US009359296B2

(12) United States Patent
Wang et al.

(10) Patent No.: US 9,359,296 B2
(45) Date of Patent: Jun. 7, 2016

(54) 7-SUBSTITUTED INDOLE MCL-1 INHIBITORS

(71) Applicant: AbbVie Inc., North Chicago, IL (US)

(72) Inventors: Xilu Wang, Grayslake, IL (US);
Xiaohong Song, Grayslake, IL (US);
Steven W. Elmore, Northbrook, IL (US);
Milan Bruncko, Green Oaks, IL (US);
David J. Madar, Miami, FL (US);
Andrew J. Souers, Evanston, IL (US);
Lisa A. Hasvold, Grayslake, IL (US); Le Wang, Vernon Hills, IL (US); Zhi-Fu Tao, Gurnee, IL (US); Aaron R. Kunzer, Shaumburg, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

(21) Appl. No.: 14/683,839

(22) Filed: Apr. 10, 2015

(65) Prior Publication Data
US 2015/0284328 A1 Oct. 8, 2015

Related U.S. Application Data

(63) Continuation of application No. 13/868,951, filed on Apr. 23, 2013, now Pat. No. 9,035,047, which is a continuation of application No. 12/104,294, filed on Apr. 16, 2008, now Pat. No. 8,445,679.

(60) Provisional application No. 60/949,650, filed on Jul. 13, 2007, provisional application No. 60/912,038, filed on Apr. 16, 2007.

(51) Int. Cl.
*C07D 401/06* (2006.01)
*C07D 401/14* (2006.01)
*C07D 209/42* (2006.01)
*A61K 31/5377* (2006.01)
*C07D 413/14* (2006.01)
*C07D 209/34* (2006.01)
*C07D 401/12* (2006.01)
*C07D 413/06* (2006.01)
*C07D 417/04* (2006.01)
*C07D 401/04* (2006.01)
*C07D 413/12* (2006.01)
*C07D 405/06* (2006.01)
*C07D 491/113* (2006.01)

(52) U.S. Cl.
CPC .......... *C07D 209/42* (2013.01); *A61K 31/5377* (2013.01); *C07D 209/34* (2013.01); *C07D 401/04* (2013.01); *C07D 401/06* (2013.01); *C07D 401/12* (2013.01); *C07D 401/14* (2013.01); *C07D 405/06* (2013.01); *C07D 413/06* (2013.01); *C07D 413/12* (2013.01); *C07D 413/14* (2013.01); *C07D 417/04* (2013.01); *C07D 491/113* (2013.01)

(58) Field of Classification Search
CPC ........................... C07D 401/06; C07D 401/14
See application file for complete search history.

(56) References Cited

U.S. PATENT DOCUMENTS

| 3,303,195 | A | 2/1967 | Velluz |
| 3,578,669 | A | 5/1971 | Zenitz |
| 4,014,883 | A | 3/1977 | Fryer et al. |
| 5,180,400 | A | 1/1993 | Baudry et al. |
| 6,787,651 | B2 | 9/2004 | Stolle et al. |
| 7,268,159 | B2 | 9/2007 | Hu et al. |
| 7,947,696 | B2 | 5/2011 | Eggenweiler et al. |
| 7,981,888 | B2 | 7/2011 | Song et al. |
| 8,853,209 | B2 | 10/2014 | Song et al. |
| 2005/0159427 | A1 | 7/2005 | Bruncko et al. |
| 2006/0160879 | A1 | 7/2006 | Olofsson et al. |
| 2009/0124616 | A1 | 5/2009 | Song et al. |

FOREIGN PATENT DOCUMENTS

| AU | 199891705 B2 | 5/2002 |
| CS | 270491 B1 | 10/2008 |
| EP | 0673937 B1 | 9/1995 |
| EP | 0791582 A1 | 8/1997 |
| EP | 0281242 A1 | 2/2002 |
| EP | 1852420 A1 | 7/2007 |
| EP | 1873144 A1 | 2/2008 |
| GB | 888426 | 4/1958 |
| JP | S4969698 | 7/1974 |
| JP | S63196563 A | 8/1988 |
| JP | H0598584 A | 4/1993 |
| JP | 2001513494 A | 9/2001 |
| JP | 2001517667 A | 10/2001 |
| JP | 2002521001 A | 7/2002 |
| JP | 2004505085 A | 2/2004 |
| JP | 2005514365 A | 5/2005 |
| JP | 2007500722 A | 1/2007 |
| JP | 2007501793 A | 2/2007 |
| JP | 2009519291 A | 5/2009 |

(Continued)

OTHER PUBLICATIONS

Amundson et al., "An Informatics Approach Identifying Markers of Chemosensitivity in Human Cancer Cell Lines," Cancer Research, (Nov. 1, 2000), pp. 6101-6110, vol. 60.

Backus et al., "Rb, mcl-1 and p53 expression correlate with clinical outcome in patients with liver metastases from colorectal cancer," Annals of Oncology, (2001), pp. 779-785, vol. 12.

Baekelandt et al., "Expression of Apoptosis-Related Proteins Is an Independent Determinant of Patient Prognosis in Advanced Ovarian Cancer," Journal of Clinical Oncology, (Nov. 15, 2000), pp. 3775-3781, vol. 18, No. 22.

Chung et al., "Expression of apoptotic regulators and their significance in cervical cancer," Cancer Letters, (2002), pp. 63-68, vol. 180.

(Continued)

*Primary Examiner* — Robert Havlin
(74) *Attorney, Agent, or Firm* — Jones Day

(57) ABSTRACT

Compounds which inhibit the activity of anti-apoptotic Mcl-1 protein, compositions containing the compounds, and methods of treating diseases involving overexpressed or unregulated Mcl-1 protein are disclosed.

2 Claims, No Drawings

(56) References Cited

FOREIGN PATENT DOCUMENTS

| WO | 9706141 A1 | 2/1997 |
|---|---|---|
| WO | 9838188 A1 | 9/1998 |
| WO | 9907351 A2 | 2/1999 |
| WO | 0210169 A1 | 2/2002 |
| WO | 0230895 A1 | 4/2002 |
| WO | 03044014 A1 | 5/2003 |
| WO | 2005013996 A2 | 2/2005 |
| WO | 2005016893 A2 | 2/2005 |
| WO | 2006041961 A1 | 4/2006 |
| WO | 2006090817 A1 | 8/2006 |
| WO | 2006112549 A1 | 10/2006 |
| WO | 2006122631 A1 | 11/2006 |
| WO | 2007008627 A2 | 1/2007 |
| WO | 2007068621 A1 | 6/2007 |
| WO | 2008131000 A2 | 10/2008 |

OTHER PUBLICATIONS

Cross et al., "Rules for the Nomenclature of Organic Chemistry, Section E: Stereochemistry," Pure and Applied Chemistry, (1976), pp. 11-30, vol. 45.
Deininger et al., "Antiapoptotic Bcl-2 Family Protein Expression Increases with Progression of Oligodendroglioma," Cancer, (1999), pp. 1832-1839, 86(9), vol. 86(9).
Eerola et al., "Accelerated Apoptosis and Low Bcl-2 Expression Associated with Neuroendocrine Differentiation Predict Shortened Survival in Operated Large Cell Carcinoma of the Lung," Pathology Oncology Research, (1999), pp. 179-186. vol. 5(3).
Fong et al., "Mcl-1 Expression in Gestational Trophoblastic Disease Correlates with Clinical Outcome," Cancer, (2005), pp. 268-276, vol. 103, No. 2.
Gomez-Bougie et al., "The imbalance between Bim and Mcl-1 expression controls the survival of human myeloma cells," European Journal of Immunology, (2004), pp. 3156-3164, vol. 34.
Greene et al., "Protective Groups in Organic Synthesis," (1999), 3rd Ed., John Wiley & Sons.
Holzelova et al., "Autoimmune Lymphoproliferative Syndrome with Somatic Fas Mutations," The New England Journal of Medicine, (2004), pp. 1409-1418, vol. 351, No. 14.
Hotz et al., "Spontaneous Apoptosis and the Expression of p53 and Bcl-2 Family Proteins in Locally Advanced Head and Neck Cancer," Arch Otolaryngol Head Neck Surg, (Apr. 1999), pp. 417-422, vol. 125.
International Searching Authority, "International Search Report and Written Opinion for International Application No. PCT/US2008/060472," (Oct. 21, 2008), pp. 11.
Kubinyi, H., "Ligand-Protein Interactions and Molecular Similarity," 3D QSAR in Drug Design: Theory Methods and Applications, (1998), Table of Contents, pp. 4, and pp. 243-244, vol. 2-3.
Kunori, "CAPLUS Abstract of: Studies on related indole compounds. I. Bromination of indole-2-carboxylic acid," Nippon Kagaku Zasshi, (1957), pp. 1798-1800, vol. 78.
Kuramoto et al., "High Expression of MCL 1 gene related to vascular endothelial growth factor is associated with poor outcome in non-Hodgkin's lymphoma," British Journal of Haematology, (2002), pp. 158-161, vol. 116.
Maddirala et al., "Fischer indolization of 2,6-dialkyl- and 2,4,6-trialkylphenylhydrazones of diketones and keto esters," Tetrahedron Letters, (2003), pp. 5665-5668, vol. 44, No. 30.
Maeta et al., "Expression of Mcl-1 and p53 proteins predicts the survival of patients with T3 gastric carcinoma," Gastric Cancer, (2004), pp. 78-84, vol. 7.
Marion et al., "The Synthesis and the Characterization of Monomethyl-and Dimethylindoles," Canadian Journal of Research, Chemical Sciences, (1947), pp. 1-13, vol. 25B, No. 1.
Moshynska, et al., "Prognostic Significance of a Short Sequence Insertion in the MCL-1 Promoter in Chronic Lymphocytic Leukemia," Journal of the National Cancer Institute, (May 5, 2004), pp. 673-682, vol. 96, No. 9.
Packham et al., "Bodyguards and assassins: Bcl-2 family proteins and apoptosis control in chronic lymphocytic leukaemia," Immunology, (2005), pp. 441-449, vol. 114.
Pelchowicz et al., "Substituted Tryptamines and Their Derivatives," Journal of the Chemical Society, (Nov. 1960), pp. 4699-4701.
Puck et al., "Immune Disorders Caused by Defects in the Caspase Cascade," Current Allergy and Asthma Reports, (2003), pp. 378-384, vol. 3.
Rassidakis et al., "BCL-2 family proteins in peripheral T-cell lymphomas: correlation with tumour apoptosis and proliferation," Journal of Pathology, (2003), pp. 240-248, vol. 200.
Rengan et al., "Actin cytoskeletal function is spared, but apoptosis is increased, in WAS patient hematopoietic cells," Blood, (2000), pp. 1283-1292, vol. 95, No. 4.
Shi et al., "Acquired Resistance of Pancraatic Cancer Cells towards 5-Fiuorouracll and Gemcitabine is Associated with Altered Expression of Apoptosis-Regulating Genes," Oncology, (2002), pp. 354-362, vol. 62.
Shimazaki et al., "Evaluation of apoptosis as a prognostic factor in myelodysplastic syndromes," British Journal of Haematology, (Jan. 26, 2000), pp. 584-590, vol. 110.
Soini et al., "Apoptosis and Expression of Apoptosis Regulating Proteins bcl-2, mcl-1, bcl-X and bax in Malignant Mesothelioma," Clinical Cancer Research, (Nov. 1999), pp. 3508-3515, vol. 5.
Strik et al., "BCL-2 Family protein expression in initial and recurrent glioblastomas: modulation by radiochemotherapy," J Neural Neurosurg Psychiatry, (1999), pp. 763-768, vol. 67.
Wermuth, "Electronic Screening: Leading Finding from Database Mining," The Practice of Medicinal Chemistry, 2nd Edition, (2003), Chapters 9-10.
Zhang et al., "Fragment-based design, synthesis, and biological evaluation of N-substituted-5-(4-isopropylthiophenol)-2-hydroxynicotinamide derivatives as novel Mcl-1 inhibitors," European Journal of Medicinal Chemistry, (2013), pp. 410-420, vol. 60.
Kauffman et al., "Elevated Expression of the Apoptotic Regulator Mcl-1 at the Time of Leukemic Relapse," Blood, (Feb. 1, 1998), pp. 991-1000, vol. 91, No. 3.

7-SUBSTITUTED INDOLE MCL-1 INHIBITORS

CROSS-REFERENCE SECTION TO RELATED APPLICATIONS

This application is a continuation of U.S. application Ser. No. 13/868,951, filed Apr. 23, 2013, which is a continuation of U.S. application Ser. No. 12/104,294, filed Apr. 16, 2008; which claims the benefit of U.S. Provisional Patent Application No. 60/949,650, filed Jul. 13, 2007, now expired, and U.S. Provisional Patent Application No. 60/912,038, filed Apr. 16, 2007, now expired, which are hereby incorporated by reference in their entireties inot this application.

SEQUENCE LISTING

The content of the following submission on ASCII text file is incorporated herein by reference in its entirety a computer readable form (CRF) of the Sequence Listing, entitled 8976USC2_12655-121-999_SEQ_LISTING.txt, of size 1048 bytes, and created on Apr. 8, 2015.

FIELD OF THE INVENTION

This invention pertains to compounds which inhibit the activity of anti-apoptotic Mcl-1 protein, compositions containing the compounds, and methods of treating diseases involving overexpressed or unregulated Mcl-1 protein.

BACKGROUND OF THE INVENTION

Mcl-1 protein is associated with a number of diseases. There is therefore an existing need in the therapeutic arts for compounds which bind to and inhibit the activity of Mcl-1 protein.

SUMMARY OF THE INVENTION

One embodiment of this invention, therefore, pertains to compounds which inhibit the activity of Mcl-1 protein, the compounds having Formula I,

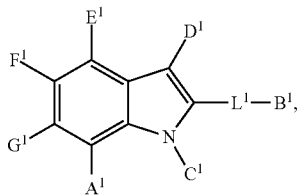

(I)

and therapeutically acceptable salts thereof, wherein $A^1$ is $A^2$, $OA^2$, $SA^2$, $S(O)A^2$, $SO_2A^2$, $NH_2$, $NHA^2$, $N(A^2)_2$, $C(O)A^2$, $C(O)NH_2$, $C(O)NHA^2$, $C(O)N(A^2)_2$, $NHC(O)A^2$, $NA^2C(O)A^2$, $NHSO_2A^2$, $NA^2SO_2A^2$, $NHC(O)OA^2$, $NA^2C(O)OA^2$, $SO_2NH_2$, $SO_2NHA^2$, $SO_2N(A^2)_2$, $NHC(O)NH_2$, $NHC(O)A^2$ $NHC(O)N(A^2)_2$, $NA^2C(O)N(A^2)_2$F, Cl, Br, or I;

$A^2$ is $R^1$, $R^2$, $R^3$, or $R^4$;

$R^1$ is phenyl which is unfused or fused with benzene, heteroarene or $R^{1A}$; $R^{1A}$ is cycloalkane, cycloalkene, heterocycloalkane or heterocycloalkene;

$R^2$ is heteroaryl which is unfused or fused with benzene, heteroarene or $R^{2A}$; $R^{2A}$ is cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene or $R^{3A}$; $R^{3A}$ is cycloalkane, cycloalkene, heterocycloalkane or heterocycloalkene;

$R^4$ is alkyl, alkenyl, or alkynyl, each of which is unsubstituted or substituted with one, two, three, four or five of independently selected $R^5$, $OR^5$, $SR^5$, $S(O)R^5$, $SO_2R^5$, $NH_2$, $NHR^5$, $N(R^5)_2$, $C(O)R^5$, $C(O)NH_2$, $C(O)NHR^5$, $C(O)N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $SO_2NH_2$, $SO_2NHR^5$, $SO_2N(R^5)_2$, $NHC(O)NH_2$, $NHC(O)R^5$, $NHC(O)N(R^5)_2$, $NR^5C(O)N(R^5)_2$, OH, (O), $C(O)OH$, CN, $CF_3$, $OCF_3$, $CF_2CF_3$, F, Cl, Br or I;

$R^5$ is $R^6$, $R^7$ or $R^8$;

$R^6$ is phenyl which is unfused or fused with benzene, heteroarene or $R^{6A}$; $R^{6A}$ is cycloalkane, cycloalkene, heterocycloalkane or heterocycloalkene;

$R^7$ is heteroaryl which is unfused or fused with benzene, heteroarene or $R^{7A}$; $R^{7A}$ is cycloalkane, cycloalkene, heterocycloalkane or heterocycloalkene;

$R^8$ is cycloalkyl, cycloalkenyl, heterocycloalkyl or heterocycloalkenyl, each of which is unfused or fused with benzene, heteroarene or $R^{8A}$; $R^{8A}$ is cycloalkane, cycloalkene, heterocycloalkane or heterocycloalkene;

$L^1$ is a bond or is alkylene, alkenylene, alkynylene or $L^2$; and $B^1$ is $C(O)OH$ or a bioisostere thereof or is $C(O)OR^1$, $C(O)OR^2$, $C(O)OR^3$ or $C(O)OR^4$;

$L^2$ is $C_2$-$C_6$-alkylene, $C_4$-$C_6$-alkenylene or $C_4$-$C_6$-alkynylene, each of which has one $CH_2$ moiety replaced with O, S, S(O), $SO_2$, NH or $N(W^1)$;

$W^1$ is alkyl, alkenyl or alkynyl;

$C^1$ and $D^1$ are independently H, $R^9$, $R^{10}$, $R^{11}$, $R^{12}$, $C(O)OR^{12}$, F, Cl, Br, I, or one of $C^1$ and $D^1$ is H, and the other is $R^9$, $R^{10}$, $R^{11}$ $R^{12}$, $C(O)OR^{12}$, F, Cl, Br, or I;

$R^9$ is phenyl which is unfused or fused with benzene, heteroarene or $R^{9A}$; $R^{9A}$ is cycloalkane, cycloalkene, heterocycloalkane or heterocycloalkene;

$R^{10}$ is heteroaryl which is unfused or fused with benzene, heteroarene or $R^{10A}$; $R^{10A}$ is cycloalkane, cycloalkene, heterocycloalkane or heterocycloalkene;

$R^{11}$ is cycloalkyl, cycloalkenyl, heterocycloalkyl or heterocycloalkenyl, each of which is unfused or fused with benzene, heteroarene or $R^{11A}$; $R^{11A}$ is cycloalkane, cycloalkene, heterocycloalkane or heterocycloalkene;

$R^{12}$ is alkyl, alkenyl, or alkynyl, each of which is unsubstituted or substituted with one, two, three, four or five of independently selected $R^{13}$, $OR^{13}$, $SR^{13}$, $S(O)R^{13}$, $SO_2R^{13}$, $NH_2$, $NHR^{13}$, $N(R^{13})_2$, $C(O)R^{13}$, $C(O)NH_2$, $C(O)NHR^{13}$, $C(O)N(R^{13})_2$, $NHC(O)R^{13}$, $NR^{13}C(O)R^{13}$, $NHC(O)R^{13}$, $NR^{13}C(O)R^{13}$, $NHSO_2R^{13}$, $NR^{13}SO_2R^{13}$, $NHC(O)OR^{13}$, $NR^{13}C(O)OR^{13}$, $SO_2NH_2$, $SO_2NHR^{13}$, $SO_2N(R^{13})_2$, $NHC(O)NH_2$, $NHC(O)R^{13}$, $NHC(O)N(R^{13})_2$, $NR^{13}C(O)N(R^{13})_2$, OH, (O), $C(O)OH$, CN, $CF_3$, $OCF_3$, $CF_2CF_3$, F, Cl, Br or I;

$R^{13}$ is $R^{14}$, $R^{15}$ $R^{16}$, or $R^{16A}$;

$R^{14}$ is phenyl which is unfused or fused with benzene, heteroarene or $R^{14A}$; $R^{14A}$ is cycloalkane, cycloalkene, heterocycloalkane or heterocycloalkene; each of which is unfused or fused with $R^{14B}$; $R^{14B}$ is cycloalkane, cycloalkene, heterocycloalkane or heterocycloalkene;

$R^{15}$ is heteroaryl which is unfused or fused with benzene, heteroarene or $R^{15A}$; $R^{15A}$ is cycloalkane, cycloalkene, heterocycloalkane or heterocycloalkene;

$R^{16}$ is cycloalkyl, cycloalkenyl, heterocycloalkyl or heterocycloalkenyl, each of which is unfused or fused with benzene, heteroarene or $R^{16A}$; $R^{16A}$ cycloalkane, cycloalkene, heterocycloalkane or heterocycloalkene;

$R^{16A}$ alkyl, alkenyl, or alkynyl; and one or two or each of $E^1$ and $F^1$ and $G^1$ are independently H, $CF_3$, F, Cl, Br or I, and the remainder are independently $R^{17}$, $R^{18}$, $R^{19}$, $R^{20}$ or $OR^{20}$;

$R^{17}$ is phenyl which is unfused or fused with benzene, heteroarene or $R^{17A}$; $R^{17A}$ is cycloalkane, cycloalkene, heterocycloalkane or heterocycloalkene;

$R^{18}$ is heteroaryl which is unfused or fused with benzene, heteroarene or $R^{18A}$; $R^{18A}$ is cycloalkane, cycloalkene, heterocycloalkane or heterocycloalkene;

$R^{19}$ is cycloalkyl, cycloalkenyl, heterocycloalkyl or heterocycloalkenyl, each of which is unfused or fused with benzene, heteroarene or $R^{19A}$; $R^{19A}$ is cycloalkane, cycloalkene, heterocycloalkane or heterocycloalkene;

$R^{20}$ is alkyl, alkenyl, or alkynyl, each of which is unsubstituted or substituted with one, two, three, four or five of independently selected $R^{20}$, $OR^{20}$, $SR^{20}$, $S(O)R^{20}$, $SO_2R^{20}$, $NH_2$, $NHR^{20}$, $N(R^{20})_2$, $C(O)R^{20}$, $C(O)NH_2$, $C(O)NHR^{20}$, $C(O)N(R^2)_2$, $NHC(O)R^{20}$, $NHC(O)R^{20}$, $NR^{20}C(O)R^{20}$, $NR^{20}C(O)R^{20}$, $NHSO_2R^{20}$, $NR^{20}SO_2R^{20}$, $NHC(O)OR^{20}$, $NR^{20}C(O)OR^{20}$, $SO_2NH_2$, $SO_2NHR^{20}$, $SO_2N(R^{20})_2$, $NHC(O)NH_2$, $NHC(O)R^{20}$, $NHC(O)N(R^{20})_2$, $NR^{20}C(O)N(R^{20})_2$, OH, (O), C(O)OH, CN, $CF_3$, $OCF_3$, $CF_2CF_3$, F, Cl, Br or I;

$R^{20}$ is $R^{21}$, $R^{22}$ or $R^{23}$;

$R^{21}$ is phenyl which is unfused or fused with benzene, heteroarene or $R^{21A}$; $R^{21A}$ is cycloalkane, cycloalkene, heterocycloalkane or heterocycloalkene;

$R^{22}$ is heteroaryl which is unfused or fused with benzene, heteroarene or $R^{22A}$; $R^{22A}$ is cycloalkane, cycloalkene, heterocycloalkane or heterocycloalkene;

$R^{23}$ is cycloalkyl, cycloalkenyl, heterocycloalkyl or heterocycloalkenyl, each of which is unfused or fused with benzene, heteroarene or $R^{23A}$; $R^{23A}$ is cycloalkane, cycloalkene, heterocycloalkane or heterocycloalkene;

wherein each foregoing cyclic moiety is independently unsubstituted or substituted with one or two or three or four or five of independently selected spiroheteroalkyl, $R^{30}$, $OR^{30}$, $OCH_2R^{30}$, $SR^{30}$, $S(O)R^{30}$, $SO_2R^{30}$, $C(O)R^{30}$, $CO(O)R^{30}$, $OC(O)R^{30}$, $OC(O)OR^{30}$, NO, $NO_2$, $NH_2$, $NHR^{30}$, $N(R^{30})_2$, $CH_2R^{30}$, $C(O)NH_2$, $C(O)NHR^{30}$, $C(O)N(R^{30})_2$, $NHC(O)R^{30}$ $NR^{30}C(O)R^{30}$, $C(O)NHOH$, $C(O)NHOR^{30}$, $C(O)NHSO_2R^{30}$, $C(O)NR^{30}SO_2R^{30}$, $SO_2NH_2$, $SO_2NHR^{30}$, $SO_2N(R^{30})_2$, $CF_3$, $CF_2CF_3$, C(O)H, C(O)OH, $C(N)NH_2$, $C(N)NHR^{30}$, $C(N)N(R^{30})_2$, =NO-(alkylene)-$C(O)CF_3$, CNOH, $CNOCH_3$, OH, (O), CN, $N_3$, $CF_3$, $CF_2CF_3$, $OCF_3$, $OCF_2CF_3$, F, Cl, Br, or I;

$R^{30}$ is $R^{31}$, $R^{32}$, $R^{33}$ or $R^{34}$;

$R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocycloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl, or alkynyl, each of which is unsubstituted or substituted with one, two, three, four or five of independently selected $R^{35}$, $OR^{35}$, $SR^{35}$, $S(O)R^{35}$, $SO_2R^{35}$, $NH_2$, $NHR^{35}$, $N(R^{35})_2$, $C(O)R^{35}$, $C(O)NH_2$, $C(O)NHR^{35}$, $C(O)N(R^{35})_2$, $NHC(O)R^{35}$, $NR^{35}C(O)R^{35}$, $NHSO_2R^{35}$, $NR^{35}SO_2R^{35}$, $NHC(O)OR^{35}$, $NR^{35}C(O)OR^{35}$, $SO_2NH_2$, $SO_2NHR^{35}$, $SO_2N(R^{35})_2$, $NHC(O)NH_2$, $NHC(O)R^{35}$ NHC(O)N(R^{35})_2$, $NR^{35}C(O)N(R^{35})_2$, OH, (O), C(O)OH, CN, $CF_3$, $OCF_3$, $CF_2CF_3$, F, Cl, Br or I;

$R^{35}$ is $R^{36}$, $R^{37}$, $R^{38}$ or $R^{39}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is heteroaryl which is unfused or fused with benzene, heteroarene or $R^{37A}$; $R^{37A}$ is cycloalkane, cycloalkene, heterocycloalkane or heterocycloalkene;

$R^{38}$ is cycloalkyl, cycloalkenyl, heterocycloalkyl or heterocycloalkenyl, each of which is unfused or fused with benzene, heteroarene or $R^{38A}$; $R^{38A}$ is cycloalkane, cycloalkene, heterocycloalkane or heterocycloalkene;

$R^{39}$ is alkyl, alkenyl or alkynyl, each of which is unsubstituted or substituted with $NH_2$, $N(R^{40})_2$, $OR^{40}$, or $R^{40}$;

$R^{40}$ is alkyl, alkenyl, alkynyl, phenyl, heteroaryl, cycloalkyl, cycloalkenyl or heterocycloalkyl;

wherein the moieties represented by $R^{31}$, $R^{32}$, $R^{33}$ $R^{36}$, $R^{37}$, $R^{38}$ and $R^{40}$ are independently unsubstituted or substituted with one or two or three of independently selected $R^{50}$, $OR^{50}$, $C(O)R^{50}$, $C(O)OR^{50}$, $SO_2R^{50}$, $NHC(O)R^{50}$, F, Cl, Br, I, C(O)OH, CN, $NO_2$, $NH_2$, $CF_3$, (O) or OH;

$R^{50}$ is $R^{51}$, $R^{52}$, $R^{53}$ or $R^{54}$;

$R^{51}$ is phenyl which is unfused or fused with benzene, heteroarene or $R^{51A}$; $R^{51A}$ is cycloalkane, cycloalkene, heterocycloalkane or heterocycloalkene;

$R^{52}$ is heteroaryl which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl, or alkynyl; each of which is unsubstituted or substituted with one, two, three, four or five of independently selected F, Cl, Br, I, C(O)OH, CN, $NO_2$, $NH_2$, $CF_3$, (O), OH, phenyl, heteroaryl, cycloalkyl, cycloalkenyl or heterocycloalkyl and wherein the moieties represented by $R^{51}$, $R^{52}$, and $R^{53}$ are independently unsubstituted or substituted with one or two or three of independently selected $R^{55}$, $OR^{55}$, $OCH_2R^{55}$, $SR^{55}$, $S(O)R^{55}$, $SO_2R^{55}$, $C(O)R^{55}$, $CO(O)R^{55}$, $OC(O)R^{55}$, $OC(O)OR^{55}$, $NO_2$, $NH_2$, $NHR^{55}$, $N(R^{55})_2$, $CH_2R^{55}$, $C(O)NH_2$, $C(O)NHR^{55}$, $C(O)N(R^{55})_2$, $NHC(O)R^{55}$, $NR^{55}C(O)R^{55}$, C(O)NHOH, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $CF_3$, $CF_2CF_3$, C(O)H, C(O)OH, $C(N)NH_2$, $C(N)NHR^{55}$, $C(N)N(R^{55})_2$, =NO-(alkylene)-$C(O)CF_3$, CNOH, $CNOCH_3$, OH, (O), CN, $N_3$, $CF_3$, $CF_2CF_3$, $OCF_3$, $OCF_2CF_3$, F, Cl, Br or I; and $R^{55}$ is alkyl, alkenyl, alkynyl, phenyl, heteroaryl, cycloalkyl, cycloalkenyl or heterocycloalkyl.

Another embodiment pertains to compounds having Formula I,

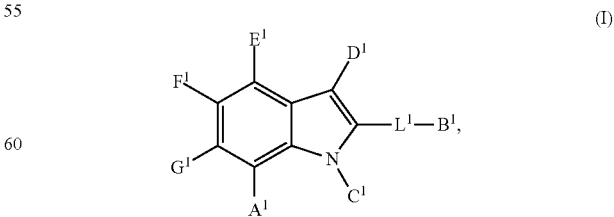

(I)

and therapeutically acceptable salts thereof, wherein $A^1$ is $A^2$, $OA^2$, $SA^2$, $S(O)A^2$, $SO_2A^2$, $NH_2$, $NHA^2$, $N(A^2)_2$, $C(O)A^2$, $C(O)NH_2$, $C(O)NHA^2$, $C(O)N(A^2)_2$, $NHC(O)A^2$, $NA^2C(O)A^2$, $NHSO_2A^2$, $NA^2SO_2A^2$, $NHC(O)OA^2$, $NA^2C$ (O)OA², SO₂NH₂, SO₂NHA², SO₂N(A²)₂, NHC(O)NH₂, NHC(O)A²NHC(O)N(A²)₂, NA²C(O)N(A²)₂F, Cl, Br, or I;

$A^2$ is $R^1$, $R^2$, $R^3$, or $R^4$;

$R^1$ is phenyl which is unfused or fused with benzene, heteroarene or $R^{1A}$; $R^{1A}$ is cycloalkane, cycloalkene, heterocycloalkane or heterocycloalkene;

$R^2$ is heteroaryl which is unfused or fused with benzene, heteroarene or $R^{2A}$; $R^{2A}$ is cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene or $R^{3A}$; $R^{3A}$ is cycloalkane, cycloalkene, heterocycloalkane or heterocycloalkene;

$R^4$ is alkyl, alkenyl, or alkynyl, each of which is unsubstituted or substituted with one, two, three, four or five of independently selected $R^5$, $OR^5$, $SR^5$, $S(O)R^5$, $SO_2R^5$, $NH_2$, $NHR^5$, $N(R^5)_2$, $C(O)R^5$, $C(O)NH_2$, $C(O)NHR^5$, $C(O)N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $SO_2NH_2$, $SO_2NHR^5$, $SO_2N(R^5)_2$, $NHC(O)NH_2$, $NHC(O)R^5$, $NHC(O)N(R^5)_2$, $NR^5C(O)N(R^5)_2$, OH, (O), C(O)OH, CN, $CF_3$, $OCF_3$, $CF_2CF_3$, F, Cl, Br or I;

$R^5$ is $R^6$, $R^7$ or $R^8$;

$R^6$ is phenyl which is unfused or fused with benzene, heteroarene or $R^{6A}$; $R^{6A}$ is cycloalkane, cycloalkene, heterocycloalkane or heterocycloalkene;

$R^7$ is heteroaryl which is unfused or fused with benzene, heteroarene or $R^{7A}$; $R^{7A}$ is cycloalkane, cycloalkene, heterocycloalkane or heterocycloalkene;

$R^8$ is cycloalkyl, cycloalkenyl, heterocycloalkyl or heterocycloalkenyl, each of which is unfused or fused with benzene, heteroarene or $R^{8A}$; $R^{8A}$ is cycloalkane, cycloalkene, heterocycloalkane or heterocycloalkene;

$L^1$ is a bond or is alkylene, alkenylene, alkynylene or $L^2$; and $B^1$ is C(O)OH or a bioisostere thereof or is $C(O)OR^1$, $C(O)OR^2$, $C(O)OR^3$ or $C(O)OR^4$;

$L^2$ is $C_2$-$C_6$-alkylene, $C_4$-$C_6$-alkenylene or $C_4$-$C_6$-alkynylene, each of which has one $CH_2$ moiety replaced with O, S, S(O), $SO_2$, NH or $N(W^1)$;

$W^1$ is alkyl, alkenyl or alkynyl;

$C^1$ and $D^1$ are independently H, $R^9$, $R^{10}$, $R^{11}$, $R^{12}$, $C(O)OR^{12}$, F, Cl, Br, I, or
one of $C^1$ and $D^1$ is H, and the other is $R^9$, $R^{10}$, $R^{11}R^{12}$, $C(O)OR^{12}$, F, Cl, Br, or I;

$R^9$ is phenyl which is unfused or fused with benzene, heteroarene or $R^{9A}$; $R^{9A}$ is cycloalkane, cycloalkene, heterocycloalkane or heterocycloalkene;

$R^{10}$ is heteroaryl which is unfused or fused with benzene, heteroarene or $R^{10A}$; $R^{10A}$ is cycloalkane, cycloalkene, heterocycloalkane or heterocycloalkene;

$R^{11}$ is cycloalkyl, cycloalkenyl, heterocycloalkyl or heterocycloalkenyl, each of which is unfused or fused with benzene, heteroarene or $R^{11A}$; $R^{11A}$ is cycloalkane, cycloalkene, heterocycloalkane or heterocycloalkene;

$R^{12}$ is alkyl, alkenyl, or alkynyl, each of which is unsubstituted or substituted with one, two, three, four or five of independently selected $R^{13}$, $OR^{13}$, $SR^{13}$, $S(O)R^{13}$, $SO_2R^{13}$, $NH_2$, $NHR^{13}$, $N(R^{13})_2$, $C(O)R^{13}$, $C(O)NH_2$, $C(O)NHR^{13}$, $C(O)N(R^{13})_2$, $NHC(O)R^{13}$, $NR^{13}C(O)R^{13}$, $NHC(O)R^{13}$, $NR^{13}C(O)R^{13}$, $NHSO_2R^{13}$, $NR^{13}SO_2R^{13}$, $NHC(O)OR^{13}$, $NR^{13}C(O)OR^{13}$, $SO_2NH_2$, $SO_2NHR^{13}$, $SO_2N(R^{13})_2$, $NHC(O)NH_2$, $NHC(O)R^{13}$, $NHC(O)N(R^{13})_2$, $NR^{13}C(O)N(R^{13})_2$, OH, (O), C(O)OH, CN, $CF_3$, $OCF_3$, $CF_2CF_3$, F, Cl, Br or I;

$R^{13}$ is $R^{14}$, $R^{15}$ $R^{16}$, or $R^{16A}$;

$R^{14}$ is phenyl which is unfused or fused with benzene, heteroarene or $R^{14A}$; $R^{14A}$ is cycloalkane, cycloalkene, heterocycloalkane or heterocycloalkene; each of which is unfused or fused with $R^{14B}$; $R^{14B}$ is cycloalkane, cycloalkene, heterocycloalkane or heterocycloalkene;

$R^{15}$ is heteroaryl which is unfused or fused with benzene, heteroarene or $R^{15A}$; $R^{15A}$ is cycloalkane, cycloalkene, heterocycloalkane or heterocycloalkene;

$R^{16}$ is cycloalkyl, cycloalkenyl, heterocycloalkyl or heterocycloalkenyl, each of which is unfused or fused with benzene, heteroarene or $R^{16A}$; $R^{16A}$ cycloalkane, cycloalkene, heterocycloalkane or heterocycloalkene;

$R^{16A}$ is alkyl, alkenyl, or alkynyl; and one or two or each of $E^1$ and $F^1$ and $G^1$ are independently H, $CF_3$, F, Cl, Br or I, and the remainder are independently $R^{17}$, $R^{18}$, $R^{19}$, $R^{20}$ or $OR^{20}$;

$R^{17}$ is phenyl which is unfused or fused with benzene, heteroarene or $R^{17A}$; $R^{17A}$ is cycloalkane, cycloalkene, heterocycloalkane or heterocycloalkene;

$R^{18}$ is heteroaryl which is unfused or fused with benzene, heteroarene or $R^{18A}$; $R^{18A}$ is cycloalkane, cycloalkene, heterocycloalkane or heterocycloalkene;

$R^{19}$ is cycloalkyl, cycloalkenyl, heterocycloalkyl or heterocycloalkenyl, each of which is unfused or fused with benzene, heteroarene or $R^{19A}$; $R^{19A}$ is cycloalkane, cycloalkene, heterocycloalkane or heterocycloalkene;

$R^{20}$ is alkyl, alkenyl, or alkynyl, each of which is unsubstituted or substituted with one, two, three, four or five of independently selected $R^{20}$, $OR^{20}$, $SR^{20}$, $S(O)R^{20}$, $SO_2R^{20}$, $NH_2$, $NHR^{20}$, $N(R^{20})_2$, $C(O)R^{20}$, $C(O)NH_2$, $C(O)NHR^{20}$, $C(O)N(R^{20})_2$, $NHC(O)R^{20}$, $NHC(O)R^{20}$, $NR^{20}C(O)R^{20}$, $NR^{20}C(O)R^{20}$, $NHSO_2R^{20}$, $NR^{20}SO_2R^{20}$, $NHC(O)OR^{20}$, $NR^{20}C(O)OR^{20}$, $SO_2NH_2$, $SO_2NHR^{20}$, $SO_2N(R^2)_2$, $NHC(O)NH_2$, $NHC(O)R^{20}$, $NHC(O)N(R^{20})_2$, $NR^{20}C(O)N(R^{20})_2$, OH, (O), C(O)OH, CN, $CF_3$, $OCF_3$, $CF_2CF_3$, F, Cl, Br or I;

$R^{20}$ is $R^{21}$, $R^{22}$ or $R^{23}$;

$R^{21}$ is phenyl which is unfused or fused with benzene, heteroarene or $R^{21A}$; $R^{21A}$ is cycloalkane, cycloalkene, heterocycloalkane or heterocycloalkene;

$R^{22}$ is heteroaryl which is unfused or fused with benzene, heteroarene or $R^{22A}$; $R^{22A}$ is cycloalkane, cycloalkene, heterocycloalkane or heterocycloalkene;

$R^{23}$ is cycloalkyl, cycloalkenyl, heterocycloalkyl or heterocycloalkenyl, each of which is unfused or fused with benzene, heteroarene or $R^{23A}$; $R^{23A}$ is cycloalkane, cycloalkene, heterocycloalkane or heterocycloalkene;

wherein each foregoing cyclic moiety is independently unsubstituted or substituted with one or two or three or four or five of independently selected spiroheteroalkyl, $R^{30}$, $OR^{30}$, $SO_2R^{30}$, $C(O)R^{30}$, NO, $NO_2$, $NH_2$, $N(R^{30})_2$, $C(O)NH_2$, $C(O)NHR^{30}$, $NHC(O)R^{30}$, $C(O)NHSO_2R^{30}$, $SO_2NH_2$, C(O)OH, OH, (O), CN, $CF_3$, $OCF_3$, F, Cl, Br, or I;

$R^{30}$ is $R^{31}$, $R^{32}$, $R^{33}$ or $R^{34}$;

$R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocycloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl, or alkynyl, each of which is unsubstituted or substituted with one, two, three, four or five of independently selected $R^{35}$, $OR^{35}$, $SR^{35}$, $S(O)R^{35}$, $SO_2R^{35}$, $NH_2$, $NHR^{35}$, $N(R^{35})_2$, $C(O)R^{35}$, $C(O)NH_2$, $C(O)NHR^{35}$, $C(O)N(R^{35})_2$, $NHC(O)R^{35}$, $NR^{35}C(O)R^{35}$, $NHSO_2R^{35}$, $NR^{35}SO_2R^{35}$, $NHC(O)OR^{35}$, $NR^{35}C(O)OR^{35}$, $SO_2NH_2$, $SO_2NHR^{35}$, $SO_2N(R^{35})_2$, $NHC(O)NH_2$, $NHC(O)R^{35}NHC$ (O)N(R$^{35}$)$_2$, NR$^{35}$C(O)N(R$^{35}$)$_2$, OH, (O), C(O)OH, CN, CF$_3$, OCF$_3$, CF$_2$CF$_3$, F, Cl, Br or I;

R$^{35}$ is R$^{36}$, R$^{37}$, R$^{38}$ or R$^{39}$;

R$^{36}$ is phenyl which is unfused or fused with benzene, heteroarene or R$^{36A}$; R$^{36A}$ is cycloalkane, cycloalkene, heterocycloalkane or heterocycloalkene;

R$^{37}$ is heteroaryl which is unfused or fused with benzene, heteroarene or R$^{37A}$; R$^{37A}$ is cycloalkane, cycloalkene, heterocycloalkane or heterocycloalkene;

R$^{38}$ is cycloalkyl, cycloalkenyl, heterocycloalkyl or heterocycloalkenyl, each of which is unfused or fused with benzene, heteroarene or R$^{38A}$; R$^{38A}$ is cycloalkane, cycloalkene, heterocycloalkane or heterocycloalkene;

R$^{39}$ is alkyl, alkenyl or alkynyl, each of which is unsubstituted or substituted with NH$_2$, N(R$^{40}$)$_2$, OR$^{40}$, or R$^{40}$;

R$^{40}$ is alkyl, alkenyl, alkynyl, phenyl, heteroaryl, cycloalkyl, cycloalkenyl or heterocycloalkyl;

wherein the moieties represented by R$^{31}$, R$^{32}$, R$^{33}$ R$^{36}$, R$^{37}$, R$^{38}$ and R$^{40}$ are independently unsubstituted or substituted with one or two or three of independently selected R$^{50}$, OR$^{50}$, C(O)R$^{50}$, C(O)OR$^{50}$, SO$_2$R$^{50}$, NHC(O)R$^{50}$, F, Cl, Br, I, C(O)OH, CN, NO$_2$, NH$_2$, CF$_3$, (O) or OH;

R$^{50}$ is R$^{51}$, R$^{52}$, R$^{53}$ or R$^{54}$;

R$^{51}$ is phenyl which is unfused or fused with benzene, heteroarene or R$^{51A}$; R$^{51A}$ is cycloalkane, cycloalkene, heterocycloalkane or heterocycloalkene;

R$^{52}$ is heteroaryl which is unfused or fused with benzene, heteroarene or R$^{52A}$; R$^{52A}$ is cycloalkane, cycloalkene, heterocycloalkane or heterocycloalkene;

R$^{53}$ is cycloalkyl, cycloalkenyl, heterocycloalkyl or heterocycloalkenyl, each of which is unfused or fused with benzene, heteroarene or R$^{53A}$; R$^{53A}$ is cycloalkane, cycloalkene, heterocycloalkane or heterocycloalkene;

R$^{54}$ is alkyl, alkenyl, or alkynyl; each of which is unsubstituted or substituted with one, two, three, four or five of independently selected F, Cl, Br, I, C(O)OH, CN, NO$_2$, NH$_2$, CF$_3$, (O), OH, phenyl, heteroaryl, cycloalkyl, cycloalkenyl or heterocycloalkyl and wherein the moieties represented by R$^{51}$, R$^{52}$, and R$^{53}$ are independently unsubstituted or substituted with one or two or three of independently selected CO(O)R$^{55}$, C(O)OH, (O), F, Cl, Br or I; and R$^{55}$ is alkyl, alkenyl, alkynyl, phenyl, heteroaryl, cycloalkyl, cycloalkenyl or heterocycloalkyl.

Still another embodiment pertains to compounds having formula (I)

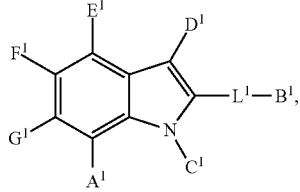

(I)

and therapeutically acceptable salts thereof, wherein

A$^1$ is A$^2$, OA$^2$, SA$^2$, S(O)A$^2$, SO$_2$A$^2$, NH$_2$, NHA$^2$, N(A$^2$)$_2$, C(O)A$^2$, C(O)NH$_2$, C(O)NHA$^2$, C(O)N(A$^2$)$_2$, NHC(O)A$^2$, NA$^2$C(O)A$^2$, NHSO$_2$A$^2$, NA$^2$SO$_2$A$^2$, NHC(O)OA$^2$, NA$^2$C(O)OA$^2$, SO$_2$NH$_2$, SO$_2$NHA$^2$, SO$_2$N(A$^2$)$_2$, NHC(O)NH$_2$, NHC(O)A$^2$NHC(O)N(A$^2$)$_2$, NA$^2$C(O)N(A$^2$)$_2$F, Cl, Br, or I;

A$^2$ is R$^1$, R$^2$, R$^3$, or R$^4$;

R$^1$ is phenyl which is unfused or fused with benzene, heteroarene or R$^{1A}$; R$^{1A}$ is cycloalkane, heterocycloalkane or heterocycloalkene;

R$^2$ is heteroaryl which is unfused or fused with benzene or heteroarene;

R$^3$ is cycloalkyl, cycloalkenyl, heterocycloalkyl or heterocycloalkenyl, each of which is unfused or fused with benzene;

R$^4$ is alkyl, alkenyl, or alkynyl, each of which is unsubstituted or substituted with one, two, three, four or five of independently selected R$^5$, OR$^5$, SR$^5$, S(O)R$^5$, SO$_2$R$^5$, NH$_2$, NHR$^5$, N(R$^5$)$_2$, C(O)R$^5$, C(O)NH$_2$, C(O)NHR$^5$, C(O)N(R$^5$)$_2$, NHC(O)R$^5$, NR$^5$C(O)R$^5$, NHSO$_2$R$^5$, NR$^5$SO$_2$R$^5$, NHC(O)OR$^5$, NR$^5$C(O)OR$^5$, SO$_2$NH$_2$, SO$_2$NHR$^5$, SO$_2$N(R$^5$)$_2$, NHC(O)NH$_2$, NHC(O)R$^5$, NHC(O)N(R$^5$)$_2$, NR$^5$C(O)N(R$^5$)$_2$, OH, (O), C(O)OH, CN, CF$_3$, OCF$_3$, CF$_2$CF$_3$, F, Cl, Br or I;

R$^5$ is R$^6$, R$^7$ or R$^8$;

R$^6$ is phenyl which is unfused or fused with benzene;

R$^7$ is heteroaryl;

R$^8$ is cycloalkyl, cycloalkenyl, heterocycloalkyl or heterocycloalkenyl;

L$^1$ is a bond or is alkylene, alkenylene, alkynylene or L$^2$; and B$^1$ is C(O)OH or a bioisostere thereof or is C(O)OR$^1$, C(O)OR$^2$, C(O)OR$^3$ or C(O)OR$^4$;

L$^2$ is C$_2$-C$_6$-alkylene, C$_4$-C$_6$-alkenylene or C$_4$-C$_6$-alkynylene, each of which has one CH$_2$ moiety replaced with O, S, S(O), SO$_2$, NH or N(W$^1$);

W$^1$ is alkyl, alkenyl or alkynyl;

C$^1$ and D$^1$ are independently H, R$^9$, R$^{10}$, R$^{11}$, R$^{12}$, C(O)OR$^{12}$, F, Cl, Br, I, or one of C$^1$ and D$^1$ is H, and the other is R$^9$, R$^{10}$, R$^{11}$R$^{12}$, C(O)OR$^{12}$, F, Cl, Br, or I;

R$^9$ is phenyl;

R$^{10}$ is heteroaryl;

R$^{11}$ is cycloalkyl, cycloalkenyl, heterocycloalkyl or heterocycloalkenyl;

R$^{12}$ is alkyl, alkenyl, or alkynyl, each of which is unsubstituted or substituted with one, two, three, four or five of independently selected R$^{13}$, OR$^{13}$, SR$^{13}$, S(O)R$^{13}$, SO$_2$R$^{13}$NH$_2$, NHR$^{13}$, N(R$^{13}$)$_2$, C(O)R$^{13}$, C(O)NH$_2$, C(O)NHR$^{13}$, C(O)N(R$^{13}$)$_2$, NHC(O)R$^{13}$, NR$^{13}$C(O)R$^{13}$, NHC(O)R$^{13}$, NR$^{13}$C(O)R$^{13}$, NHSO$_2$R$^{13}$, NR$^{13}$SO$_2$R$^{13}$, NHC(O)OR$^{13}$, NR$^{13}$C(O)OR$^{13}$, SO$_2$NH$_2$, SO$_2$NHR$^{13}$, SO$_2$N(R$^{13}$)$_2$, NHC(O)NH$_2$, NHC(O)R$^{13}$, NHC(O)N(R$^{13}$)$_2$, NR$^{13}$C(O)N(R$^{13}$)$_2$, OH, (O), C(O)OH, CN, CF$_3$, OCF$_3$, CF$_2$CF$_3$, F, Cl, Br or I;

R$^{13}$ is R$^{14}$, R$^{15}$ R$^{16}$, or R$^{16A}$;

R$^{14}$ is phenyl which is unfused or fused with benzene, heteroarene or R$^{14A}$; R$^{14A}$ is cycloalkane, or heterocycloalkane; each of which is unfused or fused with R$^{14B}$; R$^{14B}$ is cycloalkane;

R$^{15}$ is heteroaryl which is unfused or fused with benzene or heteroarene;

R$^{16}$ is cycloalkyl, cycloalkenyl, heterocycloalkyl or heterocycloalkenyl, each of which is unfused or fused with benzene;

R$^{16A}$ alkyl, alkenyl, or alkynyl; and one or two or each of E$^1$ and F$^1$ and G$^1$ are independently H, CF$_3$, F, Cl, Br or I, and the remainder are independently R$^{17}$, R$^{18}$, R$^{19}$, R$^{20}$ or OR$^{20}$;

R$^{17}$ is phenyl which is unfused or fused with benzene;

R$^{18}$ is heteroaryl;

R$^{19}$ is cycloalkyl, cycloalkenyl, heterocycloalkyl or heterocycloalkenyl;

R$^{20}$ is alkyl, alkenyl, or alkynyl, each of which is unsubstituted or substituted with one, two, three, four or five of independently selected R$^{20}$, OR$^{20}$, SR$^{20}$, S(O)R$^{20}$, SO$_2$R$^{20}$, NH$_2$, NHR$^{20}$, N(R$^{20}$)$_2$, C(O)R$^{20}$, C(O)NH$_2$, C(O)NHR$^{20}$, C(O)N(R$^{20}$)$_2$, NHC(O)R$^{20}$, NHC(O)R$^{20}$, NR$^{20}$C(O)R$^{20}$, NR$^{20}$C(O)R$^{20}$, NHSO$_2$R$^{20}$, NR$^2$SO$_2$R$^{20}$, NHC(O)OR$^{20}$, NR$^{20}$C(O)OR$^{20}$, SO$_2$NH$_2$, SO$_2$NHR$^{20}$, SO$_2$N(R$^{20}$)$_2$, NHC(O)NH$_2$, NHC(O)R$^{20}$, NHC(O)N(R$^{20}$)$_2$, NR$^{20}$C(O)N(R$^{20}$)$_2$, OH, (O), C(O)OH, CN, CF$_3$, OCF$_3$, CF$_2$CF$_3$, F, Cl, Br or I;

R$^{20}$ is R$^{21}$, R$^{22}$ or R$^{23}$;

R$^{21}$ is phenyl which is unfused or fused with benzene;

R$^{22}$ is heteroaryl;

R$^{23}$ is cycloalkyl, cycloalkenyl, heterocycloalkyl or heterocycloalkenyl;

wherein each foregoing cyclic moiety is independently unsubstituted or substituted with one or two or three or four or five of independently selected spiroheteroalkyl, R$^{30}$, OR$^{30}$, SO$_2$R$^{30}$, C(O)R$^{30}$, NO, NO$_2$, NH$_2$, N(R$^{30}$)$_2$, C(O)NH$_2$, C(O)NHR$^{30}$, NHC(O)R$^{30}$, C(O)NHSO$_2$R$^{30}$, SO$_2$NH$_2$, C(O)OH, OH, (O), CN, CF$_3$, OCF$_3$, F, Cl, Br, or I;

R$^{30}$ is R$^{31}$, R$^{32}$, R$^{33}$ or R$^{34}$;

R$^{31}$ is phenyl which is unfused or fused with benzene;

R$^{32}$ is heteroaryl;

R$^{33}$ is cycloalkyl, cycloalkenyl, heterocycloalkyl or heterocycloalkenyl, each of which is unfused or fused with benzene;

R$^{34}$ is alkyl, alkenyl, or alkynyl, each of which is unsubstituted or substituted with one, two, three, four or five of independently selected R$^{35}$, OR$^{35}$, SR$^{35}$, S(O)R$^{35}$, SO$_2$R$^{35}$, NH$_2$, NHR$^{35}$, N(R$^{35}$)$_2$, C(O)R$^{35}$, C(O)NH$_2$, C(O)NHR$^{35}$, C(O)N(R$^{35}$)$_2$, NHC(O)R$^{35}$, NR$^{35}$C(O)R$^{35}$, NHSO$_2$R$^{35}$, NR$^{35}$SO$_2$R$^{35}$, NHC(O)R$^{35}$, NR$^{35}$C(O)OR$^{35}$, SO$_2$NH$_2$, SO$_2$NHR$^{35}$, SO$_2$N(R$^{35}$)$_2$, NHC(O)NH$_2$, NHC(O)R$^{35}$ NHC(O)N(R$^{35}$)$_2$, NR$^{35}$C(O)N(R$^{35}$)$_2$, OH, (O), C(O)OH, CN, CF$_3$, OCF$_3$, CF$_2$CF$_3$, F, Cl, Br or I;

R$^{35}$ is R$^{36}$, R$^{37}$, R$^{38}$ or R$^{39}$;

R$^{36}$ is phenyl which is unfused or fused with benzene or R$^{36A}$; R$^{36A}$ is cycloalkene;

R$^{37}$ is heteroaryl which is unfused or fused with benzene;

R$^{38}$ is cycloalkyl, cycloalkenyl, heterocycloalkyl or heterocycloalkenyl, each of which is unfused or fused with benzene;

R$^{39}$ is alkyl, alkenyl or alkynyl, each of which is unsubstituted or substituted with NH$_2$, N(R$^{40}$)$_2$, OR$^{40}$, or R$^{40}$;

R$^{40}$ is alkyl, alkenyl, alkynyl, phenyl, heteroaryl, cycloalkyl, cycloalkenyl or heterocycloalkyl;

wherein the moieties represented by R$^{31}$, R$^{32}$, R$^{33}$ R$^{36}$, R$^{37}$, R$^{38}$ and R$^{40}$ are independently unsubstituted or substituted with one or two or three of independently selected R$^{50}$, OR$^{50}$, C(O)R$^{50}$, C(O)OR$^{50}$, SO$_2$R$^{50}$, NHC(O)R$^{50}$, F, Cl, Br, I, C(O)OH, CN, NO$_2$, NH$_2$, CF$_3$, (O) or OH;

R$^{50}$ is R$^{51}$, R$^{52}$, R$^{53}$ or R$^{54}$;

R$^{51}$ is phenyl;

R$^{52}$ is heteroaryl;

R$^{53}$ is cycloalkyl, cycloalkenyl, heterocycloalkyl or heterocycloalkenyl;

R$^{54}$ is alkyl, alkenyl, or alkynyl; each of which is unsubstituted or substituted with one, two, three, four or five of independently selected F, Cl, Br, I, C(O)OH, CN, NO$_2$, NH$_2$, CF$_3$, (O), OH, phenyl, heteroaryl, cycloalkyl, cycloalkenyl or heterocycloalkyl and wherein the moieties represented by R$^{51}$, R$^{52}$, and R$^{53}$ are independently unsubstituted or substituted with one or two or three of independently selected CO(O)R$^{55}$, C(O)OH, (O), F, Cl, Br or I; and R$^{55}$ is alkyl, alkenyl, alkynyl, phenyl, heteroaryl, cycloalkyl, cycloalkenyl or heterocycloalkyl.

Still another embodiment pertains to compounds having formula (I)

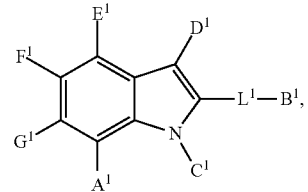

(I)

and therapeutically acceptable salts thereof, wherein

A$^1$ is A$^2$, NHA$^2$, N(A$^2$)$_2$, F, Cl, Br, or I;

A$^2$ is R$^1$, R$^2$, R$^3$, or R$^4$;

R$^1$ is phenyl which is unfused or fused with benzene, heteroarene or R$^{1A}$; R$^{1A}$ is cycloalkane, heterocycloalkane or heterocycloalkene;

R$^2$ is heteroaryl which is unfused or fused with benzene or heteroarene;

R$^3$ is cycloalkenyl, heterocycloalkyl or heterocycloalkenyl, each of which is unfused or fused with benzene;

R$^4$ is alkyl or alkenyl, each of which is unsubstituted or substituted with one, two, three, four or five of independently selected R$^5$, OR$^5$, SR$^5$, C(O)OH, F, Cl, Br or I;

R$^5$ is R$^6$, R$^7$ or R$^8$;

R$^6$ is phenyl which is unfused or fused with benzene;

R$^7$ is heteroaryl;

R$^8$ is cycloalkyl;

L$^1$ is a bond and B$^1$ is C(O)OH or a bioisostere thereof or is C(O)OR$^4$;

C$^1$ and D$^1$ are independently H, R$^9$, R$^{12}$, C(O)OR$^{12}$, F, Cl, Br, I, or one of C$^1$ and D$^1$ is H, and the other is R$^{12}$, F, Cl, Br, or I;

R$^9$ is phenyl;

R$^{12}$ is alkyl, alkenyl, or alkynyl, each of which is unsubstituted or substituted with one, two, three, four or five of independently selected R$^{13}$, OR$^{13}$, SR$^{13}$, NHR$^{13}$, N(R$^{13}$)$_2$, C(O)R$^{13}$, C(O)N(R$^{13}$)$_2$, C(O)OH, F, Cl, Br or I;

R$^{13}$ is R$^{14}$, R$^{15}$ R$^{16}$, or R$^{16A}$;

R$^{14}$ is phenyl which is unfused or fused with benzene, heteroarene or R$^{14A}$; R$^{14A}$ is cycloalkane, or heterocycloalkane; each of which is unfused or fused with R$^{14B}$; R$^{14B}$ is cycloalkane;

R$^{15}$ is heteroaryl which is unfused or fused with benzene or heteroarene;

R$^{16}$ is cycloalkyl or heterocycloalkyl, each of which is unfused or fused with benzene;

R$^{16A}$ alkyl; and one or two or each of E$^1$ and F$^1$ and G$^1$ are independently H, CF$_3$, F, Cl, Br or I, and the remainder are independently R$^{17}$, R$^{20}$ or OR$^{20}$;

R$^{17}$ is phenyl which is unfused or fused with benzene;

R$^{18}$ is heteroaryl;

R$^{19}$ is cycloalkyl, cycloalkenyl, heterocycloalkyl or heterocycloalkenyl;

R$^{20}$ is alkyl or alkenyl, each of which is unsubstituted or substituted with one, two, three, four or five of independently selected R$^{20}$, OR$^{20}$, F, Cl, Br or I;

R$^{20}$ is R$^{21}$;

R$^{21}$ is phenyl which is unfused or fused with benzene;

wherein each foregoing cyclic moiety is independently unsubstituted or substituted with one or two or three or four or five of independently selected spiroheteroalkyl, R$^{30}$, OR$^{30}$, SO$_2$R$^{30}$, C(O)R$^{30}$, NO, NO$_2$, NH$_2$, N(R$^{30}$)$_2$, C(O)NH$_2$, C(O)NHR$^{30}$, NHC(O)R$^{30}$, C(O)NHSO$_2$R$^{30}$, SO$_2$NH$_2$, C(O)OH, OH, (O), CN, CF$_3$, OCF$_3$, F, Cl, Br, or I;

R$^{30}$ is R$^{31}$, R$^{32}$, R$^{33}$ or R$^{34}$;

R$^{31}$ is phenyl which is unfused or fused with benzene;

R$^{32}$ is heteroaryl;

R$^{33}$ is cycloalkyl, cycloalkenyl, or heterocycloalkyl, each of which is unfused or fused with benzene;

R³⁴ is alkyl, alkenyl, or alkynyl, each of which is unsubstituted or substituted with one, two, three, four or five of independently selected R³⁵, OR³⁵, SR³⁵, S(O)R³⁵, SO₂R³⁵, NH₂, N(R³⁵)₂, C(O)NHR³⁵, OH, C(O)OH, F, Cl, Br or I;

R³⁵ is R³⁶, R³⁷, R³⁸ or R³⁹;

R³⁶ is phenyl which is unfused or fused with benzene or R³⁶ᴬ; R³⁶ᴬ is cycloalkene;

R³⁷ is heteroaryl which is unfused or fused with benzene;

R³⁸ is cycloalkyl, or heterocycloalkyl, each of which is unfused or fused with benzene;

R³⁹ is alkyl, each of which is unsubstituted or substituted with NH₂, N(R⁴⁰)₂, or OR⁴⁰;

R⁴⁰ is alkyl or phenyl;

wherein the moieties represented by R³¹, R³², R³³ R³⁶, R³⁷, R³⁸ and R⁴⁰ are independently unsubstituted or substituted with one or two or three of independently selected R⁵⁰, OR⁵⁰, C(O)R⁵⁰, C(O)OR⁵⁰, SO₂R⁵⁰, NHC(O)R⁵⁰, F, Cl, Br, I, C(O)OH, CN, NO₂, NH₂, (O) or OH;

R⁵⁰ is R⁵¹, R⁵², R⁵³ or R⁵⁴;

R⁵¹ is phenyl;

R⁵² is heteroaryl;

R⁵³ is heterocycloalkyl;

R⁵⁴ is alkyl; each of which is unsubstituted or substituted with one, two, three, four or five of independently selected OH, phenyl, or heteroaryl;

wherein the moieties represented by R⁵¹ and R⁵³ are independently unsubstituted or substituted with one or two or three of independently selected CO(O)R⁵⁵, C(O)OH, (O), F, Cl, Br or I; and R⁵⁵ is alkyl.

Still another embodiment pertains to compositions comprising an excipient and a therapeutically effective amount of a compound having Formula I.

Still another embodiment pertains to 3-(3-(1-naphthyloxy)propyl)-7-((E)-2-phenylvinyl)-1H-indole-2-carboxylic acid;

3-(3-(1-naphthyloxyl)propyl)-7-phenyl-1H-indole-2-carboxylic acid;

3-(3-(1-naphthyloxyl)propyl)-7-((1E)-3-phenylprop-1-enyl)-1H-indole-2-carboxylic acid;

7-((E)-2-cyclohexylvinyl)-3-(3-(1-naphthyloxyl)propyl)-1H-indole-2-carboxylic acid;

7-(3-(benzyloxy)phenyl)-3-(3-(1-naphthyloxy)propyl)-1H-indole-2-carboxylic acid;

7-(4-fluorophenyl)-3-(3-(1-naphthyloxy)propyl)-1H-indole-2-carboxylic acid;

7-(2-naphthyl)-3-(3-(1-naphthyloxy)propyl)-1H-indole-2-carboxylic acid;

7-(1-naphthyl)-3-(3-(1-naphthyloxy)propyl)-1H-indole-2-carboxylic acid;

7-(1,1'-biphenyl-2-yl)-3-(3-(1-naphthyloxy)propyl)-1H-indole-2-carboxylic acid;

7-(2-morpholin-4-ylphenyl)-3-(3-(1-naphthyloxy)propyl)-1H-indole-2-carboxylic acid;

7-(2-fluoro-1,1'-biphenyl-4-yl)-3-(3-(1-naphthyloxy)propyl)-1H-indole-2-carboxylic acid;

7-(4-(benzyloxy)phenyl)-3-(3-(1-naphthyloxy)propyl)-1H-indole-2-carboxylic acid;

7-(3-morpholin-4-ylphenyl)-3-(3-(1-naphthyloxy)propyl)-1H-indole-2-carboxylic acid;

3-(3-(1-naphthyloxy)propyl)-7-pyridin-3-yl-1H-indole-2-carboxylic acid;

3-(3-(1-naphthyloxy)propyl)-7-pyridin-4-yl-1H-indole-2-carboxylic acid;

3-(3-(1-naphthyloxy)propyl)-7-((1E)-5-phenylpent-1-enyl)-1H-indole-2-carboxylic acid;

7-(2-methylphenyl)-3-(3-(1-naphthyloxy)propyl)-1H-indole-2-carboxylic acid;

7-(3-methylphenyl)-3-(3-(1-naphthyloxy)propyl)-1H-indole-2-carboxylic acid;

7-(4-methylphenyl)-3-(3-(1-naphthyloxy)propyl)-1H-indole-2-carboxylic acid;

7-(4-carboxyphenyl)-3-(3-(1-naphthyloxy)propyl)-1H-indole-2-carboxylic acid;

7-(3-carboxyphenyl)-3-(3-(1-naphthyloxy)propyl)-1H-indole-2-carboxylic acid;

7-(2-(benzyloxy)phenyl)-3-(3-(1-naphthyloxy)propyl)-1H-indole-2-carboxylic acid;

7-(2-ethoxyphenyl)-3-(3-(1-naphthyloxy)propyl)-1H-indole-2-carboxylic acid;

7-(2-ethylphenyl)-3-(3-(1-naphthyloxy)propyl)-1H-indole-2-carboxylic acid;

7-(2-methoxyphenyl)-3-(3-(1-naphthyloxy)propyl)-1H-indole-2-carboxylic acid;

7-(2-isopropoxyphenyl)-3-(3-(1-naphthyloxy)propyl)-1H-indole-2-carboxylic acid;

3-(3-(1-naphthyloxy)propyl)-7-(2-phenoxyphenyl)-1H-indole-2-carboxylic acid;

7-(2-carboxyphenyl)-3-(3-(1-naphthyloxy)propyl)-1H-indole-2-carboxylic acid;

3-(3-(1-naphthyloxy)propyl)-7-(2-((5,6,7,8-tetrahydronaphthalen-1-yloxy)methyl)phenyl)-1H-indole-2-carboxylic acid;

7-(4-cyclohexylphenyl)-3-(3-(1-naphthyloxy)propyl)-1H-indole-2-carboxylic acid;

7-(2-chlorophenyl)-3-(3-(1-naphthyloxy)propyl)-1H-indole-2-carboxylic acid;

7-(3-chloropyridin-4-yl)-3-(3-(1-naphthyloxy)propyl)-1H-indole-2-carboxylic acid;

7-(2,5-dichlorophenyl)-3-(3-(1-naphthyloxy)propyl)-1H-indole-2-carboxylic acid;

7-(3,5-dichlorophenyl)-3-(3-(1-naphthyloxy)propyl)-1H-indole-2-carboxylic acid;

7-(2,3-dimethoxyphenyl)-3-(3-(1-naphthyloxy)propyl)-1H-indole-2-carboxylic acid;

7-(2,4-dimethoxyphenyl)-3-(3-(1-naphthyloxy)propyl)-1H-indole-2-carboxylic acid;

7-(2,5-dimethoxyphenyl)-3-(3-(1-naphthyloxy)propyl)-1H-indole-2-carboxylic acid;

7-(2,6-dimethoxyphenyl)-3-(3-(1-naphthyloxy)propyl)-1H-indole-2-carboxylic acid;

7-(4-methoxypyridin-3-yl)-3-(3-(1-naphthyloxy)propyl)-1H-indole-2-carboxylic acid;

7-(2-methoxypyridin-3-yl)-3-(3-(1-naphthyloxy)propyl)-1H-indole-2-carboxylic acid;

3-(3-(1-naphthyloxy)propyl)-7-quinolin-4-yl-1H-indole-2-carboxylic acid;

7-(4-hydroxy-2-methylphenyl)-3-(3-(1-naphthyloxy)propyl)-1H-indole-2-carboxylic acid;

7-(2-(4-methylpiperazin-1-yl)phenyl)-3-(3-(1-naphthyloxy)propyl)-1H-indole-2-carboxylic acid;

7-(2,4-dichlorophenyl)-3-(3-(1-naphthyloxy)propyl)-1H-indole-2-carboxylic acid;

7-(4-carboxy-2-methylphenyl)-3-(3-(1-naphthyloxy)propyl)-1H-indole-2-carboxylic acid;

7-(2-methoxyphenyl)-3-(3-((2-methyl-1-naphthyl)oxy)propyl)-1H-indole-2-carboxylic acid;

7-(4-fluoro-2-isopropoxyphenyl)-3-(3-(1-naphthyloxy)propyl)-1H-indole-2-carboxylic acid;

7-(2-ethoxy-1-naphthyl)-3-(3-(1-naphthyloxy)propyl)-1H-indole-2-carboxylic acid;

7-(4-amino-2-methylphenyl)-3-(3-(1-naphthyloxy)propyl)-1H-indole-2-carboxylic acid;

7-(4-(((2-(dimethylamino)ethyl)amino)carbonyl)-2-methylphenyl)-3-(3-(1-naphthyloxy)propyl)-1H-indole-2-carboxylic acid;

7-(4-chloro-2-methylphenyl)-3-(3-(1-naphthyloxy)propyl)-1H-indole-2-carboxylic acid;

7-(2,3-dichlorophenyl)-3-(3-(1-naphthyloxy)propyl)-1H-indole-2-carboxylic acid;

3-(3-(1-naphthyloxy)propyl)-7-(2-(trifluoromethyl)phenyl)-1H-indole-2-carboxylic acid;

7-(3-chloro-2-fluorophenyl)-3-(3-(1-naphthyloxy)propyl)-1H-indole-2-carboxylic acid;

7-(2,3-difluorophenyl)-3-(3-(1-naphthyloxy)propyl)-1H-indole-2-carboxylic acid;

7-cyclopent-1-en-1-yl-3-(3-(1-naphthyloxyl)propyl)-1H-indole-2-carboxylic acid;

7-cyclohex-1-en-1-yl-3-(3-(1-naphthyloxyl)propyl)-1H-indole-2-carboxylic acid;

3-(3-(1-naphthyloxy)propyl)-7-(2-phenylcyclohex-1-en-1-yl)-1H-indole-2-carboxylic acid;

7-(2-cyclohexylphenyl)-3-(3-(1-naphthyloxy)propyl)-1H-indole-2-carboxylic acid;

7-(6-carboxypyridin-3-yl)-3-(3-(1-naphthyloxy)propyl)-1H-indole-2-carboxylic acid;

7-(3-methyl-5-nitropyridin-2-yl)-3-(3-(1-naphthyloxy)propyl)-1H-indole-2-carboxylic acid;

7-(2,3-dihydro-1,4-benzodioxin-6-yl)-3-(3-(1-naphthyloxy)propyl)-1H-indole-2-carboxylic acid;

7-(1,3-benzodioxol-5-yl)-3-(3-(1-naphthyloxy)propyl)-1H-indole-2-carboxylic acid;

3-(3-((4-chloro-1-naphthyl)oxy)propyl)-7-(2-methoxyphenyl)-1H-indole-2-carboxylic acid;

3-(3-(2-bromophenoxyl)propyl)-7-(2-methoxyphenyl)-1H-indole-2-carboxylic acid;

7-(2-methyl-4-(((2-morpholin-4-ylethyl)amino)carbonyl)phenyl)-3-(3-(1-naphthyloxy)propyl)-1H-indole-2-carboxylic acid;

7-(3-methylquinolin-2-yl)-3-(3-(1-naphthyloxy)propyl)-1H-indole-2-carboxylic acid;

7-(4-(hydroxymethyl)phenyl)-3-(3-(1-naphthyloxy)propyl)-1H-indole-2-carboxylic acid;

7-(3-(hydroxymethyl)phenyl)-3-(3-(1-naphthyloxy)propyl)-1H-indole-2-carboxylic acid;

5-chloro-7-(2-methylphenyl)-3-(3-(1-naphthyloxy)propyl)-1H-indole-2-carboxylic acid;

7-(3-methylpyridin-2-yl)-3-(3-(1-naphthyloxy)propyl)-1H-indole-2-carboxylic acid;

7-(2,6-dimethylpyridin-3-yl)-3-(3-(1-naphthyloxy)propyl)-1H-indole-2-carboxylic acid;

7-(6-amino-2-methylpyridin-3-yl)-3-(3-(1-naphthyloxy)propyl)-1H-indole-2-carboxylic acid;

3-(3-(1-naphthyloxy)propyl)-7-(2-piperazin-1-ylphenyl)-1H-indole-2-carboxylic acid;

7-(4-(3-chlorophenyl)piperazin-1-yl)-3-(3-(1-naphthyloxy)propyl)-1H-indole-2-carboxylic acid;

7-(2-methylphenyl)-1-(2-morpholin-4-ylethyl)-3-(3-(1-naphthyloxy)propyl)-1H-indole-2-carboxylic acid;

7-(2-methylphenyl)-3-(3-(5,6,7,8-tetrahydronaphthalen-1-yloxy)propyl)-1H-indole-2-carboxylic acid;

5-chloro-3-(3-(1-naphthyloxy)propyl)-7-phenyl-1H-indole-2-carboxylic acid;

5-chloro-7-(4-chloro-2-methylphenyl)-3-(3-(1-naphthyloxy)propyl)-1H-indole-2-carboxylic acid;

5-chloro-7-cyclopent-1-en-1-yl-3-(3-(1-naphthyloxy)propyl)-1H-indole-2-carboxylic acid;

7-(3,5-dichloropyridin-2-yl)-3-(3-(1-naphthyloxy)propyl)-1H-indole-2-carboxylic acid;

7-(5-(aminocarbonyl)pyridin-2-yl)-3-(3-(1-naphthyloxy)propyl)-1H-indole-2-carboxylic acid;

7-(3-chloro-5-(trifluoromethyl)pyridin-2-yl)-3-(3-(1-naphthyloxy)propyl)-1H-indole-2-carboxylic acid;

7-(5-amino-2-(trifluoromethoxy)phenyl)-3-(3-(1-naphthyloxy)propyl)-1H-indole-2-carboxylic acid;

7-(5-carboxy-2-methoxyphenyl)-3-(3-(1-naphthyloxy)propyl)-1H-indole-2-carboxylic acid;

7-(4-carboxy-2-nitrophenyl)-3-(3-(1-naphthyloxy)propyl)-1H-indole-2-carboxylic acid;

7-(5-carboxy-2-chlorophenyl)-3-(3-(1-naphthyloxy)propyl)-1H-indole-2-carboxylic acid;

7-(1-benzyl-3-methyl-1,2,3,6-tetrahydropyridin-4-yl)-3-(3-(1-naphthyloxy)propyl)-1H-indole-2-carboxylic acid;

7-(4-amino-2-(trifluoromethyl)phenyl)-3-(3-(1-naphthyloxy)propyl)-1H-indole-2-carboxylic acid;

7-(1,4-dioxa-8-azaspiro(4.5)dec-8-yl)-3-(3-(1-naphthyloxy)propyl)-1H-indole-2-carboxylic acid;

7-(3-carboxypiperidin-1-yl)-3-(3-(1-naphthyloxy)propyl)-1H-indole-2-carboxylic acid;

7-(4-carboxypiperidin-1-yl)-3-(3-(1-naphthyloxy)propyl)-1H-indole-2-carboxylic acid;

3-(3-(1-naphthyloxy)propyl)-7-pyrrolidin-1-yl-1H-indole-2-carboxylic acid;

7-morpholin-4-yl-3-(3-(1-naphthyloxy)propyl)-1H-indole-2-carboxylic acid;

3-(3-(1-naphthyloxy)propyl)-7-piperidin-1-yl-1H-indole-2-carboxylic acid;

7-(4-(aminosulfonyl)-2-(trifluoromethyl)phenyl)-3-(3-(1-naphthyloxy)propyl)-1H-indole-2-carboxylic acid;

4-(2-(ethoxycarbonyl)-3-(3-(1-naphthyloxy)propyl)-1H-indol-7-yl)-3-methylbenzoic acid;

7-(2-methyl-4-(morpholin-4-ylcarbonyl)phenyl)-3-(3-(1-naphthyloxy)propyl)-1H-indole-2-carboxylic acid;

7-(4-((4-carboxypiperidin-1-yl)carbonyl)-2-methylphenyl)-3-(3-(1-naphthyloxy)propyl)-1H-indole-2-carboxylic acid;

7-(4-((3-carboxypiperidin-1-yl)carbonyl)-2-methylphenyl)-3-(3-(1-naphthyloxy)propyl)-1H-indole-2-carboxylic acid;

7-(4-(carboxymethylcarbamoyl)-2-methylphenyl)-3-(3-(naphthalen-1-yloxy)propyl)-1H-indole-2-carboxylic acid;

3-(3-(3,4-dihydroquinolin-1(2H)-yl)propyl)-7-(2-(trifluoromethyl)phenyl)-1H-indole-2-carboxylic acid;

7-(2-methylphenyl)-3-(3-(3-phenoxyphenoxyl)propyl)-1H-indole-2-carboxylic acid;

3-(3-(2,3-dimethylphenoxyl)propyl)-7-(2-methylphenyl)-1H-indole-2-carboxylic acid;

7-(4-methylpyridin-3-yl)-3-(3-(1-naphthyloxy)propyl)-1H-indole-2-carboxylic acid;

7-(2-methylbenzyl)-3-(3-(1-naphthyloxy)propyl)-1H-indole-2-carboxylic acid;

3,3'-bis(3-(1-naphthyloxy)propyl)-1H, 1'H-7,7'-biindole-2,2'-dicarboxylic acid;

3-(4-(3,4-dihydroquinolin-1(2H)-yl)butyl)-7-(2-(trifluoromethyl)phenyl)-1H-indole-2-carboxylic acid;

7-(4-carboxy-2-methylphenyl)-3-(4-(3,4-dihydroquinolin-1(2H)-yl)butyl)-1H-indole-2-carboxylic acid;

7-(2-methylphenyl)-3-(4-(1-naphthyl)butyl)-1H-indole-2-carboxylic acid;

7-(2-methylphenyl)-3-(4-(1-naphthyloxy)butyl)-1H-indole-2-carboxylic acid;

3-(3-(2,4-dimethylphenoxyl)propyl)-7-(2-methylphenyl)-1H-indole-2-carboxylic acid;

3-(3-(2,5-dimethylphenoxyl)propyl)-7-(2-methylphenyl)-1H-indole-2-carboxylic acid;

7-(1,1'-biphenyl-2-yl)-3-(4-(1-naphthyloxy)butyl)-1H-indole-2-carboxylic acid;
7-(4-((2-carboxypiperidin-1-yl)carbonyl)-2-methylphenyl)-3-(3-(1-naphthyloxy)propyl)-1H-indole-2-carboxylic acid;
7-(4-((S)-1-carboxy-2-methylpropylcarbamoyl)-2-methylphenyl)-3-(3-(naphthalen-1-yloxy)propyl)-1H-indole-2-carboxylic acid;
N-(4-(2-carboxy-3-(3-(1-naphthyloxy)propyl)-1H-indol-7-yl)-3-methylbenzoyl)-4-chlorophenylalanine;
N-(4-(2-carboxy-3-(3-(1-naphthyloxy)propyl)-1H-indol-7-yl)-3-methylbenzoyl)-L-tryptophan;
(3S)-2-(4-(2-carboxy-3-(3-(1-naphthyloxy)propyl)-1H-indol-7-yl)-3-methylbenzoyl)-1,2,3,4-tetrahydroisoquinoline-3-carboxylic acid;
N-(4-(2-carboxy-3-(3-(1-naphthyloxy)propyl)-1H-indol-7-yl)-3-methylbenzoyl)-L-tyrosine;
7-(4-((R)-2-carboxypyrrolidine-1-carbonyl)-2-methylphenyl)-3-(3-(naphthalen-1-yloxy)propyl)-1H-indole-2-carboxylic acid;
7-(4-((S)-1-carboxyethylcarbamoyl)-2-methylphenyl)-3-(3-(naphthalen-1-yloxy)propyl)-1H-indole-2-carboxylic acid;
N-(4-(2-carboxy-3-(3-(1-naphthyloxy)propyl)-1H-indol-7-yl)-3-methylbenzoyl)-4-nitro-L-phenylalanine;
N-(4-(2-carboxy-3-(3-(1-naphthyloxy)propyl)-1H-indol-7-yl)-3-methylbenzoyl)-L-phenylalanine;
7-(4-((((S)-carboxy(phenyl)methyl)amino)carbonyl)-2-methylphenyl)-3-(3-(1-naphthyloxy)propyl)-1H-indole-2-carboxylic acid;
7-(4-carboxy-2-methylphenyl)-3-(3-(2,4,5-trichlorophenoxyl)propyl)-1H-indole-2-carboxylic acid;
7-(4-carboxy-2-methylphenyl)-3-(3-(2,3,4-trichlorophenoxyl)propyl)-1H-indole-2-carboxylic acid;
7-(4-carboxy-2-methylphenyl)-3-(3-(2,3,5-trimethylphenoxyl)propyl)-1H-indole-2-carboxylic acid;
3-(3-(2-tert-butylphenoxy)propyl)-7-(4-carboxy-2-methylphenyl)-1H-indole-2-carboxylic acid;
7-(4-carboxy-2-methylphenyl)-3-(3-(2-(trifluoromethyl)phenoxy)propyl)-1H-indole-2-carboxylic acid;
7-(4-carboxy-2-methylphenyl)-3-(3-(quinolin-8-yloxy)propyl)-1H-indole-2-carboxylic acid;
7-(4-carboxy-2-methylphenyl)-3-(3-((5-oxo-5,6,7,8-tetrahydronaphthalen-1-yl)oxy)propyl)-1H-indole-2-carboxylic acid;
3-(3-(3-benzoylphenoxy)propyl)-7-(4-carboxy-2-methylphenyl)-1H-indole-2-carboxylic acid;
7-(2-methylphenyl)-1-(2-morpholin-4-ylethyl)-3-(3-(5,6,7,8-tetrahydronaphthalen-1-yloxy)propyl)-1H-indole-2-carboxylic acid;
7-(4-(cyclohexyloxy)phenyl)-3-(4-(1-naphthyloxy)butyl)-1H-indole-2-carboxylic acid;
7-(1,1'-biphenyl-2-yl)-1-(2-morpholin-4-ylethyl)-3-(3-(5,6,7,8-tetrahydronaphthalen-1-yloxy)propyl)-1H-indole-2-carboxylic acid;
3-(3-(3,4-dimethylphenoxyl)propyl)-7-(2-methylphenyl)-1H-indole-2-carboxylic acid;
3-(3-(3,5-dimethylphenoxyl)propyl)-7-(2-methylphenyl)-1H-indole-2-carboxylic acid;
3-(3-(2,3-dimethoxyphenoxy)propyl)-7-(2-methylphenyl)-1H-indole-2-carboxylic acid;
7-(2-methylphenyl)-3-(3-(1-naphthylamino)propyl)-1H-indole-2-carboxylic acid;
1-(carboxymethyl)-7-(2-methylphenyl)-3-(3-(1-naphthyloxy)propyl)-1H-indole-2-carboxylic acid;
3-(3-(3-(dimethylamino)phenoxy)propyl)-7-(2-methylphenyl)-1H-indole-2-carboxylic acid;
3-(4-(3,4-dihydroquinolin-1(2H)-yl)butyl)-7-(4-(morpholin-4-ylcarbonyl)-2-(trifluoromethyl)phenyl)-1H-indole-2-carboxylic acid;
3-(4-(2-methyl-3,4-dihydroquinolin-1(2H)-yl)butyl)-7-(4-(morpholin-4-ylcarbonyl)-2-(trifluoromethyl)phenyl)-1H-indole-2-carboxylic acid;
3-(4-(6-methyl-3,4-dihydroquinolin-1(2H)-yl)butyl)-7-(4-(morpholin-4-ylcarbonyl)-2-(trifluoromethyl)phenyl)-1H-indole-2-carboxylic acid;
3-(4-(6-methoxy-3,4-dihydroquinolin-1(2H)-yl)butyl)-7-(4-(morpholin-4-ylcarbonyl)-2-(trifluoromethyl)phenyl)-1H-indole-2-carboxylic acid;
3-(4-(ethyl(1-naphthyl)amino)butyl)-7-(4-(morpholin-4-ylcarbonyl)-2-(trifluoromethyl)phenyl)-1H-indole-2-carboxylic acid;
3-(4-(2,3-dihydro-1H-indol-1-yl)butyl)-7-(4-(morpholin-4-ylcarbonyl)-2-(trifluoromethyl)phenyl)-1H-indole-2-carboxylic acid;
3-(4-(2-methyl-2,3-dihydro-1H-indol-1-yl)butyl)-7-(4-(morpholin-4-ylcarbonyl)-2-(trifluoromethyl)phenyl)-1H-indole-2-carboxylic acid;
7-(4-(morpholin-4-ylcarbonyl)-2-(trifluoromethyl)phenyl)-3-(4-(5-nitro-2,3-dihydro-1H-indol-1-yl)butyl)-1H-indole-2-carboxylic acid;
3-(4-(5-bromo-2,3-dihydro-1H-indol-1-yl)butyl)-7-(4-(morpholin-4-ylcarbonyl)-2-(trifluoromethyl)phenyl)-1H-indole-2-carboxylic acid;
3-(4-(2,3-dihydro-4H-1,4-benzoxazin-4-yl)butyl)-7-(4-(morpholin-4-ylcarbonyl)-2-(trifluoromethyl)phenyl)-1H-indole-2-carboxylic acid;
7-(2-methylphenyl)-3-(3-(2,3,5-trimethylphenoxy)propyl)-1H-indole-2-carboxylic acid;
7-(2-methylphenyl)-3-(3-(2,3,6-trimethylphenoxy)propyl)-1H-indole-2-carboxylic acid;
3-(3-(2,3-dichlorophenoxy)propyl)-7-(2-methylphenyl)-1H-indole-2-carboxylic acid;
7-(2-methylphenyl)-3-(5-(5,6,7,8-tetrahydronaphthalen-1-yloxy)pentyl)-1H-indole-2-carboxylic acid;
7-(2-methylphenyl)-3-(5-(1-naphthyloxy)pentyl)-1H-indole-2-carboxylic acid;
7-(2,3-dimethylphenyl)-3-(3-(1-naphthyloxy)propyl)-1H-indole-2-carboxylic acid;
7-(2-methylphenyl)-3-(3-(1-naphthyloxy)propyl)-1-(pyridin-4-ylmethyl)-1H-indole-2-carboxylic acid;
7-(2-(4-fluorophenyl)cyclohex-1-en-1-yl)-3-(3-(1-naphthyloxy)propyl)-1H-indole-2-carboxylic acid;
7-(3,5-dimethyl-1-(2-(2-oxopyrrolidin-1-yl)ethyl)-1H-pyrazol-4-yl)-3-(3-(1-naphthyloxy)propyl)-1H-indole-2-carboxylic acid;
1-(tert-butoxycarbonyl)-7-(2-methylphenyl)-3-(3-(1-naphthyloxy)benzyl)-1H-indole-2-carboxylic acid;
7-(2-methylphenyl)-3-(3-(1-naphthyloxy)benzyl)-1H-indole-2-carboxylic acid;
7-(2-methylphenyl)-4-((E)-2-phenylvinyl)-1H-indole-2-carboxylic acid;
7-(2-methylphenyl)-4-(1-naphthyl)-1H-indole-2-carboxylic acid;
7-(2-methylphenyl)-4-(2-naphthyl)-1H-indole-2-carboxylic acid;
7-(2-methylphenyl)-4-(3-(2-naphthyloxyl)propyl)-1H-indole-2-carboxylic acid;
7-(2-methylphenyl)-4-(4-(1-naphthyloxy)butyl)-1H-indole-2-carboxylic acid;
7-(2-methylphenyl)-4-(4-(2-naphthyloxyl)butyl)-1H-indole-2-carboxylic acid;
7-(2-methylphenyl)-4-(2-(2-naphthyl)ethyl)-1H-indole-2-carboxylic acid;

3-(3-(1-naphthyloxy)propyl)-7-thien-3-yl-1H-indole-2-carboxylic acid;
7-((3-(aminocarbonyl)phenyl)amino)-3-(3-(1-naphthyloxy)propyl)-1H-indole-2-carboxylic acid;
7-((3-cyanophenyl)amino)-3-(3-(1-naphthyloxy)propyl)-1H-indole-2-carboxylic acid;
7-((2-benzylphenyl)amino)-3-(3-(1-naphthyloxy)propyl)-1H-indole-2-carboxylic acid;
7-(1,1'-biphenyl-2-ylamino)-3-(3-(1-naphthyloxy)propyl)-1H-indole-2-carboxylic acid;
7-((2-ethylphenyl)amino)-3-(3-(1-naphthyloxy)propyl)-1H-indole-2-carboxylic acid;
3-(3-(1-naphthyloxy)propyl)-7-((2-propylphenyl)amino)-1H-indole-2-carboxylic acid;
7-(5-carboxy-3-methylthien-2-yl)-3-(3-(1-naphthyloxy)propyl)-1H-indole-2-carboxylic acid;
7-((2-carboxyphenyl)amino)-3-(3-(1-naphthyloxy)propyl)-1H-indole-2-carboxylic acid;
7-((3-carboxyphenyl)amino)-3-(3-(1-naphthyloxy)propyl)-1H-indole-2-carboxylic acid;
7-(2-morpholin-4-yl-5-nitropyridin-3-yl)-3-(3-(1-naphthyloxy)propyl)-1H-indole-2-carboxylic acid;
7-(5-amino-2-morpholin-4-ylpyridin-3-yl)-3-(3-(1-naphthyloxy)propyl)-1H-indole-2-carboxylic acid;
7-((3-chloropyridin-4-yl)amino)-3-(3-(1-naphthyloxy)propyl)-1H-indole-2-carboxylic acid;
7-((2-isopropylphenyl)amino)-3-(3-(1-naphthyloxy)propyl)-1H-indole-2-carboxylic acid;
7-(2-morpholin-4-ylpyridin-3-yl)-3-(3-(1-naphthyloxy)propyl)-1H-indole-2-carboxylic acid;
7-(5-(aminocarbonyl)-1,2-dimethyl-6-oxo-1,6-dihydropyridin-3-yl)-3-(3-(1-naphthyloxy)propyl)-1H-indole-2-carboxylic acid;
7-(5-cyano-1,2-dimethyl-6-oxo-1,6-dihydropyridin-3-yl)-3-(3-(1-naphthyloxy)propyl)-1H-indole-2-carboxylic acid;
7-(5-amino-4-chloro-2-morpholin-4-ylpyridin-3-yl)-3-(3-(1-naphthyloxy)propyl)-1H-indole-2-carboxylic acid;
2-methyl-3'-(3-(1-naphthyloxy)propyl)-2,3-dihydro-1'H-1,7'-biindole-2'-carboxylic acid;
7-(2-fluoro-5-methylpyridin-4-yl)-3-(3-(1-naphthyloxy)propyl)-1H-indole-2-carboxylic acid;
7-((2-methoxypyridin-3-yl)amino)-3-(3-(1-naphthyloxy)propyl)-1H-indole-2-carboxylic acid;
7-(5-methyl-2-oxo-1,2-dihydropyridin-4-yl)-3-(3-(1-naphthyloxy)propyl)-1H-indole-2-carboxylic acid;
7-(5-methyl-2-(2-pyrrolidin-1-ylethoxy)pyridin-4-yl)-3-(3-(1-naphthyloxy)propyl)-1H-indole-2-carboxylic acid;
7-(2-(dimethylamino)-5-nitropyridin-3-yl)-3-(3-(1-naphthyloxy)propyl)-1H-indole-2-carboxylic acid;
7-(2-(2-(dimethylamino)ethoxy)-5-methylpyridin-4-yl)-3-(3-(1-naphthyloxy)propyl)-1H-indole-2-carboxylic acid;
7-(5-methyl-2-(2-morpholin-4-ylethoxy)pyridin-4-yl)-3-(3-(1-naphthyloxy)propyl)-1H-indole-2-carboxylic acid;
7-(2-(1,4-dioxa-8-azaspiro(4.5)dec-8-yl)-5-nitropyridin-3-yl)-3-(3-(1-naphthyloxy)propyl)-1H-indole-2-carboxylic acid;
3-(3-(1-naphthyloxy)propyl)-7-(5-nitro-2-(4-oxopiperidin-1-yl)pyridin-3-yl)-1H-indole-2-carboxylic acid;
7-(5-amino-2-(dimethylamino)pyridin-3-yl)-3-(3-(1-naphthyloxy)propyl)-1H-indole-2-carboxylic acid;
7-(2-(4-hydroxypiperidin-1-yl)-5-nitropyridin-3-yl)-3-(3-(1-naphthyloxy)propyl)-1H-indole-2-carboxylic acid;
7-(6-methoxy-4-methylpyridin-3-yl)-3-(3-(1-naphthyloxy)propyl)-1H-indole-2-carboxylic acid;
7-(2-fluoro-5-methylpyridin-4-yl)-1-(2-morpholin-4-ylethyl)-3-(3-(1-naphthyloxy)propyl)-1H-indole-2-carboxylic acid;
3-(3-(1-naphthyloxy)propyl)-7-(1,3,5-trimethyl-1H-pyrazol-4-yl)-1H-indole-2-carboxylic acid;
7-((2-morpholin-4-ylpyridin-3-yl)amino)-3-(3-(1-naphthyloxy)propyl)-1H-indole-2-carboxylic acid;
7-(5-methyl-2-(2-phenylethoxy)pyridin-4-yl)-3-(3-(1-naphthyloxy)propyl)-1H-indole-2-carboxylic acid;
7-(5-methyl-2-(2-pyridin-3-ylethoxy)pyridin-4-yl)-3-(3-(1-naphthyloxy)propyl)-1H-indole-2-carboxylic acid;
7-((2-morpholin-4-ylphenyl)amino)-3-(3-(1-naphthyloxy)propyl)-1H-indole-2-carboxylic acid;
7-((4-carboxypyridin-3-yl)amino)-3-(3-(1-naphthyloxy)propyl)-1H-indole-2-carboxylic acid;
3-(3-(1-naphthyloxy)propyl)-7-((4-(trifluoromethyl)pyridin-3-yl)amino)-1H-indole-2-carboxylic acid;
7-(2-(3-aminopropoxy)-5-methylpyridin-4-yl)-3-(3-(1-naphthyloxy)propyl)-1H-indole-2-carboxylic acid;
7-(5-methyl-2-(tetrahydrofuran-3-ylmethoxy)pyridin-4-yl)-3-(3-(1-naphthyloxy)propyl)-1H-indole-2-carboxylic acid;
7-(5-methyl-2-(4-phenylbutoxy)pyridin-4-yl)-3-(3-(1-naphthyloxy)propyl)-1H-indole-2-carboxylic acid;
7-(2-(3-methoxyphenyl)cyclohex-1-en-1-yl)-3-(3-(1-naphthyloxy)propyl)-1H-indole-2-carboxylic acid;
7-(1-(carboxymethyl)-3,5-dimethyl-1H-pyrazol-4-yl)-3-(3-(1-naphthyloxy)propyl)-1H-indole-2-carboxylic acid;
7-(1-benzyl-1H-imidazol-5-yl)-3-(3-(1-naphthyloxy)propyl)-1H-indole-2-carboxylic acid;
7-(2-(2-methylphenyl)cyclohex-1-en-1-yl)-3-(3-(1-naphthyloxy)propyl)-1H-indole-2-carboxylic acid;
7-(3,5-dimethyl-1-(2-morpholin-4-ylethyl)-1H-pyrazol-4-yl)-3-(3-(1-naphthyloxy)propyl)-1H-indole-2-carboxylic acid;
3-(3-(1-naphthyloxy)propyl)-7-(2-(4-nitrophenyl)cyclohex-1-en-1-yl)-1H-indole-2-carboxylic acid;
7-(4,4-dimethyl-2-phenylcyclohex-1-en-1-yl)-3-(3-(1-naphthyloxy)propyl)-1H-indole-2-carboxylic acid;
1-ethyl-7-(ethyl(phenyl)amino)-3-(3-(1-naphthyloxy)propyl)-1H-indole-2-carboxylic acid;
7-anilino-3-(3-(1-naphthyloxy)propyl)-1H-indole-2-carboxylic acid;
7-(5-methyl-2-(tetrahydro-2H-pyran-3-ylmethoxy)pyridin-4-yl)-3-(3-(1-naphthyloxy)propyl)-1H-indole-2-carboxylic acid;
7-(5-methyl-2-(2-(2-oxopyrrolidin-1-yl)ethoxy)pyridin-4-yl)-3-(3-(1-naphthyloxy)propyl)-1H-indole-2-carboxylic acid;
7-(5-methyl-2-(2-(4-methylpiperazin-1-yl)ethoxy)pyridin-4-yl)-3-(3-(1-naphthyloxy)propyl)-1H-indole-2-carboxylic acid;
3-(3-(1-naphthyloxy)propyl)-7-(2-(2-oxocyclohexyl)pyridin-3-yl)-1H-indole-2-carboxylic acid;
7-(2-fluoro-5-methylpyridin-4-yl)-1-(2-(4-methylpiperazin-1-yl)ethyl)-3-(3-(1-naphthyloxy)propyl)-1H-indole-2-carboxylic acid;
7-(5,5-dimethyl-2-phenylcyclohex-1-en-1-yl)-3-(3-(1-naphthyloxy)propyl)-1H-indole-2-carboxylic acid;
3-(3-(1-naphthyloxy)propyl)-7-(pyridin-3-ylamino)-1H-indole-2-carboxylic acid;
3-(3-(1-naphthyloxy)propyl)-7-(phenyl(propyl)amino)-1-propyl-1H-indole-2-carboxylic acid;
7-(3-cyclohex-1-en-1-ylpyridin-2-yl)-3-(3-(1-naphthyloxy)propyl)-1H-indole-2-carboxylic acid;
3-(3-(1-naphthyloxy)propyl)-7-(2-pyridin-3-ylcyclohex-1-en-1-yl)-1H-indole-2-carboxylic acid;
3-(3-((8-chloroquinazolin-4-yl)oxy)propyl)-7-(2-methylphenyl)-1H-indole-2-carboxylic acid;

1-butyl-7-(butyl(phenyl)amino)-3-(3-(1-naphthyloxy)propyl)-1H-indole-2-carboxylic acid;
3-(3-(7-chloro-1H-pyrrolo(2,3-c)pyridin-1-yl)propyl)-7-(2-methylphenyl)-1H-indole-2-carboxylic acid;
7-(3-cyclohexylpyridin-2-yl)-3-(3-(1-naphthyloxy)propyl)-1H-indole-2-carboxylic acid;
3-(3-(1-naphthyloxy)propyl)-7-(1-(1,3-thiazol-5-ylmethyl)-1H-pyrrolo(2,3-c)pyridin-3-yl)-1H-indole-2-carboxylic acid;
7-(1-(3,3-dimethyl-2-oxobutyl)-1H-pyrrolo(2,3-c)pyridin-3-yl)-3-(3-(1-naphthyloxy)propyl)-1H-indole-2-carboxylic acid;
7-(4-cyclohex-1-en-1-ylpyridin-3-yl)-3-(3-(1-naphthyloxy)propyl)-1H-indole-2-carboxylic acid;
7-(1-(3,5-difluorobenzyl)-1H-pyrrolo(2,3-c)pyridin-3-yl)-3-(3-(1-naphthyloxy)propyl)-1H-indole-2-carboxylic acid;
3-(3-(1-naphthyloxy)propyl)-7-(1-phenylvinyl)-1H-indole-2-carboxylic acid;
3-(3-(1-naphthyloxy)propyl)-7-(1H-pyrrolo(2,3-c)pyridin-7-yl)-1H-indole-2-carboxylic acid;
7-(4-cyclohexylpyridin-3-yl)-3-(3-phenoxypropyl)-1H-indole-2-carboxylic acid;
7-(2,4-dimethyl-1,3-thiazol-5-yl)-3-(3-(1-naphthyloxy)propyl)-1H-indole-2-carboxylic acid;
7-(1-(carboxymethyl)-1H-pyrrolo(2,3-c)pyridin-3-yl)-3-(3-(1-naphthyloxy)propyl)-1H-indole-2-carboxylic acid;
3-(3-(1-naphthyloxy)propyl)-7-(1-phenylethyl)-1H-indole-2-carboxylic acid;
7-(1-benzyl-3,5-dimethyl-1H-pyrazol-4-yl)-3-(3-(1-naphthyloxy)propyl)-1H-indole-2-carboxylic acid;
7-(2-(2-chlorophenyl)cyclohex-1-en-1-yl)-3-(3-(1-naphthyloxy)propyl)-1H-indole-2-carboxylic acid;
3-(3-(1-naphthyloxy)propyl)-1H, 1'H-7,7'-biindole-2-carboxylic acid;
3-(3-(1-naphthyloxy)propyl)-7-(1-(2-(2-oxopyrrolidin-1-yl)ethyl)-1H-pyrrolo(2,3-c)pyridin-7-yl)-1H-indole-2-carboxylic acid;
7-(5-methyl-3-phenyl-1H-pyrazol-4-yl)-3-(3-(1-naphthyloxy)propyl)-1H-indole-2-carboxylic acid;
7-(2-methylphenyl)-4-(2-(1-naphthyloxy)ethyl)-1H-indole-2-carboxylic acid;
7-(2-methylphenyl)-4-(2-(2-naphthyloxyl)ethyl)-1H-indole-2-carboxylic acid;
4-(2-(2,3-dichlorophenoxy)ethyl)-7-(2-methylphenyl)-1H-indole-2-carboxylic acid;
3-(3-(1H-indol-4-yloxy)propyl)-7-(2-methylphenyl)-1H-indole-2-carboxylic acid;
4-(2-(2-chloro-3-(trifluoromethyl)phenoxy)ethyl)-7-(2-methylphenyl)-1H-indole-2-carboxylic acid;
1-methyl-3-(3-(((1-methyl-1H-indol-4-yl)oxy)propyl)-7-(2-methylphenyl)-1H-indole-2-carboxylic acid;
7-(2-(4-ethylphenyl)cyclohex-1-en-1-yl)-3-(3-(1-naphthyloxy)propyl)-1H-indole-2-carboxylic acid;
7-(2-(4-isopropylphenyl)cyclohex-1-en-1-yl)-3-(3-(1-naphthyloxyl)propyl)-1H-indole-2-carboxylic acid;
7-(1,3-dimethyl-5-phenyl-1H-pyrazol-4-yl)-3-(3-(1-naphthyloxy)propyl)-1H-indole-2-carboxylic acid;
7-(1,5-dimethyl-3-phenyl-1H-pyrazol-4-yl)-3-(3-(1-naphthyloxy)propyl)-1H-indole-2-carboxylic acid;
7-(3,5-dimethyl-1-((3-methyloxetan-3-yl)methyl)-1H-pyrazol-4-yl)-3-(3-(1-naphthyloxy)propyl)-1H-indole-2-carboxylic acid;
7-(3,5-dimethyl-1-tetrahydrofuran-3-yl-1H-pyrazol-4-yl)-3-(3-(1-naphthyloxy)propyl)-1H-indole-2-carboxylic acid;
7-(3,5-dimethyl-1-pyridin-2-yl-1H-pyrazol-4-yl)-3-(3-(1-naphthyloxy)propyl)-1H-indole-2-carboxylic acid;
7-(2-chloro-4-methylpyridin-3-yl)-3-(3-(1-naphthyloxy)propyl)-1H-indole-2-carboxylic acid;
7-(4-methyl-2-(2-(2-oxopyrrolidin-1-yl)ethoxy)pyridin-3-yl)-3-(3-(1-naphthyloxy)propyl)-1H-indole-2-carboxylic acid;
7-(3,5-dimethyl-1-(tetrahydrofuran-3-ylmethyl)-1H-pyrazol-4-yl)-3-(3-(1-naphthyloxy)propyl)-1H-indole-2-carboxylic acid;
7-(1-cyclopentyl-3,5-dimethyl-1H-pyrazol-4-yl)-3-(3-(1-naphthyloxy)propyl)-1H-indole-2-carboxylic acid;
7-(1-((2,2-dimethyl-1,3-dioxolan-4-yl)methyl)-3,5-dimethyl-1H-pyrazol-4-yl)-3-(3-(1-naphthyloxyl)propyl)-1H-indole-2-carboxylic acid;
7-(4-methyl-2-(2-morpholin-4-ylethoxy)pyridin-3-yl)-3-(3-(1-naphthyloxy)propyl)-1H-indole-2-carboxylic acid;
7-(4-methyl-2-morpholin-4-ylpyridin-3-yl)-3-(3-(1-naphthyloxy)propyl)-1H-indole-2-carboxylic acid;
7-(2-chloro-4-methylpyridin-3-yl)-3-(3-(1-naphthyloxy)propyl)-1-(pyridin-3-ylmethyl)-1H-indole-2-carboxylic acid;
7-(2-(1H-imidazol-1-yl)-4-methylpyridin-3-yl)-3-(3-(1-naphthyloxy)propyl)-1H-indole-2-carboxylic acid;
7-(1-(2,3-dihydroxypropyl)-3,5-dimethyl-1H-pyrazol-4-yl)-3-(3-(1-naphthyloxy)propyl)-1H-indole-2-carboxylic acid;
3-(3-(1-naphthyloxy)propyl)-7-(3-phenyl-5-(2-phenylethyl)-1H-pyrazol-4-yl)-1H-indole-2-carboxylic acid;
7-(4-methyl-2-phenylpyridin-3-yl)-3-(3-(1-naphthyloxy)propyl)-1H-indole-2-carboxylic acid;
7-(4-methyl-2-vinylpyridine-3-yl)-3-(3-(1-naphthyloxy)propyl)-1H-indole-2-carboxylic acid;
7-(4-methyl-2-((1E)-prop-1-enyl)pyridin-3-yl)-3-(3-(1-naphthyloxy)propyl)-1H-indole-2-carboxylic acid;
7-(2-ethyl-4-methylpyridin-3-yl)-3-(3-(1-naphthyloxy)propyl)-1H-indole-2-carboxylic acid;
7-(3,5-dimethyl-1-(pyridin-3-ylmethyl)-1H-pyrazol-4-yl)-3-(3-(1-naphthyloxy)propyl)-1H-indole-2-carboxylic acid;
7-(2-isopropenyl-4-methylpyridin-3-yl)-3-(3-(1-naphthyloxy)propyl)-1H-indole-2-carboxylic acid;
7-(4-methyl-2-pentylpyridine-3-yl)-3-(3-(1-naphthyloxy)propyl)-1H-indole-2-carboxylic acid;
7-(4-methyl-2-propylpyridine-3-yl)-3-(3-(1-naphthyloxy)propyl)-1H-indole-2-carboxylic acid;
7-(2-isopropyl-4-methylpyridin-3-yl)-3-(3-(1-naphthyloxy)propyl)-1H-indole-2-carboxylic acid;
7-(3,5-diisopropyl-1-methyl-1H-pyrazol-4-yl)-3-(3-(1-naphthyloxy)propyl)-1H-indole-2-carboxylic acid;
7-(5-carboxy-1,3-dimethyl-1H-pyrazol-4-yl)-3-(3-(1-naphthyloxy)propyl)-1H-indole-2-carboxylic acid;
7-(4-methyl-2-(2-methylprop-1-enyl)pyridin-3-yl)-3-(3-(1-naphthyloxy)propyl)-1H-indole-2-carboxylic acid;
7-(4-carboxy-1-phenyl-1H-pyrazol-5-yl)-3-(3-(1-naphthyloxy)propyl)-1H-indole-2-carboxylic acid;
7-(2-isobutyl-4-methylpyridin-3-yl)-3-(3-(1-naphthyloxy)propyl)-1H-indole-2-carboxylic acid;
7-(4-methyl-2,3'-bipyridine-3-yl)-3-(3-(1-naphthyloxy)propyl)-1H-indole-2-carboxylic acid;
7-(2-(4-methoxyphenyl)-4-methylpyridin-3-yl)-3-(3-(1-naphthyloxy)propyl)-1H-indole-2-carboxylic acid;
7-(4-methyl-2-(1-methyl-1H-pyrazol-4-yl)pyridin-3-yl)-3-(3-(1-naphthyloxy)propyl)-1H-indole-2-carboxylic acid;
7-(3-(hydroxymethyl)-1,5-dimethyl-1H-pyrazol-4-yl)-3-(3-(1-naphthyloxy)propyl)-1H-indole-2-carboxylic acid;
3-bromo-7-(1,3-dimethyl-5-phenyl-1H-pyrazol-4-yl)-1H-indole-2-carboxylic acid;

7-(1,3-dimethyl-5-(phenoxymethyl)-1H-pyrazol-4-yl)-3-(3-(1-naphthyloxy)propyl)-1H-indole-2-carboxylic acid;

7-(1-methyl-1H-pyrazol-4-yl)-3-(3-(1-naphthyloxy)propyl)-1H-indole-2-carboxylic acid;

3-bromo-7-(2-((E)-2-cyclohexylvinyl)-4-methylpyridin-3-yl)-1H-indole-2-carboxylic acid;

7-(3-isopropyl-1-methyl-5-(phenoxymethyl)-1H-pyrazol-4-yl)-3-(3-(1-naphthyloxy)propyl)-1H-indole-2-carboxylic acid;

7-(1,5-dimethyl-3-(phenoxymethyl)-1H-pyrazol-4-yl)-3-(3-(1-naphthyloxy)propyl)-1H-indole-2-carboxylic acid;

7-(4-(anilinocarbonyl)-1-phenyl-1H-pyrazol-5-yl)-3-(3-(1-naphthyloxy)propyl)-1H-indole-2-carboxylic acid;

7-(3-((3-chlorophenoxy)methyl)-1,5-dimethyl-1H-pyrazol-4-yl)-3-(3-(1-naphthyloxy)propyl)-1H-indole-2-carboxylic acid;

7-(1,5-dimethyl-3-((3-phenoxyphenoxy)methyl)-1H-pyrazol-4-yl)-3-(3-(1-naphthyloxy)propyl)-1H-indole-2-carboxylic acid;

3-bromo-4-(2-((4-bromo-1-naphthyl)oxy)ethyl)-7-(2-methylphenyl)-1H-indole-2-carboxylic acid;

7-(1,5-dimethyl-3-((4-morpholin-4-ylphenoxy)methyl)-1H-pyrazol-4-yl)-3-(3-(1-naphthyloxy)propyl)-1H-indole-2-carboxylic acid;

7-(3-(((5-chloropyridin-3-yl)oxy)methyl)-1,5-dimethyl-1H-pyrazol-4-yl)-3-(3-(1-naphthyloxy)propyl)-1H-indole-2-carboxylic acid;

7-(3,5-dimethyl-1-(2-nitrophenyl)-1H-pyrazol-4-yl)-3-(3-(1-naphthyloxy)propyl)-1H-indole-2-carboxylic acid;

3-(3-(1-naphthyloxy)propyl)-7-((2-(phenylthio)ethyl)amino)-1H-indole-2-carboxylic acid;

7-(3-((2-cyanophenoxy)methyl)-1,5-dimethyl-1H-pyrazol-4-yl)-3-(3-(1-naphthyloxy)propyl)-1H-indole-2-carboxylic acid;

7-(3-((4-(4-acetylpiperazin-1-yl)phenoxy)methyl)-1,5-dimethyl-1H-pyrazol-4-yl)-3-(3-(1-naphthyloxy)propyl)-1H-indole-2-carboxylic acid;

3-bromo-7-(2-methylphenyl)-4-(2-(1-naphthyloxy)ethyl)-1H-indole-2-carboxylic acid;

7-(1-(2-aminophenyl)-3,5-dimethyl-1H-pyrazol-4-yl)-3-(3-(1-naphthyloxy)propyl)-1H-indole-2-carboxylic acid;

7-(3-(1H-imidazol-1-ylmethyl)-1,5-dimethyl-1H-pyrazol-4-yl)-3-(3-(1-naphthyloxy)propyl)-1H-indole-2-carboxylic acid;

7-(2-methylphenyl)-4-(2-(1-naphthyloxy)ethyl)-3-vinyl-1H-indole-2-carboxylic acid;

7-(4-((benzylamino)carbonyl)-1-phenyl-1H-pyrazol-5-yl)-3-(3-(1-naphthyloxy)propyl)-1H-indole-2-carboxylic acid;

3-(3-(1-naphthyloxy)propyl)-7-(1-phenyl-4-(((3-pyrrolidin-1-ylpropyl)amino)carbonyl)-1H-pyrazol-5-yl)-1H-indole-2-carboxylic acid;

7-(4,6-dimethylpyrimidin-5-yl)-3-(3-(1-naphthyloxy)propyl)-1H-indole-2-carboxylic acid;

7-(4,6-dimethylpyrimidin-5-yl)-3-(3-(1-naphthyloxy)propyl)-1-(pyridin-3-ylmethyl)-1H-indole-2-carboxylic acid;

7-(2-ethyl-4-methylpyridin-3-yl)-3-(3-(1-naphthyloxy)propyl)-1-(pyridin-3-ylmethyl)-1H-indole-2-carboxylic acid;

7-(2-ethyl-4-methylpyridin-3-yl)-3-(3-(1-naphthyloxy)propyl)-1-(1,3-thiazol-4-ylmethyl)-1H-indole-2-carboxylic acid;

7-(2-chloro-4-((4-morpholin-4-ylphenoxy)methyl)pyridin-3-yl)-3-(3-(1-naphthyloxy)propyl)-1H-indole-2-carboxylic acid;

7-(5-isopropyl-1-methyl-3-((4-morpholin-4-ylphenoxy)methyl)-1H-pyrazol-4-yl)-3-(3-(1-naphthyloxy)propyl)-1H-indole-2-carboxylic acid;

7-(3-isopropyl-1-methyl-5-((4-morpholin-4-ylphenoxy)methyl)-1H-pyrazol-4-yl)-3-(3-(1-naphthyloxy)propyl)-1H-indole-2-carboxylic acid;

7-(2-isopropenyl-4-methylpyridin-3-yl)-3-(3-(1-naphthyloxy)propyl)-1-(pyridin-2-ylmethyl)-1H-indole-2-carboxylic acid;

7-(1,5-dimethyl-3-((4-morpholin-4-ylphenoxy)methyl)-1H-pyrazol-4-yl)-3-(3-(1-naphthyloxy)propyl)-1-(pyridin-3-ylmethyl)-1H-indole-2-carboxylic acid;

7-(2-ethyl-4-((4-morpholin-4-ylphenoxy)methyl)pyridin-3-yl)-3-(3-(1-naphthyloxy)propyl)-1H-indole-2-carboxylic acid;

7-(4-methyl-2-pyrimidin-5-ylpyridin-3-yl)-3-(3-(1-naphthyloxy)propyl)-1H-indole-2-carboxylic acid;

7-(4-methyl-6'-morpholin-4-yl-2,3'-bipyridin-3-yl)-3-(3-(1-naphthyloxy)propyl)-1H-indole-2-carboxylic acid;

7-(4,6-dimethylpyrimidin-5-yl)-3-(3-(1-naphthyloxy)propyl)-1-(pyridin-2-ylmethyl)-1H-indole-2-carboxylic acid;

7-(4,6-dimethylpyrimidin-5-yl)-1-(2-(4-methylpiperazin-1-yl)-2-oxoethyl)-3-(3-(1-naphthyloxy)propyl)-1H-indole-2-carboxylic acid;

1-(2-(dimethylamino)-2-oxoethyl)-7-(4,6-dimethylpyrimidin-5-yl)-3-(3-(1-naphthyloxy)propyl)-1H-indole-2-carboxylic acid;

7-(3-((4-(1,1-dioxidothiomorpholin-4-yl)phenoxy)methyl)-1,5-dimethyl-1H-pyrazol-4-yl)-3-(3-(1-naphthyloxy)propyl)-1H-indole-2-carboxylic acid;

7-(4,6-dimethylpyrimidin-5-yl)-1-(2-morpholin-4-ylethyl)-3-(3-(1-naphthyloxy)propyl)-1H-indole-2-carboxylic acid;

7-(1,5-dimethyl-3-((4-piperazin-1-ylphenoxy)methyl)-1H-pyrazol-4-yl)-3-(3-(1-naphthyloxy)propyl)-1H-indole-2-carboxylic acid;

7-(3-((4-(4-acetylpiperazin-1-yl)phenoxy)methyl)-1,5-dimethyl-1H-pyrazol-4-yl)-3-(3-(1-naphthyloxy)propyl)-1-(pyridin-3-ylmethyl)-1H-indole-2-carboxylic acid;

7-(4,6-dimethylpyrimidin-5-yl)-1-(2-(4-methylpiperazin-1-yl)ethyl)-3-(3-(1-naphthyloxy)propyl)-1H-indole-2-carboxylic acid;

7-(3-((4-(4-(tert-butoxycarbonyl)piperazin-1-yl)phenoxy)methyl)-1,5-dimethyl-1H-pyrazol-4-yl)-3-(3-(1-naphthyloxy)propyl)-1H-indole-2-carboxylic acid;

1-(2-(dimethylamino)ethyl)-7-(4,6-dimethylpyrimidin-5-yl)-3-(3-(1-naphthyloxy)propyl)-1H-indole-2-carboxylic acid;

3-(3-(1-naphthyloxy)propyl)-7-(4-(1H-pyrazol-1-yl)phenyl)-1H-indole-2-carboxylic acid;

3-(3-(1-naphthyloxy)propyl)-7-(2,3,4-trifluorophenyl)-1H-indole-2-carboxylic acid;

7-(4-hydroxy-3-methoxyphenyl)-3-(3-(1-naphthyloxy)propyl)-1H-indole-2-carboxylic acid;

3-(3-(1-naphthyloxy)propyl)-7-(3,4,5-trimethoxyphenyl)-1H-indole-2-carboxylic acid;

3-(3-(1-naphthyloxy)propyl)-7-(4-(trifluoromethoxy)phenyl)-1H-indole-2-carboxylic acid;

7-(2-methoxy-5-methylphenyl)-3-(3-(1-naphthyloxy)propyl)-1H-indole-2-carboxylic acid;

7-(3-fluoro-4-methoxyphenyl)-3-(3-(1-naphthyloxy)propyl)-1H-indole-2-carboxylic acid;

3-(3-(1-naphthyloxy)propyl)-7-(4-(5-oxo-2,5-dihydro-1H-pyrazol-3-yl)phenyl)-1H-indole-2-carboxylic acid;

7-(3-(morpholin-4-ylmethyl)phenyl)-3-(3-(1-naphthyloxy)propyl)-1H-indole-2-carboxylic acid;

7-(4-(morpholin-4-ylmethyl)phenyl)-3-(3-(1-naphthyloxy)propyl)-1H-indole-2-carboxylic acid;

7-(4-isopropoxy-2-methylphenyl)-3-(3-(1-naphthyloxy)propyl)-1H-indole-2-carboxylic acid;

3-(3-(1-naphthyloxy)propyl)-7-(4-(1H-pyrazol-5-yl)phenyl)-1H-indole-2-carboxylic acid;

7-(2,5-dimethylphenyl)-3-(3-(1-naphthyloxy)propyl)-1H-indole-2-carboxylic acid;

3-(3-(1-naphthyloxy)propyl)-7-(2,4,5-trimethylphenyl)-1H-indole-2-carboxylic acid;

3-(3-(1-naphthyloxy)propyl)-7-(3-(trifluoromethoxy)phenyl)-1H-indole-2-carboxylic acid;

7-(2-methyl-4-propoxyphenyl)-3-(3-(1-naphthyloxy)propyl)-1H-indole-2-carboxylic acid;

7-(3-cyanophenyl)-3-(3-(1-naphthyloxy)propyl)-1H-indole-2-carboxylic acid;

3-(3-(1-naphthyloxy)propyl)-7-(2,3,5,6-tetramethylphenyl)-1H-indole-2-carboxylic acid;

7-(3-cyano-2-methylphenyl)-3-(3-(1-naphthyloxy)propyl)-1H-indole-2-carboxylic acid;

7-(3-ethynyl-2-methylphenyl)-3-(3-(1-naphthyloxy)propyl)-1H-indole-2-carboxylic acid;

7-(5-(((3-(dimethylamino)propyl)amino)carbonyl)-2-methylphenyl)-3-(3-(1-naphthyloxy)propyl)-1H-indole-2-carboxylic acid;

7-(2-isopropylphenyl)-3-(3-(1-naphthyloxy)propyl)-1H-indole-2-carboxylic acid;

7-(5-(((2-(dimethylamino)ethyl)amino)carbonyl)-2-methylphenyl)-3-(3-(1-naphthyloxy)propyl)-1H-indole-2-carboxylic acid;

7-(2-methyl-5-(((2-morpholin-4-ylethyl)amino)carbonyl)phenyl)-3-(3-(1-naphthyloxy)propyl)-1H-indole-2-carboxylic acid;

7-(2-methyl-5-(((3-morpholin-4-ylpropyl)amino)carbonyl)phenyl)-3-(3-(1-naphthyloxy)propyl)-1H-indole-2-carboxylic acid;

7-(2-methyl-5-(((2-phenylethyl)amino)carbonyl)phenyl)-3-(3-(1-naphthyloxy)propyl)-1H-indole-2-carboxylic acid;

7-(1H-indazol-5-yl)-3-(3-(1-naphthyloxy)propyl)-1H-indole-2-carboxylic acid;

7-(5-((((1S,4R)-bicyclo(2.2.1)hept-2-ylmethyl)amino)carbonyl)-2-methylphenyl)-3-(3-(1-naphthyloxy)propyl)-1H-indole-2-carboxylic acid;

7-(2-methyl-5-(((3-phenylpropyl)amino)carbonyl)phenyl)-3-(3-(1-naphthyloxy)propyl)-1H-indole-2-carboxylic acid;

7-(2-((2-isopropyl-5-methylphenoxy)methyl)phenyl)-3-(3-(1-naphthyloxy)propyl)-1H-indole-2-carboxylic acid;

7-(2-chloro-6-methylphenyl)-3-(3-(1-naphthyloxy)propyl)-1H-indole-2-carboxylic acid;

7-(2-benzylphenyl)-3-(3-(1-naphthyloxy)propyl)-1H-indole-2-carboxylic acid;

3-(3-(1-naphthyloxy)propyl)-7-(2,4,6-triisopropylphenyl)-1H-indole-2-carboxylic acid;

3-(3-(1-naphthyloxy)propyl)-7-(1-oxo-2,3-dihydro-1H-inden-4-yl)-1H-indole-2-carboxylic acid;

7-(2-cyclopentylphenyl)-3-(3-(1-naphthyloxy)propyl)-1H-indole-2-carboxylic acid;

7-(2',6'-dimethoxy-1,1'-biphenyl-2-yl)-3-(3-(1-naphthyloxy)propyl)-1H-indole-2-carboxylic acid;

3-(3-(1-naphthyloxy)propyl)-7-(5,6,7,8-tetrahydronaphthalen-1-yl)-1H-indole-2-carboxylic acid;

7-(4'-tert-butyl-1,1'-biphenyl-2-yl)-3-(3-(1-naphthyloxy)propyl)-1H-indole-2-carboxylic acid;

7-(5-fluoro-2-methyl-3-((methylsulfonyl)methyl)phenyl)-3-(3-(1-naphthyloxy)propyl)-1H-indole-2-carboxylic acid;

7-(5-(((2-hydroxy-1,1-dimethylethyl)amino)carbonyl)-2,3,4-trimethylphenyl)-3-(3-(1-naphthyloxy)propyl)-1H-indole-2-carboxylic acid;

7-(2-(4-(ethoxycarbonyl)piperazin-1-yl)phenyl)-3-(3-(1-naphthyloxy)propyl)-1H-indole-2-carboxylic acid;

7-(2-methyl-6-nitrophenyl)-3-(3-(1-naphthyloxy)propyl)-1H-indole-2-carboxylic acid;

3-(3-(1-naphthyloxy)propyl)-7-(2-(4-propionylpiperazin-1-yl)phenyl)-1H-indole-2-carboxylic acid;

7-(2-methyl-6-thien-2-ylphenyl)-3-(3-(1-naphthyloxy)propyl)-1H-indole-2-carboxylic acid;

3-(3-(1-naphthyloxy)propyl)-7-(2-(4-(1,3-thiazol-4-ylmethyl)piperazin-1-yl)phenyl)-1H-indole-2-carboxylic acid;

7-(2-(4-(2-hydroxyethyl)piperazin-1-yl)phenyl)-3-(3-(1-naphthyloxy)propyl)-1H-indole-2-carboxylic acid;

7-(2-(4-(methylsulfonyl)piperazin-1-yl)phenyl)-3-(3-(1-naphthyloxy)propyl)-1H-indole-2-carboxylic acid;

7-(2-((4-(tert-butoxycarbonyl)piperazin-1-yl)sulfonyl)phenyl)-3-(3-(1-naphthyloxy)propyl)-1H-indole-2-carboxylic acid;

7-(2-((4-ethylpiperazin-1-yl)sulfonyl)phenyl)-3-(3-(1-naphthyloxy)propyl)-1H-indole-2-carboxylic acid;

3-(3-(1-naphthyloxy)propyl)-7-(2-((4-(2-oxopyrrolidin-1-yl)piperidin-1-yl)sulfonyl)phenyl)-1H-indole-2-carboxylic acid;

7-(3-((1S,4R)-2-hydroxybicyclo(2.2.1)hept-2-yl)-2-methylphenyl)-3-(3-(1-naphthyloxy)propyl)-1H-indole-2-carboxylic acid;

7-((1E)-1-ethylbut-1-enyl)-3-(3-(1-naphthyloxy)propyl)-1H-indole-2-carboxylic acid;

7-((Z)-2-carboxy-1-pentylvinyl)-3-(3-(1-naphthyloxy)propyl)-1H-indole-2-carboxylic acid;

7-(5,7-dimethylpyrazolo(1,5-a)pyrimidin-3-yl)-3-(3-(1-naphthyloxy)propyl)-1H-indole-2-carboxylic acid;

7-(4-(4-fluorophenyl)-5-(4-(methylsulfonyl)phenyl)thien-2-yl)-3-(3-(1-naphthyloxy)propyl)-1H-indole-2-carboxylic acid;

3-(3-(1-naphthyloxy)propyl)-1-(pyridin-4-ylmethyl)-7-(2-(trifluoromethyl)phenyl)-1H-indole-2-carboxylic acid;

7-(5-(((2-(dimethylamino)ethyl)(pyridin-2-yl)amino)methyl)thien-2-yl)-3-(3-(1-naphthyloxy)propyl)-1H-indole-2-carboxylic acid;

7-(2-morpholin-4-yl-6-(trifluoromethyl)phenyl)-3-(3-(1-naphthyloxy)propyl)-1H-indole-2-carboxylic acid;

7-(4-methoxy-2-phenyl-1-benzofuran-3-yl)-3-(3-(1-naphthyloxy)propyl)-1H-indole-2-carboxylic acid;

4-fluoro-7-(2-morpholin-4-ylphenyl)-3-(3-(1-naphthyloxy)propyl)-1H-indole-2-carboxylic acid;

4-fluoro-7-(2-methylphenyl)-3-(3-(1-naphthyloxy)propyl)-1H-indole-2-carboxylic acid;

7-(2-(((2-adamantylamino)carbonyl)-6-methylimidazo(1,2-a)pyridin-8-yl)-3-(3-(1-naphthyloxy)propyl)-1H-indole-2-carboxylic acid;

7-(1-(1-adamantyl)-3-carboxy-1H-pyrazol-4-yl)-3-(3-(1-naphthyloxy)propyl)-1H-indole-2-carboxylic acid;

7-(2-(1-hydroxy-4-methoxycyclohexyl)-1-benzothien-3-yl)-3-(3-(1-naphthyloxy)propyl)-1H-indole-2-carboxylic acid;

7-(5-chloro-3-methyl-1-tetrahydro-2H-pyran-2-yl-1H-pyrazol-4-yl)-3-(3-(1-naphthyloxy)propyl)-1H-indole-2-carboxylic acid;

3-(3-(1-naphthyloxy)propyl)-7-(2,2,4-trimethyl-1-(phenylsulfonyl)-1,2-dihydroquinolin-3-yl)-1H-indole-2-carboxylic acid;

7-(7,8-dimethyl-2-(1-methyl-1-phenylethyl)imidazo(1,2-a)pyridin-6-yl)-3-(3-(1-naphthyloxy)propyl)-1H-indole-2-carboxylic acid;

7-(1-(4-((2-fluorobenzoyl)amino)phenyl)-3-(trifluoromethyl)-1H-pyrazol-5-yl)-3-(3-(1-naphthyloxy)propyl)-1H-indole-2-carboxylic acid;

7-(5-amino-3-(piperidin-1-ylcarbonyl)-1H-pyrazol-4-yl)-3-(3-(1-naphthyloxy)propyl)-1H-indole-2-carboxylic acid;

7-(3-methyl-1-(2-nitrophenyl)-5-phenyl-1H-pyrazol-4-yl)-3-(3-(1-naphthyloxy)propyl)-1H-indole-2-carboxylic acid;

7-(5-methyl-1-(2-oxo-2-((2-phenylethyl)amino)ethyl)-3-(trifluoromethyl)-1H-pyrazol-4-yl)-3-(3-(i-naphthyloxy)propyl)-1H-indole-2-carboxylic acid;

7-(2-(1-adamantyl)imidazo(1,2-a)pyridin-5-yl)-3-(3-(1-naphthyloxy)propyl)-1H-indole-2-carboxylic acid;

7-(1,1-dioxido-1-benzothien-3-yl)-3-(3-(1-naphthyloxy)propyl)-1H-indole-2-carboxylic acid;

7-(2-cyclohexyl-6-methylphenyl)-3-(3-(1-naphthyloxy)propyl)-1H-indole-2-carboxylic acid;

7-(4-(((2-(2-(2-aminoethoxy)ethoxy)ethyl)amino)carbonyl)-2-methylphenyl)-3-(3-(1-naphthyloxy)propyl)-1H-indole-2-carboxylic acid;

7-(1-methyl-3,5-diphenyl-1H-pyrazol-4-yl)-3-(3-(1-naphthyloxy)propyl)-1H-indole-2-carboxylic acid;

7-((Z)-2-(1H-imidazol-1-yl)-1-phenylvinyl)-3-(3-(1-naphthyloxy)propyl)-1H-indole-2-carboxylic acid;

7-(1-benzyl-2-methyl-4-nitro-1H-imidazol-5-yl)-3-(3-(1-naphthyloxy)propyl)-1H-indole-2-carboxylic acid;

3-(3-(1-naphthyloxy)propyl)-7-(2-prop-1-ynylphenyl)-1H-indole-2-carboxylic acid;

3-(3-(1-naphthyloxy)propyl)-7-(2-(phenylethynyl)phenyl)-1H-indole-2-carboxylic acid;

3,7-bis(3-(1-naphthyloxy)propyl)-1H-indole-2-carboxylic acid;

1-(2-(dimethylamino)-2-oxoethyl)-7-(2-methylphenyl)-3-(3-(1-naphthyloxy)propyl)-1H-indole-2-carboxylic acid;

1-(2-methylbenzyl)-7-(2-methylphenyl)-3-(3-(1-naphthyloxy)propyl)-1H-indole-2-carboxylic acid;

1-(3-methylbenzyl)-7-(2-methylphenyl)-3-(3-(1-naphthyloxy)propyl)-1H-indole-2-carboxylic acid;

1-(4-methylbenzyl)-7-(2-methylphenyl)-3-(3-(1-naphthyloxy)propyl)-1H-indole-2-carboxylic acid;

7-(2-methylphenyl)-1-(3-morpholin-4-ylpropyl)-3-(3-(1-naphthyloxy)propyl)-1H-indole-2-carboxylic acid;

7-(2-methylphenyl)-1-(2-(4-methylpiperazin-1-yl)-2-oxoethyl)-3-(3-(1-naphthyloxy)propyl)-1H-indole-2-carboxylic acid;

7-(2-methylphenyl)-1-(2-(4-methylpiperazin-1-yl)ethyl)-3-(3-(1-naphthyloxy)propyl)-1H-indole-2-carboxylic acid;

1-(1,1'-biphenyl-2-ylmethyl)-7-(2-methylphenyl)-3-(3-(1-naphthyloxy)propyl)-1H-indole-2-carboxylic acid;

1-(1,1'-biphenyl-3-ylmethyl)-7-(2-methylphenyl)-3-(3-(1-naphthyloxy)propyl)-1H-indole-2-carboxylic acid;

1-(1,1'-biphenyl-4-ylmethyl)-7-(2-methylphenyl)-3-(3-(1-naphthyloxy)propyl)-1H-indole-2-carboxylic acid;

1-(2,4-dimethylbenzyl)-7-(2-methylphenyl)-3-(3-(1-naphthyloxy)propyl)-1H-indole-2-carboxylic acid;

1-(4-carboxybenzyl)-7-(2-methylphenyl)-3-(3-(1-naphthyloxy)propyl)-1H-indole-2-carboxylic acid;

1-(1,1'-biphenyl-2-ylmethyl)-7-(2-morpholin-4-ylphenyl)-3-(3-(1-naphthyloxy)propyl)-1H-indole-2-carboxylic acid;

1-(1,1'-biphenyl-3-ylmethyl)-7-(2-morpholin-4-ylphenyl)-3-(3-(1-naphthyloxy)propyl)-1H-indole-2-carboxylic acid;

1-(1,1'-biphenyl-4-ylmethyl)-7-(2-morpholin-4-ylphenyl)-3-(3-(1-naphthyloxy)propyl)-1H-indole-2-carboxylic acid;

1-(2,4-dimethylbenzyl)-7-(2-morpholin-4-ylphenyl)-3-(3-(1-naphthyloxy)propyl)-1H-indole-2-carboxylic acid;

1-(2,6-dichlorobenzyl)-7-(2-morpholin-4-ylphenyl)-3-(3-(1-naphthyloxy)propyl)-1H-indole-2-carboxylic acid;

1-(4-carboxybenzyl)-7-(2-morpholin-4-ylphenyl)-3-(3-(1-naphthyloxy)propyl)-1H-indole-2-carboxylic acid;

7-(6,6-dimethylcyclohex-1-en-1-yl)-3-(3-(1-naphthyloxy)propyl)-1H-indole-2-carboxylic acid;

7-(5,5-dimethylcyclopent-1-en-1-yl)-3-(3-(1-naphthyloxy)propyl)-1H-indole-2-carboxylic acid;

3-(3-(1-naphthyloxy)propyl)-7-(7-phenylcyclohept-1-en-1-yl)-1H-indole-2-carboxylic acid;

3-(3-(1-naphthyloxy)propyl)-7-tricyclo(4.3.1.1$^{3,8}$)undec-4-en-4-yl-1H-indole-2-carboxylic acid;

3-(3-(1-naphthyloxy)propyl)-7-(2-phenylcyclohept-1-en-1-yl)-1H-indole-2-carboxylic acid;

3-(3-(1-naphthyloxy)propyl)-7-(2,6,6-trimethylcyclohex-1-en-1-yl)-1H-indole-2-carboxylic acid;

3-(3-(1-naphthyloxy)propyl)-7-((1R,4R)-1,7,7-trimethylbicyclo(2.2.1)hept-2-en-2-yl)-1H-indole-2-carboxylic acid;

7-(2-methylphenyl)-3-(3-(1-naphthyloxy)propyl)-4-(trifluoromethyl)-1H-indole-2-carboxylic acid;

7-(2-morpholin-4-ylphenyl)-3-(3-(1-naphthyloxy)propyl)-4-(trifluoromethyl)-1H-indole-2-carboxylic acid;

1-(2-(dimethylamino)ethyl)-7-(2-methylphenyl)-3-(3-(1-naphthyloxy)propyl)-1H-indole-2-carboxylic acid;

7-(1,1'-biphenyl-2-ylmethyl)-3-(3-(1-naphthyloxy)propyl)-1H-indole-2-carboxylic acid;

7-(1,1'-biphenyl-3-ylmethyl)-3-(3-(1-naphthyloxy)propyl)-1H-indole-2-carboxylic acid;

7-(1-(2-(1-naphthyloxy)ethyl)vinyl)-3-(3-(1-naphthyloxy)propyl)-1H-indole-2-carboxylic acid;

3-(3-(1-naphthyloxy)propyl)-7-(2-(phenoxymethyl)benzyl)-1H-indole-2-carboxylic acid;

3-(3-(1-naphthyloxy)propyl)-7-(2-(2-phenoxyethyl)phenyl)-1H-indole-2-carboxylic acid;

3-(3-(1-naphthyloxy)propyl)-7-(2-(2-phenoxyethyl)phenyl)-1H-indole-2-carboxylic acid;

3-(3-(1-naphthyloxy)propyl)-7-(2-(3-phenoxypropyl)phenyl)-1H-indole-2-carboxylic acid;

3-(3-(1-naphthyloxy)propyl)-7-(3-(3-phenoxypropyl)phenyl)-1H-indole-2-carboxylic acid;

3-(3-(3-hydroxy-2-methylphenoxy)propyl)-7-(2-methylphenyl)-1H-indole-2-carboxylic acid;

3-(3-(3-(2-methoxyethoxy)-2-methylphenoxy)propyl)-7-(2-methylphenyl)-1H-indole-2-carboxylic acid;

7-(1,2-dimethylprop-1-enyl)-3-(3-(1-naphthyloxy)propyl)-1H-indole-2-carboxylic acid;

3-(3-(2-methyl-3-(2-morpholin-4-ylethoxy)phenoxy)propyl)-7-(2-methylphenyl)-1H-indole-2-carboxylic acid;

3-(3-(2,3-dichlorophenoxy)propyl)-7-(2-morpholin-4-ylphenyl)-1H-indole-2-carboxylic acid;

1-(2-morpholin-4-ylethyl)-7-(2-morpholin-4-ylphenyl)-3-(3-(5,6,7,8-tetrahydronaphthalen-1-yloxy)propyl)-1H-indole-2-carboxylic acid;

7-(2-methylphenyl)-3-(3-(1-naphthylthio)propyl)-1H-indole-2-carboxylic acid;

3-(3-(3-(2-methoxyethoxy)-5-methylphenoxy)propyl)-7-(2-methylphenyl)-1H-indole-2-carboxylic acid;

7-(2-morpholin-4-ylphenyl)-3-(3-(5,6,7,8-tetrahydronaphthalen-1-yloxy)propyl)-1H-indole-2-carboxylic acid;

3-(3-(3-methyl-5-(3-morpholin-4-ylpropoxy)phenoxy)propyl)-7-(2-methylphenyl)-1H-indole-2-carboxylic acid;

3-(3-(3-(3-cyclohexylpropoxy)-5-methylphenoxy)propyl)-7-(2-methylphenyl)-1H-indole-2-carboxylic acid;

3-(3-(3-(3-(2-carboxy-1H-indol-3-yl)propoxy)-5-methylphenoxy)propyl)-7-(2-morpholin-4-ylphenyl)-1H-indole-2-carboxylic acid;

7-bromo-3-(3-(1-naphthyloxy)propyl)-1-(pyridin-4-ylmethyl)-1H-indole-2-carboxylic acid;

7-(2-morpholin-4-ylphenyl)-3-(3-(1-naphthyloxy)propyl)-1-(pyridin-4-ylmethyl)-1H-indole-2-carboxylic acid;
7-(1,1'-bi(cyclohexan)-2-en-2-yl)-3-(3-(1-naphthyloxy)propyl)-1H-indole-2-carboxylic acid;
3-(3-(2,3-dichlorophenoxy)propyl)-7-(1,2-dimethylprop-1-enyl)-1H-indole-2-carboxylic acid;
7-(2-methylphenyl)-3-(3-(1-naphthyloxy)propyl)-1-(pyridin-2-ylmethyl)-1H-indole-2-carboxylic acid;
7-(2-methyl-4-(trifluoromethyl)phenyl)-3-(3-(2,3,5-trimethylphenoxy)propyl)-1H-indole-2-carboxylic acid;
7-(4-fluoro-2-methylphenyl)-3-(3-(2,3,5-trimethylphenoxy)propyl)-1H-indole-2-carboxylic acid;
7-(4-methoxy-2-methylphenyl)-3-(3-(2,3,5-trimethylphenoxy)propyl)-1H-indole-2-carboxylic acid;
7-(2-methylphenyl)-3-(3-(1-naphthyloxy)propyl)-1-(pyridin-3-ylmethyl)-1H-indole-2-carboxylic acid;
6-methyl-7-(2-methylphenyl)-3-(3-(1-naphthyloxy)propyl)-1H-indole-2-carboxylic acid;
3-(3-(2,3-dichlorophenoxy)propyl)-7-(2-methylphenyl)-1-(pyridin-2-ylmethyl)-1H-indole-2-carboxylic acid;
7-(2-methylphenyl)-1-(2-morpholin-4-yl-2-oxoethyl)-3-(3-(1-naphthyloxy)propyl)-1H-indole-2-carboxylic acid;
3-(3-(3,5-dichlorophenoxyl)propyl)-7-(2-methylphenyl)-1H-indole-2-carboxylic acid;
1-methyl-7-(2-methylphenyl)-3-(3-(1-naphthyloxy)propyl)-1H-indole-2-carboxylic acid;
1-methyl-7-(2-morpholin-4-ylphenyl)-3-(3-(1-naphthyloxy)propyl)-1H-indole-2-carboxylic acid;
1-(3-(aminomethyl)benzyl)-7-(2-methylphenyl)-3-(3-(1-naphthyloxy)propyl)-1H-indole-2-carboxylic acid;
1-(3-(aminomethyl)benzyl)-7-(2-morpholin-4-ylphenyl)-3-(3-(1-naphthyloxy)propyl)-1H-indole-2-carboxylic acid;
7-((E)-2-(2-((E)-2-cyclohexylvinyl)phenyl)vinyl)-3-(3-(1-naphthyloxy)propyl)-1H-indole-2-carboxylic acid;
7-(2-(3-carboxyphenyl)ethyl)-3-(3-(1-naphthyloxy)propyl)-1H-indole-2-carboxylic acid;
3-(3-(1-naphthyloxy)propyl)-7-((E)-2-(2-pyridin-3-ylphenyl)vinyl)-1H-indole-2-carboxylic acid;
3-(3-(1-naphthyloxy)propyl)-7-(2-(3-(((phenylsulfonyl)amino)carbonyl)phenyl)ethyl)-1H-indole-2-carboxylic acid;
7-(2-(3-((4-methylpiperidin-1-yl)carbonyl)phenyl)ethyl)-3-(3-(1-naphthyloxy)propyl)-1H-indole-2-carboxylic acid;
3-(3-(1-naphthyloxy)propyl)-7-(2-(3-(((2-pyrrolidin-1-ylethyl)amino)carbonyl)phenyl)ethyl)-1H-indole-2-carboxylic acid;
7-(2-(3-(((2-morpholin-4-ylethyl)amino)carbonyl)phenyl)ethyl)-3-(3-(1-naphthyloxy)propyl)-1H-indole-2-carboxylic acid;
7-(2-(3-(((2-(dimethylamino)ethyl)amino)carbonyl)phenyl)ethyl)-3-(3-(1-naphthyloxy)propyl)-1H-indole-2-carboxylic acid;
3-(3-(1-naphthyloxy)propyl)-7-((E)-2-(3-(((phenylsulfonyl)amino)carbonyl)phenyl)vinyl)-1H-indole-2-carboxylic acid;
3-(3-(1-naphthyloxy)propyl)-7-((E)-2-(2-pyridin-4-ylphenyl)vinyl)-1H-indole-2-carboxylic acid;
7-((E)-2-(3-chlorophenyl)vinyl)-3-(3-(1-naphthyloxy)propyl)-1H-indole-2-carboxylic acid;
7-((E)-2-(3-((cyclohexylamino)carbonyl)phenyl)vinyl)-3-(3-(1-naphthyloxy)propyl)-1H-indole-2-carboxylic acid;
3-(3-(1-naphthyloxy)propyl)-7-((E)-2-(3-(((2-phenoxyethyl)amino)carbonyl)phenyl)vinyl)-1H-indole-2-carboxylic acid;
7-((E)-2-(3-(((2-(2-(2-aminoethoxy)ethoxy)ethyl)amino)carbonyl)phenyl)vinyl)-3-(3-(1-naphthyloxy)propyl)-1H-indole-2-carboxylic acid;
7-((E)-2-(3-((4-benzylpiperidin-1-yl)carbonyl)phenyl)vinyl)-3-(3-(1-naphthyloxy)propyl)-1H-indole-2-carboxylic acid;
3-(3-(1-naphthyloxy)propyl)-7-((E)-2-(3-((4-phenylpiperazin-1-yl)carbonyl)phenyl)vinyl)-1H-indole-2-carboxylic acid;
7-((E)-2-(3-((3-methylpiperidin-1-yl)carbonyl)phenyl)vinyl)-3-(3-(1-naphthyloxy)propyl)-1H-indole-2-carboxylic acid;
7-(2-(3-(((2-(2-(2-aminoethoxy)ethoxy)amino)carbonyl)phenyl)ethyl)-3-(3-(1-naphthyloxy)propyl)-1H-indole-2-carboxylic acid;
3-(3-(1-naphthyloxy)propyl)-7-((E)-2-(3-((E)-2-phenylvinyl)phenyl)vinyl)-1H-indole-2-carboxylic acid;
7-((E)-2-(1,1'-biphenyl-3-yl)vinyl)-3-(3-(1-naphthyloxy)propyl)-1H-indole-2-carboxylic acid;
3-(3-(1-naphthyloxy)propyl)-7-((E)-2-(3-((1E)-3-phenylprop-1-enyl)phenyl)vinyl)-1H-indole-2-carboxylic acid;
3-(3-(1-naphthyloxy)propyl)-7-((E)-2-(4-((E)-2-phenylvinyl)phenyl)vinyl)-1H-indole-2-carboxylic acid;
3-(3-(1-naphthyloxy)propyl)-7-((E)-2-(4-((1E)-3-phenylprop-1-enyl)phenyl)vinyl)-1H-indole-2-carboxylic acid;
7-((E)-2-(1,1'-biphenyl-4-yl)vinyl)-3-(3-(1-naphthyloxy)propyl)-1H-indole-2-carboxylic acid;
7-(2-(1,1'-biphenyl-3-yl)ethyl)-3-(3-(1-naphthyloxy)propyl)-1H-indole-2-carboxylic acid;
3-(3-(1-naphthyloxy)propyl)-7-(2-(3-(3-phenylpropyl)phenyl)ethyl)-1H-indole-2-carboxylic acid;
7-((E)-2-(2-chlorophenyl)vinyl)-3-(3-(1-naphthyloxy)propyl)-1H-indole-2-carboxylic acid;
7-((E)-2-(1,1'-biphenyl-2-yl)vinyl)-3-(3-(1-naphthyloxy)propyl)-1H-indole-2-carboxylic acid;
3-(3-(1-naphthyloxy)propyl)-7-((E)-2-(2-((E)-2-phenylvinyl)phenyl)vinyl)-1H-indole-2-carboxylic acid;
3-(3-(1-naphthyloxy)propyl)-7-(2-phenylethyl)-1H-indole-2-carboxylic acid;
7-(2-(2-chlorophenyl)ethyl)-3-(3-(1-naphthyloxy)propyl)-1H-indole-2-carboxylic acid;
7-(2-(1,1'-biphenyl-4-yl)ethyl)-3-(3-(1-naphthyloxy)propyl)-1H-indole-2-carboxylic acid;
3-(3-(1-naphthyloxy)propyl)-7-(2-(4-(2-phenylethyl)phenyl)ethyl)-1H-indole-2-carboxylic acid;
3-(3-(1-naphthyloxy)propyl)-7-(2-(4-(3-phenylpropyl)phenyl)ethyl)-1H-indole-2-carboxylic acid;
7-(4-carboxy-2-methylphenyl)-3-(3-((2-cyanoquinoline-8-yl)oxy)propyl)-1H-indole-2-carboxylic acid;
3-(3-((2-acetyl-1-benzofuran-7-yl)oxy)propyl)-7-(4-carboxy-2-methylphenyl)-1H-indole-2-carboxylic acid;
7-(4-carboxy-2-methylphenyl)-3-(3-((2,2-dimethyl-2,3-dihydro-1-benzofuran-7-yl)oxy)propyl)-1H-indole-2-carboxylic acid;
7-(4-carboxy-2-methylphenyl)-3-(3-(2,3-difluorophenoxyl)propyl)-1H-indole-2-carboxylic acid;
7-(4-carboxy-2-methylphenyl)-3-(3-(3-methyl-2-nitrophenoxy)propyl)-1H-indole-2-carboxylic acid;
7-(4-carboxy-2-methylphenyl)-3-(3-(2-methyl-3-nitrophenoxy)propyl)-1H-indole-2-carboxylic acid;
7-(4-carboxy-2-methylphenyl)-3-(3-(2-chloro-3-(trifluoromethyl)phenoxy)propyl)-1H-indole-2-carboxylic acid;
7-(4-carboxy-2-methylphenyl)-3-(3-(2-fluoro-3-(trifluoromethyl)phenoxy)propyl)-1H-indole-2-carboxylic acid;
7-(2-chlorophenyl)-3-(3-(ethyl(1-naphthyl)amino)propyl)-1H-indole-2-carboxylic acid;
7-(4-(morpholin-4-ylcarbonyl)-2-(trifluoromethyl)phenyl)-3-(4-(5-oxo-2,3,4,5-tetrahydro-1H-1-benzazepin-1-yl)butyl)-1H-indole-2-carboxylic acid;

7-(4-(morpholin-4-ylcarbonyl)-2-(trifluoromethyl)phenyl)-3-(4-(2,3,4,5-tetrahydro-1H-1-benzazepin-1-yl)butyl)-1H-indole-2-carboxylic acid;

3-(4-(2,3-dihydro-4H-1,4-benzothiazin-4-yl)butyl)-7-(4-(morpholin-4-ylcarbonyl)-2-(trifluoromethyl)phenyl)-1H-indole-2-carboxylic acid;

3-(4-(3,4-dihydroquinolin-1(2H)-yl)butyl)-7-(2-methylphenyl)-1H-indole-2-carboxylic acid;

3-(4-(2-methyl-3,4-dihydroquinolin-1(2H)-yl)butyl)-7-(2-methylphenyl)-1H-indole-2-carboxylic acid;

3-(4-(6-methyl-3,4-dihydroquinolin-1(2H)-yl)butyl)-7-(2-methylphenyl)-1H-indole-2-carboxylic acid;

3-(4-(8-methyl-3,4-dihydroquinolin-1(2H)-yl)butyl)-7-(2-methylphenyl)-1H-indole-2-carboxylic acid;

3-(4-(2-methyl-2,3-dihydro-1H-indol-1-yl)butyl)-7-(2-methylphenyl)-1H-indole-2-carboxylic acid;

7-(2-methylphenyl)-3-(4-(2,3,4,5-tetrahydro-1H-1-benzazepin-1-yl)butyl)-1H-indole-2-carboxylic acid;

3-(4-(3-methyl-3,4-dihydroquinolin-1(2H)-yl)butyl)-7-(2-methylphenyl)-1H-indole-2-carboxylic acid;

3-(4-(3-(hydroxymethyl)-3,4-dihydroquinolin-1(2H)-yl)butyl)-7-(2-methylphenyl)-1H-indole-2-carboxylic acid;

3-(4-(2,3-dihydro-4H-1,4-benzothiazin-4-yl)butyl)-7-(2-methylphenyl)-1H-indole-2-carboxylic acid;

4-methoxy-7-(2-methylphenyl)-3-(3-(1-naphthyloxy)propyl)-1H-indole-2-carboxylic acid;

3-(3-(((1R,4S)-8-hydroxy-1,2,3,4-tetrahydro-1,4-methanonaphthalen-5-yl)oxy)propyl)-7-(2-methylphenyl)-1H-indole-2-carboxylic acid;

7-(2-methylphenyl)-3-(3-((1R,4S)-1,2,3,4-tetrahydro-1,4-methanonaphthalen-5-yloxy)propyl)-1H-indole-2-carboxylic acid;

3-(3-((4-methoxy-1-naphthyl)oxy)propyl)-7-(2-methylphenyl)-1H-indole-2-carboxylic acid;

7-(2-methylphenyl)-3-(3-((2-nitro-1-naphthyl)oxy)propyl)-1H-indole-2-carboxylic acid;

3-(3-((3-hydroxy-1-naphthyl)oxy)propyl)-7-(2-methylphenyl)-1H-indole-2-carboxylic acid;

7-(3,5-dimethylisoxazol-4-yl)-3-(3-(2,3,6,7-tetrahydro-1H,5H-pyrido(3,2,1-ij)quinolin-8-yloxy)propyl)-1H-indole-2-carboxylic acid;

7-(2-methylphenyl)-3-(3-(2,3,6,7-tetrahydro-1H,5H-pyrido(3,2,1-ij)quinolin-8-yloxy)propyl)-1H-indole-2-carboxylic acid;

7-(2-methylphenyl)-3-(3-((2-nitroso-1-naphthyl)oxy)propyl)-1H-indole-2-carboxylic acid;

3-(3-((5-hydroxy-1-naphthyl)oxy)propyl)-7-(2-methylphenyl)-1H-indole-2-carboxylic acid;

7-(2-methylphenyl)-3-(3-(2,3,4-trifluorophenoxyl)propyl)-1H-indole-2-carboxylic acid;

3-(3-(3-chloro-2-methylphenoxy)propyl)-7-(2-methylphenyl)-1H-indole-2-carboxylic acid;

3-(3-((8-hydroxy-1-naphthyl)oxy)propyl)-7-(2-methylphenyl)-1H-indole-2-carboxylic acid;

3-(3-(3-chloro-2-cyanophenoxy)propyl)-7-(2-methylphenyl)-1H-indole-2-carboxylic acid;

3-(3-(2-bromo-3-methylphenoxy)propyl)-7-(2-methylphenyl)-1H-indole-2-carboxylic acid;

7-(2-methylphenyl)-3-(3-(3-methyl-2-vinylphenoxy)propyl)-1H-indole-2-carboxylic acid;

3-(3-(3-methyl-2-nitrophenoxy)propyl)-7-(2-methylphenyl)-1H-indole-2-carboxylic acid;

3-(3-(2-amino-3-methylphenoxy)propyl)-7-(2-methylphenyl)-1H-indole-2-carboxylic acid;

7-(4-(morpholin-4-ylcarbonyl)-2-(trifluoromethyl)phenyl)-3-(3-(1-naphthyloxy)propyl)-1H-indole-2-carboxylic acid;

3-(3-((6-amino-1-naphthyl)oxy)propyl)-7-(2-methylphenyl)-1H-indole-2-carboxylic acid;

7-(2-methylphenyl)-3-(3-(1,2,3,4-tetrahydronaphthalen-1-yloxy)prop-1-ynyl)-1H-indole-2-carboxylic acid;

3-(3-((6-(acryloylamino)-1-naphthyl)oxy)propyl)-7-(2-methylphenyl)-1H-indole-2-carboxylic acid;

7-(2-methylphenyl)-3-(3-((6-(propionylamino)-1-naphthyl)oxy)propyl)-1H-indole-2-carboxylic acid;

7-(2-methylphenyl)-3-(3-(1,2,3,4-tetrahydronaphthalen-1-yloxy)propyl)-1H-indole-2-carboxylic acid;

3-(3-((6-methoxy-1-naphthyl)oxy)propyl)-7-(2-methylphenyl)-1H-indole-2-carboxylic acid;

1-(4-methoxybenzyl)-7-(2-methylphenyl)-3-(3-(1-naphthyloxy)prop-1-ynyl)-1H-indole-2-carboxylic acid;

3-(3-((2,3,4,5,6,7,8-heptafluoro-1-naphthyl)oxy)propyl)-7-(2-methylphenyl)-1H-indole-2-carboxylic acid;

3-(3-(1-benzothien-7-yloxy)propyl)-7-(2-methylphenyl)-1H-indole-2-carboxylic acid;

3-(3-((4-fluoro-1-naphthyl)oxy)propyl)-7-(2-methylphenyl)-1H-indole-2-carboxylic acid;

3-(3-((8-fluoro-1-naphthyl)oxy)propyl)-7-(2-methylphenyl)-1H-indole-2-carboxylic acid;

3-(3-((5-fluoro-1-naphthyl)oxy)propyl)-7-(2-methylphenyl)-1H-indole-2-carboxylic acid;

7-fluoro-3-(2-isopropylphenyl)-1-(3-(1-naphthyloxy)propyl)-1H-indole-2-carboxylic acid;

7-fluoro-3-(2-methylphenyl)-1-(3-(1-naphthyloxy)propyl)-1H-indole-2-carboxylic acid;

3-(3-((5-fluoro-1-naphthyl)oxy)propyl)-7-(1,3,5-trimethyl-1H-pyrazol-4-yl)-1H-indole-2-carboxylic acid;

3-(3-(1-naphthyloxy)propyl)-1-(pyridin-4-ylmethyl)-7-(1,3,5-trimethyl-1H-pyrazol-4-yl)-1H-indole-2-carboxylic acid;

3-(3-(1-naphthyloxy)propyl)-1-(pyridin-2-ylmethyl)-7-(1,3,5-trimethyl-1H-pyrazol-4-yl)-1H-indole-2-carboxylic acid;

3-(3-(1-naphthyloxy)propyl)-1-(pyridin-3-ylmethyl)-7-(1,3,5-trimethyl-1H-pyrazol-4-yl)-1H-indole-2-carboxylic acid;

7-(2-methylphenyl)-3-(3-(1-naphthyloxy)propyl)-2-(1H-tetraazol-5-yl)-1H-indole;

1-(4-methoxybenzyl)-7-(2-methylphenyl)-3-(3-(1-naphthyloxy)propyl)-2-(1H-tetraazol-5-yl)-1H-indole;

7-(1-methyl-1H-imidazol-5-yl)-3-(3-(1-naphthyloxy)propyl)-1H-indole-2-carboxylic acid;

1-(2-(dimethylamino)-2-oxoethyl)-3-(3-(1-naphthyloxy)propyl)-7-(1,3,5-trimethyl-1H-pyrazol-4-yl)-1H-indole-2-carboxylic acid;

1-(2-(4-methylpiperazin-1-yl)-2-oxoethyl)-3-(3-(1-naphthyloxy)propyl)-7-(1,3,5-trimethyl-1H-pyrazol-4-yl)-1H-indole-2-carboxylic acid;

7-(4,6-dimethylpyrimidin-5-yl)-1-(2-morpholin-4-yl-2-oxoethyl)-3-(3-(1-naphthyloxy)propyl)-1H-indole-2-carboxylic acid;

1-(2-(4-methylpiperazin-1-yl)ethyl)-3-(3-(1-naphthyloxy)propyl)-7-(1,3,5-trimethyl-1H-pyrazol-4-yl)-1H-indole-2-carboxylic acid;

1-(2-morpholin-4-ylethyl)-3-(3-(1-naphthyloxy)propyl)-7-(1,3,5-trimethyl-1H-pyrazol-4-yl)-1H-indole-2-carboxylic acid;

1-(2-morpholin-4-yl-2-oxoethyl)-3-(3-(1-naphthyloxy)propyl)-7-(1,3,5-trimethyl-1H-pyrazol-4-yl)-1H-indole-2-carboxylic acid;

1-(2-(dimethylamino)ethyl)-3-(3-(1-naphthyloxy)propyl)-7-(1,3,5-trimethyl-1H-pyrazol-4-yl)-1H-indole-2-carboxylic acid;

7-(2-methylimidazo(1,2-a)pyridin-3-yl)-3-(3-(1-naphthyloxy)propyl)-1H-indole-2-carboxylic acid;
7-(2-(1H-imidazol-1-yl)-4-methylpyridin-3-yl)-3-(3-(1-naphthyloxy)propyl)-1-(pyridin-2-ylmethyl)-1H-indole-2-carboxylic acid;
7-(2-ethyl-4-methylpyridin-3-yl)-3-(3-(1-naphthyloxy)propyl)-1-(pyridin-2-ylmethyl)-1H-indole-2-carboxylic acid;
7-(2-ethyl-4-methylpyridin-3-yl)-3-(3-(1-naphthyloxy)propyl)-1-((1-(pyridin-4-ylmethyl)pyridinium-4-yl)methyl)-1H-indole-2-carboxylate;
7-(2-ethyl-4-methylpyridin-3-yl)-3-(3-(1-naphthyloxy)propyl)-1-(pyridin-4-ylmethyl)-1H-indole-2-carboxylic acid;
7-(2-ethyl-4-methylpyridin-3-yl)-1-(2-morpholin-4-yl-2-oxoethyl)-3-(3-(1-naphthyloxy)propyl)-1H-indole-2-carboxylic acid;
1-(2-(dimethylamino)-2-oxoethyl)-7-(2-ethyl-4-methylpyridin-3-yl)-3-(3-(1-naphthyloxy)propyl)-1H-indole-2-carboxylic acid;
7-(2-ethyl-4-methylpyridin-3-yl)-1-(2-(4-methylpiperazin-1-yl)-2-oxoethyl)-3-(3-(1-naphthyloxy)propyl)-1H-indole-2-carboxylic acid;
7-(2-ethyl-4-methylpyridin-3-yl)-1-(2-morpholin-4-ylethyl)-3-(3-(1-naphthyloxy)propyl)-1H-indole-2-carboxylic acid;
1-(2-(dimethylamino)ethyl)-7-(2-ethyl-4-methylpyridin-3-yl)-3-(3-(1-naphthyloxy)propyl)-1H-indole-2-carboxylic acid;
7-(2-ethyl-4-methylpyridin-3-yl)-1-(2-(4-methylpiperazin-1-yl)ethyl)-3-(3-(1-naphthyloxy)propyl)-1H-indole-2-carboxylic acid;
7-(2-((4-(4-carboxyphenyl)piperazin-1-yl)methyl)phenyl)-3-(3-(1-naphthyloxy)propyl)-1H-indole-2-carboxylic acid;
3-(3-(1-naphthyloxy)propyl)-7-(2-piperazin-1-ylpyridin-3-yl)-1H-indole-2-carboxylic acid;
1-(2-(dimethylamino)-2-oxoethyl)-7-(2-(1H-imidazol-1-yl)-4-methylpyridin-3-yl)-3-(3-(1-naphthyloxyl)propyl)-1H-indole-2-carboxylic acid;
7-(2-(1H-imidazol-1-yl)-4-methylpyridin-3-yl)-3-(3-(1-naphthyloxyl)propyl)-1-(pyridin-3-ylmethyl)-1H-indole-2-carboxylic acid;
7-(2-(1H-imidazol-1-yl)-4-methylpyridin-3-yl)-1-(2-morpholin-4-yl-2-oxoethyl)-3-(3-(1-naphthyloxyl)propyl)-1H-indole-2-carboxylic acid;
7-(2-(1H-imidazol-1-yl)-4-methylpyridin-3-yl)-3-(3-(1-naphthyloxyl)propyl)-1-(2-oxo-2-piperazin-1-ylethyl)-1H-indole-2-carboxylic acid;

and therapeutically acceptable salts, prodrugs, esters, amides, salts of prodrugs, salts of esters, and salts of amides thereof.

Still another embodiment pertains to methods for treating mammals having a disease characterized by overexpression or unregulation of Mcl-1 protein comprising administering thereto a therapeutically effective amount of a compound having Formula I,

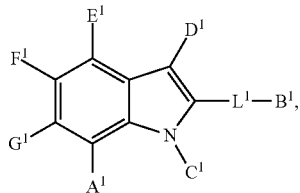

(I)

and therapeutically acceptable salts thereof, wherein
$A^1$ is $A^2$, $OA^2$, $SA^2$, $S(O)A^2$, $SO_2A^2$, $NH_2$, $NHA^2$, $N(A^2)_2$, $C(O)A^2$, $C(O)NH_2$, $C(O)NHA^2$, $C(O)N(A^2)_2$, $NHC(O)A^2$, $NA^2C(O)A^2$, $NHSO_2A^2$, $NA^2SO_2A^2$, $NHC(O)OA^2$, $NA^2C(O)OA^2$, $SO_2NH_2$, $SO_2NHA^2$, $SO_2N(A^2)_2$, $NHC(O)NH_2$, $NHC(O)A^2NHC(O)N(A^2)_2$, $NA^2C(O)N(A^2)_2$;

$A^2$ is $R^1$, $R^2$, $R^3$, $R^4$, $R^1$ is phenyl which is unfused or fused with benzene, heteroarene or $R^{1A}$; $R^{1A}$ is cycloalkane, cycloalkene, heterocycloalkane or heterocycloalkene;

$R^2$ is heteroaryl which is unfused or fused with benzene, heteroarene or $R^{2A}$; $R^{2A}$ is cycloalkane, cycloalkene, heterocycloalkane or heterocycloalkene;

$R^3$ is cycloalkyl, cycloalkenyl, heterocycloalkyl or heterocycloalkenyl, each of which is unfused or fused with benzene, heteroarene or $R^{3A}$; $R^{3A}$ is cycloalkane, cycloalkene, heterocycloalkane or heterocycloalkene;

$R^4$ is alkyl, alkenyl, or alkynyl, each of which is unsubstituted or substituted with one, two, three, four or five of independently selected $R^5$, $OR^5$, $SR^5$, $S(O)R^5$, $SO_2R^5$, $NH_2$, $NHR^5$, $N(R^5)_2$, $C(O)R^5$, $C(O)NH_2$, $C(O)NHR^5$, $C(O)N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $SO_2NH_2$, $SO_2NHR^5$, $SO_2N(R^5)_2$, $NHC(O)NH_2$, $NHC(O)R^5$, $NHC(O)N(R^5)_2$, $NR^5C(O)N(R^5)_2$, $OH$, $(O)$, $C(O)OH$, $CN$, $CF_3$, $OCF_3$, $CF_2CF_3$, $F$, $Cl$, $Br$ or $I$;

$R^5$ is $R^6$, $R^7$ or $R^8$;

$R^6$ is phenyl which is unfused or fused with benzene, heteroarene or $R^{6A}$; $R^{6A}$ is cycloalkane, cycloalkene, heterocycloalkane or heterocycloalkene;

$R^7$ is heteroaryl which is unfused or fused with benzene, heteroarene or $R^{7A}$; $R^{7A}$ is cycloalkane, cycloalkene, heterocycloalkane or heterocycloalkene;

$R^8$ is cycloalkyl, cycloalkenyl, heterocycloalkyl or heterocycloalkenyl, each of which is unfused or fused with benzene, heteroarene or $R^{8A}$; $R^{8A}$ is cycloalkane, cycloalkene, heterocycloalkane or heterocycloalkene;

$L^1$ is a bond or is alkylene, alkenylene, alkynylene or $L^2$; and $B^1$ is $C(O)OH$ or a bioisostere thereof or is $C(O)OR^1$, $C(O)OR^2$, $C(O)OR^3$ or $C(O)OR^4$;

$L^2$ is $C_2$-$C_6$-alkylene, $C_4$-$C_6$-alkenylene or $C_4$-$C_6$-alkynylene, each of which has one $CH_2$ moiety replaced with O, S, S(O), $SO_2$, NH or $N(W^1)$;

$W^1$ is alkyl, alkenyl or alkynyl:

$C^1$ and $D^1$ are independently H, $R^9$, $R^{10}$, $R^{11}$ or $R^{12}$; or one of $C^1$ and $D^1$ is H, and the other is $R^9$, $R^{10}$, $R^{11}$ or $R^{12}$;

$R^9$ is phenyl which is unfused or fused with benzene, heteroarene or $R^{9A}$; $R^{9A}$ is cycloalkane, cycloalkene, heterocycloalkane or heterocycloalkene;

$R^{10}$ is heteroaryl which is unfused or fused with benzene, heteroarene or $R^{10A}$; $R^{10A}$ is cycloalkane, cycloalkene, heterocycloalkane or heterocycloalkene;

$R^{11}$ is cycloalkyl, cycloalkenyl, heterocycloalkyl or heterocycloalkenyl, each of which is unfused or fused with benzene, heteroarene or $R^{11A}$; $R^{11A}$ is cycloalkane, cycloalkene, heterocycloalkane or heterocycloalkene;

$R^{12}$ is alkyl, alkenyl, or alkynyl, each of which is unsubstituted or substituted with one, two, three, four or five of independently selected $R^{13}$, $OR^{13}$, $SR^{13}$, $S(O)R^{11}$, $SO_2R^{13}$, $NH_2$, $NHR^{13}$, $N(R^{13})_2$, $C(O)R^{13}$, $C(O)NH_2$, $C(O)NHR^{13}$, $C(O)N(R^{13})_2$, $NHC(O)R^{30}$, $NR^{13}C(O)R^{13}$, $NHC(O)R^{13}$, $NR^{13}C(O)R^{13}$, $NHSO_2R^{13}$, $NR^{13}SO_2R^{13}$, $NHC(O)OR^{13}$, $NR^{13}C(O)OR^{13}$, $SO_2NH_2$, $SO_2NHR^{13}$, $SO_2N(R^{13})_2$, $NHC(O)NH_2$, $NHC(O)R^{30}$, $NHC(O)N(R^{13})_2$, $NR^{13}C(O)N(R^{13})_2$, $OH$, $(O)$, $C(O)OH$, $CN$, $CF_3$, $OCF_3$, $CF_2CF_3$, $F$, $Cl$, $Br$ or $I$;

$R^{13}$ is $R^{14}$, $R^{15}$ or $R^{16}$;

$R^{14}$ is phenyl which is unfused or fused with benzene, heteroarene or $R^{14A}$; $R^{14A}$ is cycloalkane, cycloalkene, heterocycloalkane or heterocycloalkene;

$R^{15}$ is heteroaryl which is unfused or fused with benzene, heteroarene or $R^{15A}$; $R^{15A}$ is cycloalkane, cycloalkene, heterocycloalkane or heterocycloalkene;

$R^{16}$ is cycloalkyl, cycloalkenyl, heterocycloalkyl or heterocycloalkenyl, each of which is unfused or fused with benzene, heteroarene or $R^{16A}$; $R^{16A}$ cycloalkane, cycloalkene, heterocycloalkane or heterocycloalkene; and one or two or each of $E^1$ and $F^1$ and $G^1$ are independently H, F, Cl, Br or I, and the remainder are independently $R^{17}$, $R^{18}$, $R^{19}$ or $R^{20}$;

$R^{17}$ is phenyl which is unfused or fused with benzene, heteroarene or $R^{17A}$; $R^{17A}$ is cycloalkane, cycloalkene, heterocycloalkane or heterocycloalkene;

$R^{18}$ is heteroaryl which is unfused or fused with benzene, heteroarene or $R^{18A}$; $R^{18A}$ is cycloalkane, cycloalkene, heterocycloalkane or heterocycloalkene;

$R^{19}$ is cycloalkyl, cycloalkenyl, heterocycloalkyl or heterocycloalkenyl, each of which is unfused or fused with benzene, heteroarene or $R^{19A}$; $R^{19A}$ is cycloalkane, cycloalkene, heterocycloalkane or heterocycloalkene;

$R^{20}$ is alkyl, alkenyl, or alkynyl, each of which is unsubstituted or substituted with one, two, three, four or five of independently selected $R^{21}$, $OR^{20}$, $SR^{20}$, $S(O)R^{20}$, $SO_2R^{20}$, $NH_2$, $NHR^{20}$, $N(R^{20})_2$, $C(O)R^{20}$, $C(O)NH_2$, $C(O)NHR^{20}$, $C(O)N(R^{20})_2$, $NHC(O)R^{20}$, $NHC(O)R^{20}$, $NR^{20}C(O)R^{20}$, $NR^{20}C(O)R^{20}$, $NHSO_2R^{20}$, $NR^{20}SO_2R^{20}$, $NHC(O)OR^{20}$, $NR^{20}C(O)OR^{20}$, $SO_2NH_2$, $SO_2NHR^{20}$, $SO_2N(R^2)_2$, $NHC(O)NH_2$, $NHC(O)R^{20}$, $NHC(O)N(R^{20})_2$, $NR^{20}C(O)N(R^{20})_2$, OH, (O), C(O)OH, CN, $CF_3$, $OCF_3$, $CF_2CF_3$, F, Cl, Br or I;

$R^{20}$ is $R^{21}$, $R^{22}$ or $R^{23}$;

$R^{21}$ is phenyl which is unfused or fused with benzene, heteroarene or $R^{21A}$; $R^{21A}$ is cycloalkane, cycloalkene, heterocycloalkane or heterocycloalkene;

$R^{22}$ is heteroaryl which is unfused or fused with benzene, heteroarene or $R^{22A}$; $R^{22A}$ is cycloalkane, cycloalkene, heterocycloalkane or heterocycloalkene;

$R^{23}$ is cycloalkyl, cycloalkenyl, heterocycloalkyl or heterocycloalkenyl, each of which is unfused or fused with benzene, heteroarene or $R^{23A}$; $R^{23A}$ is cycloalkane, cycloalkene, heterocycloalkane or heterocycloalkene;

wherein each foregoing cyclic moiety is independently unsubstituted or substituted with one or two or three or four or five of independently selected spiroheteroalkyl, $R^{30}$, $OR^{30}$, $OCH_2R^{30}$, $SR^{30}$, $S(O)R^{30}$, $SO_2R^{30}$, $C(O)R^{30}$, $CO(O)R^{30}$, $OC(O)R^{30}$, $OC(O)OR^{30}$, $NO_2$, $NH_2$, $NHR^{30}$, $N(R^{30})_2$, $CH_2R^{30}$, $C(O)NH_2$, $C(O)NHR^{30}$, $C(O)N(R^{30})_2$, $NHC(O)R^{30}$, $NR^{30}C(O)R^{30}$, $C(O)NHOH$, $C(O)NHOR^{30}$, $C(O)NHSO_2R^{30}$, $C(O)NR^{30}SO_2R^{30}$, $SO_2NH_2$, $SO_2NHR^{30}$, $SO_2N(R^{30})_2$, $CF_3$, $CF_2CF_3$, $C(O)H$, $C(O)OH$, $C(N)NH_2$, $C(N)NHR^{30}$, $C(N)N(R^{30})_2$, =NO-(alkylene)-$C(O)CF_3$, CNOH, $CNOCH_3$, OH, (O), $N_3$, $CF_3$, $CF_2CF_3$, $OCF_3$, $OCF_2CF_3$, F, Cl, Br or I;

$R^{30}$ is $R^{31}$, $R^{32}$, $R^{33}$ or $R^{34}$;

$R^{31}$ is phenyl which is unfused or fused with benzene, heteroarene or $R^{31A}$; $R^{31A}$ is cycloalkane, cycloalkene, heterocycloalkane or heterocycloalkene;

$R^{32}$ is heteroaryl which is unfused or fused with benzene, heteroarene or $R^{32A}$; $R^{32A}$ is cycloalkane, cycloalkene, heterocycloalkane or heterocycloalkene;

$R^{33}$ is cycloalkyl, cycloalkenyl, heterocycloalkyl or heterocycloalkenyl, each of which is unfused or fused with benzene, heteroarene or $R^{33A}$; $R^{33A}$ is cycloalkane, cycloalkene, heterocycloalkane or heterocycloalkene;

$R^{34}$ is alkyl, alkenyl, or alkynyl, each of which is unsubstituted or substituted with one, two, three, four or five of independently selected $R^{35}$, $OR^{35}$, $SR^{35}$, $S(O)R^{35}$, $SO_2R^{35}$, $NH_2$, $NHR^{35}$, $N(R^{35})_2$, $C(O)R^{35}$, $C(O)NH_2$, $C(O)NHR^{35}$, $C(O)N(R^{35})_2$, $NHC(O)R^{35}$, $NR^{35}C(O)R^{35}$, $NHSO_2R^{35}$, $NR^{35}SO_2R^{35}$, $NHC(O)OR^{35}$, $NR^{35}C(O)OR^{35}$, $SO_2NH_2$, $SO_2NHR^{35}$, $SO_2N(R^{35})_2$, $NHC(O)NH_2$, $NHC(O)R^{35}$ $NHC(O)N(R^{35})_2$, $NR^{35}C(O)N(R^{35})_2$, OH, (O), C(O)OH, CN, $CF_3$, $OCF_3$, $CF_2CF_3$, F, Cl, Br or I;

$R^{35}$ is $R^{36}$, $R^{37}$, $R^{38}$ or $R^{39}$;

$R^{36}$ is phenyl which is unfused or fused with benzene, heteroarene or $R^{36A}$; $R^{36A}$ is cycloalkane, cycloalkene, heterocycloalkane or heterocycloalkene;

$R^{37}$ is heteroaryl which is unfused or fused with benzene, heteroarene or $R^{37A}$; $R^{37A}$ is cycloalkane, cycloalkene, heterocycloalkane or heterocycloalkene;

$R^{38}$ is cycloalkyl, cycloalkenyl, heterocycloalkyl or heterocycloalkenyl, each of which is unfused or fused with benzene, heteroarene or $R^{38A}$; $R^{38A}$ is cycloalkane, cycloalkene, heterocycloalkane or heterocycloalkene;

$R^{39}$ is alkyl, alkenyl or alkenyl, each of which is unsubstituted or substituted with $R^{40}$;

$R^{40}$ is phenyl, heteroaryl, cycloalkyl, cycloalkenyl or heterocycloalkyl;

wherein the moieties represented by $R^{31}$, $R^{32}$, $R^{33}R^{36}$, $R^{37}$, $R^{38}$ and $R^{40}$ are independently unsubstituted or substituted with one or two or three of independently selected $R^{50}$, F, Cl, Br, I, C(O)OH, $NO_2$, $NH_2$, $CF_3$, (O) or OH;

$R^{50}$ is $R^{51}$, $R^{52}$, $R^{53}$ or $R^{54}$;

$R^{51}$ is phenyl which is unfused or fused with benzene, heteroarene or $R^{51A}$; $R^{51A}$ is cycloalkane, cycloalkene, heterocycloalkane or heterocycloalkene;

$R^{52}$ is heteroaryl which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene; and $R^{54}$ is alkyl, alkenyl, or alkynyl, with or without administering one or more than one additional therapeutic agents and with or without also administering radiotherapy thereto.

Still another embodiment comprises methods of treating mammals having a disease characterized by overexpression or unregulation of Mcl-1 protein comprising administering thereto therapeutically effective amounts of a compound having Formula I and one or more than one additional therapeutic agents, with or without also administering radiotherapy thereto.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all combinations herein, that monovalent moieties having more than one atom are attached through their left ends, and that divalent moieties are drawn from left to right.

It is also meant to be understood that a specific embodiment of a variable moiety may be the same or different as another specific embodiment having the same identifier.

The term "alkenyl," as used herein, means monovalent, straight or branched chain hydrocarbon moieties having one or more than one carbon-carbon double bonds, such as $C_2$-alkenyl, $C_3$-alkenyl, $C_4$-alkenyl, $C_5$-alkenyl, $C_6$-alkenyl and the like.

The term "alkenylene," as used herein, means divalent, straight or branched chain hydrocarbon moieties having one or more than one carbon-carbon double bonds, such as $C_2$-alkenylene, $C_3$-alkenylene, $C_4$-alkenylene, $C_5$-alkenylene, $C_6$-alkenylene and the like.

The term "alkyl," as used herein, means monovalent, saturated, straight or branched chain hydrocarbon moieties, such as $C_1$-alkyl, $C_2$-alkyl, $C_3$-alkyl, $C_4$-alkyl, $C_5$-alkyl, $C_6$-alkyl and the like.

The term "alkylene," as used herein, means divalent, saturated, straight or branched chain hydrocarbon moieties, such as $C_1$-alkylene, $C_2$-alkylene, $C_3$-alkylene, $C_4$-alkylene, $C_5$-alkylene, $C_6$-alkylene and the like.

The term "alkynyl," as used herein, means monovalent, straight or branched chain hydrocarbon moieties having one or more than one carbon-carbon triple bonds, such as $C_2$-alkynyl, $C_3$-alkynyl, $C_4$-alkynyl, $C_5$-alkynyl, $C_6$-alkynyl and the like.

The term "alkynylene," as used herein, means divalent, straight or branched chain hydrocarbon moieties having one or more than one carbon-carbon triple bonds, such as $C_2$-alkynylene, $C_3$-alkynylene, $C_4$-alkynylene, $C_5$-alkynylene, $C_6$-alkynylene and the like.

The term "C(O)OH bioisostere, as used herein, means a moiety with a substantially similar physical or chemical property that imparts similar biological properties to the compound having Formula (I). Examples of C(O)OH bioisosteres include monovalent radicals derived from removal of one hydrogen atom from a molecule such as isothiazol-3(2H)-one 1,1-dioxide, isothiazolidin-3-one 1,1-dioxide, 1,2,4-oxadiazol-5(2H)-one, 1,2,5-thiadiazolidin-3-one 1,1-dioxide, 1,2,5-thiadiazol-3-ol, 1,2,4-oxadiazolidine-3,5-dione, 2H-tetraazole and the like.

The term "cycloalkane," as used herein, means saturated cyclic or bicyclic hydrocarbon moieties, such as $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane and the like.

The term "cycloalkyl," as used herein, means monovalent, saturated cyclic and bicyclic hydrocarbon moieties, such as $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl and the like.

The term "cycloalkene," as used herein, means cyclic and bicyclic hydrocarbon moieties having one or more than one carbon-carbon double bonds, such as $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene and the like.

The term "cycloalkenyl," as used herein, means monovalent, cyclic hydrocarbon moieties having one or more than one carbon-carbon double bonds, such as $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl and the like.

The term "heteroarene," as used herein, means furan, imidazole, isothiazole, isoxazole, 1,2,3-oxadiazole, 1,2,5-oxadiazole, 1,3,4-oxadiazole, oxazole, pyrazine, pyrazole, pyridazine, pyridine, pyrimidine, pyrrole, thiazole, 1,3,4-thiadiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, 1,3,4-oxadiazolyl, oxazolyl, pyrazinyl, pyrazolyl, pyridazinyl, pyridinyl, pyrimidinyl, pyrrolyl, tetrazolyl, thiazolyl, 1,2,3-thiadiazoyl, 1,2,5-thiadiazolyl, 1,3,4-thiadiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "spiroalkyl," as used herein, means saturated, divalent hydrocarbon moieties having both ends attached to the same carbon atom, such as $C_2$-spiroalkyl, $C_3$-spiroalkyl, four $C_4$-spiroalkyl, $C_5$-spiroalkyl and the like.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl, phenyl and spiroalkyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention containing NH, C(O)H, C(O)OH, C(O)NH$_2$, OH or SH moieties may have attached thereto prodrug-forming moieties. The prodrug-forming moieties are removed by metabolic processes and release the compounds having the freed NH, C(O)H, C(O)OH, C(O)NH$_2$, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I, produced by in vitro or in vivo metabolic processes, may also have utility for treating diseases caused or exacerbated by overexpressed or unregulated Mcl-1 protein.

Certain precursor compounds of compounds having Formula I may be metabolized in vitro or in vivo to form compounds having Formula I and may thereby also have utility for treating diseases caused or exacerbated by overexpressed or unregulated Mcl-1 protein.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide, or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.001 to about 200 mg/kg body weight. Single dose compositions contain these amounts or a combination of sub-multiples thereof.

Compounds having Formula I may be administered with or without an excipient. Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Compounds having Formula I may be radiolabeled with a radioactive isotope such as carbon (i.e. $^{13}C$), hydrogen (i.e. $^{3}H$), nitrogen (i.e. $^{15}N$), phosphorus (i.e. $^{32}P$), sulfur (i.e. $^{35}S$), iodide (i.e. $^{125}I$) and the like. Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications and for in vivo and in vitro imaging.

Compounds having Formula I may be incorporated into devices such as, but not limited to, arterio-venous grafts, billiary stents, by-pass grafts, catheters, central nervous system shunts, coronary stents, drug delivery balloons, peripheral stents and ureteural stents, each of which may be used in areas such as, but not limited to, the vasculature for introduction of a compound having Formula I into selected tissues or organs in the body. One measure of the effectiveness of compounds having Formula I is reduction or elimination of device-associated thrombi and complications associated therewith.

Compounds having Formula I can used as a radiosensitizers which enhance the efficacy of radiotherapy. Examples of radiotherapy include, but are not limited to, external beam radiotherapy, teletherapy, brachtherapy and sealed and unsealed source radiotherapy.

Excipients for preparation of compositions comprising a compound having Formula I to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having Formula I to be administered ophthalmically or orally include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having Formula I to be administered osmotically include, for example, chlorofluoro-hydrocarbons, ethanol, water and mixtures thereof. Excipients for preparation of compositions comprising a compound having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound having Formula I to be administered rectally or vaginally include, for example, cocoa butter, polyethylene glycol, wax and mixtures thereof.

ASSAY (Fam)-NoxaCF (6-FAM)-GELEVEFATQLRRFGD-KLNF-amide) (SEQ ID NO:1) was made on a 433A automated synthesizer (Applied Biosystems, Foster City, Calif.) using standard FASTMOC™ deprotection/coupling cycles with 0.25 mmol MBHA Rink amide resin (SynPep, Dublin, Calif.). Cartridges containing $N^\alpha$ Fmoc-amino acids (1 mmol) with side chain protection (Arg: 2,2,5,7,8-pentamethylchroman-6-sulfonyl; Asp and Glu: tert butyl ester; Asn, Cys, Gln, and His: trityl; Lys and Trp: tert butyloxycarbonyl; Ser, Thr, and Tyr: tert-butyl ether were activated with O benzotriazol-1-yl-N,N,N',N'-tetramethyluronium hexafluorophosphate (1 mmol), 1 hydroxybenzotriazole (1 mmol) and diisopropylethylamine (2 mmol) in N methylpyrrolidone (NMP). The activated amino acid was coupled for 30 minutes following removal of the N-terminal Fmoc group with 20% piperidine in NMP. Labeling was accomplished by suspending the resin-bound, N terminally deprotected side-chain protected peptide resin (0.04 mmol) and 6 carboxyfluorescein-NHS ester (57 mg) in anhydrous dimethylformamide (2 mL) containing 0.02 mL diisopropylethylamine (DIEA) and shaking at ambient temperature overnight. The resin was drained, washed 3 times with 1:1 dichloromethane/methanol and dried. The labeled resin was cleaved and deprotected by mixing with TFA:water:thioanisole:phenol:3,6-dioxa-1,8-octanedithiol:triisopropylsilane, 80:5:5:5:2.5:2.5 for 3 hours at ambient temperature. Following evaporation under reduced pressure, the crude peptide was recovered by precipitation with ether. The product was purified on a preparative HPLC running Unipoint® analysis software (Gilson, Inc., Middleton, Wis.) on a 25 mm×200 mm radial compression column containing Delta-Pak® $C_{18}$ packing (Waters, Inc., Taunton, Mass.) with a flow rate of 20 mL/min. The peptides were eluted with a linear gradient of 0.1% TFA/water and acetonitrile. Fractions containing the pproduct were combined and lyophilized. The purity of the final products were confirmed by reverse-phase analytical HPLC on a Hewlett-Packard 1050 series system with diode-array and fluorescence detection (Agilent Technologies, Palo Alto, Calif.) eluted with a linear gradient of 0.1% trifluoroacetic acid/water and acetonitrile on a 4.6×250 mm YMC ODS-AQ, 5 μm, 120 Å column (Waters Inc.) to give the product (45.6 mg) as a yellow powder following lyophilization. The identity of the product was confirmed by matrix-assisted laser desorption ionization mass spectrography (MALDI-MS) on a Voyager DE-PRO (Applied Biosystems), m/z 1470.00 and 1448.01 (M+H)+.

A fluorescence polarization assay was used for $IC_{50}$ determination of representative compounds having Formula I against recombinant Mcl-1 protein. Compounds were series diluted in DMSO starting at 10 μM and transferred (5 μL) into a 96 well plate. Then, 120 μL of a mixture containing 10 nM fluorescent Noxa BH3 peptide and 80 nM Mcl-1 protein was added to each well. For each assay, free peptide controls (fluorescent peptide only) and bound peptide controls (fluorescent peptide in the presence of Mcl-1) were included on each assay plate. The plate was mixed on a shaker for 1 minute and incubated at room temperature for an additional 15 minutes. The polarization (in mP) was measured at room temperature with excitation wavelength at 485 nm and emission wavelength at 530 nm using an Analyst (LJL, Molecular Dynamic, Sunnyvale, Calif.). The percentage inhibition was calculated by % inhibition=100×(1−(mP−$mP_f$)/($mP_b$−$mP_f$)) in which $mP_f$ is the free peptide control and $mP_b$ is the bound peptide control. Based on percentage of inhibition, the $IC_{50}$ (inhibitor concentration at which 50% of bound peptide is displaced), obtained by fitting the inhibition data using Prism 3.0 software (Graphpad Software Inc, San Diego, Calif.). The results are shown in TABLE 1.

TABLE 1

$IC_{50}$'s (in μM) For Representative Compounds Having Formula I For Inhibition of Mcl-1 protein

| | | | | |
|---|---|---|---|---|
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| <0.030 | <0.030 | <0.030 | <0.030 | <0.030 |
| 0.030 | 0.030 | 0.030 | 0.031 | 0.031 |
| 0.031 | 0.031 | 0.031 | 0.031 | 0.031 |
| 0.032 | 0.032 | 0.032 | 0.032 | 0.032 |
| 0.032 | 0.033 | 0.033 | 0.033 | 0.033 |
| 0.033 | 0.033 | 0.034 | 0.034 | 0.035 |
| 0.035 | 0.035 | 0.036 | 0.036 | 0.037 |
| 0.037 | 0.037 | 0.037 | 0.037 | 0.038 |
| 0.038 | 0.038 | 0.038 | 0.038 | 0.039 |
| 0.039 | 0.039 | 0.039 | 0.040 | 0.040 |
| 0.040 | 0.041 | 0.041 | 0.041 | 0.042 |
| 0.042 | 0.043 | 0.043 | 0.043 | 0.044 |
| 0.044 | 0.044 | 0.044 | 0.044 | 0.044 |
| 0.045 | 0.045 | 0.045 | 0.045 | 0.045 |
| 0.045 | 0.045 | 0.045 | 0.046 | 0.046 |
| 0.047 | 0.047 | 0.047 | 0.047 | 0.047 |
| 0.048 | 0.048 | 0.048 | 0.049 | 0.050 |
| 0.050 | 0.050 | 0.050 | 0.051 | 0.051 |
| 0.051 | 0.051 | 0.051 | 0.052 | 0.052 |
| 0.052 | 0.052 | 0.052 | 0.053 | 0.053 |
| 0.053 | 0.053 | 0.053 | 0.054 | 0.054 |
| 0.054 | 0.054 | 0.054 | 0.055 | 0.056 |
| 0.057 | 0.057 | 0.057 | 0.057 | 0.058 |
| 0.058 | 0.058 | 0.058 | 0.058 | 0.059 |
| 0.059 | 0.059 | 0.060 | 0.060 | 0.060 |
| 0.061 | 0.061 | 0.062 | 0.062 | 0.062 |
| 0.063 | 0.063 | 0.063 | 0.064 | 0.065 |
| 0.065 | 0.065 | 0.067 | 0.067 | 0.067 |
| 0.068 | 0.068 | 0.069 | 0.069 | 0.070 |
| 0.071 | 0.072 | 0.072 | 0.072 | 0.073 |
| 0.074 | 0.074 | 0.074 | 0.075 | 0.076 |
| 0.077 | 0.077 | 0.078 | 0.078 | 0.079 |
| 0.079 | 0.079 | 0.080 | 0.080 | 0.081 |
| 0.082 | 0.083 | 0.084 | 0.085 | 0.085 |
| 0.085 | 0.086 | 0.086 | 0.087 | 0.088 |
| 0.089 | 0.089 | 0.089 | 0.090 | 0.090 |
| 0.090 | 0.090 | 0.090 | 0.091 | 0.091 |
| 0.093 | 0.093 | 0.095 | 0.096 | 0.096 |
| 0.097 | 0.097 | 0.097 | 0.098 | 0.100 |
| 0.101 | 0.101 | 0.101 | 0.101 | 0.103 |
| 0.104 | 0.104 | 0.105 | 0.105 | 0.106 |
| 0.106 | 0.107 | 0.108 | 0.108 | 0.110 |
| 0.111 | 0.112 | 0.114 | 0.118 | 0.119 |
| 0.121 | 0.121 | 0.122 | 0.123 | 0.125 |
| 0.127 | 0.128 | 0.130 | 0.132 | 0.132 |
| 0.133 | 0.134 | 0.136 | 0.137 | 0.137 |
| 0.138 | 0.139 | 0.143 | 0.145 | 0.145 |
| 0.148 | 0.148 | 0.151 | 0.154 | 0.155 |
| 0.156 | 0.156 | 0.156 | 0.157 | 0.163 |
| 0.163 | 0.165 | 0.165 | 0.166 | 0.166 |
| 0.168 | 0.169 | 0.170 | 0.173 | 0.173 |
| 0.173 | 0.174 | 0.175 | 0.175 | 0.176 |
| 0.179 | 0.180 | 0.180 | 0.182 | 0.183 |
| 0.185 | 0.186 | 0.186 | 0.186 | 0.186 |
| 0.186 | 0.187 | 0.191 | 0.197 | 0.200 |
| 0.200 | 0.201 | 0.203 | 0.206 | 0.207 |
| 0.208 | 0.209 | 0.210 | 0.212 | 0.212 |
| 0.213 | 0.215 | 0.216 | 0.218 | 0.219 |
| 0.220 | 0.220 | 0.222 | 0.222 | 0.223 |
| 0.224 | 0.224 | 0.227 | 0.228 | 0.229 |
| 0.230 | 0.232 | 0.234 | 0.235 | 0.235 |

TABLE 1-continued

IC$_{50}$'s (in μM) For Representative Compounds Having Formula I For Inhibition of Mcl-1 protein

| | | | | |
|---|---|---|---|---|
| 0.240 | 0.240 | 0.241 | 0.242 | 0.244 |
| 0.245 | 0.256 | 0.257 | 0.261 | 0.265 |
| 0.268 | 0.271 | 0.272 | 0.273 | 0.273 |
| 0.277 | 0.277 | 0.279 | 0.279 | 0.282 |
| 0.282 | 0.283 | 0.283 | 0.288 | 0.288 |
| 0.293 | 0.300 | 0.301 | 0.301 | 0.316 |
| 0.318 | 0.320 | 0.322 | 0.326 | 0.334 |
| 0.338 | 0.338 | 0.340 | 0.340 | 0.350 |
| 0.363 | 0.370 | 0.373 | 0.378 | 0.378 |
| 0.379 | 0.381 | 0.383 | 0.391 | 0.398 |
| 0.399 | 0.400 | 0.409 | 0.430 | 0.439 |
| 0.440 | 0.440 | 0.447 | 0.449 | 0.459 |
| 0.475 | 0.480 | 0.482 | 0.489 | 0.497 |
| 0.502 | 0.505 | 0.514 | 0.525 | 0.532 |
| 0.540 | 0.545 | 0.547 | 0.553 | 0.558 |
| 0.562 | 0.565 | 0.566 | 0.573 | 0.598 |
| 0.601 | 0.611 | 0.623 | 0.628 | 0.630 |
| 0.633 | 0.635 | 0.684 | 0.704 | 0.716 |
| 0.738 | 0.751 | 0.757 | 0.782 | 0.814 |
| 0.820 | 0.851 | 0.885 | 0.886 | 0.910 |
| 0.952 | 0.973 | 1.002 | 1.003 | 1.026 |
| 1.030 | 1.053 | 1.085 | 1.097 | 1.123 |
| 1.145 | 1.175 | 1.193 | 1.246 | 1.256 |
| 1.326 | 1.349 | 1.353 | 1.359 | 1.364 |
| 1.385 | 1.386 | 1.491 | 1.557 | 1.576 |
| 1.591 | 1.765 | 1.992 | 2.019 | 2.054 |
| 2.058 | 2.121 | 2.186 | 2.242 | 2.336 |
| 2.449 | 2.483 | 2.570 | 2.682 | 2.683 |
| 2.694 | 2.727 | 2.734 | 2.757 | 2.759 |
| 2.929 | 2.962 | 2.982 | 3.156 | 3.373 |
| 3.388 | 3.557 | 3.586 | 3.763 | 3.846 |
| 4.743 | 4.890 | 4.900 | 4.946 | 5.105 |
| 5.184 | 5.199 | 5.448 | 5.480 | 5.539 |
| 6.283 | 6.610 | 6.760 | 7.270 | 7.302 |
| 8.638 | | | | |

These data demonstrate the utility of representative compounds having Formula I as inhibitors of the activity of Mcl-1 protein.

These data demonstrate the utility of representative compounds having Formula I as inhibitors of the activity of Mcl-1 protein.

Accordingly, compounds having Formula I are expected to have utility in treatment of diseases during which anti-apopotic Mcl-1 is expressed and also utility in treatment of diseases in which anti-apopotic family protein members having close structural homology to Mcl-1 such as, for example, Bcl-X$_L$ protein, Bcl-2 protein and Bcl-w protein are expressed.

Overexpression of Mcl-1 correlates with resistance to chemotherapy, clinical outcome, disease progression, overall prognosis or a combination thereof in various hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphagioendothelio-sarcoma, lymphangiosarcoma, lymphoblastic leukemia, lymphoma (lymphoma, including Diffuse Large B-cell lymphoma, follicular lymphoma Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, testicular cancer (including germ cell testicular cancer) thyroid cancer, Waldenström's macroglobulinemia, testicular tumors, uterine cancer, Wilms' tumor and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Involvement of Mcl-1 in acute lymphoblastic leukemia is reported in Blood 1998, 91, 991-1000.

Involvement of Mcl-1 in acute myelogenous leukemia is also reported in Blood 1998, 91, 991-1000.

Involvement of Mcl-1 in cervical cancer is reported in Cancer Letters (Shannon, Ireland) 2002, 180, 63-68.

Involvement of Mcl-1 in chronic lymphocytic leukemia is reported in Journal of the National Cancer Institute 2004, 96, 673-682 and Immunology 2005, 114, 441-449.

Involvement of Mcl-1 in colorectal cancer, is reported in Annals of oncology: Official Journal of the European Society for Medical Oncology/ESMO 2001, 12, 779-785.

Involvement of Mcl-1 in gastric carcinoma, is reported in Gastric Cancer 2004, 7, 78-84.

Involvement of Mcl-1 in gestational trophobalstic disease is reported in Cancer 2005, 103, 268-276.

Involvement of Mcl-1 in glioblastoma is reported in Journal of Neurology, Neurosurgery, and Psychiatry 1999, 67, 763-768.

Involvement of Mcl-1 in head and neck cancer is reported in Archives of Otolaryngology-Head and Neck Surgery 1999, 125, 417-422.

Involvement of Mcl-1 in lung cancer is reported in Pathology Oncology Research: POR 1999, 5, 179-186.

Involvement of Mcl-1 in mesothioloma, is reported in Clinical Cancer Research 1999, 5, 3508-3515.

Involvement of Mcl-1 in multiple myeloma is reported in European Journal of Immunology 2004, 34, 3156-3164.

Involvement of Mcl-1 in non-Hodgkin's lymphoma is reported in British Journal of Haematology 2002, 116, 158-161.

Involvement of Mcl-1 in oligodenroglioma is reported in Cancer (New York) 1999, 86, 1832-1839.

Involvement of Mcl-1 in ovarian cancer is reported in Journal of Clinical Oncology: Official Journal of the American Society of Clinical Oncology 2000, 18, 3775-3781.

Involvement of Mcl-1 in pancreatic cancer is reported in Oncology 2002, 62, 354-362.

Involvement of Mcl-1 in peripheral T-cell lymphoma is reported in Journal of Pathology 2003, 200, 240-248.

Compounds having Formula I are expected to be useful when used with alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w, Bfl-1) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcl protein family member inhibitors include AT-101 ((−) gossypol), GENASENSE® (G3139 or oblimersen (Bcl-2-targeting antisense oglionucleotide)), IPI-194, IPI-565, N-(4-(4-((4'-chloro(1,1'-biphenyl)-2-yl)methyl)piperazin-1-yl) benzoyl)-4-(((1R)-3-(dimethylamino)-1-((phenylsulfanyl) methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin®(trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCI, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN®(bexarotene), LGD-1550 and the like.

Plant alkaloids include, but are not limited to, vincristine, vinblastine, vindesine, vinorelbine and the like.

Proteasome inhibitors include VELCADE® (bortezomib), MG 132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU 100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having Formula I may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB (389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafamib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 February 15; 95(4): 1283-92; and New England Journal of Medicine 2004 September; 351(14): 1409-1418).

Compounds having Formula I may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties such as C(O)OH, C(O) and C(O)H, NH, C(O)NH$_2$, OH and SH moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

A discussion protecting groups is provided in T. H. Greene and P. G. M. Wuts, Protective Groups in Organic Synthesis, 3rd Ed., John Wiley & Sons, New York (1999).

The following abbreviations have the meanings indicated. ADDP means 1,1'-(azodicarbonyl)dipiperidine; AD-mix-β means a mixture of (DHQD)$_2$PHAL, K$_3$Fe(CN)$_6$, K$_2$CO$_3$ and K$_2$SO$_4$); 9-BBN means 9-borabicyclo(3.3.1)nonane; (DHQD)$_2$PHAL means hydroquinidine 1,4-phthalazinediyl diethyl ether; DBU means 1,8-diazabicyclo(5.4.0)undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; d means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporus triethylammonium methylpolystyrene cyanoborohydride; PyBOP means benzotriazol-1-yloxytripyrrolidinophosphonium hexafluorophosphate; TEA means triethylamine; TFA means trifluoroacetic acid; THF means tetrahydrofuran; NCS means N-chlorosuccinimide; NMM means N-methylmorpholine; NMP means N-methylpyrrolidine and PPh$_3$ means triphenylphosphine.

SCHEME 1

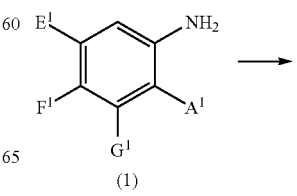

(1)

-continued

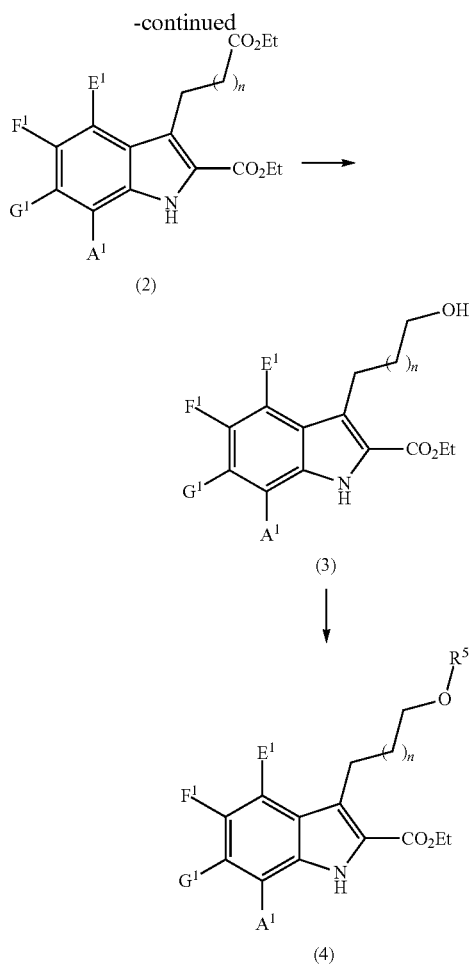

nilines of Formula (1) can be reacted as shown in SCHEME (1) and then subsequently reacted using methods described in the literature (such as those described in Palladium Reagents And Catalysts: New Perspectives For The 21st Century, By J. Tsuji, John Wiley & Sons, Ltd., Chichester, 2004, 1-670) and known by those skilled in the art for palladium catalyzed carbon cross coupling reactions.

SCHEME 2

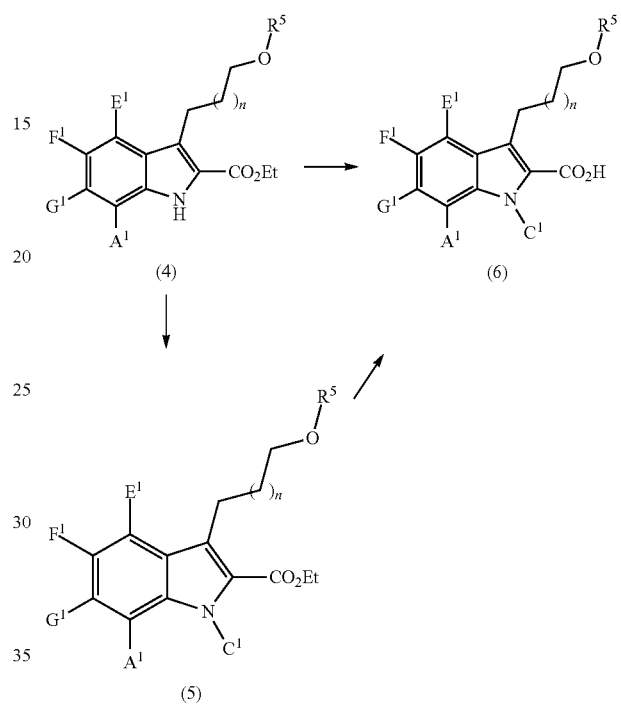

As shown in SCHEME 1, compounds of Formula (1) can be converted to compounds of Formula (2) by reacting the former with sodium nitrate and an aqueous acid followed by the addition of aqueous sodium acetate and an appropriate 2-oxocycloalkylester.

Examples of acids include hydrochloric acid and the like.

Examples of appropriate 2-oxocycloalkylesters include ethyl 2-oxocyclohexanecarboxylate, ethyl 2-oxocyclopentanecarboxylate and the like.

The reaction is initially conducted at about 0° C., over about 30 minutes to about one hour, and then warmed to between about 15° C. and 25° C. for about one to four hours, in water.

Compounds of Formula (2) can be converted to compounds of Formula (3) by reacting the former with a solution of borane.

The reaction is typically conducted at ambient temperature over about 8 hours to about 20 hours in a solvent such as but not limited to THF.

Compounds of Formula (3) can be converted to compounds of Formula (4) by reacting the former with $R^5OH$, triphenylphosphine, and a reagent such as but not limited to DEAD or TBAD.

The addition is typically conducted below room temperature before warming to ambient temperature for about 8-72 hours in a solvent such as but not limited to THF.

Introduction of moieties represented by $E^1$, $F^1$, $G^1$, and $A^1$ can be accomplished by reacting substituted anilines of Formula (1) as shown in SCHEME (1). Alternatively, bromoa- As shown in SCHEME 2, compounds of Formula (4) can be converted to compounds of Formula (5) by reacting the former with a base followed by an appropriate compound of Formula $C^1Br$ (5a) or $C^1Cl$ (5b).

Examples of a base include sodium hydride, potassium carbonate and the like.

Examples of appropriate compounds of Formula (5a) include 1-(3-bromopropoxyl)naphthalene and the like.

Examples of appropriate compounds of Formula (5b) include 2-chloro-1-morpholinoethanone and the like.

The reaction is typically conducted at or below ambient temperature for about 15 minutes to one hour during the addition of the base, and then from about 20° C. to 80° C. for about one to eight hours after the addition of the compound of Formula (5a) or (5b) in a solvent such as but not limited to DMF.

Compounds of Formula (5) can be converted to compounds of Formula (6) by reacting the former with a base.

Examples of bases include lithium hydroxide, sodium hydroxide, potassium hydroxide and the like.

The reaction is typically conducted over about 1 hour to about 48 hours, between about 0° C. and 35° C., in solvents such as water, methanol, ethanol, isopropanol, mixtures thereof and the like.

Compounds of Formula (4), wherein $C^1$ is H, can be converted to compounds of Formula (6) by reacting the former with a base.

Examples of bases include lithium hydroxide, sodium hydroxide, potassium hydroxide and the like.

The reaction is typically conducted over about 1 hour to about 48 hours, between about 0° C. and 35° C., in solvents such as water, methanol, ethanol, isopropanol, mixtures thereof and the like.

SCHEME 3

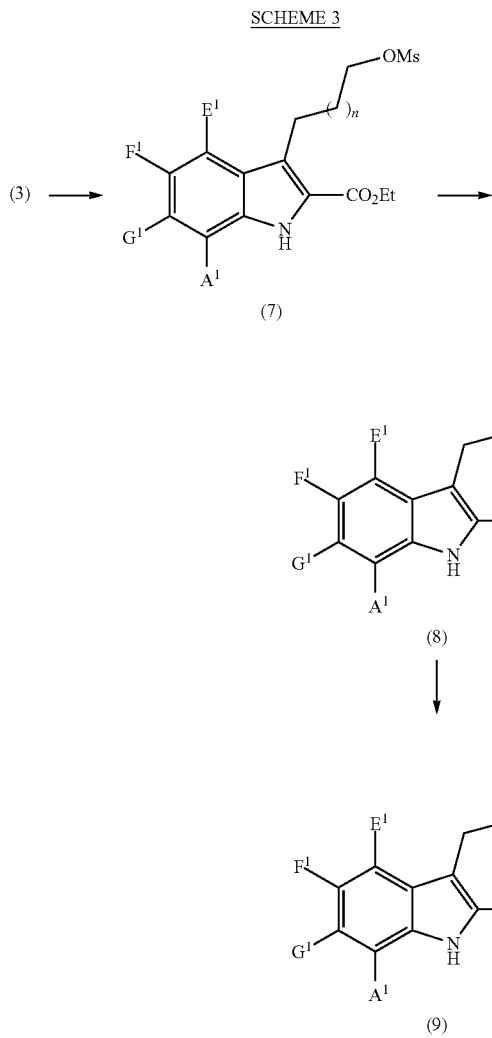

As shown in SCHEME 3, compounds of Formula (3) can be converted to compounds of Formula (7) by reacting the former with a base followed by methanesulfonyl chloride.

Examples of bases include TEA, pyridine and the like.

The reaction is typically conducted over about 30 minutes to about three hours, between about 0° C. and 20° C., in acetonitrile.

Compounds of Formula (7) can be converted to compounds of Formula (8) by reacting the former with a compound of Formula $R^5SH$, and a base.

Examples of bases include potassium carbonate and sodium carbonate.

The reaction is typically conducted over one to five days between about 50° C. and 100° C., in a solvent such as but not limited to acetonitrile.

Compounds of Formula (8) can be converted to compounds of Formula (9) as described in SCHEME 2 for the conversion of compounds of Formula (4) to compounds of Formula (6).

SCHEME 4

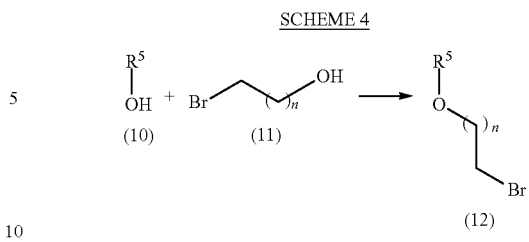

As shown in SCHEME 4, compounds of Formula (10) can be converted to compounds of Formula (12) by reacting the former with compounds of Formula (11), triphenylphosphine, and a reagent such as but not limited to DEAD or TBAD.

The addition may be conducted below room temperature before warming to ambient temperature for about 8-72 hours in a solvent such as but not limited to THF.

SCHEME 5

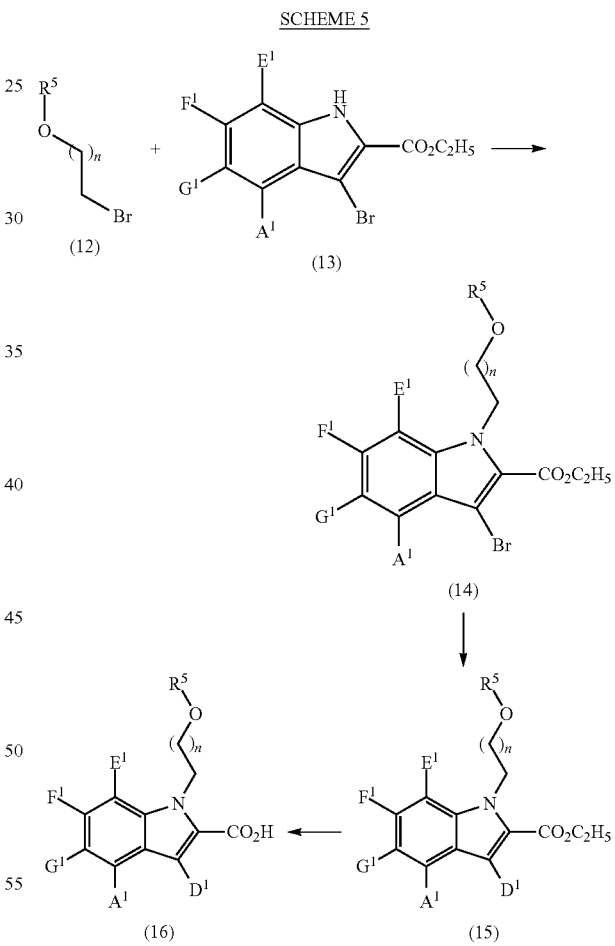

As shown in SCHEME 5, compounds of Formula (12) can be converted to compounds of Formula (14) by reacting the former, a compound of Formula (13) and a base.

Examples of bases include sodium hydride and potassium carbonate and the like.

The reaction is typically conducted at or below ambient temperature for 15 minutes to one hour during the addition of the base, and then from about 20° C. to 80° C. for about one to eight hours after the addition of the compound of Formula (13) in a solvent such as but not limited to DMF.

Compounds of Formula (14) can be converted to compounds of Formula (15) using methods described in the literature (such as those described in Palladium Reagents And Catalysts: New Perspectives For The 21st Century, By J. Tsuji, John Wiley & Sons, Ltd., Chichester, 2004, 1-670) and known by those skilled in the art for palladium catalyzed carbon cross coupling reactions.

Compounds of Formula (15) can be converted to compounds of Formula (16) as described in SCHEME 2 for the conversion of compounds of Formula (4) to compounds of Formula (6).

The reaction is initially conducted over about one hour at about 60° C. to about 100° C. after the addition of the base and then cooled to about 10° C. to about 25° C. and treated with a compounds of Formula (17). After about 10 minutes to about 20 minutes, the compound of Formula $R^5C(O)H$ is added and the mixture is again heated at about 60° C. to about 100° C. for about one to eight hours.

Compounds of Formula (18) can be converted to compounds of Formula (19) by reacting the former with a hydrogen source and a catalyst.

Examples of hydrogen sources include hydrazine and hydrogen gas.

SCHEME 6

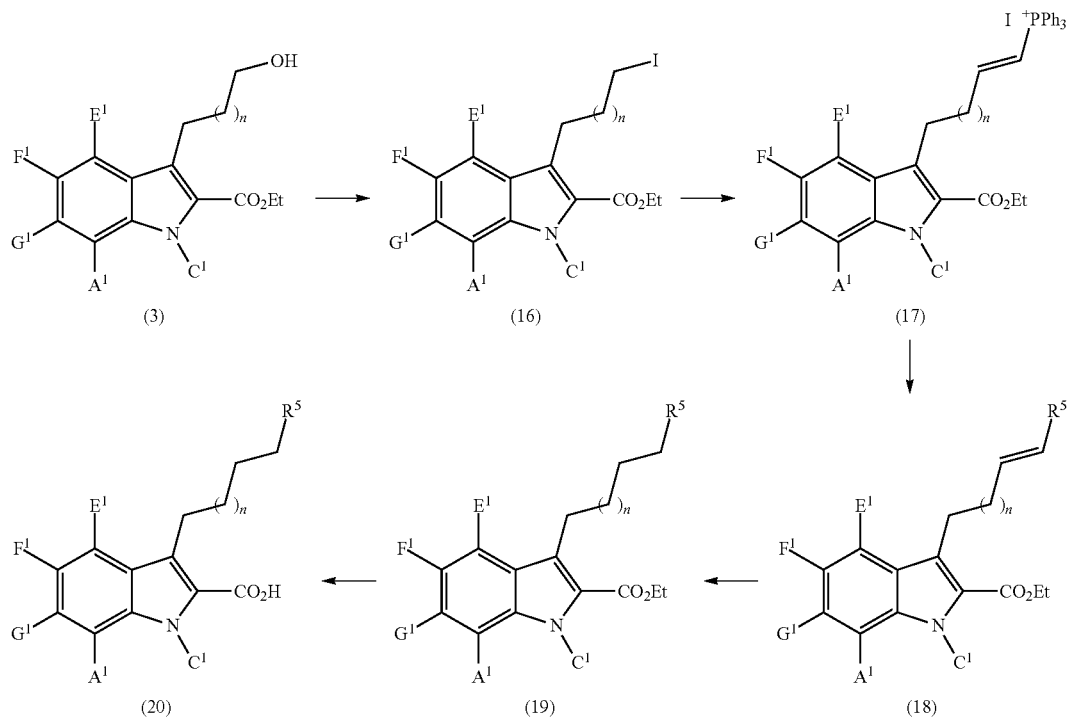

As shown in SCHEME 6, compounds of Formula (3) can be converted to compounds of Formula (16) by reacting the former, iodine, triphenyphosphine and imidazole, followed by a base.

Examples of bases include sodium carbonate and the like.

The reaction is typically conducted from about −10° C. to about 10° C. for about 15 minutes to one hour and then continued for an additional 30 minutes to one hour after addition of the base, in a solvent such as but not limited to dichloromethane.

Compounds of Formula (16) can be converted to compounds of Formula (17) by reacting the former and triphenyphosphine.

The reaction is typically conducted over about 8 to about 48 hours at reflux, in a solvent such as but not limited to acetonitrile or dichloromethane.

Compounds of Formula (17) can be converted to compounds of Formula (18) by reacting the former, a base, and a compound of Formula $R^5C(O)H$.

Examples of bases include sodium hydride and n-butyllithium.

Examples of catalysts include Pd/C and Raney Nickel and the like.

Temperature and pressure vary depending on the hydrogenation method and the substrates employed. Typical solvents include methanol, ethanol, ethyl acetate, and the like.

Compounds of Formula (19) can be converted to compounds of Formula (20) as described in SCHEME 2 for the conversion of compounds of Formula (4) to compounds of Formula (6).

SCHEME 7

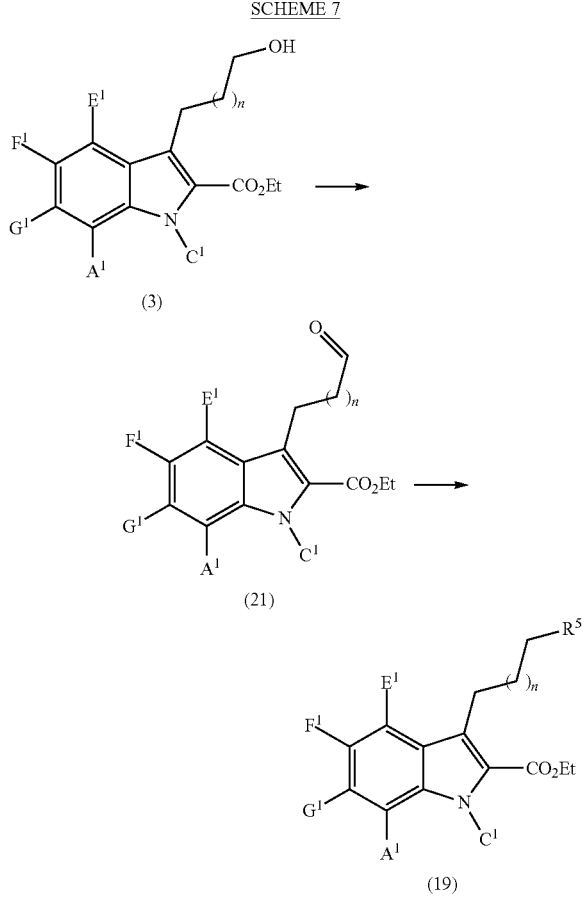

As shown in SCHEME 7, compounds of Formula (3) can be converted to compounds of Formula (21) by reacting the former, DMSO, a base, and a dehydration agent.

Examples of bases include triethylamine, diisopropylamine, and the like.

Examples of dehydration agents include oxalyl chloride, trifluoroacetic anhydride, and pyridine sulfate.

The reaction is typically conducted over about one to about eight hours at about −60° C. to about 0° C. depending on the substrate and method employed.

The following examples are presented to provide what is believed to be the most useful and readily understood description of procedures and conceptual aspects of this invention.

EXAMPLE 1A ethyl 7-bromo-3-(3-ethoxy-3-oxopropyl)-1H-indole-2-carboxylate

A mixture of 2-bromoaniline (34.2 g) in 5M HCl (50 mL) and water (250 mL) at 0° C. was treated with $NaNO_2$ (13.8 g) in water (200 mL). After addition, sodium acetate (92.3 g) in water (250 mL) and 2-oxo-cyclopentanecarboxylic acid ethyl ester (30 mL) were added. The mixture was stirred for 15 minutes, warmed to 19° C. over two hours and extracted with dichloromethane. The extract was dried ($MgSO_4$), filtered and concentrated. The concentrate was dissolved in 1.1:1 $H_2SO_4$:ethanol (30 mL), refluxed overnight, cooled to room temperature, quenched with water (1.5 L), and filtered. The filtrant was dissolved in dichloromethane (200 mL) and filtered through a Flash 75 cartridge with dichloromethane. After concentration, the product was recrystallized from hexane.

EXAMPLE 1B ethyl 7-bromo-3-(3-hydroxypropyl)-1H-indole-2-carboxylate

To a mixture of EXAMPLE 1A (1.85 g) in THF (50 mL) was added 1M borane THF (30 mL). The mixture was stirred at room temperature for 16 hours, quenched with methanol (10 mL) and concentrated. The concentrate was purified by flash column chromatography on silica gel with 5-25% ethyl acetate/hexanes.

EXAMPLE 1C ethyl 7-bromo-3-(3-(naphthalen-1-yloxy)propyl)-1H-indole-2-carboxylate To a mixture of Example 1B (10.87 g), 1-naphthol (5.77 g) and triphenylphosphine (10.5 g) in THF (100 mL) was added di-tert-butyl azodicarboxylate (9.21 g). The mixture was stirred for 3 days, concentrated, redissolved in dichloromethane, washed with water and brine and dried (MgSO4), filtered and concentrated. The concentrate was purified by flash column chromatography on silica gel with 0-10% ethyl acetate in hexanes. The product was recrystallized from hexanes.

EXAMPLE 1D 3-(3-(1-naphthyloxy)propyl)-7-((E)-2-phenylvinyl)-1H-indole-2-carboxylic acid A mixture of EXAMPLE 1C (0.034 g), (E)-styrylboronic acid (0.1 g), bis(triphenylphosphine)palladium(II) dichloride (4 mg), and 2M $Na_2CO_3$ (0.5 mL) in 7:2:3 dimethoxyethane/ethanol/water (3 mL) was heated under microwave (CEM Discover) at 150° C. for 30 minutes, quenched with 1M HCl (0.4 mL) and extracted with ethyl acetate. The extract was filtered through a drying cartridge ($MgSO_4$, Alltech Assoc., 2 g) and concentrated. The concentrate was purified by reverse phase HPLC (Zorbax SB-C18, 20-100% acetonitrile/water/0.1% TFA). $^1$H NMR (400 MHz, DMSO-$d_6$) δ 13.03 (brs, 1H), 11.68 (s, 1H), 8.23 (m, 1H), 8.14 (d, 1H), 7.86 (m, 1H), 7.76 (d, 1H), 7.68 (d, 1H), 7.61 (d, 1H), 7.52 (m, 2H), 7.41 (m, 4H), 7.29 (m, 2H), 7.01 (t, 1H), 6.88 (d, 1H), 4.17 (t, 2H), 2.22 (m, 2H).

EXAMPLE 2

3-(3-(1-naphthyloxyl)propyl)-7-phenyl-1H-indole-2-carboxylic acid

This example was prepared by substituting phenylboronic acid for (E)-styrylboronic acid in EXAMPLE 1D. $^1$H NMR (400 MHz, DMSO-$d_6$) δ 12.97 (s, 1H), 10.29 (s, 1H), 8.23 (m, 1H), 7.86 (m, 1H), 7.69 (d, 1H), 7.64 (m, 2H), 7.52 (m, 4H), 7.41 (m, 3H), 7.25 (m, 1H), 7.10 (t, 1H), 6.89 (d, 1H), 4.20 (t, 2H), 3.37 (m, 2H), 2.24 (m, 2H).

EXAMPLE 3

3-(3-(1-naphthyloxy)propyl)-7-((1E)-3-phenylprop-1-enyl)-1H-indole-2-carboxylic acid This example was prepared by substituting (E)-3-phenylprop-1-enylboronic acid for (E)-styrylboronic acid in EXAMPLE 1D. ¹H NMR (400 MHz, DMSO-$d_6$) δ 13.02 (brs, 1H), 11.38 (s, 1H), 8.20 (m, 1H), 7.85 (m, 1H), 7.36 (m, 12H), 6.93 (t, 1H), 6.86 (d, 1H), 6.44 (m, 1H), 4.15 (t, 2H), 3.58 (d, 2H), 2.20 (m, 2H).

EXAMPLE 4

7-((E)-2-cyclohexylvinyl)-3-(3-(1-naphthyloxyl) propyl)-1H-indole-2-carboxylic acid This example was prepared by substituting (E)-2-cyclohexyl-vinylboronic acid for (E)-styrylboronic acid in EXAMPLE 1D. ¹H NMR (400 MHz, DMSO-$d_6$) δ 13.02 (brs, 1H), 11.37 (s, 1H), 8.21 (m, 1H), 7.85 (m, 1H), 7.51 (m, 3H), 7.44 (m, 1H), 7.36 (m, 2H), 7.19 (d, 1H), 6.89 (m, 2H), 6.30 (m, 1H), 4.15 (t, 2H), 2.19 (m, 3H), 1.77 (m, 5H), 1.27 (m, 5H).

EXAMPLE 5

7-(3-(benzyloxy)phenyl)-3-(3-(1-naphthyloxy)propyl)-1H-indole-2-carboxylic acid

This example was prepared by substituting 3-(benzyloxy)-phenylboronic acid for (E)-styrylboronic acid in EXAMPLE 1D. ¹H NMR (400 MHz, DMSO-$d_6$) δ 12.99 (brs, 1H), 10.34 (s, 1H), 8.22 (m, 1H), 7.86 (m, 1H), 7.69 (d, 1H), 7.36 (m, 13H), 7.07 (m, 2H), 6.89 (d, 1H), 5.19 (s, 2H), 4.20 (t, 2H), 3.37 (t, 2H), 2.24 (m, 2H).

EXAMPLE 6

7-(4-fluorophenyl)-3-(3-(1-naphthyloxy)propyl)-1H-indole-2-carboxylic acid

This example was prepared by substituting 4-fluorophenyl-boronic acid for (E)-styrylboronic acid in EXAMPLE 1D. ¹H NMR (400 MHz, DMSO-$d_6$) δ 13.00 (brs, 1H), 10.54 (s, 1H), 8.22 (m, 1H), 7.86 (m, 1H), 7.70 (d, 1H), 7.64 (m, 2H), 7.49 (m, 3H), 7.34 (m, 3H), 7.21 (d, 1H), 7.08 (t, 1H), 6.89 (d, 1H), 4.19 (t, 2H), 3.37 (t, 2H), 2.24 (m, 2H).

EXAMPLE 7

7-(2-naphthyl)-3-(3-(1-naphthyloxy)propyl)-1H-indole-2-carboxylic acid

This example was prepared by substituting 2-naphthylboronic acid for (E)-styrylboronic acid in EXAMPLE 1D. ¹H NMR (500 MHz, DMSO-$d_6$) δ 13.01 (brs, 1H), 10.69 (s, 1H), 8.25 (m, 1H), 8.17 (s, 1H), 8.01 (m, 3H), 7.87 (m, 1H), 7.74 (m, 2H), 7.55 (m, 4H), 7.45 (d, 1H), 7.36 (m, 2H), 7.13 (t, 1H), 6.90 (d, 1H), 4.21 (t, 2H), 3.39 (t, 2H), 2.26 (m, 2H).

EXAMPLE 8

7-(1-naphthyl)-3-(3-(1-naphthyloxyl)propyl)-1H-indole-2-carboxylic acid

This example was prepared by substituting 1-naphthylboronic acid for (E)-styrylboronic acid in EXAMPLE 1D. ¹H NMR (500 MHz, DMSO-$d_6$) δ 12.90 (brs, 1H), 10.54 (s, 1H), 8.27 (m, 1H), 8.01 (m, 2H), 7.88 (m, 1H), 7.79 (d, 1H), 7.61 (t, 1H), 7.50 (m, 5H), 7.40 (m, 3H), 7.20 (d, 1H), 7.15 (t, 1H), 6.92 (d, 1H), 4.23 (s, 2H), 3.40 (m, 2H), 2.27 (m, 2H).

EXAMPLE 9

7-(1,1'-biphenyl-2-yl)-3-(3-(1-naphthyloxy)propyl)-1H-indole-2-carboxylic acid

This example was prepared by substituting biphenyl-2-ylboronic acid for (E)-styrylboronic acid in EXAMPLE 1D. ¹H NMR (500 MHz, DMSO-$d_6$) δ 12.90 (brs, 1H), 10.22 (s, 1H), 8.24 (m, 1H), 7.86 (m, 1H), 7.50 (m, 8H), 7.38 (t, 1H), 7.09 (m, 5H), 6.86 (m, 3H), 4.14 (t, 2H), 2.18 (m, 2H).

EXAMPLE 10

7-(2-morpholin-4-ylphenyl)-3-(3-(1-naphthyloxyl) propyl)-1H-indole-2-carboxylic acid This example was prepared by substituting 2-morpholinophenyl-boronic acid for (E)-styrylboronic acid in EXAMPLE 1D. ¹H NMR (500 MHz, DMSO-$d_6$) δ 13.11 (brs, 1H), 10.07 (s, 1H), 8.24 (d, 1H), 7.85 (m, 1H), 7.74 (d, 1H), 7.44 (m, 7H), 7.14 (m, 3H), 6.86 (d, 1H), 4.18 (t, 2H), 3.25 (m, 4H), 2.78 (m, 4H), 2.26 (m, 2H).

EXAMPLE 11

7-(2-fluoro-1,1'-biphenyl-4-yl)-3-(3-(1-naphthyloxy) propyl)-1H-indole-2-carboxylic acid This example was prepared by substituting 2-fluorobiphenyl-4-ylboronic acid for (E)-styrylboronic acid in EXAMPLE 1D. ¹H NMR (500 MHz, DMSO-$d_6$) δ 13.07 (brs, 1H), 10.86 (s, 1H), 8.23 (m, 1H), 7.87 (m, 1H), 7.74 (d, 1H), 7.65 (m, 3H), 7.53 (m, 6H), 7.41 (m, 3H), 7.32 (d, 1H), 7.11 (t, 1H), 6.90 (d, 1H), 4.20 (t, 2H), 3.38 (t, 2H), 2.24 (m, 2H).

EXAMPLE 12

7-(4-(benzyloxy)phenyl)-3-(3-(1-naphthyloxyl)propyl)-1H-indole-2-carboxylic acid This example was prepared by substituting 4-(benzyloxy)-phenylboronic acid for (E)-styrylboronic acid in EXAMPLE 1D. ¹H NMR (500 MHz, DMSO-$d_6$) δ 13.04 (brs, 1H), 10.27 (s, 1H), 8.23 (m, 1H), 7.87 (m, 1H), 7.65 (d, 1H), 7.54 (m, 6H), 7.39 (m, 5H), 7.18 (m, 3H), 7.07 (t, 1H), 6.90 (d, 1H), 5.19 (s, 2H), 4.19 (t, 2H), 2.23 (m, 2H).

EXAMPLE 13

7-(3-morpholin-4-ylphenyl)-3-(3-(1-naphthyloxyl) propyl)-1H-indole-2-carboxylic acid This example was prepared by substituting 3-morpholinophenyl-boronic acid for (E)-styrylboronic acid in EXAMPLE 1D. ¹H NMR (500 MHz, DMSO-$d_6$) δ 13.03 (brs, 1H), 10.21 (s, 1H), 8.22 (m, 1H), 7.86 (m, 1H), 7.68 (d, 1H), 7.52 (m, 2H), 7.45 (d, 1H), 7.38 (d, 2H), 7.25 (d, 1H), 7.06 (m, 4H), 6.89 (d, 1H), 4.19 (t, 2H), 3.76 (t, 4H), 3.19 (t, 4H), 2.23 (m, 2H).

EXAMPLE 14

3-(3-(1-naphthyloxyl)propyl)-7-pyridin-3-yl-1H-indole-2-carboxylic acid

This example was prepared as a TFA salt by substituting 3-pyridylboronic acid for (E)-styrylboronic acid in EXAMPLE 1D. $^1$H NMR (500 MHz, DMSO-$d_6$) δ 13.13 (brs, 1H), 11.30 (s, 1H), 8.96 (s, 1H), 8.76 (m, 1H), 8.31 (d, 1H), 8.22 (d, 1H), 7.84 (m, 3H), 7.52 (m, 2H), 7.45 (d, 1H), 7.38 (t, 1H), 7.29 (d, 1H), 7.14 (t, 1H), 6.89 (d, 1H), 4.19 (t, 2H), 3.38 (t, 2H), 2.24 (m, 2H).

EXAMPLE 15

3-(3-(1-naphthyloxyl)propyl)-7-pyridin-4-yl-1H-indole-2-carboxylic acid

This example was prepared as a TFA salt by substituting 4-pyridylboronic acid for (E)-styrylboronic acid in EXAMPLE 1D. $^1$H NMR (500 MHz, DMSO-$d_6$) δ 13.18 (brs, 1H), 11.18 (s, 1H), 8.84 (m, 2H), 8.21 (d, 1H), 7.98 (m, 2H), 7.86 (d, 2H), 7.45 (m, 5H), 7.16 (m, 1H), 6.89 (d, 1H), 4.19 (t, 2H), 3.39 (t, 2H), 2.24 (m, 2H).

EXAMPLE 16

3-(3-(1-naphthyloxy)propyl)-7-((1E)-5-phenylpent-1-enyl)-1H-indole-2-carboxylic acid This example was prepared by substituting (E)-5-phenyl-pent-1-enylboronic acid for (E)-styrylboronic acid in EXAMPLE 1D. $^1$H NMR (500 MHz, DMSO-$d_6$) δ 13.00 (brs, 1H), 11.38 (s, 1H), 8.22 (m, 1H), 7.85 (m, 1H), 7.52 (m, 3H), 7.40 (m, 3H), 7.23 (m, 6H), 6.94 (t, 1H), 6.85 (d, 1H), 6.37 (m, 1H), 4.15 (t, 2H), 2.66 (t, 2H), 2.28 (m, 2H), 2.19 (m, 2H), 1.82 (m, 2H).

EXAMPLE 17

7-(2-methylphenyl)-3-(3-(1-naphthyloxy)propyl)-1H-indole-2-carboxylic acid

This example was prepared by substituting 2-methylphenylboronic acid for (E)-styrylboronic acid in EXAMPLE 1D. $^1$H NMR (500 MHz, DMSO-$d_6$) δ 12.95 (brs, 1H), 10.49 (s, 1H), 8.26 (d, 1H), 7.87 (d, 1H), 7.69 (d, 1H), 7.53 (m, 2H), 7.45 (d, 1H), 7.39 (t, 1H), 7.26 (m, 4H), 7.06 (m, 2H), 6.90 (d, 1H), 4.21 (t, 2H), 2.24 (m, 2H), 2.06 (s, 3H).

EXAMPLE 18

7-(3-methylphenyl)-3-(3-(1-naphthyloxyl)propyl)-1H-indole-2-carboxylic acid

This example was prepared by substituting 3-methylphenyl-boronic acid for (E)-styrylboronic acid in EXAMPLE 1D. $^1$H NMR (500 MHz, DMSO-$d_6$) δ 13.02 (brs, 1H), 10.32 (s, 1H), 8.22 (m, 1H), 7.87 (m, 1H), 7.68 (d, 1H), 7.52 (m, 2H), 7.41 (m, 5H), 7.23 (m, 2H), 7.09 (t, 1H), 6.89 (d, 1H), 4.19 (t, 2H), 2.41 (s, 3H), 2.24 (m, 2H).

EXAMPLE 19

7-(4-methylphenyl)-3-(3-(1-naphthyloxy)propyl)-1H-indole-2-carboxylic acid

This example was prepared by substituting 4-methylphenyl-boronic acid for (E)-styrylboronic acid in EXAMPLE 1D. $^1$H NMR (500 MHz, DMSO-$d_6$) δ 13.05 (brs, 1H), 10.25 (s, 1H), 8.22 (m, 1H), 7.86 (m, 1H), 7.67 (d, 1H), 7.50 (m, 5H), 7.36 (m, 3H), 7.22 (m, 1H), 7.08 (t, 1H), 6.89 (d, 1H), 4.19 (t, 2H), 2.39 (s, 3H), 2.23 (m, 2H).

EXAMPLE 20

7-(4-carboxyphenyl)-3-(3-(1-naphthyloxyl)propyl)-1H-indole-2-carboxylic acid This example was prepared by substituting 4-(methoxycarbonyl)-phenylboronic acid for (E)-styrylboronic acid in EXAMPLE 1D. $^1$H NMR (500 MHz, DMSO-$d_6$) δ 13.01 (brs, 2H), 10.73 (s, 1H), 8.23 (m, 1H), 8.06 (d, 2H), 7.87 (m, 1H), 7.74 (m, 3H), 7.50 (m, 3H), 7.38 (t, 1H), 7.11 (t, 1H), 6.89 (d, 1H), 4.19 (t, 2H), 2.24 (m, 2H).

EXAMPLE 21

7-(3-carboxyphenyl)-3-(3-(1-naphthyloxyl)propyl)-1H-indole-2-carboxylic acid This example was prepared by substituting 3-(methoxycarbonyl)-phenylboronic acid for (E)-styrylboronic acid in EXAMPLE 1D. $^1$H NMR (500 MHz, DMSO-$d_6$) δ 13.02 (brs, 2H), 10.84 (s, 1H), 8.23 (m, 1H), 8.12 (m, 1H), 7.98 (m, 1H), 7.85 (m, 2H), 7.72 (d, 1H), 7.63 (t, 1H), 7.52 (m, 2H), 7.45 (d, 1H), 7.39 (t, 1H), 7.24 (d, 1H), 7.10 (t, 1H), 6.90 (d, 1H), 4.19 (t, 2H), 3.38 (t, 2H), 2.24 (m, 2H).

EXAMPLE 22

7-(2-(benzyloxy)phenyl)-3-(3-(1-naphthyloxy)propyl)-1H-indole-2-carboxylic acid This example was prepared by substituting 2-(benzyloxy)-phenylboronic acid for (E)-styrylboronic acid in EXAMPLE 1D. $^1$H NMR (500 MHz, DMSO-$d_6$) δ 12.95 (brs, 1H), 10.35 (s, 1H), 8.27 (m, 1H), 7.87 (m, 1H), 7.67 (d, 1H), 7.53 (m, 2H), 7.40 (m, 4H), 7.24 (d, 1H), 7.10 (m, 8H), 6.87 (d, 1H), 5.09 (s, 2H), 4.17 (t, 2H), 2.24 (m, 2H).

EXAMPLE 23

7-(2-ethoxyphenyl)-3-(3-(1-naphthyloxy)propyl)-1H-indole-2-carboxylic acid

This example was prepared by substituting 2-ethoxyphenyl-boronic acid for (E)-styrylboronic acid in EXAMPLE 1D. $^1$H NMR (500 MHz, DMSO-$d_6$) δ 13.01 (brs, 1H), 9.93 (s, 1H), 8.25 (m, 1H), 7.87 (m, 1H), 7.70 (d, 1H), 7.44 (m, 6H), 7.17 (m, 2H), 7.06 (m, 2H), 6.89 (d, 1H), 4.19 (t, 2H), 4.09 (q, 2H), 2.24 (m, 2H), 1.15 (t, 3H).

EXAMPLE 24

7-(2-ethylphenyl)-3-(3-(1-naphthyloxy)propyl)-1H-indole-2-carboxylic acid

This example was prepared by substituting 2-ethylphenyl-boronic acid for (E)-styrylboronic acid in EXAMPLE 1D. $^1$H NMR (500 MHz, DMSO-$d_6$) δ 12.93 (brs, 1H), 10.40 (s, 1H), 8.26 (m, 1H), 7.87 (m, 1H), 7.69 (d, 1H), 7.53 (m, 2H), 7.45 (d, 1H), 7.38 (m, 3H), 7.26 (m, 1H), 7.18 (d, 1H), 7.05 (m, 2H), 6.91 (d, 1H), 4.21 (t, 2H), 2.33 (m, 4H), 0.94 (t, 3H).

EXAMPLE 25

7-(2-methoxyphenyl)-3-(3-(1-naphthyloxyl)propyl)-1H-indole-2-carboxylic acid This example was prepared by substituting 2-methoxyphenyl-boronic acid for (E)-styrylboronic acid in EXAMPLE 1D. ¹H NMR (500 MHz, DMSO-d₆) δ 12.97 (brs, 1H), 10.09 (s, 1H), 8.26 (m, 1H), 7.87 (m, 1H), 7.68 (d, 1H), 7.53 (m, 2H), 7.42 (m, 3H), 7.29 (m, 1H), 7.15 (m, 2H), 7.06 (m, 2H), 6.91 (d, 1H), 4.20 (t, 2H), 3.74 (s, 3H), 2.24 (m, 2H).

EXAMPLE 26

7-(2-isopropoxyphenyl)-3-(3-(1-naphthyloxyl)propyl)-1H-indole-2-carboxylic acid

This example was prepared by substituting 2-isopropoxyphenyl-boronic acid for (E)-styrylboronic acid in EXAMPLE 1D. ¹H NMR (500 MHz, DMSO-d₆) δ 13.04 (brs, 1H), 9.73 (s, 1H), 8.24 (m, 1H), 7.86 (m, 1H), 7.70 (d, 1H), 7.52 (m, 2H), 7.45 (d, 1H), 7.38 (m, 3H), 7.20 (m, 2H), 7.08 (m, 2H), 6.89 (d, 1H), 4.62 (m, 1H), 4.19 (t, 2H), 3.37 (t, 2H), 2.24 (m, 2H), 1.13 (d, 6H).

EXAMPLE 27

3-(3-(1-naphthyloxy)propyl)-7-(2-phenoxyphenyl)-1H-indole-2-carboxylic acid

This example was prepared by substituting 2-phenoxyphenyl-boronic acid for (E)-styrylboronic acid in EXAMPLE 1D. ¹H NMR (300 MHz, DMSO-d₆) δ 13.00 (brs, 1H), 10.56 (s, 1H), 8.25 (m, 1H), 7.86 (m, 1H), 7.64 (d, 1H), 7.45 (m, 6H), 7.23 (m, 4H), 6.94 (m, 6H), 4.17 (t, 2H), 2.21 (m, 2H).

EXAMPLE 28

7-(2-carboxyphenyl)-3-(3-(1-naphthyloxyl)propyl)-1H-indole-2-carboxylic acid

This example was prepared by substituting 2-(diethylcarbamoyl)phenylboronic acid for (E)-styrylboronic acid in EXAMPLE 1D. ¹H NMR (300 MHz, DMSO-d₆) δ 12.90 (brs, 1H), 12.42 (brs, 1H), 10.56 (s, 1H), 8.27 (m, 1H), 7.87 (m, 2H), 7.52 (m, 8H), 7.03 (m, 2H), 6.92 (d, 1H), 4.21 (t, 2H), 2.23 (m, 2H).

EXAMPLE 30

3-(3-(1-naphthyloxyl)propyl)-7-(2-((5,6,7,8-tetrahydronaphthalen-1-yloxy)methyl)phenyl)-1H-indole-2-carboxylic acid This example was prepared by substituting 2-((5,6,7,8-tetrahydronaphthalen-1-yloxy)methyl)phenylboronic acid for (E)-styrylboronic acid in EXAMPLE 1D. ¹H NMR (300 MHz, DMSO-d₆) δ 12.94 (brs, 1H), 10.49 (s, 1H), 8.24 (m, 1H), 7.86 (m, 1H), 7.66 (m, 2H), 7.44 (m, 7H), 7.08 (m, 2H), 6.85 (m, 2H), 6.56 (d, 1H), 6.37 (d, 1H), 4.80 (brs, 2H), 4.18 (t, 2H), 2.60 (m, 2H), 2.39 (m, 2H), 2.24 (m, 2H), 1.62 (m, 4H).

EXAMPLE 31

7-(4-cyclohexylphenyl)-3-(3-(1-naphthyloxyl)propyl)-1H-indole-2-carboxylic acid

This example was prepared by substituting 4-cyclohexylphenyl-boronic acid for (E)-styrylboronic acid in EXAMPLE 1D. ¹H NMR (300 MHz, DMSO-d₆) δ 13.04 (brs, 1H), 10.26 (s, 1H), 8.23 (m, 1H), 7.86 (m, 1H), 7.67 (d, 1H), 7.45 (m, 8H), 7.23 (m, 1H), 7.08 (t, 1H), 6.89 (d, 1H), 4.19 (t, 2H), 3.37 (t, 2H), 2.59 (m, 1H), 2.24 (m, 2H), 1.80 (m, 5H), 1.39 (m, 5H).

EXAMPLE 32

7-(2-chlorophenyl)-3-(3-(1-naphthyloxy)propyl)-1H-indole-2-carboxylic acid

This example was prepared by substituting 2-chlorophenyl-boronic acid for (E)-styrylboronic acid in EXAMPLE 1D. ¹H NMR (500 MHz, DMSO-d₆) δ 12.97 (brs, 1H), 10.91 (s, 1H), 8.27 (m, 1H), 7.87 (m, 1H), 7.73 (m, 1H), 7.54 (m, 3H), 7.42 (m, 5H), 7.08 (m, 2H), 6.91 (d, 1H), 4.21 (t, 2H), 3.37 (t, 2H), 2.23 (m, 2H).

EXAMPLE 33

7-(3-chloropyridin-4-yl)-3-(3-(1-naphthyloxy)propyl)-1H-indole-2-carboxylic acid This example was prepared as a TFA salt by substituting 2-chloropyrid-4-yl-boronic acid for (E)-styrylboronic acid in EXAMPLE 1D. ¹H NMR (500 MHz, DMSO-d₆) δ 13.03 (brs, 1H), 11.28 (s, 1H), 8.72 (s, 1H), 8.57 (d, 1H), 8.25 (m, 1H), 7.87 (m, 1H), 7.79 (d, 1H), 7.53 (m, 2H), 7.45 (m, 2H), 7.39 (t, 1H), 7.11 (m, 2H), 6.91 (d, 1H), 4.20 (t, 2H), 2.23 (m, 2H).

EXAMPLE 34

7-(2,5-dichlorophenyl)-3-(3-(1-naphthyloxyl)propyl)-1H-indole-2-carboxylic acid

This example was prepared by substituting 2,5-dichlorophenyl-boronic acid for (E)-styrylboronic acid in EXAMPLE 1D. ¹H NMR (500 MHz, DMSO-d₆) δ 12.96 (brs, 1H), 11.43 (s, 1H), 8.24 (m, 1H), 7.86 (m, 1H), 7.65 (d, 1H), 7.52 (m, 2H), 7.45 (d, 1H), 7.38 (m, 2H), 7.21 (t, 1H), 6.95 (t, 1H), 6.87 (d, 1H), 4.16 (t, 2H), 2.21 (m, 2H).

EXAMPLE 35

7-(3,5-dichlorophenyl)-3-(3-(1-naphthyloxyl)propyl)-1H-indole-2-carboxylic acid

This example was prepared by substituting 3,5-dichlorophenyl-boronic acid for (E)-styrylboronic acid in EXAMPLE 1D. ¹H NMR (500 MHz, DMSO-d₆) δ 12.94 (brs, 1H), 11.02 (s, 1H), 8.27 (m, 1H), 7.86 (m, 2H), 7.67 (m, 2H), 7.53 (m, 2H), 7.46 (d, 1H), 7.39 (m, 2H), 7.03 (m, 2H), 6.91 (d, 1H), 4.21 (t, 2H), 2.24 (m, 2H).

EXAMPLE 36

7-(2,3-dimethoxyphenyl)-3-(3-(1-naphthyloxy)propyl)-1H-indole-2-carboxylic acid

This example was prepared by substituting 2,3-dimethoxyphenyl-boronic acid for (E)-styrylboronic acid in EXAMPLE 1D. ¹H NMR (500 MHz, DMSO-d₆) δ 13.05 (brs, 1H), 10.03 (s, 1H), 8.25 (m, 1H), 7.87 (m, 1H), 7.71 (d, 1H), 7.52 (m, 2H), 7.45 (d, 1H), 7.39 (t, 1H), 7.14 (m, 4H), 6.92 (m, 2H), 4.20 (t, 2H), 3.88 (s, 3H), 3.43 (s, 3H), 2.24 (m, 2H).

EXAMPLE 37

7-(2,4-dimethoxyphenyl)-3-(3-(1-naphthyloxy)propyl)-1H-indole-2-carboxylic acid This example was prepared by substituting 2,4-dimethoxyphenyl-boronic acid for (E)-styrylboronic acid in EXAMPLE 1D. $^1$H NMR (500 MHz, DMSO-$d_6$) δ 12.96 (brs, 1H), 9.99 (s, 1H), 8.27 (m, 1H), 7.87 (m, 1H), 7.64 (d, 1H), 7.53 (m, 2H), 7.46 (d, 1H), 7.39 (t, 1H), 7.21 (m, 1H), 7.10 (m, 1H), 7.03 (m, 1H), 6.90 (m, 1H), 6.71 (m, 1H), 6.65 (m, 1H), 4.19 (t, 2H), 3.84 (s, 3H), 3.74 (s, 3H), 2.24 (m, 2H).

EXAMPLE 38

7-(2,5-dimethoxyphenyl)-3-(3-(1-naphthyloxyl)propyl)-1H-indole-2-carboxylic acid This example was prepared by substituting 2,5-dimethoxyphenyl-boronic acid for (E)-styrylboronic acid in EXAMPLE 1D. $^1$H NMR (500 MHz, DMSO-$d_6$) δ 12.99 (brs, 1H), 10.08 (s, 1H), 8.26 (m, 1H), 7.87 (m, 1H), 7.68 (d, 1H), 7.53 (m, 2H), 7.46 (d, 1H), 7.39 (t, 1H), 7.17 (d, 1H), 7.07 (m, 2H), 6.98 (m, 1H), 6.90 (d, 1H), 6.87 (d, 1H), 4.20 (t, 2H), 3.75 (s, 3H), 3.68 (s, 3H), 2.24 (m, 2H).

EXAMPLE 39

7-(2,6-dimethoxyphenyl)-3-(3-(1-naphthyloxyl)propyl)-1H-indole-2-carboxylic acid This example was prepared by substituting 2,6-dimethoxyphenyl-boronic acid for (E)-styrylboronic acid in EXAMPLE 1D. $^1$H NMR (500 MHz, DMSO-$d_6$) δ 12.87 (brs, 1H), 10.18 (s, 1H), 8.30 (m, 1H), 7.88 (m, 1H), 7.62 (m, 1H), 7.53 (m, 2H), 7.46 (d, 1H), 7.38 (m, 2H), 7.01 (m, 2H), 6.93 (d, 1H), 6.76 (d, 2H), 4.22 (s, 2H), 3.62 (s, 6H), 2.23 (m, 2H).

EXAMPLE 40

7-(4-methoxypyridin-3-yl)-3-(3-(1-naphthyloxy)propyl)-1H-indole-2-carboxylic acid This example was prepared as a TFA salt by substituting 4-methoxypyrid-3-yl-boronic acid for (E)-styrylboronic acid in EXAMPLE 1D. $^1$H NMR (500 MHz, DMSO-$d_6$) δ 13.02 (brs, 1H), 10.94 (s, 1H), 8.37 (m, 1H), 8.24 (m, 1H), 7.88 (m, 2H), 7.70 (d, 1H), 7.52 (m, 2H), 7.45 (d, 1H), 7.38 (t, 1H), 7.19 (d, 1H), 7.07 (t, 1H), 6.94 (d, 1H), 6.89 (d, 1H), 4.19 (t, 2H), 3.93 (s, 3H), 2.23 (m, 2H).

EXAMPLE 41

7-(2-methoxypyridin-3-yl)-3-(3-(1-naphthyloxy)propyl)-1H-indole-2-carboxylic acid This example was prepared as a TFA salt by substituting 2-methoxypyrid-3-yl-boronic acid for (E)-styrylboronic acid in EXAMPLE 1D. $^1$H NMR (400 MHz, DMSO-$d_6$) δ 13.00 (brs, 1H), 10.85 (s, 1H), 8.25 (m, 2H), 7.87 (m, 1H), 7.68 (m, 2H), 7.53 (m, 2H), 7.46 (d, 1H), 7.39 (t, 1H), 7.08 (m, 3H), 6.90 (m, 1H), 4.20 (t, 2H), 3.83 (s, 3H), 2.22 (m, 2H).

EXAMPLE 42

3-(3-(1-naphthyloxyl)propyl)-7-quinolin-4-yl-1H-indole-2-carboxylic acid

This example was prepared as a TFA salt by substituting quinolin-4-ylboronic acid for (E)-styrylboronic acid in EXAMPLE 1D. $^1$H NMR (400 MHz, DMSO-$d_6$) δ 12.96 (brs, 1H), 11.01 (s, 1H), 9.06 (d, 1H), 8.25 (m, 1H), 8.18 (d, 1H), 7.86 (m, 3H), 7.64 (d, 1H), 7.47 (m, 6H), 7.22 (m, 2H), 6.92 (m, 1H), 4.23 (t, 2H), 2.27 (m, 2H).

EXAMPLE 43A ethyl 3-(3-(naphthalen-1-yloxy)propyl)-7-(4,4,5,5-tetramethyl-1,3,2-dioxaborolan-2-yl)-1H-indole-2-carboxylate A mixture of EXAMPLE 1C (1.0 g), bis(pinacolato)diboron (674 mg), potassium acetate (998 mg) and (1,1'-bis(diphenylphosphino)ferrocene)dichloropalladium(II) (81 mg) in DMF (10 mL) was heated at 60° C. overnight and concentrated. The concentrate was partitioned between dichloromethane and water. The extract washed with water and brine and dried (Na$_2$SO$_4$), filtered and concentrated. The concentrate was loaded on a silica gel cartridge and eluted with 5% ethyl acetate/hexanes.

EXAMPLE 43B

7-(4-hydroxy-2-methylphenyl)-3-(3-(1-naphthyloxy)propyl)-1H-indole-2-carboxylic acid To a mixture of EXAMPLE 43A (50 mg) and 4-bromo-3-methylphenol (22 mg) in THF (2 mL) was added tris(dibenzylideneacetone)dipalladium(0) (4.6 mg), and tri-tert-butylphosphine tetrafluoroborate (1.45 mg). The mixture was stirred at ambient temperature overnight and partitioned between ethyl acetate (150 mL) and water (50 mL). The extract was washed with brine, dried over sodium sulfate, and filtered. The filtrate was concentrated, and the concentrate was loaded on a silica gel cartridge and eluted with ethyl acetate (5%) in hexanes to provide a product which was dissolved in THF (2 mL), methanol (1 mL) and water (1 mL) and hydrolyzed with LiOH (100 mg) overnight. The mixture was acidified with 5% aqueous HCl and extracted with ethyl acetate. The exteact was washed with water and brine and dried (Na$_2$SO$_4$), filtered and concentrated. The concentrate was purified by reverse phase HPLC as described in Example 1D. $^1$H NMR (300 MHz, CDCl$_3$) δ 8.39 (d, 1H), 8.35 (d, 1H), 7.77 (d, 1H), 7.72 (dd, 1H), 7.13-7.50 (m, 6H), 6.85 (d, 1H), 6.76 (t, 2H), 4.21 (t, 2H), 3.47 (t, 2H), 2.38 (m, 2H), 2.13 (s, 3H).

EXAMPLE 44

7-(2-(4-methylpiperazin-1-yl)phenyl)-3-(3-(1-naphthyloxyl)propyl)-1H-indole-2-carboxylic acid This example was prepared as a TFA salt by substituting EXAMPLE 43A for (E)-styrylboronic acid and 1-(2-bromophenyl)-4-methylpiperazine for EXAMPLE 1C in EXAMPLE 1D. $^1$H NMR (300 MHz, DMSO-$d_6$) δ 13.10 (brs, 1H), 10.43 (s, 1H), 8.25 (m, 1H), 7.87 (m, 1H), 7.74 (d, 1H), 7.46 (m, 6H), 7.31 (dd, 1H), 7.15 (m, 3H), 6.90 (m, 1H), 4.19 (t, 2H), 3.19 (m, 4H), 2.82 (m, 2H), 2.59 (s, 3H), 2.25 (m, 2H).

EXAMPLE 45

7-(2,4-dichlorophenyl)-3-(3-(1-naphthyloxyl)propyl)-1H-indole-2-carboxylic acid

This example was prepared by substituting 2,4-dichlorophenyl-boronic acid for (E)-styrylboronic acid in EXAMPLE 1D. $^1$H NMR (500 MHz, DMSO-$d_6$) δ 13.06 (brs, 1H), 10.70 (s, 1H), 8.22 (m, 1H), 7.87 (m, 1H), 7.71 (d, 1H), 7.62 (m, 2H), 7.53 (m, 3H), 7.45 (d, 1H), 7.38 (t, 1H), 7.22 (d, 1H), 7.09 (t, 1H), 6.89 (d, 1H), 4.19 (t, 2H), 2.23 (m, 2H).

EXAMPLE 46

7-(4-carboxy-2-methylphenyl)-3-(3-(1-naphthyloxyl)propyl)-1H-indole-2-carboxylic acid This example was prepared by substituting 4-(methoxycarbonyl)-2-methylphenylboronic acid for (E)-styrylboronic acid in EXAMPLE 1D. $^1$H NMR (500 MHz, DMSO-$d_6$) δ 13.02 (brs, 2H), 10.87 (s, 1H), 8.25 (m, 1H), 7.86 (m, 3H), 7.73 (d, 1H), 7.53 (m, 2H), 7.46 (d, 1H), 7.39 (m, 1H), 7.32 (d, 1H), 7.07 (m, 2H), 6.91 (d, 1H), 4.21 (t, 2H), 2.24 (m, 2H), 2.10 (s, 3H).

EXAMPLE 47A ethyl 3-(3-hydroxypropyl)-7-(2-methoxyphenyl)-1H-indole-2-carboxylate A mixture of EXAMPLE 1B (456 mg) and 2-methoxyphenylboronic acid (182.4 mg) in THF (10 mL), tris(dibenzylideneacetone)dipalladium(0) (46 mg), tri-tert-butylphosphine tetrafluoroborate (15 mg) and CsF (456 mg) was stirred at ambient temperature, diluted with ethyl acetate (200 mL), washed with water and brine, and dried (Na$_2$SO$_4$), filtered and concentrated. The concentrate was purified by flash column chromatography on silica gel with 20% ethyl acetate in hexanes.

EXAMPLE 47B 7-(2-methoxyphenyl)-3-(3-((2-methyl-1-naphthyl)oxy)propyl)-1H-indole-2-carboxylic acid To a mixture of EXAMPLE 47A (71 mg), 2-methyl-1-naphthol (35 mg), triphenylphosphine (58 mg) in THF (2 mL) and di-tert-butyl azodicarboxylate (55 mg) was stirred at ambient temperature overnight and partitioned between ethyl acetate (150 mL) and water (50 mL). The organic layer was washed with brine and a dried (Na$_2$SO$_4$), filtered and concentrated. The concentrate was purified by flash chromatography on silica gel with 5% ethyl acetate in hexanes to provide an intermediate which was dissolved in THF (2 mL), methanol (1 mL) and water (1 mL) and hydrolyzed with LiOH (100 mg) overnight. The mixture was acidified with 5% HCl and extracted with ethyl acetate. The extract was washed with water and brine and dried (Na$_2$SO$_4$), filtered and concentrated. The concentrate was purified by reverse phase HPLC (C-18, 30 to 100% acetonitrile/water/0.1% TFA). $^1$H NMR (300 MHz, CDCl$_3$) δ 8.74 (s, 1H), 8.12 (dd, 1H), 7.82 (d, 1H), 7.77 (d, 1H), 7.52 (d, 1H), 7.36-7.47 (m, 5H), 7.27 (d, 1H), 7.09 (t, 2H), 4.10 (t, 2H), 3.83 (s, 3H), 3.48 (t, 2H), 2.46 (s, 3H), 2.38 (m, 2H).

EXAMPLE 48

7-(4-fluoro-2-isopropoxyphenyl)-3-(3-(1-naphthyloxy)propyl)-1H-indole-2-carboxylic acid This example was prepared by substituting 4-fluoro-2-isopropoxyphenylboronic acid for (E)-styrylboronic acid in EXAMPLE 1D. $^1$H NMR (300 MHz, DMSO-$d_6$) δ 12.98 (brs, 1H), 10.03 (s, 1H), 8.24 (m, 1H), 7.87 (m, 1H), 7.68 (d, 1H), 7.43 (m, 5H), 7.15 (d, 1H), 7.04 (m, 2H), 6.86 (m, 2H), 4.66 (m, 1H), 4.18 (t, 2H), 2.23 (m, 2H), 1.14 (s, 3H), 1.12 (s, 3H).

EXAMPLE 49

7-(2-ethoxy-1-naphthyl)-3-(3-(1-naphthyloxy)propyl)-1H-indole-2-carboxylic acid

This example was prepared by substituting 2-ethoxynaphthalen-1-ylboronic acid for (E)-styrylboronic acid in EXAMPLE 1D. $^1$H NMR (300 MHz, DMSO-$d_6$) δ 12.81 (brs, 1H), 10.42 (brs, 1H), 8.29 (m, 1H), 8.00 (d, 1H), 7.89 (m, 2H), 7.75 (m, 1H), 7.41 (m, 7H), 7.13 (m, 3H), 6.91 (m, 1H), 4.24 (t, 2H), 4.10 (q, 2H), 3.39 (t, 2H), 2.27 (m, 2H), 1.02 (m, 3H).

EXAMPLE 50

7-(4-amino-2-methylphenyl)-3-(3-(1-naphthyloxy)propyl)-1H-indole-2-carboxylic acid This example was prepared by substituting 4-bromo-3-methylaniline for 4-bromo-3-methylphenol in EXAMPLE 43B. $^1$H NMR (300 MHz, DMSO-$d_6$) δ 10.48 (s, 1H), 8.25 (dd, 1H), 7.88 (dd, 1H), 7.71 (d, 1H), 7.37-7.57 (m, 6H), 7.27 (d, 1H), 7.09 (m, 3H), 6.92 (d, 1H), 4.21 (t, 2H), 2.26 (m, 2H), 2.01 (s, 3H).

EXAMPLE 51A 4-bromo-N-(2-(dimethylamino)ethyl)-3-methylbenzamide

A mixture of 4-bromo-3-methylbenzoic acid (430 mg), N,N-dimethylethylenediamine (180 mg), 1-ethyl-3-(3-(dimethylamino)propyl)carbodiimide hydrochloride (600 mg) and 4-dimethylaminopyridine (244 mg) in dichloromethane (20 mL) was stirred at ambient temperature for 4 hours, diluted with ethyl acetate (200 mL), washed with water and brine, and dried (Na$_2$SO$_4$), filtered and concentrated. The concentrate was purified by flash column chromatography with 10% ethyl acetate in ammonia saturated dichloromethane.

EXAMPLE 51B 7-(4-(((2-(dimethylamino)ethyl)amino)carbonyl)-2-methylphenyl)-3-(3-(1-naphthyloxyl)propyl)-1H-indole-2-carboxylic acid This example was prepared as a TFA salt by substituting EXAMPLE 51A for 4-bromo-3-methylphenol in EXAMPLE 43B. $^1$H NMR (300 MHz, DMSO-$d_6$) δ 10.65 (s, 1H), 9.32

(m, 1H), 8.69 (t, 1H), 8.25 (dd, 1H), 7.88 (dd, 1H), 7.72 (dt, 1H), 7.33-7.57 (m, 6H), 7.06 (dd, 2H), 6.91 (d, 1H), 4.21 (t, 2H), 3.63 (m, 2H), 2.50 (s, 6H), 2.26 (m, 2H), 2.12 (s, 3H).

EXAMPLE 52

7-(4-chloro-2-methylphenyl)-3-(3-(1-naphthyloxyl) propyl)-1H-indole-2-carboxylic acid This example was prepared by substituting 4-chloro-2-methylphenylboronic acid for (E)-styrylboronic acid in EXAMPLE 1D. $^1$H NMR (500 MHz, DMSO-$d_6$) δ 12.93 (brs, 1H), 10.88 (s, 1H), 8.25 (m, 1H), 7.87 (m, 1H), 7.70 (d, 1H), 7.46 (m, 5H), 7.30 (m, 1H), 7.21 (d, 1H), 7.05 (m, 2H), 6.90 (d, 1H), 4.20 (t, 2H), 2.23 (m, 2H), 2.03 (s, 3H).

EXAMPLE 53

7-(2,3-dichlorphenyl)-3-(3-(1-naphthyloxyl)propyl)-1H-indole-2-carboxylic acid

This example was prepared by substituting 2,3-dichlorophenyl-boronic acid for (E)-styrylboronic acid in EXAMPLE 1D. $^1$H NMR (500 MHz, DMSO-$d_6$) δ 12.98 (brs, 1H), 11.20 (s, 1H), 8.26 (m, 1H), 7.87 (m, 1H), 7.74 (m, 1H), 7.68 (m, 1H), 7.53 (m, 2H), 7.39 (m, 4H), 7.06 (m, 2H), 6.91 (d, 1H), 4.21 (t, 2H), 2.24 (m, 2H).

EXAMPLE 54

3-(3-(1-naphthyloxyl)propyl)-7-(2-(trifluoromethyl) phenyl)-1H-indole-2-carboxylic acid This example was prepared by substituting 2-trifluoromethyl-phenylboronic acid for (E)-styrylboronic acid in EXAMPLE 1D. $^1$H NMR (500 MHz, DMSO-$d_6$) δ 12.93 (brs, 1H), 11.04 (s, 1H), 8.27 (m, 1H), 7.86 (m, 2H), 7.71 (m, 2H), 7.64 (t, 1H), 7.53 (m, 2H), 7.46 (d, 1H), 7.39 (t, 2H), 7.04 (t, 2H), 6.91 (d, 1H), 4.21 (t, 2H), 2.24 (m, 2H).

EXAMPLE 55

7-(3-chloro-2-fluorophenyl)-3-(3-(1-naphthyloxyl) propyl)-1H-indole-2-carboxylic acid This example was prepared by substituting 3-chloro-2-fluoro-phenylboronic acid for (E)-styrylboronic acid in EXAMPLE 1D. $^1$H NMR (500 MHz, DMSO-$d_6$) δ 13.02 (brs, 1H), 11.28 (s, 1H), 8.26 (m, 1H), 7.87 (m, 1H), 7.76 (d, 1H), 7.62 (m, 1H), 7.53 (m, 2H), 7.41 (m, 3H), 7.30 (t, 1H), 7.12 (m, 2H), 6.90 (d, 1H), 4.20 (t, 2H), 3.37 (t, 2H), 2.23 (m, 2H).

EXAMPLE 56

7-(2,3-difluorophenyl)-3-(3-(1-naphthyloxy)propyl)-1H-indole-2-carboxylic acid

This example was prepared by substituting 2,3-difluoro-phenylboronic acid for (E)-styrylboronic acid in EXAMPLE 1D. $^1$H NMR (500 MHz, DMSO-$d_6$) δ 13.04 (brs, 1H), 11.24 (s, 1H), 8.26 (d, 1H), 7.87 (d, 1H), 7.77 (d, 1H), 7.47 (m, 5H), 7.28 (m, 2H), 7.19 (m, 1H), 7.09 (t, 1H), 6.90 (d, 1H), 4.20 (t, 2H), 3.38 (t, 2H), 2.24 (m, 2H).

EXAMPLE 57

7-cyclopent-1-en-1-yl-3-(3-(1-naphthyloxy)propyl)-1H-indole-2-carboxylic acid

This example was prepared by substituting 1-cyclopentene-boronic acid for (E)-styrylboronic acid in EXAMPLE 1D. $^1$H NMR (500 MHz, DMSO-$d_6$) δ 13.10 (brs, 1H), 10.12 (s, 1H), 8.22 (m, 1H), 7.85 (m, 1H), 7.60 (d, 1H), 7.51 (m, 2H), 7.45 (d, 1H), 7.37 (t, 1H), 7.17 (d, 1H), 6.98 (t, 1H), 6.87 (d, 1H), 6.33 (t, 1H), 4.16 (t, 2H), 2.79 (m, 2H), 2.60 (m, 2H), 2.21 (m, 2H), 1.98 (m, 2H).

EXAMPLE 58

7-cyclohex-1-en-1-yl-3-(3-(1-naphthyloxy)propyl)-1H-indole-2-carboxylic acid

This example was prepared by substituting 1-cyclohexene-boronic acid for (E)-styrylboronic acid in EXAMPLE 1D. $^1$H NMR (500 MHz, DMSO-$d_6$) δ 13.03 (brs, 1H), 10.44 (s, 1H), 8.22 (m, 1H), 7.86 (m, 1H), 7.46 (m, 5H), 7.05 (m, 1H), 6.95 (t, 1H), 6.88 (d, 1H), 5.96 (m, 1H), 4.17 (t, 2H), 2.38 (m, 2H), 2.20 (m, 4H), 1.73 (m, 4H).

EXAMPLE 59A 2-phenylcyclohex-1-enyl trifluoromethanesulfonate

2-Phenylcyclohexanone (0.2 g) was added to the mixture of 60% oily NaH (0.17 g) in DMF (3 mL) at 0° C. The mixture was warmed to room temperature and stirred for 30 minutes, treated with 1,1,1-trifluoro-N-phenyl-N-(trifluoromethylsulfonyl)methanesulfonamide (0.7 g), stirred for 6 hours and treated with water (20 mL) and ethyl acetate (50 mL). The extract was washed with brine (20 mL) and water (20 mL), and dried (Na$_2$SO$_4$), filtered and concentrated. The concentrate was purified by flash chromotography on silica gel with 0-30% ethyl acetate/hexane.

EXAMPLE 59B 3-(3-(1-naphthyloxy)propyl)-7-(2-phenylcyclohex-1-en-1-yl)-1H-indole-2-carboxylic acid This example was prepared by substituting EXAMPLE 43A for (E)-styrylboronic acid and EXAMPLE 59A for EXAMPLE 1C in EXAMPLE 1D. $^1$H NMR (500 MHz, DMSO-$d_6$) δ 12.92 (brs, 1H), 10.69 (s, 1H), 8.23 (m, 1H), 7.86 (m, 1H), 7.51 (m, 2H), 7.44 (d, 1H), 7.38 (m, 2H), 6.89 (m, 8H), 4.11 (t, 2H), 3.24 (t, 2H), 2.41 (m, 4H), 2.15 (m, 2H), 1.86 (m, 4H).

EXAMPLE 60

7-(2-cyclohexylphenyl)-3-(3-(1-naphthyloxy)propyl)-1H-indole-2-carboxylic acid

This example was prepared by substituting EXAMPLE 43A for (E)-styrylboronic acid and 1-bromo-2-cyclohexyl-benzene for EXAMPLE 1C in EXAMPLE 1D. $^1$H NMR (500 MHz, DMSO-$d_6$) δ 12.95 (brs, 1H), 10.28 (s, 1H), 8.26 (m, 1H), 7.87 (m, 1H), 7.70 (d, 1H), 7.53 (m, 2H), 7.41 (m, 4H), 7.24 (t, 1H), 7.17 (d, 1H), 7.07 (t, 1H), 7.00 (d, 1H), 6.89 (d, 1H), 4.20 (t, 2H), 2.29 (m, 4H), 1.55 (m, 7H), 1.18 (m, 2H), 0.86 (m, 2H).

EXAMPLE 61

7-(6-carboxypyridin-3-yl)-3-(3-(1-naphthyloxyl)propyl)-1H-indole-2-carboxylic acid This example was prepared by substituting methyl 5-bromopicolinate for 4-bromo-3-methylphenol in EXAMPLE 43B. $^1$H NMR (300 MHz, DMSO-d$_6$) δ 11.30 (s, 1H), 8.88 (s, 1H), 8.22 (dd, 1H), 8.15 (s, 1H), 7.87 (dd, 1H), 7.79 (d, 1H), 7.29-7.56 (m, 6H), 7.13 (t, 1H), 6.90 (d, 1H), 4.19 (t, 2H), 2.26 (m, 2H).

EXAMPLE 62

7-(3-methyl-5-nitropyridin-2-yl)-3-(3-(1-naphthyloxy)propyl)-1H-indole-2-carboxylic acid This example was prepared by substituting 2-bromo-3-methyl-5-nitropyridine for 4-bromo-3-methylphenol in EXAMPLE 43B. $^1$H NMR (300 MHz, CDCl$_3$) δ 9.90 (m, 1H), 9.43 (d, 1H), 8.52 (d, 1H), 8.39 (d, 1H), 7.95 (m, 1H), 7.80 (dd, 1H), 7.68 (dd, 1H), 7.13-7.60 (m, 8H), 7.00 (d, 1H), 6.68 (t, 2H), 4.21 (t, 2H), 3.10 (t, 2H), 2.67 (s, 3H), 2.18 (m, 2H).

EXAMPLE 63

7-(2,3-dihydro-1,4-benzodioxin-6-yl)-3-(3-(1-naphthyloxy)propyl)-1H-indole-2-carboxylic acid This example was prepared by substituting EXAMPLE 1C for 4-bromo-3-methylphenol and 2,3-dihydrobenzo(b)(1,4)dioxin-6-ylboronic acid for EXAMPLE 43A in EXAMPLE 43B. $^1$H NMR (300 MHz, CDCl$_3$) δ 8.87 (s, 1H), 8.35 (dd, 1H), 7.76 (dd, 1H), 7.70 (dd, 1H), 7.30-7.49 (m, 5H), 7.15 (m, 2H), 7.02 (d, 1H), 6.75 (d, 1H), 4.33 (s, 4H), 4.21 (t, 2H), 3.84 (t, 2H), 2.38 (m, 2H).

EXAMPLE 64

7-(1,3-benzodioxol-5-yl)-3-(3-(1-naphthyloxy)propyl)-1H-indole-2-carboxylic acid This example was prepared by substituting EXAMPLE 1C for 4-bromo-3-methylphenol and benzo(d)(1,3)dioxol-5-ylboronic acid for EXAMPLE 43A in EXAMPLE 43B.
$^1$H NMR (300 MHz, CDCl$_3$) δ 8.84 (s, 1H), 8.35 (dd, 1H), 7.78 (dd, 1H), 7.70 (d, 1H), 7.30-7.49 (m, 5H), 7.17 (d, 2H), 7.09 (s, 1H), 6.97 (d, 1H), 6.75 (dd, 1H), 6.05 (s, 2H), 4.21 (t, 2H), 3.49 (t, 2H), 2.38 (m, 2H).

EXAMPLE 65A ethyl 3-(3-(4-chloronaphthalen-1-yloxy)propyl)-7-(2-methoxyphenyl)-1H-indole-2-carboxylate This example was prepared by substituting EXAMPLE 47A for EXAMPLE 1B and 4-chloro-1-naphthol for 1-naphthol in EXAMPLE 1D.

EXAMPLE 65B 3-(3-(4-chloronaphthalen-1-yloxy)propyl)-7-(2-methoxyphenyl)-1H-indole-2-carboxylic acid A mixture of EXAMPLE 65A (70 mg) in THF (2 mL), methanol (1 mL) and water (1 mL) was treated with LiOH.H$_2$O (100 mg) and stirred at ambient temperature overnight. The mixture was acidified with 5% aqueous HCl and extracted with ethyl acetate. The extract was washed with water, brine and dried (Na$_2$SO$_4$), filtered and concentrated. The concentrate was dissolved in 1:1DMSO/methanol and purified by reverse phase HPLC (C18, 20 to 100% acetonitrile/water/0.1% TFA). $^1$H NMR (300 MHz, CDCl$_3$) δ 8.72 (s, 1H), 8.38 (dd, 1H), 8.15 (dd, 1H), 7.72 (d, 1H), 7.35-7.57 (m, 5H), 7.08-7.21 (m, 3H), 6.65 (d, 1H), 4.18 (t, 2H), 3.82 (s, 3H), 3.47 (t, 2H), 2.37 (m, 2H).

EXAMPLE 66A ethyl 3-(3-(2-bromophenoxyl)propyl)-7-(2-methoxyphenyl)-1H-indole-2-carboxylate This example was prepared by substituting EXAMPLE 47A for EXAMPLE 1B and 2-bromophenol for 1-naphthol in EXAMPLE 1C.

EXAMPLE 66B 3-(3-(2-bromophenoxyl)propyl)-7-(2-methoxyphenyl)-1H-indole-2-carboxylic acid This example was prepared by substituting EXAMPLE 66A for EXAMPLE 65A in EXAMPLE 65B. $^1$H NMR (300 MHz, CDCl$_3$) δ 8.72 (s, 1H), 7.79 (d, 1H), 7.55 (dd, 1H), 7.43 (t, 1H), 7.35 (dd, 1H), 7.22 (m, 3H), 7.10 (d, 1H), 6.85 (d, 1H), 6.77 (d, 1H), 4.11 (t, 2H), 3.84 (s, 3H), 3.43 (t, 2H), 2.29 (m, 2H).

EXAMPLE 67A 4-bromo-3-methyl-N-(2-morpholinoethyl)benzamide

This example was prepared by substituting 2-morpholinoethanamine for N1,N1-dimethylethane-1,2-diamine in EXAMPLE 51A.

EXAMPLE 67B 7-(2-methyl-4-(((2-morpholin-4-ylethyl)amino)carbonyl)phenyl)-3-(3-(1-naphthyloxyl)propyl)-1H-indole-2-carboxylic acid This example was prepared as a TFA salt by substituting EXAMPLE 67A for 4-bromo-3-methylphenol in EXAMPLE 43B. $^1$H NMR (300 MHz, DMSO-d$_6$) δ 12.94 (m, 1H), 10.68 (s, 1H), 9.82 (m, 1H), 8.74 (m, 1H), 8.24 (dd, 2H), 7.88 (dd, 1H), 7.82 (d, 1H), 7.72 (t, 1H), 7.34-7.55 (m, 5H), 7.07 (m, 2H), 6.91 (d, 1H), 4.11 (t, 2H), 4.00 (m, 2H), 3.17-3.67 (m, 8H), 2.26 (m, 2H), 2.12 (S, 3H).

EXAMPLE 68

7-(3-methylquinolin-2-yl)-3-(3-(1-naphthyloxyl)propyl)-1H-indole-2-carboxylic acid This example was prepared as a TFA salt by substituting 2-bromo-3-methyl-quinoline for 4-bromo-3-methylphenol in EXAMPLE 43B. ¹H NMR (300 MHz, DMSO-$d_6$) δ 13.05 (m, 1H), 11.19 (m, 1H), 8.42 (m, 1H), 8.28 (dd, 1H), 8.05 (d, 1H), 7.37-7.89 (m, 9H), 7.16 (t, 1H), 6.91 (d, 1H), 4.22 (t, 2H), 2.36 (s, 3H), 2.26 (m, 2H).

EXAMPLE 69

7-(4-(hydroxymethyl)phenyl)-3-(3-(1-naphthyloxyl) propyl)-1H-indole-2-carboxylic acid This example was prepared by substituting 4-(hydroxymethyl)-phenylboronic acid for EXAMPLE 43A and EXAMPLE 1C for 4-bromo-3-methylphenol in EXAMPLE 43B. ¹H NMR (300 MHz, DMSO-$d_6$) δ 13.05 (m, 1H), 10.28 (m, 1H), 8.22 (dd, 1H), 7.87 (dd, 1H), 7.68 (d, 1H), 7.36-7.61 (m, 6H), 7.26 (d, 1H), 7.09 (t, 1H), 6.90 (d, 1H), 5.25 (t, 1H), 4.59 (d, 2H), 4.19 (t, 2H), 2.26 (m, 2H).

EXAMPLE 70

7-(3-(hydroxymethyl)phenyl)-3-(3-(1-naphthyloxy) propyl)-1H-indole-2-carboxylic acid This example was prepared by substituting 3-(hydroxymethyl)-phenylboronic acid for EXAMPLE 43A and EXAMPLE 1C for 4-bromo-3-methylphenol in EXAMPLE 43B. ¹H NMR (300 MHz, DMSO-$d_6$) δ 13.05 (m, 1H), 10.26 (m, 1H), 8.22 (dd, 1H), 7.87 (dd, 1H), 7.69 (d, 1H), 7.36-7.61 (m, 8H), 7.26 (d, 1H), 7.09 (t, 1H), 6.90 (d, 1H), 5.22 (t, 1H), 4.59 (d, 2H), 4.20 (t, 2H), 2.25 (m, 2H).

EXAMPLE 71A ethyl 7-bromo-5-chloro-3-(3-ethoxy-3-oxopropyl)-1H-indole-2-carboxylate This example was prepared by substituting 2-bromo-4-chloroaniline for 2-bromoaniline in EXAMPLE 1A.

EXAMPLE 71B ethyl 7-bromo-5-chloro-3-(3-hydroxypropyl)-1H-indole-2-carboxylate This example was prepared by substituting EXAMPLE 71A for EXAMPLE 1A in EXAMPLE 1B.

EXAMPLE 71C ethyl 7-bromo-5-chloro-3-(3-(naphthalen-1-yloxy) propyl)-1H-indole-2-carboxylate This example was prepared by substituting EXAMPLE 71B for EXAMPLE 1B in EXAMPLE 1C.

EXAMPLE 71D 5-chloro-7-(2-methylphenyl)-3-(3-(1-naphthyloxyl) propyl)-1H-indole-2-carboxylic acid This example was prepared by substituting EXAMPLE 71C for EXAMPLE 1C and 2-methylphenylboronic acid for (E)-styrylboronic acid in EXAMPLE 1D. ¹H NMR (400 MHz, DMSO-$d_6$) δ 10.92 (s, 1H), 8.27 (m, 1H), 7.87 (m, 1H), 7.74 (d, 1H), 7.51 (m, 3H), 7.30 (m, 5H), 6.99 (d, 1H), 6.91 (d, 1H), 4.20 (t, 2H), 2.22 (m, 2H), 2.05 (s, 3H).

EXAMPLE 72

7-(3-methylpyridin-2-yl)-3-(3-(1-naphthyloxy)propyl)-1H-indole-2-carboxylic acid This example was prepared as a TFA salt by substituting 2-bromo-3-methylpyridine for 4-bromo-3-methylphenol in EXAMPLE 43B. ¹H NMR (300 MHz, DMSO-$d_6$) δ 11.20 (s, 1H), 8.71 (d, 1H), 8.26 (m, 2H), 7.88 (m, 3H), 7.37-7.56 (m, 5H), 7.17 (t, 1H), 6.90 (d, 1H), 4.20 (t, 2H), 2.27 (s, 3H), 2.24 (m, 2H).

EXAMPLE 73

7-(2,6-dimethylpyridin-3-yl)-3-(3-(1-naphthyloxyl) propyl)-1H-indole-2-carboxylic acid This example was prepared as a TFA salt by substituting 3-bromo-2,6-dimethylpyridine for 4-bromo-3-methylphenol in EXAMPLE 43B. ¹H NMR (300 MHz, DMSO-$d_6$) δ 13.10 (m, 1H), 11.31 (s, 1H), 8.23 (m, 2H), 7.88 (m, 3H), 7.36-7.54 (m, 4H), 7.15 (t, 2H), 6.90 (d, 1H), 4.20 (t, 2H), 2.76 (s, 3H), 2.36 (s, 3H), 2.24 (m, 2H).

EXAMPLE 74

7-(6-amino-2-methylpyridin-3-yl)-3-(3-(1-naphthyloxy)propyl)-1H-indole-2-carboxylic acid This example was prepared TFA salt by substituting 6-amino-3-bromo-2-methylpyridine for 4-bromo-3-methylphenol in EXAMPLE 43B. ¹H NMR (300 MHz, DMSO-$d_6$) δ 13.72 (m, 1H), 13.05 (m, 1H), 11.24 (s, 1H), 8.24 (dd, 1H), 7.88 (dd, 1H), 7.73 (m, 4H), 7.36-7.56 (m, 4H), 7.10 (d, 2H), 6.88 (t, 2H), 4.19 (t, 2H), 2.25 (m, 2H), 2.13 (s, 3H).

EXAMPLE 75

3-(3-(1-naphthyloxy)propyl)-7-(2-piperazin-1-ylphenyl)-1H-indole-2-carboxylic acid This example was prepared as a TFA salt by substituting EXAMPLE 43A for (E)-styrylboronic acid and 1-(2-bromophenyl)-piperazine for EXAMPLE 1C in EXAMPLE 1D. ¹H NMR (300 MHz, DMSO-$d_6$) δ 13.12 (brs, 1H), 10.36 (s, 1H), 8.42 (brs, 2H), 8.25 (m, 1H), 7.88 (m, 1H), 7.75 (d, 1H), 7.46 (m, 6H), 7.29 (m, 1H), 7.15 (m, 3H), 6.89 (m, 1H), 4.20 (t, 2H), 2.96 (m, 4H), 2.25 (m, 2H).

EXAMPLE 76A ethyl 7-bromo-1-(methoxymethyl)-3-(3-(naphthalen-1-yloxy)propyl)-1H-indole-2-carboxylate To an ice bath cooled mixture of EXAMPLE 1C (2.0 g) in THF (20 mL) was added 60% oily NaH (265 mg). The mixture was stirred for 30 minutes before adding chloromethyl methyl ether (0.54 mL). The mixture was stirred for 3 hours and overnight at room temperature, quenched by adding saturated NH$_4$Cl mixture and extracted with diethylether. The extract was washed with water and brine and dried (Na$_2$SO$_4$),

EXAMPLE 76B 7-(4-(3-chlorophenyl)piperazin-1-yl)-3-(3-(1-naph-thyloxyl)propyl)-1H-indole-2-carboxylic acid A mixture of EXAMPLE 76A (100 mg), 1-(3-chlorophenyl)piperazine (48 mg), tris(dibenzylideneacetone)dipalladium(0) (9.2 mg), 2,2'-bis(diphenylphosphino)-1,1'-binaphthyl (13.1 mg) and $Cs_2CO_3$ (195 mg) in toluene (5 mL) was heated at reflux overnight. The mixture was partitioned between ethyl acetate (200 mL) and water (50 mL). The organic layer was washed with brine and dried ($Na_2SO_4$), filtered and concentrated. The concentrate was purified by column chromatography on silica gel with 1:4ethyl acetate: hexanes to provide the ethyl ester. The ester was treated with 2M HCl in diethylether (5 mL), concentrated, and treated with $LiOH.H_2O$ (100 mg) in 2/1/2 THF/methanol/water, stirred overnight at room temperature and concentrated. The product was purified by reverse phase HPLC (C-18, 20 to 100% acetonitrile/water/0.1% TFA). $^1$H NMR (300 MHz, DMSO-$d_6$) δ 12.98 (m, 1H), 10.90 (s, 1H), 8.24 (dd, 1H), 7.86 (dd, 1H), 7.35-7.54 (m, 5H), 7.25 (t, 1H), 6.82-7.03 (m, 6H), 4.18 (t, 2H), 3.45 (m, 4H), 3.15 (m, 4H), 2.20 (m, 2H).

EXAMPLE 77A ethyl 7-bromo-1-(2-morpholino-2-oxoethyl)-3-(3-(naphthalen-1-yloxy)propyl)-1H-indole-2-carboxylate To a mixture of 60% oily NaH (0.03 g) in DMF (5 mL) was added EXAMPLE 1C (0.25 g) in DMF (10 mL). After stirring at room temperature for 30 minutes, 2-chloro-1-morpholinoethanone (0.1 g) was added, and the mixture was stirred for three hours. Water (20 mL) and dichloromethane were added, and the organic layer was washed with water and brine and concentrated. The concentrate was purified by preparative reverse phase HPLC (Zorbax SB, C-18 with 30%-100% acetonitrile/water/0.1% TFA).

EXAMPLE 77B ethyl 7-bromo-1-(2-morpholinoethyl)-3-(3-(naphthalen-1-yloxy)propyl)-1H-indole-2-carboxylate To a mixture of EXAMPLE 77A (0.15 g) in THF (10 mL) was added 1M $BH_3.THF$ (1.8 mL). The mixture was stirred at room temperature for 16 hours, quenched with methanol (5 mL) and concentrated. The concentrate was dissolved in ethanol (40 mL) and treated with 12N HCl (0.5 mL). After stirring for three hours, the mixture was concentrated, and the concentrate was purified by preparative reverse phase HPLC (Zorbax SB, C-18, 30% to 100% acetonitrile/water/0.1% TFA).

EXAMPLE 77C 7-(2-methylphenyl)-1-(2-morpholin-4-ylethyl)-3-(3-(1-naphthyloxyl)propyl)-1H-indole-2-carboxylic acid This example was prepared as a TFA salt by substituting EXAMPLE 77B for EXAMPLE 1C and 2-methylphenylboronic acid for (E)-styrylboronic acid in EXAMPLE 1D. $^1$H NMR (500 MHz, DMSO-$d_6$) δ 8.23 (m, 1H), 7.88 (m, 1H), 7.81 (d, 1H), 7.45 (m, 8H), 7.15 (t, 1H), 7.01 (d, 1H), 6.92 (d, 1H), 4.64 (m, 1H), 4.24 (t, 2H), 4.02 (m, 1H), 3.61 (m, 4H), 2.23 (m, 2H), 2.00 (s, 3H).

EXAMPLE 78A ethyl 7-bromo-3-(3-(5,6,7,8-tetrahydronaphthalen-1-yloxy)propyl)-1H-indole-2-carboxylate This example was prepared by substituting 5,6,7,8-tetrahydronaphthalen-1-ol for 1-naphthol in EXAMPLE 1C.

EXAMPLE 78B 7-(2-methylphenyl)-3-(3-(5,6,7,8-tetrahydronaphthalen-1-yloxy)propyl)-1H-indole-2-carboxylic This example was prepared by substituting EXAMPLE 78A for EXAMPLE 1C and 2-methylphenylboronic acid for (E)-styrylboronic acid in EXAMPLE 1D. $^1$H NMR (500 MHz, DMSO-$d_6$) δ 10.41 (brs, 1H), 7.65 (m, 1H), 7.27 (m, 4H), 7.11 (t, 1H), 7.04 (d, 1H), 6.99 (t, 1H), 6.64 (t, 2H), 3.98 (t, 2H), 3.25 (t, 2H), 2.66 (m, 4H), 2.08 (m, 5H), 1.71 (m, 4H).

EXAMPLE 79

5-chloro-3-(3-(1-naphthyloxyl)propyl)-7-phenyl-1H-indole-2-carboxylic acid

This example was prepared by substituting EXAMPLE 71C for EXAMPLE 1C and phenylboronic acid for (E)-styrylboronic acid in EXAMPLE 1D. $^1$H NMR (500 MHz, DMSO-$d_6$) δ 10.41 (s, 1H), 7.65 (m, 1H), 7.27 (m, 4H), 7.11 (t, 1H), 7.04 (d, 1H), 6.99 (t, 1H), 6.64 (t, 2H), 3.98 (t, 2H), 3.25 (t, 2H), 2.66 (m, 4H), 2.08 (m, 5H), 1.71 (m, 4H).

EXAMPLE 80

5-chloro-7-(4-chloro-2-methylphenyl)-3-(3-(1-naphthyloxy)propyl)-1H-indole-2-carboxylic acid This example was prepared by substituting EXAMPLE 71C for EXAMPLE 1C and 4-chloro-2-methylphenylboronic acid for (E)-styrylboronic acid in EXAMPLE 1D. $^1$H NMR (500 MHz, DMSO-$d_6$) δ 11.24 (s, 1H), 8.26 (m, 1H), 7.87 (m, 1H), 7.75 (d, 1H), 7.46 (m, 5H), 7.31 (m, 1H), 7.21 (d, 1H), 7.00 (d, 1H), 6.91 (d, 1H), 4.19 (t, 2H), 2.21 (m, 2H), 2.03 (s, 3H).

EXAMPLE 81

5-chloro-7-cyclopent-1-en-1-yl-3-(3-(1-naphthyloxyl)propyl)-1H-indole-2-carboxylic acid This example was prepared by substituting EXAMPLE 71C for EXAMPLE 1C and 1-cyclopenteneboronic acid for (E)-styrylboronic acid in EXAMPLE 1D. $^1$H NMR (500 MHz, DMSO-$d_6$) δ 10.49 (s, 1H), 8.22 (m, 1H), 7.86 (m, 1H), 7.62 (d, 1H), 7.49 (m, 3H), 7.38 (t, 1H), 7.09 (d, 1H), 6.87 (d, 1H), 6.39 (m, 1H), 4.15 (t, 2H), 2.77 (m, 2H), 2.59 (m, 2H), 2.19 (m, 2H), 1.98 (m, 2H).

EXAMPLE 82

7-(3,5-dichloropyridin-2-yl)-3-(3-(1-naphthyloxyl)propyl)-1H-indole-2-carboxylic acid This example was prepared as a TFA salt by substituting 2-bromo-3,5-dichloropyridine for 4-bromo-3-methylphenol in EXAMPLE 43B. $^1$H NMR (300 MHz, DMSO-d$_6$) δ 13.05 (m, 1H), 11.10 (s, 1H), 8.70 (s, 1H), 8.35 (s, 1H), 8.26 (dd, 1H), 7.87 (dd, 1H), 7.79 (d, 1H), 7.53 (m, 2H), 7.40 (d, 1H), 7.36 (t, 1H), 7.30 (d, 1H), 7.09 (t, 1H), 6.90 (d, 1H), 4.20 (t, 2H), 3.35 (m, 2H), 2.24 (m, 2H).

EXAMPLE 83

7-(5-(aminocarbonyl)pyridin-2-yl)-3-(3-(1-naphthyloxyl)propyl)-1H-indole-2-carboxylic acid This example was prepared as a TFA salt by substituting 6-bromonicotinamide for 4-bromo-3-methylphenol in EXAMPLE 43B. $^1$H NMR (300 MHz, DMSO-d$_6$) δ 13.30 (m, 1H), 11.47 (s, 1H), 9.27 (s, 1H), 8.36 (s, 2H), 8.20 (d, 2H), 8.13 (d, 1H), 7.87 (t, 2H), 7.63 (s, 1H), 7.50 (m, 3H), 7.37 (t, 1H), 7.18 (t, 1H), 6.88 (d, 1H), 4.20 (t, 2H), 3.39 (m, 2H), 2.27 (m, 2H).

EXAMPLE 84

7-(3-chloro-5-(trifluoromethyl)pyridin-2-yl)-3-(3-(1-naphthyloxyl)propyl)-1H-indole-2-carboxylic acid This example was prepared as a TFA salt by substituting 2-bromo-3-chloro-5-trifluoromethylpyridine for 4-bromo-3-methylphenol in EXAMPLE 43B. $^1$H NMR (300 MHz, DMSO-d$_6$) δ 13.10 (m, 1H), 11.17 (s, 1H), 9.04 (s, 1H), 8.57 (s, 1H), 8.26 (m, 1H), 7.85 (m, 2H), 7.36-7.57 (m, 5H), 7.11 (t, 1H), 6.89 (d, 1H), 4.20 (t, 2H), 3.39 (m, 2H), 2.25 (m, 2H).

EXAMPLE 85

7-(5-amino-2-(trifluoromethoxy)phenyl)-3-(3-(1-naphthyloxy)propyl)-1H-indole-2-carboxylic acid This example was prepared by substituting 3-bromo-4-trifluoromethoxyaniline for 4-bromo-3-methylphenol in EXAMPLE 43B. $^1$H NMR (300 MHz, DMSO-d$_6$) δ 10.47 (s, 1H), 8.26 (dd, 1H), 7.86 (dd, 1H), 7.70 (d, 1H), 7.54 (m, 2H), 7.41 (d, 1H), 8.37 (t, 1H), 7.10 (m, 3H), 6.89 (d, 1H), 6.69 (d, 1H), 6.66 (s, 1H), 4.19 (t, 2H), 2.23 (m, 2H).

EXAMPLE 86

7-(5-carboxy-2-methoxyphenyl)-3-(3-(1-naphthyloxyl)propyl)-1H-indole-2-carboxylic acid This example was prepared by substituting methyl 3-bromo-4-methoxybenzoate for 4-bromo-3-methylphenol in EXAMPLE 43B. $^1$H NMR (300 MHz, DMSO-d$_6$) δ 12.80 (m, 1H), 10.65 (s, 1H), 8.26 (m, 1H), 8.02 (dd, 1H), 7.89 (m, 1H), 7.81 (s, 1H), 7.70 (d, 1H), 7.53 (m, 3H), 7.40 (d, 1H), 7.36 (t, 1H), 7.22 (d, 1H), 7.12 (d, 1H), 7.05 (t, 1H), 6.91 (d, 1H), 4.21 (t, 2H), 3.80 (t, 3H), 2.25 (m, 2H).

EXAMPLE 87

7-(4-carboxy-2-nitrophenyl)-3-(3-(1-naphthyloxyl)propyl)-1H-indole-2-carboxylic acid This example was prepared by substituting methyl 4-bromo-3-nitrobenzoate for 4-bromo-3-methylphenol in EXAMPLE 43B. $^1$H NMR (300 MHz, DMSO-d$_6$) δ 13.60 (m, 1H), 13.00 (m, 1H), 11.31 (s, 1H), 8.56 (s, 1H), 8.26 (dd, 1H), 7.88 (m, 1H), 7.74 (m, 1H), 7.65 (d, 1H), 7.53 (m, 3H), 7.40 (d, 1H), 7.36 (t, 1H), 7.22 (d, 1H), 7.12 (d, 1H), 7.05 (m, 1H), 6.91 (d, 1H), 4.21 (t, 2H), 3.37 (t, 2H), 2.25 (m, 2H).

EXAMPLE 88

7-(5-carboxy-2-chlorophenyl)-3-(3-(1-naphthyloxyl)propyl)-1H-indole-2-carboxylic acid This example was prepared by substituting methyl 3-bromo-4-chlorobenzoate for 4-bromo-3-methylphenol in EXAMPLE 43B. $^1$H NMR (300 MHz, DMSO-d$_6$) δ 13.00 (m, 1H), 11.18 (s, 1H), 8.26 (m, 1H), 7.98 (d, 1H), 7.88 (m, 1H), 7.74 (m, 1H), 7.68 (d, 1H), 7.53 (m, 3H), 7.40 (d, 1H), 7.36 (t, 1H), 7.09 (m, 2H), 6.91 (d, 1H), 4.21 (t, 2H), 3.37 (t, 2H), 2.25 (m, 2H).

EXAMPLE 89A 1-benzyl-3-methyl-1,2,3,6-tetrahydropyridin-4-yl trifluoromethanesulfonate This example was prepared by substituting 1-benzyl-3-methylpiperidin-4-one for 2-phenylcyclohexanone in EXAMPLE 59A.

EXAMPLE 89B 7-(1-benzyl-3-methyl-1,2,3,6-tetrahydropyridin-4-yl)-3-(3-(1-naphthyloxyl)propyl)-1H-indole-2-carboxylic acid This example was prepared as a TFA salt by substituting EXAMPLE 43A for (E)-styrylboronic acid and EXAMPLE 89A for EXAMPLE 1C in EXAMPLE 1D. $^1$H NMR (500 MHz, DMSO-d$_6$) δ 13.22 (s, 1H), 10.77 (10.55) (s, 1H), 9.99 (9.54) (s, 1H), 8.22 (d, 1H), 7.86 (d, 1H), 7.63 (m, 3H), 7.45 (m, 8H), 7.03 (m, 2H), 6.88 (d, 1H), 5.82 (m, 1H), 4.51 (m, 2H), 4.18 (t, 2H), 3.80 (m, 2H), 2.98 (m, 1H), 2.20 (m, 2H), 0.92 (0.78) (d, 3H).

EXAMPLE 90

7-(4-amino-2-(trifluoromethyl)phenyl)-3-(3-(1-naphthyloxyl)propyl)-1H-indole-2-carboxylic acid This example was prepared by substituting 4-bromo-3-trifluoromethylaniline for 4-bromo-3-methylphenol in EXAMPLE 43B. $^1$H NMR (300 MHz, DMSO-d$_6$) δ 12.90 (m, 1H), 10.62 (s, 1H), 8.26 (m, 1H), 7.87 (m, 1H), 7.65 (d, 1H), 7.53 (m, 3H), 7.40 (d, 1H), 7.36 (t, 1H), 7.09 (m, 3H), 6.89 (d, 1H), 6.82 (d, 1H), 4.20 (t, 2H), 3.35 (t, 2H), 2.20 (m, 2H).

EXAMPLE 91

7-(1,4-dioxa-8-azaspiro(4.5)dec-8-yl)-3-(3-(1-naphthyloxy)propyl)-1H-indole-2-carboxylic acid This example was prepared by substituting 1,4-dioxa-8-azaspiro(4.5)decane for 1-(3-chlorophenyl)piperazine in EXAMPLE 76B. ¹H NMR (300 MHz, DMSO-d₆) δ 10.88 (s, 1H), 8.24 (m, 1H), 7.86 (m, 1H), 7.35-7.54 (m, 5H), 6.86 (m, 3H), 4.16 (t, 2H), 3.93 (s, 4H), 3.33 (t, 2H), 3.17 (m, 4H), 2.19 (m, 2H), 1.94 (m, 4H).

EXAMPLE 92

7-(3-carboxypiperidin-1-yl)-3-(3-(1-naphthyloxy)propyl)-1H-indole-2-carboxylic acid This example was prepared by substituting methyl piperidine-3-carboxylate for 1-(3-chlorophenyl)piperazine in EXAMPLE 76B. ¹H NMR (300 MHz, DMSO-d₆) δ 13.00 (m, 1H), 11.10 (s, 1H), 8.24 (m, 1H), 7.86 (m, 1H), 7.30-7.55 (m, 5H), 6.86 (m, 2H), 6.74 (d, 1H), 4.16 (t, 2H), 3.70 (m, 1H), 2.72-3.06 (m, 5H), 2.20 (m, 4H), 1.72 (m, 3H).

EXAMPLE 93

7-(4-carboxypiperidin-1-yl)-3-(3-(1-naphthyloxy)propyl)-1H-indole-2-carboxylic acid This example was prepared by substituting methyl piperidine-4-carboxylate for 1-(3-chlorophenyl)piperazine in EXAMPLE 76B. ¹H NMR (300 MHz, DMSO-d₆) δ 11.00 (m, 1H), 8.22 (m, 1H), 7.86 (m, 1H), 7.35-7.54 (m, 5H), 6.97 (m, 2H), 6.86 (d, 1H), 4.16 (t, 2H), 3.45 (m, 4H), 3.29 (t, 2H), 2.90 (m, 1H), 2.19 (t, 2H), 2.00 (m, 4H).

EXAMPLE 94

3-(3-(1-naphthyloxy)propyl)-7-pyrrolidin-1-yl-1H-indole-2-carboxylic acid

This example was prepared by substituting pyrrolidine for 1-(3-chlorophenyl)piperazine in EXAMPLE 76B. ¹H NMR (300 MHz, DMSO-d₆) δ 10.40 (m, 1H), 8.22 (m, 1H), 7.86 (m, 1H), 7.35-7.54 (m, 5H), 7.21 (d, 1H), 6.90 (m, 2H), 6.86 (d, 1H), 6.70 (m, 1H), 4.16 (t, 2H), 3.30 (t, 2H), 2.19 (t, 2H), 1.99 (m, 4H).

EXAMPLE 95

7-morpholin-4-yl-3-(3-(1-naphthyloxy)propyl)-1H-indole-2-carboxylic acid

This example was prepared by substituting morpholine for 1-(3-chlorophenyl)piperazine in EXAMPLE 76B. ¹H NMR (300 MHz, DMSO-d₆) δ 10.91 (m, 1H), 8.22 (m, 1H), 7.86 (m, 1H), 7.34-7.53 (m, 5H), 6.92 (m, 2H), 6.80 (d, 1H), 4.16 (t, 2H), 3.86 (m, 4H), 3.30 (t, 2H), 2.98 (m, 4H), 2.19 (t, 2H).

EXAMPLE 96

3-(3-(1-naphthyloxy)propyl)-7-piperidin-1-yl-1H-indole-2-carboxylic acid

This example was prepared by substituting piperidine for 1-(3-chlorophenyl)piperazine in EXAMPLE 76B. ¹H NMR (300 MHz, DMSO-d₆) δ 8.21 (m, 1H), 7.86 (m, 1H), 7.35-7.56 (m, 6H), 7.09 (m, 1H), 6.88 (d, 1H), 4.16 (t, 2H), 3.35 (t, 2H), 2.19 (m, 2H), 1.87 (m, 4H), 1.63 (m, 2H).

EXAMPLE 97

7-(4-(aminosulfonyl)-2-(trifluoromethyl)phenyl)-3-(3-(1-naphthyloxy)propyl)-1H-indole-2-carboxylic acid This example was prepared by substituting 4-bromo-3-(trifluoromethyl)benzenesulfonamide for 4-bromo-3-methylphenol in EXAMPLE 43B. ¹H NMR (300 MHz, DMSO-d₆) δ 12.98 (m, 1H), 11.31 (s, 1H), 8.26 (m, 1H), 8.23 (s, 1H), 8.08 (d, 1H), 7.86 (m, 1H), 7.76 (dd, 1H), 7.36-7.63 (m, 7H), 7.05 (m, 2H), 6.90 (d, 1H), 4.21 (t, 2H), 3.40 (t, 2H), 2.23 (m, 2H).

EXAMPLE 98A tert-butyl 4-bromo-3-methylbenzoate

To a mixture of methyl 4-bromo-3-methylbenzoate (4.85 g) and tert-butyl acetate (3 mL) was added 1M potassium tert-butoxide in THF (0.3 mL). The mixture was stirred under vacuum for 10 minutes and treated with another equivalent of tert-butyl acetate and 1 mol % of (1,1'-bis(diphenylphosphino)ferrocene)dichloropalladium(II) dichloromethane. This procedure was repeated three times. The mixture was diluted with ethyl acetate (40 mL) and washed with 5% aqueous HCl, water and brine. After drying over Na₂SO₄, the mixture was concentrated.

EXAMPLE 98B tert-butyl 3-methyl-4-(4,4,5,5-tetramethyl-1,3,2-dioxaborolan-2-yl)benzoate This example was prepared by substituting EXAMPLE 98A for EXAMPLE 1C in EXAMPLE 43A.

EXAMPLE 98C ethyl 7-(4-(tert-butoxycarbonyl)-2-methylphenyl)-3-(3-(naphthalen-1-yloxy)propyl)-1H-indole-2-carboxylate This example was prepared by substituting EXAMPLE 98B for 2-methoxyphenylboronic acid and EXAMPLE 1C for EXAMPLE 1B in EXAMPLE 47A.

EXAMPLE 98D 4-(2-(ethoxycarbonyl)-3-(3-(1-naphthyloxyl)propyl)-1H-indol-7-yl)-3-methylbenzoic acid A mixture of EXAMPLE 98C in dichoromethane (5 mL) and TFA (5 mL) was stirred at room temperature overnight and concentrated. The concentrate was partitioned between water (50 mL) and ethyl acetate (200 mL), and the organic phase was washed with brine and dried (Na₂SO₄), filtered and concentrated. ¹H NMR (300 MHz, DMSO-d₆) δ 12.88 (m, 1H), 11.00 (s, 1H), 8.22 (m, 1H), 7.85 (m, 3H), 7.86 (m, 1H), 7.73 (d, 1H), 7.32-7.55 (m, 5H), 7.08 (m, 2H), 6.92 (d, 1H), 4.25 (m, 4H), 3.36 (t, 2H), 2.24 (t, 2H), 2.10 (s, 3H), 1.26 (t, 3H).

EXAMPLE 99

7-(2-methyl-4-(morpholin-4-ylcarbonyl)phenyl)-3-(3-(1-naphthyloxy)propyl)-1H-indole-2-carboxylic acid To a mixture of EXAMPLE 98D (75 mg) and morpholine (32 mg) in dichloromethane (2 mL) was added 1-ethyl-3-(3-(dimethylamino)propyl)carbodiimide hydrochloride (58 mg) and DMAP (38 mg). The mixture was stirred at room temperature overnight and concentrated. The concentrate was diluted with ethyl acetate (150 mL), washed with 5% HCl, water and brine and dried ($Na_2SO_4$), filtered and concentrated. The concentrate was dissolved in THF (4 mL), methanol (2 mL) and water (2 mL). $LiOH.H_2O$ (100 mg) was added to the mixture and the mixture was stirred overnight. The mixture was concentrated, the concentrate was acidified with 5% HCl and extracted with ethyl acetate. The extract was washed with brine and dried ($Na_2SO_4$), filtered and concentrated. The concentrate was purified by reverse phase HPLC (C-18, 30 to 100% acetonitrile/water/0.1% TFA). $^1$H NMR (300 MHz, DMSO-$d_6$) δ 12.95 (m, 1H), 10.79 (s, 1H), 8.25 (m, 1H), 7.87 (m, 1H), 7.71 (d, 1H), 7.35-7.57 (m, 6H), 7.27 (s, 1H), 7.08 (m, 2H), 6.90 (d, 1H), 4.21 (t, 1H), 3.64 (m, 8H), 3.37 (t, 2H), 2.26 (t, 2H), 2.07 (s, 3H).

EXAMPLE 100

7-(4-((4-carboxypiperidin-1-yl)carbonyl)-2-methylphenyl)-3-(3-(1-naphthyloxy)propyl)-1H-indole-2-carboxylic acid This example was prepared by substituting methyl piperidine-4-carboxylate for morpholine in EXAMPLE 99. $^1$H NMR (300 MHz, DMSO-$d_6$) δ 10.78 (s, 1H), 8.25 (m, 1H), 7.87 (m, 1H), 7.71 (d, 1H), 7.32-7.54 (m, 5H), 7.25 (s, 1H), 7.08 (m, 2H), 6.91 (d, 1H), 4.21 (t, 2H), 3.39 (t, 2H), 3.00 (m, 4H), 2.26 (t, 2H), 2.08 (s, 3H), 1.90 (m, 1H), 1.65 (m, 4H).

EXAMPLE 101

7-(4-((3-carboxypiperidin-1-yl)carbonyl)-2-methylphenyl)-3-(3-(1-naphthyloxy)propyl)-1H-indole-2-carboxylic acid This example was prepared by substituting methyl piperidine-3-carboxylate for morpholine in EXAMPLE 99. $^1$H NMR (300 MHz, DMSO-$d_6$) δ 10.82 (s, 1H), 8.25 (m, 1H), 7.87 (m, 1H), 7.71 (d, 1H), 7.32-7.54 (m, 5H), 7.26 (s, 1H), 7.08 (m, 2H), 6.91 (d, 1H), 4.21 (t, 2H), 3.38 (t, 2H), 3.05 (m, 4H), 2.26 (t, 2H), 2.08 (s, 3H), 1.86 (m, 5H).

EXAMPLE 102

7-(4-(carboxymethylcarbamoyl)-2-methylphenyl)-3-(3-(naphthalen-1-yloxy)propyl)-1H-indole-2-carboxylic acid This example was prepared by substituting methyl 2-aminoacetate for morpholine in EXAMPLE 99. $^1$H NMR (300 MHz, DMSO-$d_6$) δ 10.83 (s, 1H), 8.83 (t, 1H), 8.25 (m, 1H), 7.87 (m, 1H), 7.85 (s, 1H), 7.71 (m, 2H), 7.32-7.54 (m, 4H), 7.29 (d, 1H), 7.08 (m, 2H), 6.91 (d, 1H), 4.21 (t, 2H), 3.96 (d, 2H), 3.37 (t, 2H), 2.24 (m, 2H), 2.11 (s, 3H).

EXAMPLE 103A ethyl 7-bromo-3-(3-oxopropyl)-1H-indole-2-carboxylate

To a cooled (0° C.) mixture of EXAMPLE 1B (3.26 g) in dichloromethane (5 mL) was added DMSO (1 mL) and triethylamine (0.835 mL) followed by pyridine sulfate (636 mg). The mixture was stirred for 2 hours, diluted with ethyl acetate (150 mL), and washed with 5% HCl, saturated $NaHCO_3$, water and brine and dried ($Na_2SO_4$), filtered and concentrated.

EXAMPLE 103B ethyl 7-bromo-3-(3-(3,4-dihydroquinolin-1(2H)-yl)propyl)-1H-indole-2-carboxylate To a mixture of EXAMPLE 103A (325 mg) and 1,2,3,4-tetrahydroquinoline (160 mg) in dichloroethane (10 mL) was added sodium acetate (310 mg). The mixture was stirred at ambient temperature overnight, diluted with ethyl acetate (200 mL) and washed with 1N NaOH, water, and brine. After drying over sodium sulfate and concentration, the concentrate was loaded on a silica gel cartridge and eluted with 5% ethyl acetate in hexane.

EXAMPLE 103C 3-(3-(3,4-dihydroquinolin-1(2H)-yl)propyl)-7-(2-(trifluoromethyl)phenyl)-1H-indole-2-carboxylic acid This example was prepared by substituting 2-trifluoromethyl-phenylboronic acid for EXAMPLE 43A and EXAMPLE 103B for 4-bromo-3-methylphenol in EXAMPLE 43B. $^1$H NMR (300 MHz, $CDCl_3$) δ 8.43 (t, 1H), 7.85 (dd, 1H), 7.57-7.67 (m, 3H), 7.44 (d, 1H), 7.01-7.26 (m, 4H), 3.43 (m, 4H), 3.26 (t, 2H), 2.85 (t, 2H), 2.10 (m, 4H).

EXAMPLE 104A ethyl 7-bromo-3-(3-(3-phenoxyphenoxyl)propyl)-1H-indole-2-carboxylate This example was prepared by substituting 3-phenoxyphenol for 1-naphthol in EXAMPLE 1C.

EXAMPLE 104B 7-(2-methylphenyl)-3-(3-(3-phenoxyphenoxyl)propyl)-1H-indole-2-carboxylic acid This example was prepared by substituting EXAMPLE 104A for EXAMPLE 1C and 2-methylphenylboronic acid for (E)-styrylboronic acid in EXAMPLE 1D. $^1$H NMR (500 MHz, DMSO-$d_6$) δ 10.45 (s, 1H), 7.64 (d, 1H), 7.30 (m, 7H), 7.05 (m, 5H), 6.70 (m, 1H), 6.53 (m, 2H), 3.97 (t, 2H), 3.21 (t, 2H), 2.06 (s, 5H).

EXAMPLE 105A ethyl 7-bromo-3-(3-(2,3-dimethylphenoxyl)propyl)-1H-indole-2-carboxylate This example was prepared by substituting 2,3-dimethylphenol for 1-naphthol in EXAMPLE 1C.

EXAMPLE 105B 3-(3-(2,3-dimethylphenoxyl)propyl)-7-(2-methylphenyl)-1H-indole-2-carboxylic acid This example was prepared by substituting EXAMPLE 105A for EXAMPLE 1C and 2-methylphenylboronic acid for (E)-styrylboronic acid in EXAMPLE 1D. $^1$H NMR (500 MHz, DMSO-$d_6$) δ 12.96 (brs, 1H), 10.46 (s, 1H), 7.66 (d, 1H), 7.27 (m, 4H), 7.11 (t, 1H), 7.01 (m, 2H), 6.73 (t, 2H), 3.98 (t, 2H), 3.27 (t, 2H), 2.22 (s, 3H), 2.13 (s, 3H), 2.10 (m, 2H), 2.06 (s, 3H)

EXAMPLE 106

7-(4-methylpyridin-3-yl)-3-(3-(1-naphthyloxy)propyl)-1H-indole-2-carboxylic acid This example was prepared as a TFA salt by substituting 4-methyl-3-pyridylboronic acid for (E)-styrylboronic acid in EXAMPLE 1D. $^1$H NMR (300 MHz, DMSO-$d_6$) δ 12.98 (brs, 1H), 11.18 (s, 1H), 8.56 (d, 1H), 8.47 (s, 1H), 8.25 (m, 1H), 7.86 (m, 1H), 7.77 (m, 1H), 7.52 (m, 3H), 7.42 (m, 2H), 7.10 (m, 2H), 6.91 (m, 1H), 4.21 (t, 2H), 2.24 (m, 2H), 2.12 (s, 3H).

EXAMPLE 107

7-(2-methylbenzyl)-3-(3-(1-naphthyloxy)propyl)-1H-indole-2-carboxylic acid

This example was prepared by substituting 2-methylbenzylbromide for EXAMPLE 1C and EXAMPLE 43A for (E)-styrylboronic acid in EXAMPLE 1D. $^1$H NMR (300 MHz, DMSO-$d_6$) δ 13.00 (brs, 1H), 11.30 (s, 1H), 8.24 (m, 1H), 7.86 (m, 1H), 7.45 (m, 5H), 7.13 (m, 3H), 6.89 (m, 3H), 6.68 (d, 1H), 4.27 (s, 2H), 4.18 (t, 2H), 2.22 (m, 5H).

EXAMPLE 108

3,3'-bis(3-(1-naphthyloxy)propyl)-1H,1'H-7,7'-biindole-2,2'-dicarboxylic acid

This example was prepared as a side product by substituting EXAMPLE 43A for (E)-styrylboronic acid in EXAMPLE 1D. $^1$H NMR (300 MHz, DMSO-$d_6$) δ 12.94 (brs, 2H), 10.26 (s, 2H), 8.27 (m, 2H), 7.87 (m, 2H), 7.76 (d, 2H), 7.43 (m, 10H), 7.14 (t, 2H), 6.92 (d, 2H), 4.23 (t, 4H), 3.40 (t, 4H), 2.27 (m, 4H).

EXAMPLE 109A ethyl 7-bromo-3-(4-ethoxy-4-oxobutyl)-1H-indole-2-carboxylate

This example was prepared by substituting ethyl 2-oxocyclohexanecarboxylate for ethyl 2-oxocyclopentanecarboxylate in EXAMPLE 1A.

EXAMPLE 109B ethyl 7-bromo-3-(4-hydroxybutyl)-1H-indole-2-carboxylate

This example was prepared by substituting EXAMPLE 109A for EXAMPLE 1A in EXAMPLE 1B.

EXAMPLE 109C ethyl 7-bromo-3-(4-oxobutyl)-1H-indole-2-carboxylate

This example was prepared by substituting EXAMPLE 109B for EXAMPLE 1B in EXAMPLE 103A.

EXAMPLE 109D ethyl 7-bromo-3-(4-(3,4-dihydroquinolin-1(2H)-yl)butyl)-1H-indole-2-carboxylate This example was prepared by substituting EXAMPLE 109C for EXAMPLE 103A in EXAMPLE 103B.

EXAMPLE 109E 3-(4-(3,4-dihydroquinolin-1(2H)-yl)butyl)-7-(2-(trifluoromethyl)phenyl)-1H-indole-2-carboxylic acid This example was prepared by substituting 2-trifluoromethyl-phenylboronic acid for EXAMPLE 43A and EXAMPLE 109D for 4-bromo-3-methylphenol in EXAMPLE 43B. $^1$H NMR (300 MHz, DMSO-$d_6$) δ 10.93 (s, 1H), 7.83 (dd, 1H), 7.63 (m, 3H), 7.39 (d, 1H), 7.10 (t, 1H), 7.02 (d, 1H), 6.95 (t, 1H), 6.85 (d, 1H), 6.52 (d, 1H), 6.42 (t, 1H), 3.21 (m, 4H), 2.63 (t, 2H), 1.84 (m, 2H), 1.62 (m, 4H).

EXAMPLE 110

7-(4-carboxy-2-methylphenyl)-3-(4-(3,4-dihydroquinolin-1(2H)-yl)butyl)-1H-indole-2-carboxylic acid This example was prepared by substituting 4-(methoxycarbonyl)-2-methylphenylboronic acid for EXAMPLE 43A and EXAMPLE 109D for 4-bromo-3-methylphenol in EXAMPLE 43B. $^1$H NMR (300 MHz, DMSO-$d_6$) δ 10.76 (s, 1H), 7.89 (s, 1H), 7.82 (dd, 1H), 7.71 (dd, 1H), 7.32 (d, 1H), 7.15 (t, 1H), 7.06 (d, 1H), 6.91 (t, 1H), 6.83 (d, 1H), 6.50 (d, 1H), 6.43 (t, 1H), 3.22 (m, 4H), 3.64 (t, 2H), 2.09 (s, 3H), 1.81 (m, 2H), 1.61 (m, 4H).

EXAMPLE 111A ethyl 7-bromo-3-(3-iodopropyl)-1H-indole-2-carboxylate

To a mixture of EXAMPLE 1B (1.116 g) in dichloromethane (30 mL) at 0° C. was added iodine (1.01 g), triphenyl phosphine (1.03 g) and imidazole (0.535 g). The mixture was stirred at 0° C. for 1 hour and treated with saturated NaHCO$_3$ (50 mL). Stirring was continued for 30 minutes, and the organic layer was washed with a saturated aqueous Na$_2$S$_2$O$_3$ (50 mL), water (20 mL), and brine (50 mL) and dried (Na$_2$SO$_4$), filtered and concentrated. The concentrate

EXAMPLE 111B (3-(7-bromo-2-(ethoxycarbonyl)-1H-indol-3-yl)propyl)triphenylphosphonium iodide To a mixture of EXAMPLE 111A (0.136 g) in CH$_3$CN (5 mL) was added triphenylphosphine (157 mg). The mixture was refluxed for 48 hours, cooled to room temperature, washed with hexanes and concentrated.

EXAMPLE 111C ethyl 7-bromo-3-(4-(naphthalen-1-yl)but-3-enyl)-1H-indole-2-carboxylate A mixture of 60% oily sodium hydride (40 mg) in DMSO (5 mL) was heated for 1 hour at 80° C., cooled to 15° C. and treated with Example 111B (0.797 g). The mixture was stirred for 10 minutes, treated with 1-napthalaldehyde (0.156 g) and heated for 3 hours at 80° C. After standing overnight at room temperature, the mixture was poured into saturated NaHSO$_4$ mixture and extracted with diethylether. The extract was washed with water and brine and dried (MgSO$_4$), filtered, and concentrated. The concentrate was purified by flash column chromatography on silica gel chromatography with 0-20% ethyl acetate in hexanes.

EXAMPLE 111D 3-(4-(naphthalen-1-yl)but-3-enyl)-7-o-tolyl-1H-indole-2-carboxylic acid This example was prepared by substituting 2-methylphenylboronic acid for (E)-styrylboronic acid and EXAMPLE 111C for EXAMPLE 1C in EXAMPLE 1D.

EXAMPLE 111E 7-(2-methylphenyl)-3-(4-(1-naphthyl)butyl)-1H-indole-2-carboxylic acid A mixture of EXAMPLE 111D and Pd/C (catalytic) in ethyl acetate/ethanol was stirred at room temperature under hydrogen (balloon) overnight. The mixture was filtered, washed with ethyl acetate/ethanol and concentrated. The concentrate was purified on reverse phase HPLC (Zorbax SB-C18, 20100% acetonitrile/water/0.1% TFA). $^1$H NMR (300 MHz, DMSO-d$_6$) δ 12.82 (brs, 1H), 10.36 (s, 1H), 8.03 (m, 1H), 7.90 (m, 1H), 7.75 (d, 1H), 7.66 (d, 1H), 7.51 (m, 2H), 7.31 (m, 6H), 7.12 (t, 1H), 7.03 (m, 1H), 3.17 (m, 2H), 3.09 (m, 2H), 2.05 (s, 3H), 1.78 (m, 4H).

EXAMPLE 112A ethyl 7-bromo-3-(4-(naphthalen-1-yloxy)butyl)-1H-indole-2-carboxylate This example was prepared by substituting EXAMPLE 109B for EXAMPLE 1B in EXAMPLE 1C.

EXAMPLE 112B 7-(2-methylphenyl)-3-(4-(1-naphthyloxy)butyl)-1H-indole-2-carboxylic acid This example was prepared by substituting 2-methylphenylboronic acid for (E)-styrylboronic acid and EXAMPLE 112A for EXAMPLE 1C in EXAMPLE 1D. $^1$H NMR (500 MHz, DMSO-d$_6$) δ 12.87 (brs, 1H), 10.42 (s, 1H), 8.12 (d, 1H), 7.85 (d, 1H), 7.70 (d, 1H), 7.37 (m, 8H), 7.12 (t, 1H), 7.05 (m, 1H), 6.94 (d, 1H), 4.19 (m, 2H), 3.22 (m, 2H), 2.06 (s, 3H), 1.93 (m, 4H).

EXAMPLE 113A ethyl 7-bromo-3-(3-(2,4-dimethylphenoxyl)propyl)-1H-indole-2-carboxylate This example was prepared by substituting 2,4-dimethylphenol for 1-naphthol in EXAMPLE 1C.

EXAMPLE 113B 3-(3-(2,4-dimethylphenoxyl)propyl)-7-(2-methylphenyl)-1H-indole-2-carboxylic acid This example was prepared by substituting 2-methylphenylboronic acid for (E)-styrylboronic acid and EXAMPLE 113A for EXAMPLE 1C in EXAMPLE 1D. $^1$H NMR (500 MHz, DMSO-d$_6$) δ 12.88 (brs, 1H), 10.45 (s, 1H), 7.65 (d, 1H), 7.27 (m, 4H), 7.10 (t, 1H), 7.04 (dd, 1H), 6.92 (m, 2H), 6.73 (d, 1H), 3.97 (t, 2H), 3.25 (t, 2H), 2.19 (s, 3H), 2.17 (s, 3H), 2.07 (m, 5H).

EXAMPLE 114A ethyl 7-bromo-3-(3-(2,5-dimethylphenoxyl)propyl)-1H-indole-2-carboxylate This example was prepared by substituting 2,5-dimethylphenol for 1-napthol in EXAMPLE 1C.

EXAMPLE 114B 3-(3-(2,5-dimethylphenoxyl)propyl)-7-(2-methylphenyl)-1H-indole-2-carboxylic acid This example was prepared by substituting 2-methylphenylboronic acid for (E)-styrylboronic acid and EXAMPLE 114A for EXAMPLE 1C in EXAMPLE 1D. $^1$H NMR (500 MHz, DMSO-d$_6$) δ 12.89 (brs, 1H), 10.45 (brs, 1H), 7.66 (d, 1H), 7.33 (m, 2H), 7.25 (m, 2H), 7.11 (t, 1H), 7.02 (m, 2H), 6.64 (m, 2H), 4.00 (t, 2H), 3.26 (t, 2H), 2.22 (s, 3H), 2.15 (s, 3H), 2.08 (m, 5H).

EXAMPLE 115

7-(1,1'-biphenyl-2-yl)-3-(4-(1-naphthyloxy)butyl)-1H-indole-2-carboxylic acid

This example was prepared by substituting 2-biphenylboronic acid for (E)-styrylboronic acid and EXAMPLE 112A for EXAMPLE 1C in EXAMPLE 1D. $^1$H NMR (500 MHz, DMSO-d$_6$) δ 12.82 (brs, 1H), 10.12 (s, 1H), 8.11 (d, 1H), 7.85 (d, 1H), 7.48 (m, 9H), 7.08 (m, 5H), 6.90 (m, 3H), 4.16 (m, 2H), 3.15 (m, 2H), 1.87 (m, 4H).

EXAMPLE 116

7-(4-((2-carboxypiperidin-1-yl)carbonyl)-2-methylphenyl)-3-(3-(1-naphthyloxy)propyl)-1H-indole-2-carboxylic acid This example was prepared by substituting methyl piperidine-2-carboxylate for morpholine in EXAMPLE 99. $^1$H NMR (300 MHz, DMSO-d$_6$) δ 12.96 (m, 1H), 10.84 (s, 1H), 8.25 (m, 1H), 7.87 (m, 1H), 7.71 (d, 1H), 7.25-7.56 (m, 8H), 7.08 (m, 2H), 6.91 (d, 1H), 4.21 (t, 2H), 3.37 (t, 2H), 2.26 (t, 2H), 2.08 (s, 3H), 1.72 (m, 3H), 1.40 (m, 2H).

EXAMPLE 117

7-(4-((S)-1-carboxy-2-methylpropylcarbamoyl)-2-methylphenyl)-3-(3-(naphthalen-1-yloxy)propyl)-1H-indole-2-carboxylic acid This example was prepared by substituting 2-amino-3-methyl-butyric acid methyl ester for morpholine in EXAMPLE 99. $^1$H NMR (300 MHz, DMSO-d$_6$) δ 10.79 (s, 1H), 8.37 (d, 1H), 8.25 (m, 1H), 7.89 (s, 1H), 7.87 (m, 1H), 7.71 (d, 1H), 7.30-7.56 (m, 4H), 7.29 (d, 1H), 7.06 (m, 2H), 6.91 (d, 1H), 4.36 (t, 1H), 4.21 (t, 2H), 3.37 (t, 2H), 2.26 (m, 2H), 2.08 (s, 3H), 0.99 (t, 6H).

EXAMPLE 118

N-(4-(2-carboxy-3-(3-(1-naphthyloxy)propyl)-1H-indol-7-yl)-3-methylbenzoyl)-4-chlorophenylalanine This example was prepared by substituting methyl 2-amino-3-(4-chlorophenyl)propanoate for morpholine in EXAMPLE 99. $^1$H NMR (300 MHz, DMSO-d$_6$) δ 12.84 (m, 1H), 10.84 (s, 1H), 8.70 (d, 1H), 8.25 (m, 1H), 7.86 (m, 1H), 7.78 (s, 1H), 7.71 (d, 1H), 7.29-7.54 (m, 8H), 7.26 (d, 1H), 7.06 (m, 2H), 6.90 (d, 1H), 4.70 (m, 1H), 4.20 (t, 2H), 3.36 (t, 2H), 3.21 (dd, 2H), 2.23 (m, 2H), 2.08 (s, 3H).

EXAMPLE 119

N-(4-(2-carboxy-3-(3-(1-naphthyloxyl)propyl)-1H-indol-7-yl)-3-methylbenzoyl)-L-tryptophan This example was prepared by substituting methyl ester (L)-tryptophan for morpholine in EXAMPLE 99. $^1$H NMR (300 MHz, DMSO-d$_6$) δ 10.81 (d, 1H), 8.60 (d, 1H), 8.25 (m, 1H), 7.86 (m, 1H), 7.79 (s, 1H), 7.70 (t, 1H), 7.64 (d, 1H), 7.22-7.54 (m, 9H), 7.04 (m, 4H), 6.90 (d, 1H), 4.75 (m, 1H), 4.20 (t, 2H), 3.36 (t, 2H), 2.23 (m, 2H), 2.08 (s, 3H).

EXAMPLE 120

(3S)-2-(4-(2-carboxy-3-(3-(1-naphthyloxy)propyl)-1H-indol-7-yl)-3-methylbenzoyl)-1,2,3,4-tetrahydroisoquinoline-3-carboxylic acid This example was prepared by substituting (3S)-methyl 1,2,3,4-tetrahydroisoquinolinecarboxylate for morpholine in EXAMPLE 99. $^1$H NMR (300 MHz, DMSO-d$^6$) δ 12.94 (m, 1H), 10.84 (d, 1H), 8.26 (m, 1H), 7.88 (m, 1H), 7.76 (m, 1H), 7.09-7.55 (m, 13H), 6.91 (d, 1H), 5.20 (t, 1H), 5.05 (d, 1H), 4.90 (m, 1H), 4.70 (dd, 1H), 4.50 (d, 1H), 4.22 (t, 2H), 3.38 (t, 2H), 2.27 (m, 2H), 2.08 (s, 3H).

EXAMPLE 121

N-(4-(2-carboxy-3-(3-(1-naphthyloxy)propyl)-1H-indol-7-yl)-3-methylbenzoyl)-L-tyrosine This example was prepared by substituting methyl ester L-tyrosine for morpholine in EXAMPLE 99. $^1$H NMR (300 MHz, DMSO-d$_6$) δ 10.84 (s, 1H), 9.17 (s, 1H), 8.60 (d, 1H), 8.25 (m, 1H), 7.87 (m, 1H), 7.79 (s, 1H), 7.74 (m, 1H), 7.53 (m, 2H), 7.40 (d, 1H), 7.36 (d, 1H), 7.26 (d, 1H), 7.08 (m, 4H), 6.90 (d, 1H), 6.66 (d, 2H), 4.60 (m, 1H), 4.20 (t, 2H), 3.36 (t, 2H), 3.00 (m, 3H), 2.23 (m, 2H), 2.08 (s, 3H).

EXAMPLE 122

7-(4-((R)-2-carboxypyrrolidine-1-carbonyl)-2-methylphenyl)-3-(3-(naphthalen-1-yloxy)propyl)-1H-indole-2-carboxylic acid This example was prepared by substituting methyl ester L-proline for morpholine in EXAMPLE 99. $^1$H NMR (300 MHz, DMSO-d$_6$) δ 10.80 (s, 1H), 8.25 (m, 1H), 7.86 (m, 1H), 7.71 (d, 1H), 7.36-7.54 (m, 6H), 7.28 (d, 1H), 7.08 (m, 2H), 6.91 (d, 1H), 4.45 (m, 1H), 4.20 (t, 2H), 3.64 (t, 2H), 2.25 (m, 2H), 2.08 (s, 3H), 1.92 (m, 3H).

EXAMPLE 123

7-(4-((S)-1-carboxyethylcarbamoyl)-2-methylphenyl)-3-(3-(naphthalen-1-yloxy)propyl)-1H-indole-2-carboxylic acid This example was prepared by substituting methyl ester L-alanine for morpholine in EXAMPLE 99. $^1$H NMR (300 MHz, DMSO-d$_6$) δ 10.81 (s, 1H), 8.66 (d, 1H), 8.25 (m, 1H), 7.87 (m, 2H), 7.78 (d, 1H), 7.71 (d, 1H), 7.36-7.54 (m, 4H), 7.30 (d, 1H), 7.06 (m, 2H), 6.91 (d, 1H), 4.47 (m, 1H), 4.21 (t, 2H), 3.37 (t, 2H), 2.25 (m, 2H), 2.08 (s, 3H), 1.42 (d, 3H).

EXAMPLE 124

N-(4-(2-carboxy-3-(3-(1-naphthyloxy)propyl)-1H-indol-7-yl)-3-methylbenzoyl)-4-nitro-L-phenylalanine This example was prepared by substituting methyl 2-amino-3-(4-nitrophenyl)propanoate for morpholine in EXAMPLE 99. $^1$H NMR (300 MHz, DMSO-d$_6$) δ 12.90 (s, 1H), 10.83 (s, 1H), 8.78 (d, 1H), 8.25 (m, 1H), 8.17 (d, 2H), 7.87 (m, 2H), 7.71 (s, 1H), 7.70 (d, 1H), 7.63 (d, 2H), 7.36-7.54 (m, 4H), 7.26 (d, 1H), 7.06 (m, 2H), 6.91 (d, 1H), 4.80 (m, 1H), 4.20 (t, 2H), 3.36 (t, 2H), 2.23 (m, 2H), 2.08 (s, 3H).

EXAMPLE 125

N-(4-(2-carboxy-3-(3-(1-naphthyloxyl)propyl)-1H-indol-7-yl)-3-methylbenzoyl)-L-phenylalanine This example was prepared by substituting methyl ester L-phenylalanine for morpholine in EXAMPLE 99. $^1$H NMR (300 MHz, DMSO-d$_6$) δ 12.80 (m, 1H), 10.84 (s, 1H), 8.68 (d, 1H), 8.25 (m, 1H), 7.87 (m, 1H), 7.78 (s, 1H), 7.72 (d, 1H), 7.22-7.54 (m, 10H), 7.06 (m, 2H), 6.91 (d, 1H), 4.70 (m, 1H), 4.20 (t, 2H), 3.36 (t, 2H), 3.21 (m, 3H), 2.23 (m, 2H), 2.08 (s, 3H).

EXAMPLE 126

7-(4-((((S)-carboxy(phenyl)methyl)amino)carbonyl)-2-methylphenyl)-3-(3-(1-naphthyloxyl)propyl)-1H-indole-2-carboxylic acid This example was prepared by substituting (S)-methyl 2-amino-2-phenylacetate for morpholine in EXAMPLE 99. $^1$H NMR (300 MHz, DMSO-d$_6$) δ 12.92 (s, 1H), 10.79 (s, 1H), 9.02 (d, 1H), 8.25 (m, 1H), 7.93 (s, 1H), 7.85 (m, 2H), 7.70 (d, 1H), 7.31-7.54 (m, 9H), 7.28 (d, 1H), 7.06 (m, 2H), 6.90 (d, 1H), 5.66 (d, 1H), 4.70 (m, 1H), 4.20 (t, 2H), 3.36 (t, 2H), 2.23 (m, 2H), 2.10 (s, 3H).

EXAMPLE 127A 3-methyl-4-(4,4,5,5-tetramethyl-(1,3,2)dioxaborolan-2-yl)-benzoic acid methyl ester This example was prepared by substituting 4-bromo-3-methyl-benzoic acid methyl ester for EXAMPLE 1C in EXAMPLE 43A.

EXAMPLE 127B 3-(3-hydroxypropyl)-7-(4-methoxycarbonyl-2-methyl-phenyl)-1H-indole-2-carboxylic acid ethyl ester This example was prepared by substituting EXAMPLE 1B for EXAMPLE 1C and EXAMPLE 127A for 2-methoxyphenylboronic acid in EXAMPLE 47A.

EXAMPLE 127C 7-(4-methoxycarbonyl-2-methyl-phenyl)-3-(3-(toluene-4-sulfonyloxy)-propyl)-1H-indole-2-carboxylic acid ethyl ester To a mixture of EXAMPLE 127B (2.0 g), toluene-2-sulfonyl chloride (1.16 g) in dichloromethane (30 mL) was added DMAP (0.305 g). The mixture was stirred at room temperature overnight. The mixture was diluted with ethyl acetate (300 mL) and washed with saturated aqueous sodium bicarbonate mixture, 3% aqueous HCl, water and brine. After drying over $Na_2SO_4$ and filtering, the mixture was concentrated.

EXAMPLE 127D 7-(4-carboxy-2-methylphenyl)-3-(3-(2,4,5-trichlorophenoxyl)propyl)-1H-indole-2-carboxylic acid To a mixture of EXAMPLE 127C (60 mg) in DMF (1 mL) was added 2,4,5-trichlorophenol (43 mg) and $Cs_2CO_3$ (500 mg). The mixture was stirred at room temperature overnight, diluted with ethyl acetate (150 mL), and washed with water and brine. After drying over $Na_2SO_4$, the combined organic layers were concentrated, and the concentrate was saponified with LiOH as described in EXAMPLE 65B. $^1$H NMR (300 MHz, DMSO-$d_6$) δ 12.92 (m, 1H), 10.88 (s, 1H), 7.89 (s, 1H), 7.82 (m, 2H), 7.38 (s, 1H), 7.32 (d, 1H), 7.10 (m, 2H), 4.13 (t, 2H), 3.25 (t, 2H), 2.13 (m, 2H), 2.10 (s, 3H).

EXAMPLE 128

7-(4-carboxy-2-methylphenyl)-3-(3-(2,3,4-trichlorophenoxyl)propyl)-1H-indole-2-carboxylic acid This example was prepared by substituting 2,3,4-trichlorophenol for 2,4,5-trichlorophenol in EXAMPLE 127D. $^1$H NMR (300 MHz, DMSO-$d_6$) δ 12.86 (m, 1H), 10.87 (s, 1H), 7.89 (s, 1H), 7.82 (dd, 2H), 7.69 (dd, 1H), 7.56 (d, 1H), 7.32 (d, 1H), 7.06 (m, 3H), 4.13 (t, 2H), 3.25 (t, 2H), 2.13 (m, 2H), 2.10 (s, 3H).

EXAMPLE 129

7-(4-carboxy-2-methylphenyl)-3-(3-(2,3,5-trimethylphenoxy)propyl)-1H-indole-2-carboxylic acid This example was prepared by substituting 2,3,5-trimethylphenol for 2,4,5-trichlorophenol in EXAMPLE 127D. $^1$H NMR (300 MHz, DMSO-$d_6$) δ 12.86 (m, 1H), 10.85 (s, 1H), 7.89 (s, 1H), 7.82 (dd, 1H), 7.69 (dd, 1H), 7.32 (d, 1H), 7.13 (t, 1H), 7.06 (d, 1H), 3.97 (t, 2H), 3.26 (t, 2H), 2.13 (m, 2H), 2.14 (s, 3H), 2.10 (s, 3H), 2.08 (S, 3H).

EXAMPLE 130

3-(3-(2-tert-butylphenoxy)propyl)-7-(4-carboxy-2-methylphenyl)-1H-indole-2-carboxylic acid This example was prepared by substituting 2-tert-butylphenol for 2,4,5-trichlorophenol in EXAMPLE 127D. $^1$H NMR (300 MHz, DMSO-$d_6$) δ 12.88 (m, 1H), 10.88 (s, 1H), 7.90 (s, 1H), 7.82 (dd, 1H), 7.72 (dd, 1H), 7.32 (d, 1H), 7.22 (d, 1H), 7.17 (t, 1H), 7.06 (d, 1H), 6.80 (m, 2H), 4.07 (t, 2H), 2.14 (m, 2H), 2.11 (s, 3H), 1.41 (s, 9H).

EXAMPLE 131

7-(4-carboxy-2-methylphenyl)-3-(3-(2-(trifluoromethyl)phenoxy)propyl)-1H-indole-2-carboxylic acid This example was prepared by substituting 2-trifluoromethylphenol for 2,4,5-trichlorophenol in EXAMPLE 127D. $^1$H NMR (300 MHz, DMSO-$d_6$) δ 12.87 (m, 1H), 10.87 (s, 1H), 7.94 (s, 1H), 7.82 (dd, 1H), 7.61 (m, 4H), 7.32 (d, 1H), 7.20 (d, 1H), 7.06 (m, 4H), 4.15 (t, 2H), 3.24 (t, 2H), 2.10 (s, 3H), 2.07 (m, 2H).

EXAMPLE 132

7-(4-carboxy-2-methylphenyl)-3-(3-(quinolin-8-yloxy)propyl)-1H-indole-2-carboxylic acid This example was prepared as a TFA salt by substituting quinolin-8-ol for 2,4,5-trichlorophenol in EXAMPLE 127D. $^1$H NMR (300 MHz, DMSO-$d_6$) δ 12.84 (m, 1H), 10.88 (s, 1H), 9.05 (dd, 1H), 8.76 (m, 1H), 7.89 (s, 1H), 7.67-7.83 (m, 5H), 7.32 (m, 2H), 7.03 (m, 2H), 4.27 (t, 2H), 3.35 (t, 2H), 2.28 (m, 2H), 2.09 (s, 3H).

EXAMPLE 133

7-(4-carboxy-2-methylphenyl)-3-(3-((5-oxo-5,6,7,8-tetrahydronaphthalen-1-yl)oxy)propyl)-1H-indole-2-carboxylic acid This example was prepared by substituting 5-hydroxy-3,4-dihydro-2H-naphthalen-1-one for 2,4,5-trichlorophenol in EXAMPLE 127D. $^1$H NMR (300 MHz, DMSO-$d_6$) δ 12.87 (m, 1H), 10.85 (s, 1H), 7.89 (s, 1H), 7.82 (d, 1H), 7.70 (d, 1H), 7.46 (d, 1H), 7.30 (m, 2H), 7.03 (m, 3H), 4.07 (t, 2H), 3.26 (t, 2H), 2.90 (t, 2H), 2.58 (t, 3H), 2.13 (m, 2H), 2.09 (s, 3H).

EXAMPLE 134

3-(3-(3-benzoylphenoxyl)propyl)-7-(4-carboxy-2-methylphenyl)-1H-indole-2-carboxylic acid This example was prepared by substituting (3-hydroxyphenyl)-phenyl-methanone for 2,4,5-trichlorophenol in EXAMPLE 127D. $^1$H NMR (300 MHz, DMSO-$d_6$) δ 12.86 (m, 1H), 10.84 (s, 1H), 7.89 (s, 1H), 7.82 (d, 1H), 7.68 (m, 3H), 7.50 (t, 2H), 7.44 (t, 1H), 7.32 (d, 2H), 7.25 (t, 2H), 7.06 (m, 2H), 4.06 (t, 2H), 3.24 (t, 2H), 2.13 (m, 2H), 2.09 (s, 3H).

EXAMPLE 135A ethyl 7-bromo-1-(2-morpholino-2-oxoethyl)-3-(3-(5,6,7,8-tetrahydronaphthalen-1-yloxy)propyl)-1H-indole-2-carboxylate This example was prepared by substituting EXAMPLE 78A for EXAMPLE 1C in EXAMPLE 77A.

EXAMPLE 135B ethyl 7-bromo-1-(2-morpholinoethyl)-3-(3-(5,6,7,8-tetrahydronaphthalen-1-yloxy)propyl)-1H-indole-2-carboxylate This example was prepared by substituting EXAMPLE 135A for EXAMPLE 77A in EXAMPLE 77B.

EXAMPLE 135C 7-(2-methylphenyl)-1-(2-morpholin-4-ylethyl)-3-(3-(5,6,7,8-tetrahydronaphthalen-1-yloxy)propyl)-1H-indole-2-carboxylic acid This example was prepared as a TFA salt by substituting 2-methylphenylboronic acid for (E)-styrylboronic acid and EXAMPLE 135B for EXAMPLE 1C in EXAMPLE 1D. $^1$H NMR (500 MHz, DMSO-$d_6$) δ 13.43 (brs, 1H), 7.77 (d, 1H), 7.41 (m, 4H), 7.20 (t, 1H), 7.01 (m, 2H), 6.65 (m, 2H), 4.66 (m, 1H), 4.02 (m, 4H), 3.26 (t, 2H), 2.66 (m, 8H), 2.05 (m, 6H), 1.72 (m, 4H).

EXAMPLE 136

7-(4-(cyclohexyloxy)phenyl)-3-(4-(1-naphthyloxy)butyl)-1H-indole-2-carboxylic acid This example was prepared by substituting 4-cyclohexyloxyphenylboronic acid for (E)-styrylboronic acid and EXAMPLE 112A for EXAMPLE 1C in EXAMPLE 1D. $^1$H NMR (500 MHz, DMSO-$d_6$) δ 12.98 (brs, 1H), 10.21 (s, 1H), 8.12 (d, 1H), 7.85 (d, 1H), 7.66 (d, 1H), 7.46 (m, 6H), 7.22 (d, 1H), 7.13 (t, 1H), 7.06 (d, 2H), 6.94 (d, 1H), 4.40 (m, 1H), 4.19 (m, 2H), 3.21 (m, 2H), 1.95 (m, 6H), 1.75 (m, 2H), 1.41 (m, 6H).

EXAMPLE 137

7-(1,1'-biphenyl-2-yl)-1-(2-morpholin-4-ylethyl)-3-(3-(5,6,7,8-tetrahydronaphthalen-1-yloxy)propyl)-1H-indole-2-carboxylic acid This example was prepared as a TFA salt by substituting 2-biphenylboronic acid for (E)-styrylboronic acid and EXAMPLE 135B for EXAMPLE 1C in EXAMPLE 1D. $^1$H NMR (500 MHz, DMSO-$d_6$) δ 13.17 (brs, 1H), 7.57 (m, 5H), 7.05 (m, 8H), 6.62 (m, 2H), 4.69 (m, 1H), 4.03 (m, 1H), 3.87 (t, 2H), 3.15 (t, 2H), 2.76 (m, 10H), 1.96 (m, 2H), 1.71 (m, 4H).

EXAMPLE 138A ethyl 7-bromo-3-(3-(3,4-dimethylphenoxyl)propyl)-1H-indole-2-carboxylate This example was prepared by substituting 3,4-dimethylphenol for 1-naphthol in EXAMPLE 1C.

EXAMPLE 138B 3-(3-(3,4-dimethylphenoxyl)propyl)-7-(2-methylphenyl)-1H-indole-2-carboxylic acid This example was prepared by substituting 2-methylphenylboronic acid for (E)-styrylboronic acid and EXAMPLE 138A for EXAMPLE 1C in EXAMPLE 1D. $^1$H NMR (500 MHz, DMSO-$d_6$) δ 12.90 (brs, 1H), 10.47 (s, 1H), 7.66 (d, 1H), 7.27 (m, 4H), 7.05 (m, 3H), 6.66 (m, 2H), 3.95 (t, 2H), 3.22 (t, 2H), 2.17 (s, 3H), 2.13 (s, 3H), 2.05 (m, 5H).

EXAMPLE 139A ethyl 7-bromo-3-(3-(3,5-dimethylphenoxyl)propyl)-1H-indole-2-carboxylate This example was prepared by substituting 3,5-dimethylphenol for 1-naphthol in EXAMPLE 1C.

EXAMPLE 139B 3-(3-(3,5-dimethylphenoxyl)propyl)-7-(2-methylphenyl)-1H-indole-2-carboxylic acid This example was prepared by substituting 2-methylphenylboronic acid for (E)-styrylboronic acid and EXAMPLE 139A for EXAMPLE 1C in EXAMPLE 1D. $^1$H NMR (500 MHz, DMSO-$d_6$) δ 12.88 (brs, 1H), 10.48 (s, 1H), 7.67 (d, 1H), 7.28 (m, 4H), 7.08 (m, 2H), 6.52 (m, 3H), 3.96 (t, 2H), 3.22 (t, 2H), 2.21 (s, 6H), 2.06 (m, 5H).

EXAMPLE 140A ethyl 7-bromo-3-(3-(2,3-dimethoxyphenoxyl)propyl)-1H-indole-2-carboxylate This example was prepared by substituting 2,3-dimethoxyphenol for 1-naphthol in EXAMPLE 1C.

EXAMPLE 140B 3-(3-(2,3-dimethoxyphenoxyl)propyl)-7-(2-methylphenyl)-1H-indole-2-carboxylic acid This example was prepared by substituting 2-methylphenylboronic acid for (E)-styrylboronic acid and EXAMPLE 140A for EXAMPLE 1C in EXAMPLE 1D. $^1$H NMR (500 MHz, DMSO-$d_6$) δ 9.92 (brs, 1H), 7.65 (m, 1H), 7.28 (m, 4H), 7.09 (m, 1H), 7.01 (d, 1H), 6.94 (m, 1H), 6.61 (m, 2H), 4.02 (t, 2H), 3.77 (s, 3H), 3.73 (s, 3H), 3.25 (t, 2H), 2.08 (m, 5H).

EXAMPLE 141A ethyl 7-bromo-3-(3-(naphthalen-1-ylamino)-3-oxo-propyl)-1H-indole-2-carboxylate A mixture of 3-(7-bromo-2-(ethoxycarbonyl)-1H-indol-3-yl)propanoic acid (0.68 g), naphthalen-1-amine (0.294 g), DMAP (0.363 g) and 1-ethyl-3-(3-(dimethylamino)propyl) carbodiimide hydrochloride (0.576 g) was stirred for 3 days at room temperature. The product precipitated and was filtered, washed with dichloromethane, and dried under vacuum.

EXAMPLE 141B ethyl 7-bromo-3-(3-(naphthalen-1-ylamino)propyl)-1H-indole-2-carboxylate To EXAMPLE 141A (0.465 g) was added a mixture of 1M $BH_3$.THF (4 mL), and the mixture was stirred for 16 hours, quenched with methanol and concentrated. The concentrate was treated with HCl and ethanol, and the mixture was concentrated. The concentrate was partitioned between saturated sodium bicarbonate and dichloromethane. The organic layer was dried ($Na_2SO_4$), filtered and concentrated. The concentrate was purified by flash column chromatography on silica gel with 0-30% ethyl acetate/hexanes.

EXAMPLE 141C 7-(2-methylphenyl)-3-(3-(1-naphthylamino)propyl)-1H-indole-2-carboxylic acid This example was prepared by substituting 2-methylphenylboronic acid for (E)-styrylboronic acid and EXAMPLE 141B for EXAMPLE 1C in EXAMPLE 1D. $^1$H NMR (300 MHz, DMSO-$d_6$) δ 12.99 (brs, 1H), 10.46 (s, 1H), 8.14 (d, 1H), 7.73 (m, 2H), 7.25 (m, 10H), 6.47 (d, 1H), 3.26 (m, 4H), 2.09 (m, 5H).

EXAMPLE 142A ethyl 7-bromo-1-(2-methoxy-2-oxoethyl)-3-(3-(naphthalen-1-yloxy)propyl)-1H-indole-2-carboxylate This example was prepared by substituting methyl 2-chloroacetate for 2-chloro-1-morpholinoethanone in EXAMPLE 77A.

EXAMPLE 142B 1-(carboxymethyl)-7-(2-methylphenyl)-3-(3-(1-naphthyloxy)propyl)-1H-indole-2-carboxylic acid This example was prepared by substituting 2-methylphenylboronic acid for (E)-styrylboronic acid and EXAMPLE 142A for EXAMPLE 1C in EXAMPLE 1D. $^1$H NMR (300 MHz, DMSO-$d_6$) δ 13.15 (brs, 1H), 12.37 (brs, 1H), 8.26 (m, 1H), 7.88 (m, 1H), 7.78 (m, 1H), 7.39 (m, 7H), 7.12 (m, 2H), 6.94 (m, 2H), 4.77 (brs, 1H), 4.49 (brs, 1H), 4.23 (t, 2H), 2.23 (m, 2H), 1.96 (s, 3H).

EXAMPLE 143A ethyl 7-bromo-3-(3-(3-dimethylaminophenoxyl)propyl)-1H-indole-2-carboxylate This example was prepared by substituting 3-dimethylaminophenol for 1-naphthol in EXAMPLE 1C.

EXAMPLE 143B 3-(3-(3-(dimethylamino)phenoxy)propyl)-7-(2-methylphenyl)-1H-indole-2-carboxylic acid This example was prepared by substituting 2-methylphenylboronic acid for (E)-styrylboronic acid and EXAMPLE 143A for EXAMPLE 1C in EXAMPLE 1D. $^1$H NMR (500 MHz, DMSO-$d_6$) δ 12.90 (brs, 1H), 10.48 (s, 1H), 7.68 (m, 1H), 7.26 (m, 4H), 7.07 (m, 3H), 6.37 (m, 3H), 3.99 (t, 2H), 3.22 (t, 2H), 2.90 (s, 6H), 2.06 (m, 5H).

EXAMPLE 144A morpholino(4-nitro-3-(trifluoromethyl)phenyl) methanone

To a mixture of 4-nitro-3-trifluoromethylbenzoic acid (10 g), morpholine (3.7 g) in dichloromethane (300 mL) was added DMAP (5.2 g) and 1-ethyl-3-(3-(dimethylamino)propyl)-carbodiimide hydrochloride (12.3 g). The mixture was stirred at room temperature overnight, washed with 5% aqueous HCl, water and brine and concentrated.

EXAMPLE 144B (4-amino-3-(trifluoromethyl)phenyl)(morpholino) methanone

A mixture of EXAMPLE 144A (13 g) and Pd/C (1.3 g, 10%) in ethanol (300 mL) was stirred under hydrogen at room temperature for two days. The catalyst was filtered off and the solvent was evaporated to provide the final compound.

EXAMPLE 144C (4-bromo-3-(trifluoromethyl)phenyl)(morpholino) methanone

To a mixture of EXAMPLE 144B (8.3 g) was added water (75 mL) and $H_2SO_4$ (25 mL). The mixture was stirred at 0° C. while $NaNO_2$ (3.13 g) in water (30 mL) was added. After stirring for 1 hour, the mixture was added to CuBr (5.45 g) in 48% HBr (200 mL). This mixture was stirred at 60° C. for 3 hours, cooled to room temperature, and partitioned between water and ethyl acetate. The organic layer was washed with aqueous $Na_2CO_3$ and dried ($Na_2SO_4$), filtered and concentrated.

EXAMPLE 144D 3-(4-oxo-butyl)-7-(4,4,5,5-tetramethyl-(1,3,2)dioxaborolan-2-yl)-1H-indole-2-carboxylic acid ethyl ester A mixture of EXAMPLE 109C (2.3 g), bis(pinacolato) diboron (2.1 g), potassium acetate (3.34 g) and (1,1'-bis (diphenylphosphino)ferrocene)dichloropalladium(II) (278 mg) in DMF (40 mL) was stirred at 60° C. overnight and concentrated. The concentrate was partitioned between dichloromethane and water. The aqueous phase was further extracted with dichloromethane. The extract was washed with water and brine and dried (Na$_2$SO$_4$), filtered and concentrated. The concentrate was purified by flash chromatography on silica gel with 5% ethyl acetate in hexanes.

EXAMPLE 144E ethyl 7-(4-(morpholine-4-carbonyl)-2-(trifluoromethyl)phenyl)-3-(4-oxobutyl)-1H-indole-2-carboxylate To a mixture of EXAMPLE 144D (1.67 g) and EXAMPLE 144C (1.53 g) in dimethoxyethane (80 mL) was added tris (dibenzylideneacetone)dipalladium(0) (201 mg), tri-tert-butylphosphine tetrafluoroborate (128 mg) and CsF (1.97 g). The mixture was stirred at ambient temperature overnight, diluted with ethyl acetate (200 mL), washed with water and brine and dried (Na$_2$SO$_4$), filtered and concentrated. The concentrate was purified on silica gel with 20% ethyl acetate in hexanes.

EXAMPLE 144F 3-(4-(3,4-dihydroquinolin-1(2H)-yl)butyl)-7-(4-(morpholin-4-ylcarbonyl)-2-(trifluoromethyl)phenyl)-1H-indole-2-carboxylic acid To a mixture of EXAMPLE 144E (52 mg) and 1,2,3,4-tetrahydroquinoline (27 mg) in dichloroethane (2 mL) was added sodium triacetoxyborohydride (50 mg). The mixture was stirred at ambient temperature overnight, diluted with ethyl acetate (200 mL), washed with water and brine, and dried over sodium sulfate. Evaporation of the solvent and flash column purification on silica gel with 20% ethyl acetate in hexanes provided the ethyl ester which was saponified with LiOH as described in EXAMPLE 65B. $^1$H NMR (300 MHz, DMSO-d$_6$) δ 11.09 (s, 1H), 8.29 (s, 1H), 8.21 (dd, 1H), 7.74 (d, 1H), 7.54 (d, 1H), 7.13 (d, 1H), 7.05 (d, 1H), 6.90 (t, 1H), 6.86 (d, 1H), 6.52 (d, 1H), 6.43 (t, 1H), 3.20 (m, 12H), 2.64 (t, 2H), 1.81 (m, 2H), 1.61 (m, 6H).

EXAMPLE 145

3-(4-(2-methyl-3,4-dihydroquinolin-1(2H)-yl)butyl)-7-(4-(morpholin-4-ylcarbonyl)-2-(trifluoromethyl)phenyl)-1H-indole-2-carboxylic acid This example was prepared by substituting 2-methyl-1,2,3,4-tetrahydroquinoline for 1,2,3,4-tetrahydroquinoline in EXAMPLE 144F. $^1$H NMR (300 MHz, DMSO-d$_6$) δ 11.09 (s, 1H), 8.29 (s, 1H), 8.22 (dd, 1H), 7.74 (d, 1H), 7.54 (d, 1H), 7.13 (t, 1H), 7.05 (d, 1H), 6.93 (t, 1H), 6.86 (d, 1H), 6.45 (m, 2H), 3.35 (m, 4H), 3.17 (m, 12H), 2.72 (m, 2H), 1.69 (m, 6H), 1.04 (d, 3H).

EXAMPLE 146

3-(4-(6-methyl-3,4-dihydroquinolin-1(2H)-yl)butyl)-7-(4-(morpholin-4-ylcarbonyl)-2-(trifluoromethyl)phenyl)-1H-indole-2-carboxylic acid This example was prepared by substituting 6-methyl-1,2,3,4-tetrahydroquinoline for 1,2,3,4-tetrahydroquinoline in EXAMPLE 144F. $^1$H NMR (300 MHz, DMSO-d$_6$) δ 11.09 (s, 1H), 8.29 (s, 1H), 8.21 (dd, 1H), 7.72 (d, 1H), 7.53 (d, 1H), 7.12 (t, 1H), 7.05 (d, 1H), 6.75 (d, 1H), 6.69 (s, 1H), 6.48 (m, 1H), 3.17 (m, 12H), 2.62 (t, 2H), 2.11 (s, 3H), 1.83 (t, 2H), 1.63 (m, 4H).

EXAMPLE 147

3-(4-(6-methoxy-3,4-dihydroquinolin-1(2H)-yl)butyl)-7-(4-(morpholin-4-ylcarbonyl)-2-(trifluoromethyl)phenyl)-1H-indole-2-carboxylic acid This example was prepared by substituting 6-methoxy-1,2,3,4-tetrahydroquinoline for 1,2,3,4-tetrahydroquinoline in EXAMPLE 144F. $^1$H NMR (300 MHz, DMSO-d$_6$) δ 11.11 (s, 1H), 8.29 (s, 1H), 8.21 (dd, 1H), 7.75 (d, 1H), 7.53 (d, 1H), 7.13 (t, 1H), 7.06 (d, 1H), 6.61 (m, 3H), 3.65 (s, 3H), 3.17 (m, 12H), 2.69 (m, 2H), 1.86 (m, 2H), 1.6 (m, 4H).

EXAMPLE 148

3-(4-(ethyl(1-naphthyl)amino)butyl)-7-(4-(morpholin-4-ylcarbonyl)-2-(trifluoromethyl)phenyl)-1H-indole-2-carboxylic acid This example was prepared by substituting ethyl-naphthalen-1-yl-amine for 1,2,3,4-tetrahydroquinoline in EXAMPLE 144F. $^1$H NMR (300 MHz, DMSO-d$_6$) δ 11.06 (s, 1H), 8.29 (s, 1H), 8.21 (dd, 1H), 7.20-8.00 (m, 8H), 7.04 (m, 3H), 3.17 (m, 12H), 1.63 (m, 5H), 0.95 (t, 3H).

EXAMPLE 149

3-(4-(2,3-dihydro-1H-indol-1-yl)butyl)-7-(4-(morpholin-4-ylcarbonyl)-2-(trifluoromethyl)phenyl)-1H-indole-2-carboxylic acid This example was prepared by substituting 2,3-dihydro-1H-indole for 1,2,3,4-tetrahydroquinoline in EXAMPLE 144F. $^1$H NMR (300 MHz, DMSO-d$_6$) δ 11.09 (s, 1H), 8.29 (s, 1H), 8.21 (dd, 1H), 7.74 (d, 1H), 7.54 (d, 1H), 6.93-7.14 (m, 4H), 6.55 (t, 1H), 6.47 (d, 1H), 3.14 (m, 12H), 2.85 (m, 3H), 1.67 (m, 5H).

EXAMPLE 150

3-(4-(2-methyl-2,3-dihydro-1H-indol-1-yl)butyl)-7-(4-(morpholin-4-ylcarbonyl)-2-(trifluoromethyl)phenyl)-1H-indole-2-carboxylic acid This example was prepared by substituting 2,3-dihydro-2-methyl-1H-indole for 1,2,3,4-tetrahydroquinoline in EXAMPLE 144F. $^1$H NMR (300 MHz, DMSO-d$_6$) δ 11.09 (s, 1H), 8.29 (s, 1H), 8.21 (dd, 1H), 7.74 (d, 1H), 7.54 (d, 1H), 7.12 (t, 1H), 7.07 (d, 1H), 6.49 (t, 1H), 6.33 (d, 1H), 3.62 (m, 2H), 3.14 (m, 12H), 1.70 (m, 5H), 1.18 (d, 3H).

EXAMPLE 151

7-(4-(morpholin-4-ylcarbonyl)-2-(trifluormethyl)phenyl)-3-(4-(5-nitro-2,3-dihydro-1H-indol-1-yl)butyl)-1H-indole-2-carboxylic acid This example was prepared by substituting 2,3-dihydro-5-nitro-1H-indole for 1,2,3,4-tetrahydroquinoline in EXAMPLE 144F. $^1$H NMR (300 MHz, DMSO-d$_6$) δ 11.09 (s, 1H), 8.29 (s, 1H), 8.21 (dd, 1H), 7.96 (dd, 1H), 7.79 (s, 1H), 7.74 (d, 1H), 7.53 (d, 1H), 7.06 (m, 3H), 6.42 (d, 1H), 3.61 (t, 3H), 3.14 (m, 10H), 3.04 (t, 2H), 1.67 (m, 5H).

EXAMPLE 152

3-(4-(5-bromo-2,3-dihydro-1H-indol-1-yl)butyl)-7-(4-(morpholin-4-ylcarbonyl)-2-(trifluoromethyl)phenyl)-1H-indole-2-carboxylic acid This example was prepared by substituting 5-bromo-2,3-dihydro-1H-indole for 1,2,3,4-tetrahydroquinoline in EXAMPLE 144F. $^1$H NMR (300 MHz, DMSO-$d_6$) δ 11.10 (s, 1H), 8.29 (s, 1H), 8.22 (dd, 1H), 7.74 (d, 1H), 7.54 (d, 1H), 7.06 (m, 4H), 6.38 (d, 1H), 3.17 (m, 10H), 3.04 (t, 2H), 2.86 (t, 2H), 1.67 (m, 5H).

EXAMPLE 153

3-(4-(2,3-dihydro-4H-1,4-benzoxazin-4-yl)butyl)-7-(4-(morpholin-4-ylcarbonyl)-2-(trifluoromethyl)phenyl)-1H-indole-2-carboxylic acid This example was prepared by substituting 3,4-dihydro-2H-benzo(1,4)oxazine for 1,2,3,4-tetrahydroquinoline in EXAMPLE 144F. $^1$H NMR (300 MHz, DMSO-$d_6$) δ 11.09 (s, 1H), 8.29 (s, 1H), 8.21 (dd, 1H), 7.74 (d, 1H), 7.53 (d, 1H), 7.12 (t, 1H), 7.05 (d, 1H), 6.71 (t, 1H), 6.65 (d, 2H), 6.46 (t, 1H), 4.12 (t, 2H), 3.14 (m, 10H), 1.65 (m, 6H).

EXAMPLE 154A ethyl 7-bromo-3-(3-(2,3,5-trimethylphenoxyl)propyl)-1H-indole-2-carboxylate This example was prepared by substituting 2,3,5-trimethylphenol for 1-naphthol in EXAMPLE 1C.

EXAMPLE 154B 7-(2-methylphenyl)-3-(3-(2,3,5-trimethylphenoxyl)propyl)-1H-indole-2-carboxylic acid This example was prepared by substituting 2-methylphenylboronic acid for (E)-styrylboronic acid and EXAMPLE 154A for EXAMPLE 1C in EXAMPLE 1D. $^1$H NMR (500 MHz, DMSO-$d_6$) δ 12.89 (brs, 1H), 10.47 (s, 1H), 7.66 (d, 1H), 7.27 (m, 4H), 7.11 (t, 1H), 7.04 (d, 1H), 6.54 (d, 2H), 3.97 (t, 2H), 3.26 (t, 2H), 2.18 (s, 3H), 2.17 (s, 3H), 2.07 (m, 8H).

EXAMPLE 155A ethyl 7-bromo-3-(3-(2,3,6-trimethylphenoxyl)propyl)-1H-indole-2-carboxylate This example was prepared by substituting 2,3,6-trimethylphenol for 1-naphthol in EXAMPLE 1C.

EXAMPLE 155B 7-(2-methylphenyl)-3-(3-(2,3,6-trimethylphenoxyl)propyl)-1H-indole-2-carboxylic acid This example was prepared by substituting 2-methylphenylboronic acid for (E)-styrylboronic acid and EXAMPLE 155A for EXAMPLE 1C in EXAMPLE 1D. $^1$H NMR (500 MHz, DMSO-$d_6$) δ 12.89 (brs, 1H), 10.47 (s, 1H), 7.71 (d, 1H), 7.28 (m, 4H), 7.15 (t, 1H), 7.05 (d, 1H), 6.89 (d, 1H), 6.80 (d, 1H), 3.76 (t, 2H), 3.27 (t, 2H), 2.16 (s, 3H), 2.16 (s, 3H), 2.11 (m, 5H), 2.06 (s, 3H).

EXAMPLE 156A ethyl 7-bromo-3-(3-(2,3-dichlorophenoxyl)propyl)-1H-indole-2-carboxylate This example was prepared by substituting 2,3-dichlorophenol for 1-naphthol in EXAMPLE 1C.

EXAMPLE 156B 3-(3-(2,3-dichlorophenoxyl)propyl)-7-(2-methylphenyl)-1H-indole-2-carboxylic acid This example was prepared by substituting 2-methylphenylboronic acid for (E)-styrylboronic acid and EXAMPLE 156A for EXAMPLE 1C in EXAMPLE 1D. $^1$H NMR (500 MHz, DMSO-$d_6$) δ 10.48 (brs, 1H), 7.66 (d, 1H), 7.30 (m, 4H), 7.21 (m, 2H), 7.06 (m, 3H), 4.12 (t, 2H), 3.27 (t, 2H), 2.12 (m, 2H), 2.05 (s, 3H).

EXAMPLE 157A 7-bromo-3-(4-ethoxycarbonyl-butyl)-1H-indole-2-carboxylic acid ethyl ester This example was prepared by substituting 2-oxo-cycloheptanecarboxylic acid ethyl ester for 2-oxo-cyclopentanecarboxylic acid ethyl ester in EXAMPLE 1A.

EXAMPLE 157B 7-bromo-3-(5-hydroxy-pentyl)-1H-indole-2-carboxylic acid ethyl ester This example was prepared by substituting EXAMPLE 157A for EXAMPLE 1A in EXAMPLE 1B.

EXAMPLE 157C 7-bromo-3-(5-(5,6,7,8-tetrahydro-naphthalen-1-yloxy)-pentyl)-1H-indole-2-carboxylic acid ethyl ester This example was prepared by substituting EXAMPLE 157A for EXAMPLE 1B and 5,6,7,8-tetrahydronaphthol for 1-naphthol in EXAMPLE 1C.

EXAMPLE 157D 7-(2-methylphenyl)-3-(5-(5,6,7,8-tetrahydronaphthalen-1-yloxy)pentyl)-1H-indole-2-carboxylic acid This example was prepared by substituting EXAMPLE 157C for EXAMPLE 1C and 2-methylphenylboronic acid for (E)-styrylboronic acid in EXAMPLE 1D. $^1$H NMR (500 MHz, DMSO-$d_6$) δ 12.82 (brs, 1H), 10.35 (s, 1H), 7.66 (d, 1H), 7.28 (m, 4H), 7.13 (t, 1H), 7.01 (m, 2H), 6.67 (d, 1H), 6.61 (d, 1H), 3.91 (t, 2H), 3.11 (t, 2H), 2.66 (m, 2H), 2.06 (s, 3H), 1.72 (m, 8H), 1.53 (m, 2H).

EXAMPLE 158A 7-bromo-3-(5-(naphthalen-1-yloxy)-pentyl)-1H-indole-2-carboxylic acid ethyl ester This example was prepared by substituting EXAMPLE 157B for EXAMPLE 1B in EXAMPLE 1C.

EXAMPLE 158B 7-(2-methylphenyl)-3-(5-(1-naphthyloxyl)pentyl)-1H-indole-2-carboxylic acid This example was prepared by substituting EXAMPLE 158A for EXAMPLE 1C and 2-methylphenylboronic acid for (E)-styrylboronic acid in EXAMPLE 1D. $^1$H NMR (500 MHz, DMSO-d$_6$) δ 12.81 (brs, 1H), 10.37 (s, 1H), 8.12 (d, 1H), 7.85 (d, 1H), 7.68 (d, 1H), 7.46 (m, 4H), 7.28 (m, 4H), 7.12 (m, 1H), 7.04 (m, 1H), 6.95 (d, 1H), 4.15 (t, 2H), 3.15 (t, 2H), 2.06 (s, 3H), 1.92 (m, 2H), 1.77 (m, 2H), 1.63 (m, 2H).

EXAMPLE 159

7-(2,3-dimethylphenyl)-3-(3-(1-naphthyloxy)propyl)-1H-indole-2-carboxylic acid $^1$H NMR (300 MHz, DMSO-d$_6$) 12.92 (s, 1H), 10.35 (s, 1H), 8.25 (m, 1H), 7.87 (m, 1H), 7.69 (dd, 1H), 7.52 (m, 2H), 7.42 (m, 2H), 7.19 (m, 2H), 7.04 (m, 3H), 6.91 (dd, 1H), 4.21 (t, 2H), 3.37 (m, 2H), 2.32 (s, 3H), 2.24 (m, 2H), 1.94 (s, 3H).

EXAMPLE 160

7-(2-methylphenyl)-3-(3-(1-naphthyloxyl)propyl)-1-(pyridin-4-ylmethyl)-1H-indole-2-carboxylic acid $^1$H NMR (400 MHz, DMSO-d$_6$) 8.37-8.45 (m, 2H), 8.19-8.26 (m, 1H), 7.84-7.91 (m, 2H), 7.36-7.57 (m, 4H), 7.13-7.28 (m, 3H), 6.83-7.00 (m, 4H), 6.59-6.67 (m, 2H), 5.52-5.63 (m, 1H), 5.17-5.30 (m, 1H), 4.26 (t, 2H), 2.24-2.35 (m, 2H), 1.76 (s, 3H).

EXAMPLE 162

7-(2-(4-fluorophenyl)cyclohex-1-en-1-yl)-3-(3-(1-naphthyloxy)propyl)-1H-indole-2-carboxylic acid $^1$H NMR (500 MHz, DMSO-d$_6$): δ 12.95 (s, 1H), 10.78 (s, 1H), 8.23-8.24 (m, 1H), 7.85-7.87 (m, 1H), 7.35-7.54 (m, 5H), 7.02-7.05 (m, 2H), 6.84 (d, J=7.63 Hz, 1H), 6.76-6.79 (m, 4H), 4.42 (t, J=6.87 Hz, 2H), 4.10-4.13 (m, 2H), 3.25 (br, 2H), 2.39-2.42 (m, 4H), 2.21-2.26 (m, 2H), 1.86 (br, 4H).

EXAMPLE 163

7-(3,5-dimethyl-1-(2-(2-oxopyrrolidin-1-yl)ethyl)-1H-pyrazol-4-yl)-3-(3-(1-naphthyloxy)propyl)-1H-indole-2-carboxylic acid $^1$H NMR (500 MHz, DMSO-d$_6$): δ 12.96 (s, 1H), 10.42 (s, 1H), 8.25-8.27 (m, 1H), 7.86-7.88 (m, 1H), 7.65 (d, J=7.63 Hz, 1H), 7.38-7.55 (m, 4H), 7.25-7.28 (m, 1H), 7.01-7.07 (m, 2H), 6.91 (d, J=7.63 Hz, 1H), 4.16-4.22 (m, 4H), 4.03 (br, 4H), 3.34-3.37 (m, 2H), 2.21-2.26 (m, 2H), 2.11-2.14 (m, 2H), 2.05 (s, 3H), 1.98 (s, 3H), 1.87-1.93 (m, 2H).

EXAMPLE 164

1-(tert-butoxycarbonyl)-7-(2-methylphenyl)-3-(3-(1-naphthyloxyl)benzyl)-1H-indole-2-carboxylic acid

EXAMPLE 164A 7-bromo-1H-indole 1-bromo-2-nitrobenzene (6.000 g, 29.7 mmol) was added to tetrahydrofuran (65 mL) and cooled to −40° C. Vinylmagnesiumbromide (1M in tetrahydrofuran, 89 mL) was added quickly. The solution was stirred for 20 minutes and then poured into a saturated aqueous solution of ammonium chloride. The solution was extracted with diethyl ether and dried with brine and anhydrous sodium sulfate. The solution was concentrated and purified by flash column chromatography on silica gel with 5% ethyl acetate in hexanes to provide the title compound.

EXAMPLE 164B 7-o-tolyl-1H-indole

EXAMPLE 164A (2.500 g), o-tolylboronic acid (1.907 g), and sodium carbonate (2M aqueous solution, 19.13 mL) were added to dioxane (43 mL). The solution was degassed and flushed with nitrogen three times. Dichloro(1,1'-bis(diphenylphosphino)ferrocene)palladium (II) dichloromethane adduct (833 mg) was added and the solution was heated at 80° C. overnight. The solution was cooled, added to 1M aqueous HCl, extracted with 20% ethyl acetate/hexanes, and dried with brine and anhydrous sodium sulfate. The solution was concentrated and purified by flash column chromatography on silica gel with 5% ethyl acetate in hexanes to provide the title compound.

EXAMPLE 164C 3-(naphthalen-1-yloxy)benzaldehyde 1-iodonaphthalene (2.000 g) and 3-hydroxybenzaldehyde (1.442 g) were added to dioxane (25 mL). The solution was degassed and flushed with nitrogen three times. Cesium carbonate (5.13 g), N,N-dimethylglycine hydrochloride (82 mg), and copper (I) iodide (30 mg) were added, and the solution was heated at 90° C. overnight. The solution was cooled, added to 1M aqueous HCl, extracted with diethyl ether, dried with brine and anhydrous sodium sulfate. The solution was concentrated and purified by flash column chromatography on silica gel with 10% ethyl acetate in hexanes to provide the title compound.

EXAMPLE 164D 3-(3-(naphthalen-1-yloxy)benzyl)-7-o-tolyl-1H-indole

EXAMPLE 164B (133 mg) and EXAMPLE 164C (175 mg) were dissolved in dichloromethane (3 mL) and added drop-wise to a solution of trifluoroacetic acid (0.074 mL, 110 mg) and triethylsilane (0.307 mL, 224 mg) in dichloromethane (3 mL), which had been cooled to 0° C. The solution was mixed for one hour at 0° C., quenched with a saturated aqueous solution of ammonium chloride, extracted with ethyl acetate, and dried with brine and anhydrous sodium sulfate. The solution was concentrated and purified by flash column chromatography on silica gel with 5% increasing to 10% ethyl acetate in hexanes to provide the title compound.

EXAMPLE 164E tert-butyl 3-(3-(naphthalen-1-yloxy)benzyl)-7-o-tolyl-1H-indole-1-carboxylate EXAMPLE 164D (158 mg) and 4-dimethylaminopyridine (4.4 mg) were added to acetonitrile (3 mL). Di-tert-butyl dicarbonate (0.088 mL, 82 mg) was added, and the solution was mixed at ambient temperature for 30 minutes. The solution was concentrated and purified by flash column chromatography on silica gel with 5% ethyl acetate in hexanes to provide the title compound.

EXAMPLE 164F 1-tert-butyl 2-methyl 3-(3-(naphthalen-1-yloxy)benzyl)-7-o-tolyl-1H-indole-1,2-dicarboxylate EXAMPLE 164E (161 mg) was added to tetrahydrofuran (3 mL). The solution was cooled to −78° C., and tert-butyl lithium (1.7M in pentane, 0.193 mL) was added slowly. The solution was mixed at −78° C. for 45 minutes, and methyl chloroformate (0.025 mL, 30.5 mg) was added. The solution was mixed at −78° C. for 30 minutes and was allowed to warm to ambient temperature. The solution was concentrated and purified by flash column chromatography on silica gel with 5% ethyl acetate in hexanes to provide the title compound.

EXAMPLE 164G 1-(tert-butoxycarbonyl)-7-(2-methylphenyl)-3-(3-(1-naphthyloxy)benzyl)-1H-indole-2-carboxylic acid EXAMPLE 164F (35 mg, 0.059 mmol) was dissolved in a mixture of tetrahydrofuran (0.6 mL), water (0.2 mL), and methanol (0.2 mL). Lithium hydroxide monohydrate (9.8 mg, 0.234 mmol) was added and the solution was mixed overnight at ambient temperature. The solution was made slightly acidic using 1M HCl, extracted with ethyl acetate, and dried with anhydrous sodium sulfate. Solvent was removed under vacuum to provide the title compound. $^1$H NMR (300 MHz, DMSO-$d_6$) δ 13.72 (br s, 1H), 8.05 (dd, 1H), 7.98 (dd, 1H), 7.73 (d, 1H), 7.66 (dd, 1H), 7.61-7.49 (m, 2H), 7.44 (t, 1H), 7.31-7.18 (m, 5H), 7.12 (dd, 2H), 7.06 (td, 2H), 6.95 (dd, 1H), 6.78 (dd, 1H), 4.35 (s, 2H), 1.99 (d, 3H), 1.17 (s, 9H).

EXAMPLE 165

7-(2-methylphenyl)-3-(3-(1-naphthyloxy)benzyl)-1H-indole-2-carboxylic acid

EXAMPLE 164G (35 mg) was dissolved in dichloromethane (2 mL). Triethylsilane (0.011 mL, 7.7 mg) and trifluoroacetic acid (0.018 mL, 27 mg) were added, and the solution was mixed overnight at ambient temperature. The solution was concentrated and purified by flash column chromatography on silica gel with 50% ethyl acetate in hexanes to provide the title compound. $^1$H NMR (300 MHz, DMSO-$d_6$) δ 12.98 (broad s, 1H), 10.61 (s, 1H), 8.05 (dd, 1H), 7.98 (dd, 1H), 7.71 (d, 1H), 7.63-7.49 (m, 3H), 7.43 (t, 1H), 7.35-7.19 (m, 6H), 7.14-7.07 (m, 2H), 7.04 (dd, 1H), 6.93 (dd, 1H), 6.75 (ddd, 1H), 4.48 (s, 2H), 1.99 (s, 3H).

EXAMPLE 166

7-(2-methylphenyl)-4-((E)-2-phenylvinyl)-1H-indole-2-carboxylic acid

EXAMPLE 166A (Z)-ethyl 2-azido-3-(5-bromo-2-chlorophenyl)acrylate

To a solution of sodium ethoxide in ethanol (15 mL) cooled to −10° C. was added dropwise a solution of 5-bromo-2-chlorobenzaldehyde (1.0 g) and ethyl 2-azidoacetate (11 mL, 18 mmol) in ethanol-tetrahydrofuran (15 mL-3 mL). The reaction mixture was stirred at −10° C. for 3 hours, allowed to warm to 10° C. over 3 hours and poured onto crushed ice. The solid was collected by filtration and dried in a vacuum oven to provide the title compound.

EXAMPLE 166B ethyl 7-bromo-4-chloro-1H-indole-2-carboxylate

To a refluxing solution of 1,2-dichlorobenzene (17 mL) was added dropwise EXAMPLE 166A (1.2 g, 3.7 mmol) over 3 hours. The solution was heated under reflux for another 2 hours. The solvent was removed under reduced pressure and the residue was purified by flash chromatography (0-20% ethyl acetate in hexanes) to provide the title compound.

EXAMPLE 166C ethyl 4-chloro-7-o-tolyl-1H-indole-2-carboxylate

To a solution of EXAMPLE 166B (610 mg), o-tolylboronic acid (330 mg), cesium fluoride (930 mg) in dioxane (5 mL) was added tetrakis(triphenylphosphine)palladium (240 mg). The resulting mixture was heated under reflux overnight and concentrated. The residue was diluted with ethyl acetate and saturated ammonium acetate, and the layers were separated. The aqueous layer was extracted with ethyl acetate (×2) and the combined organic layers were washed with brine, dried over $MgSO_4$, filtered and concentrated. The residue was purified by flash chromatography (0-20% ethyl acetate in hexanes) to provide the title compound.

EXAMPLE 166D

To a solution of EXAMPLE 166C (80 mg), (E)-styryl boronic acid (76 mg), cesium fluoride (120 mg) in dioxane-methanol (0.4 mL-0.1 mL) was added palladium acetate (5.7 mg) and (2-biphenyl)dicyclohexylphosphine (18 mg). The resulting mixture was heated under reflux overnight, treated with aqueous lithium hydroxide (0.5 mL, 2N), heated under reflux for 5 hours and concentrated. The residue was diluted with ethyl acetate and saturated ammonium acetate, and the layers were separated. The aqueous layer was extracted with ethyl acetate (×2) and the combined organic layers were washed with brine, dried over $MgSO_4$, filtered and concentrated. The residue was purified by flash chromatography (0-20% ethyl acetate in hexanes) to provide the title compound. $^1$H NMR (500 MHz, DMSO-$d_6$) δ 12.88 (br, 1H), 11.18 (s, 1H), 7.76 (m, 3H), 7.69 (d, 1H), 7.53 (d, 1H), 7.41 (m, 3H), 7.34 (d, 2H), 7.27 (m, 3H), 7.08 (d, 1H), 2.08 (s, 3H).

EXAMPLE 167

7-(2-methylphenyl)-4-(1-naphthyl)-1H-indole-2-carboxylic acid $^1$H NMR (500 MHz, DMSO-d$_6$) δ 11.32 (s, 1H), 8.04 (t, 2H), 7.71 (d, 1H), 7.66 (m, 1H), 7.61 (m, 1H), 7.56 (m, 1H), 7.46 (m, 1H), 7.34 (m, 4H), 7.22 (m, 2H), 6.60 (d, 1H), 2.18 (s, 3H).

EXAMPLE 168

7-(2-methylphenyl)-4-(2-naphthyl)-1H-indole-2-carboxylic acid $^1$H NMR (500 MHz, DMSO-d$_6$) δ 12.93 (br, 1H), 11.35 (s, 1H), 8.25 (s, 1H), 8.08 (m, 2H), 8.00 (m, 1H), 7.90 (dd, 1H), 7.57 (m, 2H), 7.36 (m, 3H), 7.31 (m, 3H), 7.19 (d, 1H), 2.13 (s, 3H).

EXAMPLE 169

7-(2-methylphenyl)-4-(3-(2-naphthyloxyl)propyl)-1H-indole-2-carboxylic acid

EXAMPLE 169A

To a solution of 2-(allyloxy)naphthalene (71 mg) in tetrahydrofuran at room temperature was added 9-Borabicyclo (3.3.1)nonane (0.5 M, 1.5 mL). The solution was stirred at 50° C. for 2 hours and cooled to room temperature. EXAMPLE 166C (100 mg), palladium acetate (7.2 mg), (2-biphenyl) dicyclohexylphosphine (22 mg) and potassium fluoride (56 mg) were added, and the resulting mixture was heated under reflux overnight. The reaction mixture was diluted with ethyl acetate and saturated ammonium chloride and the layers were separated. The aqueous layer was extracted with ethyl acetate (×2) and the combined organic layers were washed with brine, dried over MgSO$_4$, filtered and concentrated. The residue was purified by flash chromatography (20% ethyl acetate in hexanes) to provide the title compound.

EXAMPLE 169B

To a solution of EXAMPLE 169A (45 mg) in dioxane (1.0 mL) was added aqueous lithium hydroxide (2 N, 0.15 mL). The resulting mixture was heated at 60° C. overnight and diluted with ethyl acetate and saturated ammonium chloride. The layers were separated and the aqueous layer was extracted with ethyl acetate (×2). The combined organic layers were dried over MgSO4, filtered and concentrated. The residue was purified by flash chromatography (0-5% methanol in dichloromethane) to provide the title compound. $^1$H NMR (400 MHz, DMSO-d$_6$) δ 12.82 (br, 1H), 11.10 (s, 1H), 7.83 (d, 2H), 7.78 (d, 1H), 7.45 (m, 1H), 7.35 (m, 1H), 7.31 (m, 4H), 7.27 (m, 1H), 7.22 (m, 2H), 7.02 (m, 1H), 6.97 (m, 1H), 4.20 (t, 2H), 3.12 (t, 2H), 2.24 (m, 2H), 2.05 (s, 3H).

EXAMPLE 170

7-(2-methylphenyl)-4-(4-(1-naphthyloxy)butyl)-1H-indole-2-carboxylic acid $^1$H NMR (500 MHz, DMSO-d$_6$) δ 12.81 (br, 1H), 11.02 (s, 1H), 8.14 (d, 1H), 7.85 (d, 1H), 7.49 (m, 3H), 7.40 (m, 1H), 7.31 (m, 3H), 7.26 (m, 1H), 7.21 (m, 1H), 7.01 (m, 1H), 6.96 (m, 2H), 4.21 (t, 2H), 3.04 (t, 2H), 2.05 (s, 3H), 2.00 (m, 4H).

EXAMPLE 171

7-(2-methylphenyl)-4-(4-(2-naphthyloxyl)butyl)-1H-indole-2-carboxylic acid $^1$H NMR (500 MHz, DMSO-d$_6$) δ 12.81 (br, 1H), 11.01 (s, 1H), 7.80 (m, 3H), 7.44 (m, 1H), 7.31 (m, 5H), 7.25 (m, 1H), 7.20 (m, 1H), 7.17 (dd, 1H), 7.00 (m, 1H), 6.96 (m, 1H), 4.16 (t, 2H), 3.00 (t, 2H), 2.05 (s, 3H), 1.91 (m, 4H).

EXAMPLE 172

7-(2-methylphenyl)-4-(2-(2-naphthyl)ethyl)-1H-indole-2-carboxylic acid $^1$H NMR (500 MHz, DMSO-d$_6$) δ 12.83 (br, 1H), 11.05 (s, 1H), 7.86 (m, 3H), 7.80 (s, 1H), 7.53 (dd, 1H), 7.46 (m, 2H), 7.37 (d, 1H), 7.31 (d, 2H), 7.26 (m, 1H), 7.21 (m, 1H), 7.01 (m, 1H), 6.95 (d, 1H), 3.29 (m, 2H), 3.19 (m, 2H), 2.06 (s, 3H).

EXAMPLE 173

3-(3-(1-naphthyloxy)propyl)-7-thien-3-yl-1H-indole-2-carboxylic acid $^1$H NMR (500 MHz, DMSO-d$_6$): δ 13.07 (br, 1H), 10.23 (s, 1H), 8.22-8.24 (m, 1H), 7.93 (dd, J=2.9, 1.37 Hz, 1H), 7.85-7.87 (m, 1H), 7.72 (dd, J=4.88, 2.75 Hz, 1H), 7.67 (d, J=7.93 Hz, 1H), 7.79-7.55 (m, 3H), 7.44-7.46 (m, 1H), 7.36-7.40 (m, 2H), 7.05-7.08 (m, 1H), 6.89 (d, J=7.02 Hz, 1H), 4.18 (t, J=6.1 Hz, 2H), 3.75-3.78 (m, 2H), 2.21-2.26 (m, 2H).

EXAMPLE 174

7-((3-(aminocarbonyl)phenyl)amino)-3-(3-(1-naphthyloxyl)propyl)-1H-indole-2-carboxylic acid $^1$H NMR (500 MHz, DMSO-d$_6$): δ 13.07 (br, 1H), 11.22 (s, 1H), 10.23 (s, 1H), 8.20-8.24 (m, 2H), 7.92 (s, 1H), 7.85-7.87 (m, 1H), 7.68 (s, 1H), 7.49-7.54 (m, 2H), 7.44-7.46 (m, 1H), 7.30-7.40 (m, 5H), 7.23 (d, J=8.24 Hz, 1H), 7.13 (d, J=7.63 Hz, 1H), 6.88-6.93 (m, 2H), 4.18 (t, J=5.95 Hz, 2H), 3.31 (m, 2H), 2.19-2.25 (m, 2H).

EXAMPLE 175

7-((3-cyanophenyl)amino)-3-(3-(1-naphthyloxy)propyl)-1H-indole-2-carboxylic acid

EXAMPLE 175A ethyl 7-(3-cyanophenylamino)-3-(3-(naphthalen-1-yloxy)propyl)-1H-indole-2-carboxylate A mixture of ethyl 7-bromo-3-(3-(naphthalen-1-yloxy) propyl)-1H-indole-2-carboxylate (EXAMPLE 1C) (45.2 mg), 3-aminobenzonitrile (14.2 mg), 2'-(dicyclohexylphosphino)-N,N-dimethylbiphenyl-2-amine (Cy-map) (5.9 mg), tris(dibenzylideneacetone)dipalladium(0) (4.6 mg), and Cs$_2$CO$_3$ (46 mg) in dioxane (1 mL) was degassed via vacuum-nitrogen cycle three times. The reaction mixture was heated at 100 OC for 16 hours. The reaction mixture was partitioned between water and ethyl acetate. The organic layer was separated, and the aqueous layer was extracted with additional ethyl acetate. The combined organic layers were washed with brine, dried over MgSO$_4$, filtered, and concentrated in vacuo. The residue was purified with flash chromatography (1:9 EtOAc/Hex) to provide the title compound.

EXAMPLE 175B 7-((3-cyanophenyl)amino)-3-(3-(1-naphthyloxy) propyl)-1H-indole-2-carboxylic acid EXAMPLE 175A (28 mg) was treated with dioxane (3 mL) and 1.0 N LiOH (1 mL). The reaction mixture was heated at 100° C. for 3 hours. The solvents were removed in vacuo, and residue was purified with RP HPLC to give pure EXAMPLE 175B and EXAMPLE 174. $^1$H NMR (500 MHz, DMSO-d$_6$): δ 13.12 (s, 1H), 11.21 (s, 1H), 8.33 (s, 1H), 8.20-8.22 (m, 1H), 7.85-7.87 (m, 1H), 7.49-7.54 (m, 2H), 7.37-7.46 (m, 5H), 7.32 (d, J=7.93 Hz, 1H), 7.23-7.25 (m, 1H), 7.17 (d, J=7.32 Hz, 1H), 6.95 (t, J=7.78 Hz, 1H), 6.88 (d, J=7.63 Hz, 1H), 4.18 (t, J=6.1 Hz, 2H), 3.31 (m, 2H), 2.20-2.24 (m, 2H).

EXAMPLE 176

7-((2-benzylphenyl)amino)-3-(3-(1-naphthyloxy) propyl)-1H-indole-2-carboxylic acid $^1$H NMR (500 MHz, DMSO-d$_6$): δ 13.01 (s, 1H), 11.31 (s, 1H), 8.21-8.23 (m, 1H), 7.84-7.86 (m, 1H), 7.36-7.54 (m, 5H), 7.07-7.29 (m, 9H), 6.96-7.00 (m, 1H), 6.89 (d, J=7.36 Hz, 1H), 6.79 (t, J=7.83 Hz, 1H), 6.57 (d, J=7.67 Hz, 1H), 4.19 (t, J=6.14 Hz, 2H), 4.05 (s, 2H), 3.31 (m, 2H), 2.20-2.25 (m, 2H).

EXAMPLE 177

7-(1,1'-biphenyl-2-ylamino)-3-(3-(1-naphthyloxy) propyl)-1H-indole-2-carboxylic acid $^1$H NMR (500 MHz, DMSO-d$_6$): δ 12.93 (s, 1H), 11.28 (s, 1H), 8.21-8.24 (m, 1H), 7.28-7.55 (m, 13H), 7.12-7.16 (m, 1H), 6.89 (d, J=7.36 Hz, 1H), 7.01 (d, J=7.61 Hz, 1H), 6.89 (d, J=6.75 Hz, 1H), 6.81 (t, J=7.67 Hz, 1H), 6.74-6.76 (m, 1H), 4.18 (t, J=6.14 Hz, 2H), 3.31 (m, 2H), 2.17-2.24 (m, 2H).

EXAMPLE 178

7-((2-ethylphenyl)amino)-3-(3-(1-naphthyloxy)propyl)-1H-indole-2-carboxylic acid $^1$H NMR (500 MHz, DMSO-d$_6$): δ 13.04 (s, 1H), 11.36 (s, 1H), 8.22-8.24 (m, 1H), 7.85-7.88 (m, 1H), 7.15-7.54 (m, 8H), 7.02-7.09 (m, 2H), 6.89 (d, J=7.63 Hz, 1H), 6.78 (t, J=7.78 Hz, 1H), 6.50 (d, J=7.32 Hz, 1H), 4.19 (t, J=5.95 Hz, 2H), 3.31 (m, 2H), 2.68 (q, J=7.53 Hz, 2H), 2.19-2.25 (m, 2H), 1.15 (t, J=7.48 Hz, 3H).

EXAMPLE 179

3-(3-(1-naphthyloxyl)propyl)-7-((2-propylphenyl) amino)-1H-indole-2-carboxylic acid $^1$H NMR (500 MHz, DMSO-d$_6$): δ 13.03 (s, 1H), 11.36 (s, 1H), 8.22-8.24 (m, 1H), 7.85-7.87 (m, 1H), 7.50-7.54 (m, 2H), 7.44-7.46 (m, 1H), 7.39 (t, J=7.93 Hz, 1H), 7.33 (s, 1H), 7.23-7.27 (m, 1H), 7.16 (t, J=6.87 Hz, 1H), 7.08 (d, J=7.93 Hz, 1H), 7.02 (t, J=7.02 Hz, 1H), 6.89 (d, J=7.63 Hz, 1H), 6.77 (t, J=7.78 Hz, 1H), 6.50 (d, J=7.32 Hz, 1H), 4.19 (t, J=6.1 Hz, 2H), 3.31 (m, 2H), 2.63-2.66 (m, 2H), 2.19-2.25 (m, 2H), 1.55-1.59 (m, 2H), 0.88 (t, J=7.32 Hz, 3H).

EXAMPLE 180

7-(5-carboxy-3-methylthien-2-yl)-3-(3-(1-naphthyloxy)propyl)-1H-indole-2-carboxylic acid $^1$H NMR (500 MHz, DMSO-d$_6$): δ 13.01 (s, 1H), 11.02 (s, 1H), 8.22-8.24 (m, 1H), 7.86-7.88 (m, 1H), 7.77 (d, J=7.93 Hz, 1H), 7.65 (s, 1H), 7.45-7.53 (m, 1H), 7.39 (t, J=7.78 Hz, 1H), 7.21 (d, J=6.81 Hz, 1H), 7.08 (t, J=7.63 Hz, 1H), 6.90 (d, J=7.63 Hz, 1H), 4.20 (t, J=6.1 Hz, 2H), 3.34-3.38 (m, 2H), 2.21-2.26 (m, 2H).

EXAMPLE 181

7-((2-carboxyphenyl)amino)-3-(3-(1-naphthyloxy) propyl)-1H-indole-2-carboxylic acid $^1$H NMR (500 MHz, DMSO-d$_6$): δ 12.89 (s, 1H), 11.57 (s, 1H), 9.22 (s, 1H), 8.22-8.24 (m, 1H), 7.90-7.91 (m, 1H), 7.85-7.87 (m, 1H), 7.50-7.54 (m, 2H), 7.44-7.46 (m, 2H), 7.38 (t, J=7.93 Hz, 1H), 7.29-7.32 (m, 1H), 7.14 (d, J=7.32 Hz, 1H), 6.93-6.97 (m, 2H), 6.89 (d, J=7.63 Hz, 1H), 6.76 (t, J=7.32 Hz, 1H), 4.18 (t, J=5.95 Hz, 2H), 3.34-3.38 (m, 2H), 2.21-2.25 (m, 2H).

EXAMPLE 182

7-((3-carboxyphenyl)amino)-3-(3-(1-naphthyloxy) propyl)-1H-indole-2-carboxylic acid $^1$H NMR (500 MHz, DMSO-d$_6$): δ 12.99 (s, 1H), 11.22 (s, 1H), 8.26 (s, 1H), 8.22-8.23 (m, 1H), 7.85-7.87 (m, 1H), 7.76 (s, 1H), 7.49-7.54 (m, 2H), 7.37-7.46 (m, 5H), 7.26 (d, J=8.06 Hz, 1H), 7.14 (d, J=7.33 Hz, 1H), 6.94 (t, J=7.69 Hz, 1H), 4.18 (t, J=5.95 Hz, 2H), 3.34-3.38 (m, 2H), 2.21-2.25 (m, 2H).

EXAMPLE 183

7-(2-morpholin-4-yl-5-nitropyridin-3-yl)-3-(3-(1-naphthyloxy)propyl)-1H-indole-2-carboxylic acid $^1$H NMR (500 MHz, DMSO-d$_6$): δ 13.03 (s, 1H), 11.27 (s, 1H), 9.09 (d, J=2.76 Hz, 1H), 8.22-8.24 (m, 1H), 8.16 (d, J=2.76 Hz, 1H), 7.85-7.87 (m, 1H), 7.77 (d, J=7.98 Hz, 1H), 7.44-7.55 (m, 3H), 7.37 (t, J=7.98 Hz, 1H), 7.30 (d, J=7.06 Hz, 1H), 7.09 (t, J=7.67 Hz, 1H), 6.86 (d, J=7.36 Hz, 1H), 4.17 (t, J=6.14 Hz, 2H), 3.05-3.35 (m, 10H), 2.23-2.26 (m, 2H).

EXAMPLE 184

7-(5-amino-2-morpholin-4-ylpyridin-3-yl)-3-(3-(1-naphthyloxyl)propyl)-1H-indole-2-carboxylic acid $^1$H NMR (500 MHz, DMSO-d$_6$): δ 10.96 (s, 1H), 8.23-8.25 (m, 1H), 7.86-7.88 (m, 1H), 7.79 (d, J=7.93 Hz, 1H), 7.75 (s, 1H), 7.49-7.55 (m, 2H), 7.43-7.46 (m, 2H), 7.37 (t, J=7.93 Hz, 1H), 7.30 (d, J=7.32 Hz, 1H), 7.10-7.13 (m, 1H), 6.86 (d, J=7.32 Hz, 1H), 4.17 (t, J=6.14 Hz, 2H), 3.05-3.35 (m, 10H), 2.23-2.26 (m, 2H).

EXAMPLE 185

7-((3-chloropyridin-4-yl)amino)-3-(3-(1-naphthyloxy)propyl)-1H-indole-2-carboxylic acid $^1$H NMR (500 MHz, DMSO-d$_6$): δ 13.20 (s, 1H), 11.72 (s, 1H), 9.77 (s, 1H), 8.73 (s, 1H), 8.24-8.27 (m, 1H), 8.10 (d, J=6.71 Hz, 1H), 7.86-7.88 (m, 1H), 7.76 (d, J=7.93 Hz, 1H), 7.51-7.56 (m, 2H), 7.45-7.47 (m, 1H), 7.39 (t, J=7.93 Hz, 1H), 7.22 (d, J=7.32 Hz, 1H), 7.10 (t, J=7.78 Hz, 1H), 6.89 (d, J=7.32 Hz, 1H), 6.45 (d, J=6.71 Hz, 1H), 4.19 (t, J=6.1 Hz, 2H), 3.36-3.39 (m, 2H), 2.23-2.25 (m, 2H).

EXAMPLE 186

7-((2-isopropylphenyl)amino)-3-(3-(1-naphthyloxy)propyl)-1H-indole-2-carboxylic acid $^1$H NMR (500 MHz, DMSO-d$_6$): δ 12.99 (s, 1H), 11.32 (s, 1H), 8.21-8.23 (m, 1H), 7.85-7.87 (m, 1H), 7.37-7.52 (m, 6H), 7.03-7.22 (m, 4H), 6.89 (d, J=7.36 Hz, 1H), 6.75 (t, J=7.83 Hz, 1H), 6.35 (d, J=7.67 Hz, 1H), 4.19 (t, J=6.1 Hz, 2H), 3.29-3.35 (m, 2H), 2.23-2.25 (m, 3H), 1.17 (d, J=6.44 Hz, 6H).

EXAMPLE 187

7-(2-morpholin-4-ylpyridin-3-yl)-3-(3-(1-naphthyloxyl)propyl)-1H-indole-2-carboxylic acid $^1$H NMR (500 MHz, DMSO-d$_6$): δ 13.16 (s, 1H), 11.02 (s, 1H), 8.31 (dd, J=5.19, 1.83 Hz, 1H), 8.23-8.25 (m, 1H), 7.86-7.89 (m, 2H), 7.78 (d, J=7.93 Hz, 1H), 7.49-7.55 (m, 2H), 7.44-7.46 (m, 1H), 7.38 (d, J=7.93 Hz, 1H), 7.35 (t, J=7.32 Hz, 1H), 7.18-7.20 (m, 1H), 7.11-7.14 (m, 1H), 6.86 (d, J=7.63 Hz, 1H), 4.17 (t, J=6.1 Hz, 2H), 3.39 (t, J=7.32 Hz, 2H), 3.2 (br, 4H), 2.97 (br, 4H), 2.21-2.27 (m, 2H).

EXAMPLE 188

7-(5-(aminocarbonyl)-1,2-dimethyl-6-oxo-1,6-dihydropyridin-3-yl)-3-(3-(1-naphthyloxy)propyl)-1H-indole-2-carboxylic acid $^1$H NMR (500 MHz, DMSO-d$_6$): δ 13.03 (s, 1H), 11.18 (s, 1H), 9.21 (d, J=4.58 Hz, 1H), 8.22-8.24 (m, 1H), 8.06 (s, 1H), 7.86-7.88 (m, 1H), 7.72-7.74 (m, 1H), 7.49-7.55 (m, 4H), 7.44-7.46 (m, 1H), 7.69 (t, J=7.93 Hz, 1H), 7.06-7.10 (m, 2H), 6.90 (d, J=7.32 Hz, 1H), 4.20 (t, J=6.1 Hz, 2H), 3.63 (s, 3H), 3.32-3.37 (m, 2H), 2.21-2.26 (m, 2H), 2.17 (s, 3H).

EXAMPLE 189

7-(5-cyano-1,2-dimethyl-6-oxo-1,6-dihydropyridin-3-yl)-3-(3-(1-naphthyloxyl)propyl)-1H-indole-2-carboxylic acid $^1$H NMR (500 MHz, DMSO-d$_6$): δ 13.07 (s, 1H), 11.23 (s, 1H), 8.22-8.24 (m, 1H), 7.93 (s, 1H), 7.86-7.88 (m, 1H), 7.74 (dd, J=7.02, 2.14 Hz, 1H), 7.49-7.55 (m, 1H), 7.44-7.46 (m, 1H), 7.39 (t, J=7.39 Hz, 1H), 7.06-7.10 (m, 2H), 6.89 (d, J=7.32 Hz, 1H), 4.19 (t, J=6.1 Hz, 2H), 3.56 (s, 3H), 3.32-3.37 (m, 2H), 2.21-2.26 (m, 2H), 2.13 (s, 3H).

EXAMPLE 190

7-(5-amino-4-chloro-2-morpholin-4-ylpyridin-3-yl)-3-(3-(1-naphthyloxyl)propyl)-1H-indole-2-carboxylic acid $^1$H NMR (500 MHz, DMSO-d$_6$): δ 13.07 (s, 1H), 10.65 (s, 1H), 8.24 d, J=7.63 Hz, 1H), 7.86 (d, J=7.32 Hz, 1H), 7.74 (d, J=7.93 Hz, 1H), 7.49-7.54 (m, 2H), 7.45 (d, J=8.24 Hz, 1H), 7.37 (t, J=7.93 Hz, 1H), 7.28 (d, J=7.02 Hz, 1H), 7.25 (s, 1H), 7.09 (t, J=7.48 Hz, 1H), 6.86 (d, J=7.63 Hz, 1H), 4.17 (t, J=6.1 Hz, 2H), 3.39 (t, J=7.32 Hz, 2H), 3.24 (br, 4H), 2.75 (br, 4H), 2.23-2.25 (m, 2H).

EXAMPLE 191

2-methyl-3'-(3-(1-naphthyloxyl)propyl)-2,3-dihydro-1'H-1,7'-biindole-2'-carboxylic acid $^1$H NMR (500 MHz, DMSO-d$_6$): δ 13.01 (s, 1H), 10.89 (s, 1H), 8.25-8.27 (m, 1H), 7.86-7.88 (m, 1H), 7.58 (d, J=7.93 Hz, 1H), 7.50-7.55 (m, 2H), 7.45-7.47 (m, 1H), 7.39 (t, J=7.93 Hz, 1H), 7.17 (d, J=7.02 Hz, 1H), 7.12 (d, J=7.02 Hz, 1H), 7.05 (t, J=7.78 Hz, 1H), 6.91 (d, J=7.63 Hz, 1H), 6.86 (t, J=7.63 Hz, 1H), 6.60 (t, J=7.32 Hz, 1H), 5.97 (d, J=7.93 Hz, 1H), 4.51-4.54 (m, 1H), 4.21 (t, J=6.1 Hz, 2H), 3.38 (t, J=7.32 Hz, 2H), 2.79 (dd, J=15.1, 8.09 Hz, 1H), 2.21-2.27 (m, 2H).

EXAMPLE 192

7-(2-fluoro-5-methylpyridin-4-yl)-3-(3-(1-naphthyloxy)propyl)-1H-indole-2-carboxylic acid

EXAMPLE 192A methyl 7-(2-fluoro-5-methylpyridin-4-yl)-3-(3-(naphthalen-1-yloxy)propyl)-1H-indole-2-carboxylate A mixture of EXAMPLE 43A (0.40 g), 2-fluoro-4-iodo-5-methylpyridine (0.209 g), tetrakis(triphenylphosphine)palladium (46 mg) and cesium fluoride (0.365 g) in dimethoxyethane (3 mL) and methanol (1.5 mL) was heated at 120° C. for 20 minutes under microwave conditions (CEM Discovery). After cooling to room temperature, the reaction mixture was loaded onto a silica gel cartridge. The cartridge was dried in vacuum oven for 1 hour and eluted with 1:4 ethyl acetate/hexanes to give the desired product. $^1$H NMR (500 MHz, DMSO-d$_6$): 11.33 (s, 1H), 8.23-8.25 (m, 1H), 8.17 (s, 1H), 7.86-7.88 (m, 1H), 7.79-7.81 (m, 1H), 7.45-7.56 (m, 3H), 7.39 (t, J=7.93 Hz, 1H), 7.12-7.14 (m, 2H), 7.04 (d, J=2.14 Hz, 1H), 6.91 (d, J=7.32 Hz, 1H), 4.20 (t, J=5.95 Hz, 2H), 3.78 (s, 3H), 3.37 (t, J=7.48 Hz, 2H), 2.20-2.26 (m, 2H), 2.00 (s, 3H).

EXAMPLE 192B 7-(2-fluoro-5-methylpyridin-4-yl)-3-(3-(1-naphthyloxy)propyl)-1H-indole-2-carboxylic acid The title compound was synthesized according to the procedure for EXAMPLE 175B by substituting EXAMPLE 175A with EXAMPLE 192A. $^1$H NMR (500 MHz, DMSO-d$_6$): 13.00 (s, 1H), 11.21 (s, 1H), 8.23-8.25 (m, 1H), 8.16 (s, 1H), 7.86-7.88 (m, 1H), 7.76-7.79 (m, 1H), 7.50-7.55 (m, 2H), 7.45-7.47 (m, 1H), 7.39 (t, J=7.93 Hz, 1H), 7.09-7.11 (m, 2H), 7.03 (d, J=1.83 Hz, 1H), 6.90 (d, J=7.63 Hz, 1H), 4.20 (t, J=6.1 Hz, 2H), 3.37 (t, J=7.32 Hz, 2H), 2.21-2.27 (m, 2H).

EXAMPLE 193

7-((2-methoxypyridin-3-yl)amino)-3-(3-(1-naphthyloxy)propyl)-1H-indole-2-carboxylic acid $^1$H NMR (500 MHz, DMSO-$d_6$): δ 13.04 (br, 1H), 11.58 (s, 1H), 8.22-8.24 (m, 1H), 7.85-7.87 (m, 1H), 7.70 (dd, J=4.88, 1.53 Hz, 1H), 7.50-7.55 (m, 3H), 7.44-7.46 (m, 1H), 7.38 (t, J=7.93 Hz, 1H), 7.23 (d, J=7.93 Hz, 1H), 6.94 (d, J=7.02 Hz, 1H), 6.68-6.91 (m, 3H), 4.18 (t, J=6.1 Hz, 2H), 3.98 (s, 3H), 3.33 (t, J=7.32 Hz, 2H), 2.19-2.24 (m, 2H).

EXAMPLE 194

7-(5-methyl-2-oxo-1,2-dihydropyridin-4-yl)-3-(3-(1-naphthyloxyl)propyl)-1H-indole-2-carboxylic acid EXAMPLE 192 (50 mg) in acetic acid (10 ml) and water (1 mL) was heated at 100° C. for 16 hours. The solvents were removed, and the residue was purified with reverse phase (RP) HPLC to provide the title compound. $^1$H NMR (500 MHz, DMSO-$d_6$): δ 13.04 (br, 1H), 11.73 (br, 1H), 11.16 (s, 1H), 8.23-8.25 (m, 1H), 7.86-7.88 (m, 1H), 7.72 (d, J=6.1 Hz, 1H), 7.50-7.55 (m, 2H), 7.45-7.46 (m, 1H), 7.39 (t, J=7.93 Hz, 1H), 7.32 (s, 1H), 7.04-7.08 (m, 2H), 6.90 (d, J=7.32 Hz, 1H), 6.24 (s, 1H), 4.20 (t, J=5.95 Hz, 2H), 3.36 (t, J=7.32 Hz, 2H), 2.20-2.25 (m, 2H), 1.71 (s, 3H).

EXAMPLE 195

7-(5-methyl-2-(2-pyrrolidin-1-ylethoxy)pyridin-4-yl)-3-(3-(1-naphthyloxyl)propyl)-1H-indole-2-carboxylic acid 2-(Pyrrolidin-1-yl)ethanol (36.9 mg) in dioxane (2 mL) in a 4-mL vial was treated with 60% NaH (12.8 mg) at room temperature. After the bubbling ceased, EXAMPLE 192 (50 mg) was added to the solution. The vial was capped and heated at 105 OC for 3 hours. The solvent was removed, and the residue was purified with RP HPLC to provide the title compound. $^1$H NMR (500 MHz, DMSO-$d_6$): δ 11.00 (s, 1H), 11.16 (s, 1H), 9.78 (s, 1H), 8.23-8.25 (m, 1H), 8.12 (s, 1H), 7.86-7.88 (m, 1H), 7.76 (d, J=7.32 Hz, 1H), 7.50-7.55 (m, 2H), 7.45-7.47 (m, 1H), 7.39 (t, J=7.93 Hz, 1H), 7.06-7.12 (m, 2H), 6.90 (d, J=7.63 Hz, 1H), 6.76 (s, 1H), 4.58 (s, 2H), 4.20 (t, J=5.95 Hz, 2H), 3.60-3.61 (m, 4H), 3.36 (t, J=7.32 Hz, 2H), 3.13 (br, 2H), 2.20-2.25 (m, 2H), 1.97-2.01 (m, 5H), 1.87-1.91 (m, 2H).

EXAMPLE 196

7-(2-(dimethylamino)-5-nitropyridin-3-yl)-3-(3-(1-naphthyloxyl)propyl)-1H-indole-2-carboxylic acid $^1$H NMR (500 MHz, DMSO-$d_6$): δ 13.07 (s, 1H), 11.00 (s, 1H), 11.32 (s, 1H), 9.04 (d, J=2.44 Hz, 1H), 8.21-8.23 (m, 1H), 8.00 (d, J=2.75 Hz, 1H), 7.86-7.87 (m, 1H), 7.74 (d, J=7.63 Hz, 1H), 7.49-7.55 (m, 2H), 7.44-7.46 (m, 1H), 7.38 (t, J=7.78 Hz, 1H), 7.11-7.13 (m, 1H), 7.04-7.08 (m, 1H), 6.88 (d, J=7.63 Hz, 1H), 4.19 (t, J=5.95 Hz, 2H), 3.36 (t, J=7.32 Hz, 2H), 2.75 (s, 6H), 2.21-2.27 (m, 2H).

EXAMPLE 197

7-(2-(2-(dimethylamino)ethoxy)-5-methylpyridin-4-yl)-3-(3-(1-naphthyloxyl)propyl)-1H-indole-2-carboxylic acid $^1$H NMR (500 MHz, DMSO-$d_6$): δ 12.93 (br, 1H), 11.01 (s, 1H), 9.69 (s, 1H), 8.23-8.25 (m, 1H), 8.12 (s, 1H), 7.86-7.88 (m, 1H), 7.76 (d, J=7.32 Hz, 1H), 7.45-7.55 (m, 3H), 7.39 (t, J=7.93 Hz, 1H), 7.06-7.12 (m, 2H), 6.90 (d, J=7.63 Hz, 1H), 6.74 (s, 1H), 4.60 (br, 2H), 4.20 (t, J=6.1 Hz, 2H), 3.60 (br, 2H), 3.36 (t, J=7.32 Hz, 2H), 2.88 (s, 6H), 2.21-2.26 (m, 2H), 1.97 (s, 3H).

EXAMPLE 198

7-(5-methyl-2-(2-morpholin-4-ylethoxy)pyridin-4-yl)-3-(3-(1-naphthyloxy)propyl)-1H-indole-2-carboxylic acid $^1$H NMR (500 MHz, DMSO-$d_6$): δ 11.00 (s, 1H), 10.24 (s, 1H), 8.24-8.26 (m, 1H), 8.13 (s, 1H), 7.86-7.88 (m, 1H), 7.76 (d, J=6.71 Hz, 1H), 7.45-7.55 (m, 3H), 7.39 (t, J=7.93 Hz, 1H), 7.06-7.12 (m, 2H), 6.90 (d, J=7.32 Hz, 1H), 6.77 (s, 1H), 4.64 (br, 2H), 4.20 (t, J=6.1 Hz, 2H), 3.97 (br, 2H), 3.72 (br, 2H), 3.60 (t, J=4.88 Hz, 2H), 3.60 (br, 2H), 3.37 (t, J=7.32 Hz, 2H), 3.22 (br, 2H), 2.21-2.26 (m, 2H), 1.98 (s, 3H).

EXAMPLE 199

7-(2-(1,4-dioxa-8-azaspiro(4.5)dec-8-yl)-5-nitropyridin-3-yl)-3-(3-(1-naphthyloxyl)propyl)-1H-indole-2-carboxylic acid $^1$H NMR (500 MHz, DMSO-$d_6$): δ 13.02 (s, 1H), 11.25 (s, 1H), 9.07 (d, J=2.75 Hz, 1H), 8.22-8.24 (m, 1H), 8.13 (d, J=2.75 Hz, 1H), 7.85-7.87 (m, 1H), 7.76 (d, J=7.93 Hz, 1H), 7.44-7.54 (m, 3H), 7.37 (t, J=7.78 Hz, 1H), 7.29 (d, J=7.32 Hz, 1H), 7.09-7.12 (m 1H), 6.85 (d, J=7.32 Hz, 1H), 4.17 (t, J=6.1 Hz, 2H), 3.72 (s, 4H), 3.37 (m, 2H), 3.14 (br, 2H), 2.21-2.26 (m, 2H), 1.35 (br, 2H), 1.10 (br, 2H).

EXAMPLE 200

3-(3-(1-naphthyloxyl)propyl)-7-(5-nitro-2-(4-oxopiperidin-1-yl)pyridin-3-yl)-1H-indole-2-carboxylic acid $^1$H NMR (500 MHz, DMSO-$d_6$): δ 11.39 (s, 1H), 9.12 (d, J=2.75 Hz, 1H), 8.22-8.24 (m, 1H), 8.17 (d, J=2.75 Hz, 1H), 7.85-7.87 (m, 1H), 7.78 (d, J=7.93 Hz, 1H), 7.44-7.54 (m, 3H), 7.37 (t, J=7.93 Hz, 1H), 7.31 (d, J=6.41 Hz, 1H), 7.09-7.12 (m, 1H), 6.86 (d, J=7.32 Hz, 1H), 4.17 (t, J=6.1 Hz, 2H), 3.61 (br, 2H), 3.37 (m, 2H), 2.17-2.26 (m, 4H), 1.93 (br, 2H).

EXAMPLE 201

7-(5-amino-2-(dimethylamino)pyridin-3-yl)-3-(3-(1-naphthyloxy)propyl)-1H-indole-2-carboxylic acid $^1$H NMR (500 MHz, DMSO-$d_6$): δ 11.15 (br, 1H), 8.24-8.26 (m, 1H), 7.86-7.88 (m, 1H), 7.78 (d, J=7.93 Hz, 1H), 7.44-7.54 (m, 3H), 7.38 (t, J=7.93 Hz, 1H), 7.22 (d, J=7.02

Hz, 1H), 7.08-7.12 (m 1H), 6.88 (d, J=7.02 Hz, 1H), 4.18 (t, J=6.1 Hz, 2H), 3.37 (m, 2H), 2.57 (br, 6H), 2.21-2.27 (m, 2H).

EXAMPLE 202

7-(2-(4-hydroxypiperidin-1-yl)-5-nitropyridin-3-yl)-3-(3-(1-naphthyloxyl)propyl)-1H-indole-2-carboxylic acid $^1$H NMR (500 MHz, DMSO-$d_6$): δ 13.00 (s, 1H), 11.19 (br, 1H), 9.05 (d, J=2.44 Hz, 1H), 8.23-8.25 (m, 1H), 8.09 (d, J=2.45 Hz, 1H), 7.86-7.88 (m, 1H), 7.75 (d, J=7.93 Hz, 1H), 7.44-7.54 (m, 3H), 7.37 (t, J=7.78 Hz, 1H), 7.25 (d, J=6.41 Hz, 1H), 7.06-7.10 (m 1H), 6.86 (d, J=7.32 Hz, 1H), 4.17 (t, J=6.1 Hz, 2H), 3.75 (br, 6H), 3.49-3.52 (m, 1H), 3.40 (br, 2H) 2.90 (br, 2H), 2.21-2.27 (m, 2H).

EXAMPLE 203

7-(6-methoxy-4-methylpyridin-3-yl)-3-(3-(1-naphthyloxy)propyl)-1H-indole-2-carboxylic acid $^1$H NMR (500 MHz, DMSO-$d_6$): δ 11.05 (s, 1H), 8.24-8.26 (m, 1H), 7.94 (d, J=2.45 Hz, 1H), 7.86-7.88 (m, 1H), 7.71 (d, J=7.63 Hz, 1H), 7.45-7.55 (m, 3H), 7.39 (t, J=7.93 Hz, 1H), 7.03-7.09 (m, 2H), 6.91 (d, J=7.63 Hz, 1H), 6.80 (s, 1H), 4.20 (t, J=6.1 Hz, 2H), 3.90 (s, 3H), 3.35 (m, 2H), 2.21-2.27 (m, 2H), 2.00 (s, 3H).

EXAMPLE 204

7-(2-fluoro-5-methylpyridin-4-yl)-1-(2-morpholin-4-ylethyl)-3-(3-(1-naphthyloxyl)propyl)-1H-indole-2-carboxylic acid $^1$H NMR (500 MHz, DMSO-$d_6$): δ 8.22-8.24 (m, 1H), 7.87-7.91 (m, 2H), 7.46-7.56 (m, 3H), 7.39-7.42 (m, 2H), 7.19-7.22 (m, 1H), 7.08 (d, J=6.41 Hz, 1H), 6.91 (d, J=7.32 Hz, 1H), 4.77 (br, 1H), 4.23 (t, J=5.95 Hz, 2H), 3.91 (br, 1H), 3.36-3.39 (m, 2H), 2.80 (br, 4H), 2.20-2.26 (m, 2H), 1.94 (s, 3H).

EXAMPLE 205

3-(3-(1-naphthyloxy)propyl)-7-(1,3,5-trimethyl-1H-pyrazol-4-yl)-1H-indole-2-carboxylic acid $^1$H NMR (500 MHz, DMSO-$d_6$): δ 10.56 (s, 1H), 8.24-8.26 (m, 1H), 7.86-7.88 (m, 1H), 7.66 (d, J=7.32 Hz, 1H), 7.46-7.55 (m, 3H), 7.39 (t, J=7.93 Hz, 1H), 7.02-7.07 (m, 2H), 6.91 (d, J=7.32 Hz, 1H), 4.21 (t, J=6.1 Hz, 2H), 3.75 (s, 3H), 3.34-3.37 (m, 2H), 2.21-2.26 (m, 2H), 2.05 (s, 3H), 2.01 (s, 3H).

EXAMPLE 206

7-((2-morpholin-4-ylpyridin-3-yl)amino)-3-(3-(1-naphthyloxy)propyl)-1H-indole-2-carboxylic acid $^1$H NMR (500 MHz, DMSO-$d_6$): δ 13.05 (br, 1H), 11.14 (s, 1H), 8.22-8.24 (m, 1H), 7.92 (d, J=3.66 Hz, 1H), 7.86-7.87 (m, 1H), 7.44-7.56 (m, 5H), 7.38 (t, J=7.93 Hz, 1H), 7.24 (d, J=7.93 Hz, 1H), 7.00 (dd, J=7.78, 5.03 Hz, 1H), 6.85-6.88 (m, 2H), 6.74 (d, J=7.32 Hz, 1H), 4.18 (t, J=5.95 Hz, 2H), 3.63-3.64 (m, 4H), 3.33 (t, J=7.32 Hz, 2H), 3.23 (m, 4H), 2.20-2.24 (m, 2H).

EXAMPLE 207

7-(5-methyl-2-(2-phenylethoxyl)pyridin-4-yl)-3-(3-(1-naphthyloxy)propyl)-1H-indole-2-carboxylic acid $^1$H NMR (500 MHz, DMSO-$d_6$): δ 10.98 (s, 1H), 8.17 (d, J=7.63 Hz, 1H), 8.02 (s, 1H), 7.90 (d, J=7.02 Hz, 1H), 7.67 (d, J=7.02 Hz, 1H), 7.22-7.47 (m, 8H), 7.15 (t, J=6.41 Hz, 1H), 6.98-7.03 (m, 2H), 6.83 (d, J=7.32 Hz, 1H), 6.59 (s, 1H), 4.42 (t, J=6.41 Hz, 2H), 4.13 (t, J=5.64 Hz, 2H), 3.28-3.31 (m, 2H), 2.99 (t, J=6.71 Hz, 2H), 2.20-2.24 (m, 2H), 1.86 (s, 3H).

EXAMPLE 208

7-(5-methyl-2-(2-pyridin-3-ylethoxy)pyridin-4-yl)-3-(3-(1-naphthyloxy)propyl)-1H-indole-2-carboxylic acid $^1$H NMR (500 MHz, DMSO-$d_6$): δ 10.98 (s, 1H), 8.17 (d, J=7.63 Hz, 1H), 8.02 (s, 1H), 7.90 (d, J=7.02 Hz, 1H), 7.68 (d, J=7.02 Hz, 1H), 7.22-7.47 (m, 7H), 7.14 (t, J=6.41 Hz, 1H), 6.98-7.03 (m, 2H), 6.82 (d, J=7.32 Hz, 1H), 6.59 (s, 1H), 4.42 (t, J=6.41 Hz, 2H), 4.13 (t, J=5.64 Hz, 2H), 3.28-3.31 (m, 2H), 2.99 (t, J=6.71 Hz, 2H), 2.20-2.24 (m, 2H), 1.86 (s, 3H).

EXAMPLE 209

7-((2-morpholin-4-ylphenyl)amino)-3-(3-(1-naphthyloxy)propyl)-1H-indole-2-carboxylic acid $^1$H NMR (500 MHz, DMSO-$d_6$): δ 11.50 (s, 1H), 8.17 (s, 1H), 7.79 (s, 1H), 6.75-7.45 (m, 12H), 4.41 (br, 2H), 2.81 (br, 4H), 2.44 (m, 5H), 2.15 (br, 2H).

EXAMPLE 210

7-((4-carboxypyridin-3-yl)amino)-3-(3-(1-naphthyloxyl)propyl)-1H-indole-2-carboxylic acid $^1$H NMR (500 MHz, DMSO-$d_6$): δ 13.53 (br, 1H), 13.04 (br, 1H), 11.68 (s, 1H), 8.87 (s, 1H), 8.23 (s, 1H), 8.20-8.22 (m, 1H), 8.00 (d, J=4.88 Hz, 1H), 7.85-7.87 (m, 1H), 7.69 (d, J=5.19 Hz, 1H), 7.44-7.54 (m, 4H), 7.38 (t, J=7.93 Hz, 1H), 7.17 (d, J=7.32 Hz, 1H), 6.98 (t, J=7.78 Hz, 1H), 6.89 (d, J=7.32 Hz, 1H), 4.19 (t, J=6.41 Hz, 2H), 3.34-3.37 (m, 2H), 2.20-2.25 (m, 2H).

EXAMPLE 211

3-(3-(1-naphthyloxy)propyl)-7-((4-(trifluoromethyl)pyridin-3-yl)amino)-1H-indole-2-carboxylic acid $^1$H NMR (500 MHz, DMSO-$d_6$): δ 13.11 (br, 1H), 11.59 (s, 1H), 8.55 (s, 1H), 8.37 (d, J=5.19 Hz, 1H), 8.21-8.23 (m, 1H), 7.85-7.87 (m, 1H), 7.68 (d, J=5.19 Hz, 1H), 7.66 (s, 1H), 7.44-7.54 (m, 3H), 7.39 (t, J=7.93 Hz, 1H), 7.33 (d, J=7.93 Hz, 1H), 6.86-6.90 (m, 2H), 6.73 (d, J=7.32 Hz, 1H), 4.19 (t, J=6.1 Hz, 2H), 3.34-3.37 (m, 2H), 2.20-2.25 (m, 2H).

EXAMPLE 212

7-(2-(3-aminopropoxy)-5-methylpyridin-4-yl)-3-(3-(1-naphthyloxyl)propyl)-1H-indole-2-carboxylic acid $^1$H NMR (500 MHz, DMSO-$d_6$): δ 11.01 (s, 1H), 8.23-8.25 (m, 1H), 8.08 (s, 1H), 7.86-7.88 (m, 1H), 7.74-7.76 (m, 4H), 7.45-7.55 (m, 3H), 7.39 (t, J=7.93 Hz, 1H), 7.05-7.11 (m, 2H), 6.90 (d, J=7.32 Hz, 1H), 6.68 (s, 1H), 4.35 (t, J=6.1 Hz, 2H), 4.20 (t, J=6.1 Hz, 2H), 3.37 (t, J=7.48 Hz, 2H), 2.94-3.01 (m, 2H), 2.52 (m, 2H), 2.20-2.26 (m, 2H), 2.00-2.06 (m, 2H), 1.95 (s, 3H).

EXAMPLE 213

7-(5-methyl-2-(tetrahydrofuran-3-ylmethoxy)pyridin-4-yl)-3-(3-(1-naphthyloxyl)propyl)-1H-indole-2-carboxylic acid $^1$H NMR (500 MHz, DMSO-$d_6$): δ 11.07 (s, 1H), 8.24 (d, J=7.32 Hz, 1H), 8.07 (s, 1H), 7.86-7.88 (m, 1H), 7.74 (d, J=7.32 Hz, 1H), 7.45-7.54 (m, 3H), 7.39 (t, J=7.78 Hz, 1H), 7.05-7.10 (m, 2H), 6.90 (d, J=7.32 Hz, 1H), 6.67 (s, 1H), 4.16-4.27 (m, 2H), 3.75-3.80 (m, 2H), 3.67 (q, J=7.83 Hz, 1H), 3.55 (dd, J=8.54, 5.49 Hz, 1H), 3.36 (t, J=7.32 Hz, 2H), 2.67-2.71 (m, 1H), 2.21-2.26 (m, 2H), 1.99-2.04 (m, 1H), 1.93 (s, 3H), 1.64-1.70 (m, 1H).

EXAMPLE 214

7-(5-methyl-2-(4-phenylbutoxyl)pyridin-4-yl)-3-(3-(1-naphthyloxy)propyl)-1H-indole-2-carboxylic acid $^1$H NMR (500 MHz, DMSO-$d_6$): δ 12.96 (s, 1H), 11.05 (s, 1H), 8.23-8.25 (m, 1H), 8.05 (s, 1H), 7.86-7.87 (m, 1H), 7.73 (d, J=7.02 Hz, 1H), 7.45-7.54 (m, 3H), 7.39 (t, J=7.93 Hz, 1H), 7.15-7.29 (m, 5H), 7.04-7.09 (m, 2H), 6.90 (d, J=7.63 Hz, 1H), 6.63 (s, 1H), 4.29 (t, J=5.95 Hz, 2H), 4.20 (t, J=5.95 Hz, 2H), 3.36 (t, J=7.32 Hz, 2H), 2.65 (d, J=6.87 Hz, 2H), 2.21-2.26 (m, 2H), 1.92 (s, 3H), 1.70-1.78 (m, 4H).

EXAMPLE 215

7-(2-(3-methoxyphenyl)cyclohex-1-en-1-yl)-3-(3-(1-naphthyloxyl)propyl)-1H-indole-2-carboxylic acid $^1$H NMR (500 MHz, DMSO-$d_6$): δ 12.92 (s, 1H), 10.74 (s, 1H), 8.23-8.25 (m, 1H), 7.85-7.87 (m, 1H), 7.48-7.54 (m, 2H), 7.36-7.45 (m, 3H), 6.78-6.89 (m, 4H), 6.61 (d, J=7.63 Hz, 1H), 6.58 (d, J=7.63 Hz, 1H), 6.44 (dd, J=8.24, 1.83 Hz, 1H), 4.11 (t, J=6.1 Hz, 2H), 3.34 (s, 3H), 3.25 (t, J=7.32 Hz, 2H), 2.23-2.45 (m, 4H), 2.11-2.17 (m, 2H), 1.86 (m, 4H).

EXAMPLE 216

7-(1-(carboxymethyl)-3,5-dimethyl-1H-pyrazol-4-yl)-3-(3-(1-naphthyloxy)propyl)-1H-indole-2-carboxylic acid $^1$H NMR (500 MHz, DMSO-$d_6$): δ 12.98 (s, 1H), 10.32 (s, 1H), 8.24-8.26 (m, 1H), 7.86-7.88 (m, 1H), 7.66 (dd, J=7.32, 1.83 Hz, 1H), 7.45-7.55 (m, 3H), 7.39 (d, J=7.93 Hz, 1H), 7.05-7.09 (m, 2H), 6.91 (d, J=7.32 Hz, 1H), 4.88 (s, 2H), 4.21 (t, J=6.1 Hz, 2H), 3.34-3.37 (m, 2H), 2.21-2.26 (m, 2H), 2.03 (s, 3H), 2.01 (s, 3H).

EXAMPLE 217

7-(1-benzyl-1H-imidazol-5-yl)-3-(3-(1-naphthyloxy)propyl)-1H-indole-2-carboxylic acid $^1$H NMR (500 MHz, DMSO-$d_6$): δ 13.23 (s, 1H), 11.54 (s, 1H), 9.35 (s, 1H), 8.24-8.26 (m, 1H), 7.83-7.88 (m, 3H), 7.60-7.64 (m, 1H), 7.45-7.57 (m, 4H), 7.38 (d, J=7.93 Hz, 1H), 7.14-7.20 (m, 3H), 7.04-7.05 (m, 1H), 6.97-7.01 (m, 1H), 6.85-6.89 (m, 3H), 5.14 (s, 2H), 4.17 (t, J=6.1 Hz, 2H), 3.37 (t, J=7.32 Hz, 2H), 2.20-2.26 (m, 2H).

EXAMPLE 218

7-(2-(2-methylphenyl)cyclohex-1-en-1-yl)-3-(3-(1-naphthyloxyl)propyl)-1H-indole-2-carboxylic acid $^1$H NMR (500 MHz, DMSO-$d_6$): δ 12.94 (s, 1H), 10.91&10.68 (s, 1H), 8.20-8.24 (m, 1H), 7.85-7.86 (m, 1H), 7.33-7.45 (m, 5H), 6.70-7.06 (m, 7H), 4.10-4.13 (m, 2H), 3.21-3.25 (m, 2H), 2.24-2.44 (m, 4H), 2.21-2.26 (m, 5H), 1.87 (br, 4H).

EXAMPLE 219

7-(3,5-dimethyl-1-(2-morpholin-4-ylethyl)-1H-pyrazol-4-yl)-3-(3-(1-naphthyloxy)propyl)-1H-indole-2-carboxylic acid $^1$H NMR (500 MHz, DMSO-$d_6$): δ 12.98 (s, 1H), 10.46 (s, 1H), 8.24-8.26 (m, 1H), 7.86-7.88 (m, 1H), 7.67 (d, J=7.63 Hz, 1H), 7.45-7.55 (m, 3H), 7.39 (t, J=7.93 Hz, 1H), 7.08 (t, J=7.48 Hz, 1H), 7.03-7.04 (m, 1H), 6.91 (d, J=7.63 Hz, 1H), 4.42 (t, J=6.87 Hz, 2H), 4.21 (t, J=6.1 Hz, 2H), 3.87 (br, 4H), 3.61 (t, J=6.87 Hz, 2H), 3.34-3.37 (m, 2H), 2.21-2.26 (m, 2H), 2.09 (s, 3H), 2.04 (s, 3H).

EXAMPLE 221

3-(3-(1-naphthyloxy)propyl)-7-(2-(4-nitrophenyl)cyclohex-1-en-1-yl)-1H-indole-2-carboxylic acid $^1$H NMR (500 MHz, DMSO-$d_6$): δ 11.04 (s, 1H), 8.21-8.22 (m, 1H), 7.81-7.85 (m, 3H), 7.40-7.52 (m, 4H), 7.32-7.35 (m, 1H), 7.25 (d, J=8.85 Hz, 2H), 6.81 (d, J=7.63 Hz, 2H), 6.73-6.75 (m, 2H), 4.08 (t, J=5.95 Hz, 2H), 3.23 (br, 2H), 2.45 (br, 2H), 210-2.15 (m, 2H), 1.87 (br, 4H).

EXAMPLE 222

7-(4,4-dimethyl-2-phenylcyclohex-1-en-1-yl)-3-(3-(1-naphthyloxyl)propyl)-1H-indole-2-carboxylic acid $^1$H NMR (500 MHz, DMSO-$d_6$): δ 12.97 (s, 1H), 10.58 (s, 1H), 8.22-8.24 (m, 1H), 7.85-7.87 (m, 1H), 7.35-7.54 (m, 5H), 6.89-7.00 (m, 5H), 6.84 (d, J=7.63 Hz, 2H), 6.77 (d, J=4.27 Hz, 2H), 4.11 (t, J=6.1 Hz, 2H), 3.25 (t, J=7.32 Hz, 2H), 2.37 (br, 2H), 2.25 (br, 2H), 2.12-2.17 (m, 2H), 1.64 (br, 2H), 1.09 (s, 6H).

EXAMPLE 223

1-ethyl-7-(ethyl(phenyl)amino)-3-(3-(1-naphthyloxy)propyl)-1H-indole-2-carboxylic acid

EXAMPLE 223A ethyl 1-ethyl-7-(ethyl(phenyl)amino)-3-(3-(naphthalen-1-yloxy)propyl)-1H-indole-2-carboxylate EXAMPLE 224 (139 mg) in N,N-dimethylformamide (2 mL) was treated 60% NaH (36 mg, 0.9 mmol) at room temperature. After bubbling ceased, iodomethane (140 mg, 0.9 mmol) was added. The reaction was stirred for 3 hours. The reaction mixture was portioned between water and ethyl acetate. The organic layer was separated, and the aqueous layer was extracted with additional ethyl acetate. The combined organic layers were washed with brine, dried over MgSO4, filtered, and concentrated in vacuo. The residue was purified with flash chromatography on silica gel (ethyl acetate in hexanes) to give EXAMPLE 223A.

EXAMPLE 223B 1-ethyl-7-(ethyl(phenyl)amino)-3-(3-(1-naphthyloxy)propyl)-1H-indole-2-carboxylic acid The title compound was synthesized as described in EXAMPLE 175B, substituting EXAMPLE 223A for EXAMPLE 175A. $^1$H NMR (500 MHz, DMSO-$d_6$): δ 13.20 (s, 1H), 8.22-8.24 (m, 1H), 7.86-7.88 (m, 1H), 7.72 (dd, J=7.17, 1.98 Hz, 1H), 7.45-7.55 (m, 3H), 7.40 (t, J=7.78 Hz, 1H), 7.08-7.14 (m, 4H), 6.91 (d, J=7.32 Hz, 1H), 6.64 (t, J=7.32 Hz, 1H), 6.53 (d, J=8.24 Hz, 2H), 4.48-4.62 (m, 2H), 4.22 (t, J=6.1 Hz, 2H), 3.88-3.95 (m, 1H), 3.44-3.51 (m, 1H), 2.19-2.24 (m, 2H), 1.18 (t, J=7.02 Hz, 3H), 0.94 (t, J=6.87 Hz, 3H).

EXAMPLE 224

7-anilino-3-(3-(1-naphthyloxyl)propyl)-1H-indole-2-carboxylic acid $^1$H NMR (500 MHz, DMSO-$d_6$): δ 13.07 (s, 1H), 11.22 (s, 1H), 8.22-8.24 (m, 1H), 8.06 (s, 1H), 7.85-7.87 (m, 1H), 7.44-7.54 (m, 3H), 7.38 (t, J=7.93 Hz, 1H), 7.27-7.30 (m, 2H), 7.18-7.20 (m, 3H), 7.09 (d, J=7.32 Hz, 1H), 6.86-6.90 (m, 3H), 4.18 (t, J=5.95 Hz, 2H), 3.32 (m, 2H), 2.19-2.24 (m, 2H).

EXAMPLE 225

7-(5-methyl-2-(tetrahydro-2H-pyran-3-ylmethoxy)pyridin-4-yl)-3-(3-(1-naphthyloxyl)propyl)-1H-indole-2-carboxylic acid $^1$H NMR (500 MHz, DMSO-$d_6$): δ 12.95 (s, 1H), 11.07 (s, 1H), 8.23-8.25 (m, 1H), 8.06 (s, 1H), 7.86-7.88 (m, 1H), 7.74 (d, J=6.71 Hz, 1H), 7.45-7.54 (m, 3H), 7.39 (t, J=7.93 Hz, 1H), 7.05-7.11 (m, 2H), 7.18-7.20 (m, 3H), 7.09 (d, J=7.32 Hz, 1H), 6.90 (d, J=7.32 Hz, 1H), 6.65 (s, 1H), 4.09-4.21 (m, 4H), 3.87-3.90 (m, 2H), 3.73-3.75 (m, 2H), 3.24-3.37 (m, 4H), 2.21-2.26 (m, 2H), 2.01-2.05 (m, 1H), 1.93 (s, 3H), 1.93-1.95 (m, 1H), 1.59-1.60 (m, 1H), 1.51-1.53 (m, 1H), 1.36-1.39 (m 1H).

EXAMPLE 226

7-(5-methyl-2-(2-(2-oxopyrrolidin-1-yl)ethoxy)pyridin-4-yl)-3-(3-(1-naphthyloxyl)propyl)-1H-indole-2-carboxylic acid $^1$H NMR (500 MHz, DMSO-$d_6$): δ 13.03 (br, 1H), 11.06 (s, 1H), 8.23-8.25 (m, 1H), 8.09 (s, 1H), 7.86-7.88 (m, 1H), 7.74 (dd, J=7.17, 1.68 Hz, 1H), 7.45-7.54 (m, 3H), 7.39 (t, J=7.93 Hz, 1H), 7.06-7.10 (m, 2H), 6.90 (d, J=7.32 Hz, 1H), 6.68 (s, 1H), 4.38 (t, J=5.49 Hz, 2H), 4.20 (t, J=6.1 Hz, 2H), 3.56 (t, J=5.64 Hz, 2H), 3.46 (t, J=7.02 Hz, 2H), 3.37 (t, J=7.48 Hz, 2H), 2.19-2.25 (m, 4H), 1.89-1.95 (m, 5H).

EXAMPLE 227

7-(5-methyl-2-(2-(4-methylpiperazin-1-yl)ethoxy)pyridin-4-yl)-3-(3-(1-naphthyloxyl)propyl)-1H-indole-2-carboxylic acid $^1$H NMR (500 MHz, DMSO-$d_6$): δ 11.01 (s, 1H), 8.24-8.25 (m, 1H), 8.09 (s, 1H), 7.86-7.88 (m, 1H), 7.75 (d, J=7.63 Hz, 1H), 7.45-7.54 (m, 3H), 7.39 (t, J=7.93 Hz, 1H), 7.05-7.11 (m, 2H), 6.90 (d, J=7.32 Hz, 1H), 6.69 (s, 1H), 4.47 (s, 2H), 4.20 (t, J=6.1 Hz, 2H), 3.77 (br, 8H), 3.35-3.38 (m, 2H), 3.09 (m, 2H), 2.78 (s, 3H), 2.21-2.26 (m, 2H), 1.96 (s, 3H).

EXAMPLE 228

3-(3-(1-naphthyloxy)propyl)-7-(2-(2-oxocyclohexyl)pyridin-3-yl)-1H-indole-2-carboxylic acid $^1$H NMR (500 MHz, DMSO-$d_6$): δ 11.13 (s, 1H), 8.72-8.73 (m, 1H), 8.24-8.26 (m, 1H), 7.86-7.88 (m, 2H), 7.76 (d, J=8.24 Hz, 1H), 7.45-7.54 (m, 4H), 7.37-7.41 (m, 1H), 7.05 (t, J=7.48 Hz, 1H), 6.87-6.91 (m, 2H), 4.20 (t, J=5.8 Hz, 2H), 3.30-3.55 (br, 6H), 1.40-2.24 (m, 7H),

EXAMPLE 229

7-(2-fluoro-5-methylpyridin-4-yl)-1-(2-(4-methylpiperazin-1-yl)ethyl)-3-(3-(1-naphthyloxyl)propyl)-1H-indole-2-carboxylic acid $^1$H NMR (500 MHz, DMSO-$d_6$): δ 9.37 (s, 1H), 8.19-8.21 (m, 2H), 7.87 (t, J=7.02 Hz, 1H), 7.45-7.56 (m, 4H), 7.40 (t, J=7.93 Hz, 1H), 7.32 (d, J=1.83 Hz, 1H), 7.15-7.18 (m 1H), 7.04 (d, J=6.1 Hz, 1H), 6.90 (d, J=7.32 Hz, 1H), 4.46-4.50 (m, 1H), 4.21 (t, J=6.1 Hz, 2H), 3.59-3.61 (m, 1H), 2.75 (br, 2H), 2.71 (s, 3H), 2.09-2.25 (m, 6H), 1.95 (s, 3H),

EXAMPLE 230

7-(5,5-dimethyl-2-phenylcyclohex-1-en-1-yl)-3-(3-(1-naphthyloxyl)propyl)-1H-indole-2-carboxylic acid $^1$H NMR (500 MHz, DMSO-$d_6$): δ 12.95 (s, 1H), 10.24 (s, 1H), 8.21-8.23 (m, 2H), 7.85-7.86 (m, 1H), 7.35-7.54 (m, 5H), 7.01-7.03 (m, 2H), 6.95 (t, J=7.48 Hz, 1H), 6.88-6.91 (m 1H), 6.83 (d, J=7.02 Hz, 1H), 6.80-6.81 (m, 2H), 4.10 (t, J=6.1 Hz, 2H), 3.22-3.25 (m, 2H), 2.11-2.25 (m, 6H), 1.6 (br, 2H), 1.06 (s, 6H).

EXAMPLE 231

3-(3-(1-naphthyloxyl)propyl)-7-(pyridin-3-ylamino)-1H-indole-2-carboxylic acid $^1$H NMR (500 MHz, DMSO-$d_6$): δ 13.18 (s, 1H), 11.27 (s, 1H), 8.67 (s, 1H), 8.36 (d, J=2.44 Hz, 1H), 8.21-8.23 (m, 1H), 8.17 (d, J=4.58 Hz, 1H), 7.86-7.87 (m, 1H), 7.77 (dd, J=8.54, 1.83 Hz, 1H), 7.61 (dd, J=8.54, 5.19 Hz, 1H), 7.43-7.54 (m, 4H), 7.39 (t, J=7.78 Hz, 1H), 7.20 (d, J=7.32 Hz, 1H), 7.00 (t, J=7.78 Hz, 1H), 6.89 (d, J=7.32 Hz, 1H), 4.18 (t, J=6.1 Hz, 2H), 3.24 (t, J=7.32 Hz, 2H), 2.20-2.25 (m, 2H).

EXAMPLE 232

3-(3-(1-naphthyloxy)propyl)-7-(phenyl(propyl)amino)-1-propyl-1H-indole-2-carboxylic acid $^1$H NMR (500 MHz, DMSO-$d_6$): δ 13.20 (s, 1H), 8.22 (d, J=7.63 Hz, 1H), 7.87 (d, J=7.02 Hz, 1H), 7.70-7.72 (m, 1H), 7.45-7.54 (m, 3H), 7.08-7.13 (m, 4H), 6.90 (d, J=7.63 Hz, 1H), 6.64 (t, J=7.17 Hz, 1H), 6.53 (d, J=7.93 Hz, 2H), 4.44-4.50 (m, 1H), 4.32-4.37 (m, 1H), 4.21 (t, J=5.95 Hz, 2H), 3.76-3.82 (m, 1H), 2.19-2.23 (m, 2H), 1.74 (m, 1H), 1.58-1.60 (m, 1H), 1.38-1.40 (m, 1H), 1.18-1.23 (m, 1H), 0.88 (t, J=7.32 Hz, 3H), 0.45 (t, J=7.17 Hz, 3H).

EXAMPLE 233

7-(3-cyclohex-1-en-1-ylpyridin-2-yl)-3-(3-(1-naphthyloxy)propyl)-1H-indole-2-carboxylic acid $^1$H NMR (500 MHz, DMSO-$d_6$): δ 13.21 (s, 1H), 11.12 (s, 1H), 8.76 (d, J=5.19 Hz, 1H), 8.27-8.29 (m, 1H), 8.15 (s, 1H), 7.85-7.88 (m, 2H), 7.78 (s, 1H), 7.45-7.55 (m, 4H), 7.38 (t, J=7.93 Hz, 1H), 7.11 (t, J=7.63 Hz, 1H), 6.86 (d, J=7.63 Hz, 1H), 5.72 (s, 1H), 4.44-4.50 (m, 1H), 4.16 (t, J=6.1 Hz, 2H), 3.40 (t, J=7.32 Hz, 2H), 2.22-2.27 (m, 2H), 1.92 (br, 2H), 1.82 (br, 2H), 1.34-1.35 (m, 4H).

EXAMPLE 234

3-(3-(1-naphthyloxy)propyl)-7-(2-pyridin-3-ylcyclohex-1-en-1-yl)-1H-indole-2-carboxylic acid $^1$H NMR (500 MHz, DMSO-$d_6$): δ 11.07 (s, 1H), 8.33-8.35 (m, 2H), 8.22-8.23 (m, 1H), 7.93 (d, J=7.93 Hz, 1H), 7.85-7.87 (m, 1H), 7.44-7.54 (m, 5H), 7.38 (t, J=7.78 Hz, 1H), 6.89-6.90 (m, 1H), 6.82-6.86 (m, 2H), 4.11 (t, J=6.1 Hz, 2H), 3.27 (br, 2H), 2.10-2.16 (m, 2H), 1.91 (br, 4H).

EXAMPLE 235

3-(3-((8-chloroquinazolin-4-yl)oxy)propyl)-7-(2-methylphenyl)-1H-indole-2-carboxylic acid $^1$H NMR (500 MHz, DMSO-$d_6$): δ 12.95 (s, 1H), 10.48 (s, 1H), 8.85 (s, 1H), 8.13 (dd, J=7.63, 1.22 Hz, 1H), 8.10 (dd, J=8.24, 1.22 Hz, 1H), 7.70 (d, J=7.93 Hz, 1H), 7.64 (t, J=7.93 Hz, 1H), 7.25-7.34 (m, 3H), 7.19 (d, J=7.32 Hz, 1H), 7.07-7.10 (m, 1H), 7.02-7.02 (m, 1H), 4.60 (t, J=6.1 Hz, 2H), 3.34 (t, J=7.02 Hz, 2H), 2.23-2.29 (m, 2H), 2.04 (s, 3H).

EXAMPLE 236

1-butyl-7-(butyl(phenyl)amino)-3-(3-(1-naphthyloxy)propyl)-1H-indole-2-carboxylic acid $^1$H NMR (500 MHz, DMSO-$d_6$): δ 8.21 (d, J=7.67 Hz, 1H), 7.86 (d, J=7.67 Hz, 1H), 7.69-7.71 (m, 1H), 7.36-7.55 (m, 4H), 7.09-7.13 (m, 4H), 6.89 (d, J=7.67 Hz, 1H), 6.63 (t, J=7.06 Hz, 1H), 6.52 (d, J=7.98 Hz, 2H), 4.49-4.53 (m, 1H), 4.37 (m, 1H), 4.21 (t, J=5.52 Hz, 2H), 3.61 (m, 1H), 2.17-2.25 (m, 2H), 0.78-1.72 (m, 9H), 0.54 (t, J=7.36 Hz, 3H).

EXAMPLE 237

3-(3-(7-chloro-1H-pyrrolo(2,3-c)pyridin-1-yl)propyl)-7-(2-methylphenyl)-1H-indole-2-carboxylic acid $^1$H NMR (500 MHz, DMSO-$d_6$): δ 10.46 (s, 1H), 7.87 (d, J=5.22 Hz, 1H), 7.78 (d, J=3.07 Hz, 1H), 7.54-7.57 (m, 2H), 7.20-7.33 (m, 4H), 7.10-7.13 (m, 1H), 7.03-7.05 (m, 1H), 6.62 (d, J=3.07 Hz, 1H), 4.57-4.61 (m, 2H), 3.16 (t, J=7.36 Hz, 2H), 2.12-2.20 (m, 2H), 2.06 (s, 3H).

EXAMPLE 238

7-(3-cyclohexylpyridin-2-yl)-3-(3-(1-naphthyloxy)propyl)-1H-indole-2-carboxylic acid $^1$H NMR (500 MHz, DMSO-$d_6$): δ 11.27 (s, 1H), 8.70 (d, J=4.91 Hz, 1H), 8.41 (s, 1H), 8.28-8.30 (m, 1H), 7.86-7.91 (m, 3H), 7.45-7.57 (m, 3H), 7.39 (t, J=7.98 Hz, 1H), 7.29 (d, J=7.06 Hz, 1H), 7.16-7.18 (m, 1H), 6.89 (d, J=7.36 Hz, 1H), 4.20 (t, J=6.14 Hz, 2H), 3.39-3.42 (m, 2H), 2.46 (m, 2H), 2.21-2.28 (m, 2H), 0.91-1.78 (m, 10H).

EXAMPLE 239

3-(3-(1-naphthyloxyl)propyl)-7-(1-(1,3-thiazol-5-ylmethyl)-1H-pyrrolo(2,3-c)pyridin-3-yl)-1H-indole-2-carboxylic acid $^1$H NMR (500 MHz, DMSO-$d_6$): δ 13.14 (s, 1H), 10.95 (s, 1H), 9.61 (s, 1H), 9.10 (s, 1H), 8.78 (s, 1H), 8.38 (d, J=6.41 Hz, 1H), 8.22-8.24 (m, 1H), 8.15 (s, 1H), 7.93 (t, J=6.41 Hz, 1H), 7.86-7.88 (m, 1H), 7.78 (d, J=7.93 Hz, 1H), 7.35-7.54 (m, 5H), 7.12-7.16 (m, 1H), 6.90 (d, J=7.63 Hz, 1H), 6.12 (s, 2H), 4.21 (t, J=5.95 Hz, 2H), 3.40 (t, J=7.32 Hz, 2H), 2.23-2.28 (m, 2H).

EXAMPLE 240

7-(1-(3,3-dimethyl-2-oxobutyl)-1H-pyrrolo(2,3-c)pyridin-3-yl)-3-(3-(1-naphthyloxy)propyl)-1H-indole-2-carboxylic acid $^1$H NMR (500 MHz, DMSO-$d_6$): δ 13.14 (s, 1H), 10.74 (s, 1H), 9.18 (s, 1H), 8.39 (s, 1H), 8.34 (d, J=6.1 Hz, 1H), 8.22-8.24 (m, 1H), 7.93 (d, J=6.1 Hz, 1H), 7.86-7.88 (m, 1H), 7.76 (d, J=8.24 Hz, 1H), 7.35-7.53 (m, 5H), 7.14-7.18 (m, 1H), 6.90 (d, J=7.32 Hz, 1H), 5.81 (s, 2H), 4.21 (t, J=5.95 Hz, 2H), 3.39-3.41 (m, 2H), 2.23-2.28 (m, 2H), 1.30 (s, 9H).

EXAMPLE 241

7-(4-cyclohex-1-en-1-ylpyridin-3-yl)-3-(3-(1-naphthyloxy)propyl)-1H-indole-2-carboxylic acid $^1$H NMR (500 MHz, DMSO-$d_6$): δ 13.07 (s, 1H), 11.09 (s, 1H), 8.76-8.78 (m, 2H), 8.26-8.28 (m, 1H), 7.86-7.88 (m, 1H), 7.78 (d, J=7.93 Hz, 1H), 7.74 (d, J=5.8 Hz, 1H), 7.36-7.56 (m, 5H), 7.14 (d, J=6.1 Hz, 1H), 7.06-7.09 (m, 1H), 6.84-6.85 (m, 1H), 5.76 (s, 1H), 4.15 (t, J=6.1 Hz, 2H), 3.38 (t, J=7.32 Hz, 2H), 2.21-2.27 (m, 2H), 1.76-1.85 (m, 4H), 1.25-1.26 (m, 4H).

EXAMPLE 242

7-(1-(3,5-difluorobenzyl)-1H-pyrrolo(2,3-c)pyridin-3-yl)-3-(3-(1-naphthyloxyl)propyl)-1H-indole-2-carboxylic acid $^1$H NMR (500 MHz, DMSO-$d_6$): δ 10.95 (s, 1H), 9.46 (s, 1H), 8.75 (s, 1H), 8.36 (d, J=6.41 Hz, 1H), 8.23-8.25 (m, 1H), 7.91 (d, J=6.41 Hz, 1H), 7.86-7.88 (m, 1H), 7.78 (d, J=8.24

Hz, 1H), 7.37-7.54 (m, 5H), 7.13-7.25 (m, 4H), 6.90 (d, J=7.63 Hz, 1H), 5.83 (s, 2H), 4.21 (t, J=6.1 Hz, 2H), 3.39-3.41 (m, 2H), 2.24-2.29 (m, 2H).

EXAMPLE 243

3-(3-(1-naphthyloxyl)propyl)-7-(1-phenylvinyl)-1H-indole-2-carboxylic acid $^1$H NMR (500 MHz, DMSO-d$_6$): δ 13.03 (s, 1H), 9.82 (s, 1H), 8.22-8.24 (m, 1H), 7.91 (d, J=6.41 Hz, 1H), 7.86-7.88 (m, 1H), 7.45-7.55 (m, 3H), 7.30-7.40 (m, 6H), 7.09-7.11 (m, 1H), 7.04-7.07 (m, 1H), 6.90 (d, J=7.32 Hz, 1H), 5.85 (s, 1H), 5.51 (s, 1H), 4.19 (t, J=6.1 Hz, 2H), 3.34-3.36 (m, 2H), 2.20-2.25 (m, 2H).

EXAMPLE 244

3-(3-(1-naphthyloxy)propyl)-7-(1H-pyrrolo(2,3-c)pyridin-7-yl)-1H-indole-2-carboxylic acid $^1$H NMR (500 MHz, DMSO-d$_6$): δ 12.58 (s, 1H), 11.65 (s, 1H), 8.31-8.32 (m, 2H), 8.13-8.16 (m, 2H), 8.04 (d, J=7.93 Hz, 1H), 7.88-7.90 (m, 1H), 7.63 (d, J=7.62 Hz, 1H), 7.45-7.57 (m, 3H), 7.39-7.43 (m 1H), 7.26-7.29 (m, 1H), 7.03 (s, 1H), 6.92 (d, J=7.32 Hz, 1H), 4.22 (t, J=6.1 Hz, 2H), 3.43-3.45 (m, 2H), 2.24-2.30 (m, 2H).

EXAMPLE 245

7-(4-cyclohexylpyridin-3-yl)-3-(3-phenoxypropyl)-1H-indole-2-carboxylic acid $^1$H NMR (500 MHz, DMSO-d$_6$): δ 13.09 (s, 1H), 11.33 (s, 1H), 8.81 (d, J=6.1 Hz, 1H), 8.72 (s, 1H), 8.26-8.28 (m, 1H), 7.90 (d, J=5.8 Hz, 1H), 7.83-7.98 (m, 2H), 7.45-7.54 (m, 3H), 7.39 (t, J=7.93 Hz, 1H), 7.12-7.16 (m, 1H), 6.89 (d, J=7.63 Hz, 1H), 4.19 (t, J=6.26 Hz, 2H), 3.42-3.46 (m, 2H), 3.32-3.37 (m, 2H), 2.37-2.45 (m, 1H), 2.22-2.27 (m, 2H), 1.45-1.76 (m, 7H), 1.15-1.20 (m 1H), 0.81-0.99 (m, 2H).

EXAMPLE 246

7-(2,4-dimethyl-1,3-thiazol-5-yl)-3-(3-(1-naphthyloxy)propyl)-1H-indole-2-carboxylic acid $^1$H NMR (500 MHz, DMSO-d$_6$): δ 10.95 (s, 1H), 8.21-8.23 (m, 1H), 7.85-7.97 (m, 2H), 7.75 (d, J=7.98 Hz, 1H), 7.36-7.55 (m, 4H), 7.19 (t, J=6.44 Hz, 1H), 7.06-7.09 (m, 1H), 6.89 (d, J=7.37 Hz, 1H), 4.19 (t, J=6.14 Hz, 2H), 3.37 (t, J=7.52 Hz, 2H), 2.70 (s, 3H), 2.20-2.27 (m, 2H), 2.17 (s, 3H).

EXAMPLE 247

7-(1-(carboxymethyl)-1H-pyrrolo(2,3-c)pyridin-3-yl)-3-(3-(1-naphthyloxyl)propyl)-1H-indole-2-carboxylic acid $^1$H NMR (500 MHz, DMSO-d$_6$): δ 10.22 (s, 1H), 8.90 (s, 1H), 8.20-8.23 (m, 2H), 8.06 (s, 1H), 7.85-7.87 (m, 1H), 7.66-7.68 (m, 1H), 7.58-7.60 (m, 1H), 7.36-7.55 (m, 5H), 7.12-7.15 (m, 1H), 6.90 (d, J=7.67 Hz, 1H), 5.22 (s, 2H), 4.21 (t, J=6.1 Hz, 2H), 3.28 (t, J=7.52 Hz, 2H), 2.20-2.27 (m, 2H).

EXAMPLE 248

3-(3-(1-naphthyloxy)propyl)-7-(1-phenylethyl)-1H-indole-2-carboxylic acid $^1$H NMR (500 MHz, DMSO-d$_6$): δ 11.09 (s, 1H), 8.23 (d, J=7.67 Hz, 1H), 7.85-7.87 (m, 1H), 7.66-7.68 (m, 1H), 7.35-7.53 (m, 7H), 7.26 (t, J=7.52 Hz, 2H), 7.10-7.17 (m, 2H), 6.96 (t, J=7.67 Hz, 1H), 6.78 (d, J=7.37 Hz, 1H), 5.00 (d, J=7.06 Hz, 1H), 4.16 (t, J=5.98 Hz, 2H), 3.28 (t, J=7.52 Hz, 2H), 2.15-2.22 (m, 2H), 1.85 (m, 1H), 1.60 (d, J=7.06 Hz, 3H).

EXAMPLE 249

7-(1-benzyl-3,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.57 (s, 1H), 8.24-8.26 (m, 1H), 7.85-7.87 (m, 1H), 7.65 (dd, J=7.06, 1.53 Hz, 1H), 7.26-7.52 (m, 8H), 7.03-7.08 (m, 2H), 6.90 (d, J=7.67 Hz, 1H), 5.31 (d, J=7.06 Hz, 1H), 4.21 (t, J=5.98 Hz, 2H), 3.34-3.37 (m, 2H), 2.18-2.27 (m, 2H), 2.04 (s, 6H).

EXAMPLE 250

7-(2-(2-chlorophenyl)cyclohex-1-en-1-yl)-3-(3-(1-naphthyloxyl)propyl)-1H-indole-2-carboxylic acid $^1$H NMR (500 MHz, DMSO-d$_6$): δ 10.93 (s, 1H), 8.21-8.23 (m, 1H), 7.84-7.86 (m, 1H), 7.34-7.54 (m, 8H), 7.20-7.22 (m, 1H), 7.09 (dd, J=7.36, 1.84 Hz, 1H), 6.82-6.98 (m, 4H), 6.71-6.75 (m, 1H), 5.31 (d, J=7.06 Hz, 1H), 4.12 (t, J=6.14 Hz, 2H), 3.20-3.26 (m, 4H), 2.21-2.28 (m, 4H), 1.82-1.96 (m, 4H).

EXAMPLE 251

3-(3-(1-naphthyloxy)propyl)-1H,1'H-7,7'-biindole-2-carboxylic acid $^1$H NMR (500 MHz, DMSO-d$_6$): δ 13.02 (s, 1H), 10.70 (s, 1H), 9.88 (s, 1H), 8.27-8.29 (m, 1H), 7.87-7.89 (m, 1H), 7.76 (d, J=7.93 Hz, 1H), 7.62 (d, J=7.63 Hz, 1H), 7.37-7.56 (m, 5H), 7.27 (t, J=2.9 Hz, 1H), 7.21 (d, J=7.02 Hz, 1H), 7.13-7.18 (m, 2H), 6.92 (d, J=7.63 Hz, 1H), 6.55 (dd, J=3.05, 1.83 Hz, 1H), 4.23 (t, J=6.26 Hz, 2H), 3.39-3.42 (m, 2H), 2.25-2.30 (m, 2H).

EXAMPLE 252

3-(3-(1-naphthyloxy)propyl)-7-(1-(2-(2-oxopyrrolidin-1-yl)ethyl)-1H-pyrrolo(2,3-c)pyridin-7-yl)-1H-indole-2-carboxylic acid $^1$H NMR (500 MHz, DMSO-d$_6$): δ 15.03 (s, 1H), 11.85 (s, 1H), 8.35 (d, J=6.1 Hz, 1H), 8.31-8.32 (m, 1H), 8.22 (d, J=6.41 Hz, 1H), 8.20 (d, J=3.05 Hz, 1H), 8.08 (d, J=7.93 Hz, 1H), 7.88-7.90 (m, 1H), 7.61 (d, J=7.02 Hz, 1H), 7.39-7.55 (m, 5H), 7.25-7.28 (m, 1H), 7.07 (d, J=3.05 Hz, 1H), 6.92 (d, J=7.32 Hz, 1H), 4.20 (t, J=6.1 Hz, 2H), 3.83-3.88 (m, 2H), 3.56-3.60 (m, 2H), 3.42-3.45 (m, 2H), 2.23-2.28 (m, 2H), 1.94-1.98 (m, 2H), 1.64-1.71 (m, 2H).

EXAMPLE 254

7-(5-methyl-3-phenyl-1H-pyrazol-4-yl)-3-(3-(1-naphthyloxy)propyl)-1H-indole-2-carboxylic acid $^1$H NMR (500 MHz, DMSO-d$_6$): δ 10.53 (s, 1H), 8.26-8.28 (m, 1H), 7.86-7.88 (m, 1H), 7.68 (dd, J=6.87, 2.29 Hz, 1H), 7.45-7.54 (m, 3H), 7.39 (t, J=7.78 Hz, 1H), 7.29-7.31 (m, 2H), 7.15-7.17 (m, 3H), 7.01-7.05 (m, 2H), 6.90 (d, J=7.32 Hz, 1H), 4.20 (t, J=6.1 Hz, 2H), 3.33-3.36 (m, 2H), 2.21-2.26 (m, 2H), 2.03 (s, 3H).

EXAMPLE 255

7-(2-methylphenyl)-4-(2-(1-naphthyloxy)ethyl)-1H-indole-2-carboxylic acid

EXAMPLE 255A ethyl 4-(1-ethoxy-1,3-dioxobutan-2-yl)-7-o-tolyl-1H-indole-2-carboxylate A mixture of ethyl 4-chloro-7-o-tolyl-1H-indole-2-carboxylate (EXAMPLE 166C) (0.93 g), ethyl 3-oxobutanoate (0.849 g), di-tert-butyl(2'-methylbiphenyl-2-yl)phosphine (0.093 mg), K$_3$PO$_4$ (3.46 g), and palladium(II) acetate (0.033 g) in toluene (8 mL) was degassed via vacuum/nitrogen cycle three times. The reaction mixture was heated at 93° C. for 14 hours. The reaction mixture was partitioned between water and ethyl acetate. The organic layer was separated, and the aqueous layer was extracted with additional ethyl acetate. The combined organic layers were washed with brine, dried over MgSO4, filtered, and concentrated. The residue was purified with flash chromatography on silica gel (ethyl acetate in hexanes) to give the title compound.

EXAMPLE 255B methyl 4-(2-methoxy-2-oxoethyl)-7-o-tolyl-1H-indole-2-carboxylate EXAMPLE 255A (crude) in ethanol (35 mL) was treated with 20% KOH (15 mL). The mixture was heated at 100 C for 1 hour. The solvent was removed and the residue dissolved in ethyl acetate. After addition of concentrated HCl, the organic layer was separated and the aqueous layer was extracted with additional ethyl acetate. The combined organic layers were dried, and concentrated. The residue was treated with diazomethane in CH$_2$Cl$_2$ and a few drops of methanol. After bubbling ceased, the solvents were evaporated and the compound purified via flash chromatography (15:85 EtOAc/Hex) to give pure EXAMPLE 255B. $^1$H NMR (500 MHz, DMSO-d$_6$): δ 11.14 (s, 1H), 7.26-7.34 (m, 4H), 7.21 (d, J=7.32 Hz, 1H), 7.00-7.05 (m, 2H), 3.99 (s, 2H), 3.83 (s, 3H), 3.64 (s, 3H), 2.05 (s, 3H).

EXAMPLE 255C 7-(2-methylphenyl)-4-(2-(1-naphthyloxyl)ethyl)-1H-indole-2-carboxylic acid The title compound was prepared according to the procedure for EXAMPLE 164G, substituting EXAMPLE 255B for EXAMPLE 164F. $^1$H NMR (500 MHz, DMSO-d$_6$): δ 11.05 (s, 1H), 8.13 (d, J=7.98 Hz, 1H), 7.84 (d, J=7.98 Hz, 1H), 7.31-7.51 (m, 7H), 7.18-7.27 (m, 3H), 7.01 (d, J=6.75 Hz, 1H), 4.50 (t, J=6.44 Hz, 2H), 3.52 (t, J=6.44 Hz, 2H), 2.05 (s, 3H).

EXAMPLE 256

7-(2-methylphenyl)-4-(2-(2-naphthyloxyl)ethyl)-1H-indole-2-carboxylic acid $^1$H NMR (500 MHz, DMSO-d$_6$): δ 11.06 (s, 1H), 7.78-7.83 (m, 3H), 7.13-7.46 (m, 10H), 7.01 (d, J=7.06 Hz, 1H), 4.46 (t, J=6.9 Hz, 2H), 3.45 (t, J=6.75 Hz, 2H), 2.06 (s, 3H).

EXAMPLE 257

4-(2-(2,3-dichlorophenoxyl)ethyl)-7-(2-methylphenyl)-1H-indole-2-carboxylic acid $^1$H NMR (500 MHz, DMSO-d$_6$): δ 11.02 (s, 1H), 7.36 (d, J=1.84 Hz, 1H), 7.17-7.32 (m, 7H), 7.12 (d, J=7.06 Hz, 1H), 7.00 (d, J=7.36 Hz, 1H), 4.40 (t, J=6.6 Hz, 2H), 3.28-3.34 (m, 2H), 2.21-2.29 (m, 2H), 2.06 (s, 3H).

EXAMPLE 258

3-(3-(1H-indol-4-yloxy)propyl)-7-(2-methylphenyl)-1H-indole-2-carboxylic acid $^1$H NMR (500 MHz, DMSO-d$_6$): δ 11.02 (s, 1H), 10.41 (s, 1H), 7.71 (d, J=7.98 Hz, 1H), 7.20-7.33 (m, 5H), 6.93-7.11 (m, 4H), 6.47-6.49 (m, 1H), 6.42 (d, J=6.44 Hz, 1H), 4.12 (t, J=6.44 Hz, 2H), 3.40-3.42 (m, 2H), 2.06 (s, 3H).

EXAMPLE 259

4-(2-(2-chloro-3-(trifluoromethyl)phenoxy)ethyl)-7-(2-methylphenyl)-1H-indole-2-carboxylic acid $^1$H NMR (500 MHz, DMSO-d$_6$): δ 11.03 (s, 1H), 7.45-7.53 (m, 2H), 7.19-7.39 (m, 6H), 7.13 (d, J=7.36 Hz, 1H), 6.99 (d, J=7.06 Hz, 1H), 4.49 (t, J=6.75 Hz, 2H), 3.41-3.44 (m, 2H), 2.05 (s, 3H).

EXAMPLE 260

1-methyl-3-(3-((1-methyl-1H-indol-4-yl)oxy)propyl)-7-(2-methylphenyl)-1H-indole-2-carboxylic acid $^1$H NMR (500 MHz, DMSO-d$_6$): δ 13.07 (s, 1H), 7.74 (d, J=7.98 Hz, 1H), 7.27-7.37 (m, 4H), 7.20 (d, J=3.07 Hz, 1H), 7.09 (t, J=7.52 Hz, 1H), 6.98-7.05 (m, 3H), 6.49 (d, J=1.43 Hz, 1H), 6.47 (d, J=2.76 Hz, 1H), 4.13 (t, J=6.14 Hz, 2H), 3.76 (s, 3H), 3.24-3.27 (m, 2H), 2.10-2.17 (m, 2H), 2.00 (s, 3H).

EXAMPLE 261

7-(2-(4-ethylphenyl)cyclohex-1-en-1-yl)-3-(3-(1-naphthyloxy)propyl)-1H-indole-2-carboxylic acid $^1$H NMR (500 MHz, DMSO-d$_6$): δ 10.56 (s, 1H), 8.22-8.24 (m, 1H), 7.84-7.86 (m, 1H), 7.34-7.54 (m, 5H), 6.92 (d, J=8.29 Hz, 1H), 6.84 (d, J=7.67 Hz, 2H), 6.67-6.80 (m, 4H), 4.11 (t, J=6.14 Hz, 2H), 3.23-3.27 (m, 2H), 2.31-2.43 (m, 6H), 2.11-2.18 (m, 2H), 1.85 (br, 4H), 0.98 (t, J=7.52 Hz, 3H).

EXAMPLE 262

7-(2-(4-isopropylphenyl)cyclohex-1-en-1-yl)-3-(3-(1-naphthyloxyl)propyl)-1H-indole-2-carboxylic acid $^1$H NMR (500 MHz, DMSO-d$_6$): δ 10.43 (s, 1H), 8.22-8.24 (m, 1H), 7.84-7.86 (m, 1H), 7.34-7.54 (m, 5H), 6.93 (d, J=7.98 Hz, 1H), 6.79-6.84 (m, 5H), 4.10 (t, J=6.14 Hz, 2H), 3.22-3.26 (m, 2H), 2.57-2.64 (m, 1H), 2.11-2.44 (m, 6H), 1.85 (br, 4H), 0.99 (d, J=6.75 Hz, 6H).

EXAMPLE 263

7-(1,3-dimethyl-5-phenyl-1H-pyrazol-4-yl)-3-(3-(1-naphthyloxyl)propyl)-1H-indole-2-carboxylic acid $^1$H NMR (500 MHz, DMSO-d$_6$): δ 12.85 (s, 1H), 10.42 (s, 1H), 8.25 (d, J=7.63 Hz, 1H), 7.85-7.87 (m, 1H), 7.44-7.58 (m, 4H), 7.38 (t, J=7.93 Hz, 1H), 7.25-7.30 (m, 5H), 6.93-6.97 (m, 2H), 6.88 (d, J=7.63 Hz, 1H), 4.17 (t, J=6.1 Hz, 2H), 3.73 (s, 3H), 3.27-3.30 (m, 2H), 2.16-2.20 (m, 2H), 2.00 (s, 3H).

EXAMPLE 264

7-(1,5-dimethyl-3-phenyl-1H-pyrazol-4-yl)-3-(3-(1-naphthyloxyl)propyl)-1H-indole-2-carboxylic acid $^1$H NMR (500 MHz, DMSO-d$_6$): δ 12.87 (s, 1H), 10.60 (s, 1H), 8.26-8.28 (m, 1H), 7.86-7.88 (m, 1H), 7.69 (d, J=7.63 Hz, 1H), 7.45-7.55 (m, 3H), 7.39 (t, J=7.78 Hz, 1H), 7.28 (dd, J=7.32, 2.44 Hz, 2H), 7.11-7.13 (m, 3H), 6.97-7.04 (m, 2H), 6.90 (d, J=7.63 Hz, 1H), 4.20 (t, J=6.1 Hz, 2H), 3.85 (s, 3H), 3.36 (br, 2H), 2.21-2.27 (m, 2H), 2.01 (s, 3H).

EXAMPLE 265

7-(3,5-dimethyl-1-((3-methyloxetan-3-yl)methyl)-1H-pyrazol-4-yl)-3-(3-(1-naphthyloxy)propyl)-1H-indole-2-carboxylic acid $^1$H NMR (500 MHz, DMSO-d$_6$): δ 13.24 (s, 1H), 11.06 (s, 1H), 8.23 (d, J=7.63 Hz, 1H), 7.81-7.88 (m, 2H), 7.39-7.55 (m, 4H), 7.13-7.17 (m, 2H), 6.91 (d, J=7.32 Hz, 1H), 5.50 (m, 1H), 4.41-4.49 (m, 2H), 4.22-4.29 (m, 4H), 3.56 (s, 3H), 2.20-2.26 (m, 8H), 1.93 (s, 3H).

EXAMPLE 266

7-(3,5-dimethyl-1-tetrahydrofuran-3-yl-1H-pyrazol-4-yl)-3-(3-(1-naphthyloxy)propyl)-1H-indole-2-carboxylic acid $^1$H NMR (500 MHz, DMSO-d$_6$): δ 12.98 (s, 1H), 10.59 (s, 1H), 8.25-8.26 (m, 1H), 7.86-7.88 (m, 1H), 7.65 (d, J=7.93 Hz, 1H), 7.45-7.55 (m, 3H), 7.39 (t, J=7.93 Hz, 1H), 7.07-7.07 (m, 2H), 6.91 (d, J=7.63 Hz, 1H), 4.96-5.01 (m, 1H), 4.21 (t, J=6.1 Hz, 2H), 4.03-4.07 (m, 2H), 3.83-3.88 (m, 2H), 3.34-3.37 (m, 2H), 2.31-2.41 (m, 4H), 2.21-2.26 (m 2H), 2.07 (s, 3H), 2.02 (s, 3H).

EXAMPLE 267

7-(3,5-dimethyl-1-pyridin-2-yl-1H-pyrazol-4-yl)-3-(3-(1-naphthyloxy)propyl)-1H-indole-2-carboxylic acid $^1$H NMR (500 MHz, DMSO-d$_6$): δ 10.98 (s, 1H), 8.48 (d, J=4.58 Hz, 1H), 8.25-8.28 (m, 1H), 7.86-8.00 (m, 3H), 7.70 (dd, J=7.17, 1.68 Hz, 1H), 7.45-7.55 (m, 3H), 7.38-7.41 (m, 1H), 7.31-7.33 (m, 1H), 7.07-7.12 (m, 2H), 6.91 (d, J=7.32 Hz, 1H), 4.22 (t, J=5.95 Hz, 2H), 3.37 (t, J=7.63 Hz, 2H), 2.43 (s, 3H), 2.21-2.27 (m, 2H), 2.09 (s, 3H).

EXAMPLE 268

7-(2-chloro-4-methylpyridin-3-yl)-3-(3-(1-naphthyloxy)propyl)-1H-indole-2-carboxylic acid $^1$H NMR (500 MHz, DMSO-d$_6$): δ 12.99 (s, 1H), 11.40 (s, 1H), 8.26-8.31 (m, 2H), 8.25-8.28 (m, 2H), 7.86-7.88 (m, 1H), 7.76 (d, J=7.93 Hz, 1H), 7.38-7.55 (m, 5H), 7.09-7.12 (m, 1H), 7.03 (d, J=7.02 Hz, 1H), 6.91 (d, J=7.63 Hz, 1H), 4.22 (t, J=6.1 Hz, 2H), 3.37 (t, J=7.63 Hz, 2H), 2.22-2.27 (m, 2H), 1.96 (s, 3H).

EXAMPLE 269

7-(4-methyl-2-(2-(2-oxopyrrolidin-1-yl)ethoxy)pyridin-3-yl)-3-(3-(1-naphthyloxyl)propyl)-1H-indole-2-carboxylic acid $^1$H NMR (500 MHz, DMSO-d$_6$): δ 11.10 (s, 1H), 8.27-8.30 (m, 1H), 8.05 (d, J=5.22 Hz, 1H), 7.86-7.88 (m, 1H), 7.68 (d, J=7.98 Hz, 1H), 7.37-7.55 (m, 4H), 7.03-7.07 (m, 1H), 6.96-6.98 (m, 1H), 6.90 (d, J=7.36 Hz, 1H), 4.15-4.30 (m, 4H), 3.34 (m, 2H), 3.24 (t, J=4.91 Hz, 1H), 2.55-2.65 (m, 2H), 2.22-2.27 (m, 2H), 1.96 (s, 3H), 1.90 (t, J=8.13 Hz, 2H), 1.43-1.49 (m, 2H).

EXAMPLE 270

7-(3,5-dimethyl-1-(tetrahydrofuran-3-ylmethyl)-1H-pyrazol-4-yl)-3-(3-(1-naphthyloxy)propyl)-1H-indole-2-carboxylic acid $^1$H NMR (500 MHz, DMSO-d$_6$): δ 10.51 (s, 1H), 8.24-8.26 (m, 1H), 7.86-7.88 (m, 1H), 7.85-7.88 (m, 1H), 7.64-7.66 (m, 1H), 7.44-7.55 (m, 3H), 7.39 (t, J=7.83 Hz, 1H), 7.02-7.08 (m, 2H), 6.91 (d, J=7.36 Hz, 1H), 4.21 (t, J=5.98 Hz, 2H), 3.95-4.05 (m, 2H), 3.80-3.86 (m, 2H), 3.64-3.74 (m, 4H), 3.35 (t, J=7.52 Hz, 1H), 2.74-2.81 (m, 1H), 2.20-2.27 (m, 2H), 1.96-2.03 (m, 6H), 1.69-1.75 (m, 1H).

EXAMPLE 271

7-(1-cyclopentyl-3,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.47 (s, 1H), 8.24-8.26 (m, 1H), 7.85-7.88 (m, 1H), 7.85-7.88 (m, 1H), 7.65 (d, J=6.75 Hz, 1H), 7.45-7.55 (m, 3H), 7.39 (t, J=7.83 Hz, 1H), 7.01-7.07 (m, 2H), 6.91 (d, J=7.36 Hz, 1H), 4.64-4.70 (m, 1H), 4.21 (t, J=6.14 Hz, 2H), 3.33-3.37 (m, 2H), 2.21-2.26 (m, 2H), 2.02-2.08 (m, 10H), 1.85-1.88 (m, 2H), 1.64-1.66 (m, 2H).

EXAMPLE 272

7-(1-((2,2-dimethyl-1,3-dioxolan-4-yl)methyl)-3,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.34 (s, 1H), 8.23-8.26 (m, 1H), 7.85-7.88 (m, 1H), 7.65 (d, J=7.67 Hz, 1H), 7.37-

7.55 (m, 4H), 7.02-7.08 (m, 2H), 6.91 (d, J=7.36 Hz, 1H), 4.44-4.47 (m, 1H), 4.09-4.23 (m, 5H), 3.87-3.91 (m, 1H), 3.34-3.37 (m, 2H), 2.21-2.27 (m, 2H), 2.09 (s, 3H), 2.01 (s, 3H), 1.33 (s, 3H), 1.29 (s, 3H).

EXAMPLE 273

7-(4-methyl-2-(2-morpholin-4-ylethoxy)pyridin-3-yl)-3-(3-(1-naphthyloxyl)propyl)-1H-indole-2-carboxylic acid $^1$H NMR (500 MHz, DMSO-d$_6$): δ 11.11 (s, 1H), 8.91 (s, 1H), 8.26-8.28 (m, 1H), 8.10 (d, J=5.22 Hz, 1H), 7.85-7.88 (m, 1H), 7.71 (d, J=7.98 Hz, 1H), 7.45-7.55 (m, 4H), 7.39 (t, J=7.83 Hz, 1H), 7.05-7.09 (m, 1H), 6.91 (d, J=7.36 Hz, 1H), 4.55-4.59 (m, 1H), 4.40-4.46 (m, 1H), 4.21 (t, J=5.98 Hz, 2H), 3.33-3.37 (m, 2H), 2.93 (br, 2H), 2.73 (br, 2H), 2.20-2.25 (m, 2H), 1.98 (s, 3H).

EXAMPLE 274

7-(4-methyl-2-morpholin-4-ylpyridin-3-yl)-3-(3-(1-naphthyloxy)propyl)-1H-indole-2-carboxylic acid $^1$H NMR (500 MHz, DMSO-d$_6$): δ 11.28 (s, 1H), 8.27-8.29 (m, 1H), 8.20 (d, J=5.83 Hz, 1H), 7.86-7.88 (m, 1H), 7.79 (d, J=7.98 Hz, 1H), 7.45-7.55 (m, 4H), 7.37 (t, J=7.98 Hz, 1H), 7.20-7.24 (m, 2H), 7.09-7.13 (m, 1H), 6.86 (d, J=7.37 Hz, 1H), 4.18 (t, J=6.14 Hz, 2H), 3.39 (t, J=6.14 Hz, 2H), 2.87-3.17 (m, 8H), 2.21-2.28 (m, 2H), 2.12 (s, 3H).

EXAMPLE 275

7-(2-chloro-4-methylpyridin-3-yl)-3-(3-(1-naphthyloxyl)propyl)-1-(pyridin-3-ylmethyl)-1H-indole-2-carboxylic acid $^1$H NMR (500 MHz, DMSO-d$_6$): δ 8.51 (d, J=4.3 Hz, 1H), 8.25-8.29 (m, 2H), 7.93 (d, J=7.98 Hz, 1H), 7.87-7.89 (m, 1H), 7.74 (s, 1H), 7.39-7.56 (m, 5H), 7.19-7.24 (m, 2H), 7.10 (d, J=7.98 Hz, 1H), 6.99 (d, J=7.36 Hz, 1H), 6.94 (d, J=6.75 Hz, 1H), 5.29-5.46 (m, 2H), 4.28 (t, J=5.98 Hz, 2H), 3.42-3.45 (m, 2H), 2.27-2.33 (m, 2H), 1.66 (s, 3H).

EXAMPLE 276

7-(2-(1H-imidazol-1-yl)-4-methylpyridin-3-yl)-3-(3-(1-naphthyloxy)propyl)-1H-indole-2-carboxylic acid $^1$H NMR (500 MHz, DMSO-d$_6$): δ 11.37 (s, 1H), 8.75 (s, 1H), 8.60 (d, J=5.22 Hz, 1H), 8.25-8.28 (m, 1H), 7.86-7.88 (m, 1H), 7.74 (d, J=7.98 Hz, 1H), 7.70 (d, J=5.22 Hz, 1H), 7.45-7.54 (m, 3H), 7.39 (t, J=7.98 Hz, 1H), 7.30 (d, J=7.36 Hz, 2H), 7.02-7.09 (m, 2H), 6.88 (d, J=7.36 Hz, 1H), 4.17 (t, J=6.14 Hz, 2H), 3.27-3.39 (m, 2H), 2.18-2.25 (m, 2H), 2.06 (s, 3H).

EXAMPLE 277

7-(1-(2,3-dihydroxypropyl)-3,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.47 (s, 1H), 8.24-8.26 (m, 1H), 7.86-7.88 (m, 1H), 7.67 (d, J=7.36 Hz, 1H), 7.37-7.53 (m, 4H), 7.03-7.09 (m, 2H), 6.91 (d, J=7.67 Hz, 1H), 4.15-4.23 (m, 4H), 3.34-3.46 (m, 2H), 2.21-2.26 (m, 2H), 2.07 (s, 3H), 2.03 (s, 3H).

EXAMPLE 278

3-(3-(1-naphthyloxyl)propyl)-7-(3-phenyl-5-(2-phenylethyl)-1H-pyrazol-4-yl)-1H-indole-2-carboxylic acid $^1$H NMR (500 MHz, DMSO-d$_6$): δ 10.40 (s, 1H), 8.26-8.29 (m, 1H), 7.85-7.88 (m, 1H), 7.68 (d, J=8.29 Hz, 1H), 7.44-7.55 (m, 3H), 7.31-7.39 (m, 3H), 7.00-7.17 (m, 7H), 6.89-6.95 (m, 4H), 4.19 (t, J=6.14 Hz, 2H), 3.34-3.46 (m, 2H), 2.65-2.74 (m 4H), 2.21-2.26 (m, 2H).

EXAMPLE 279

7-(4-methyl-2-phenylpyridin-3-yl)-3-(3-(1-naphthyloxyl)propyl)-1H-indole-2-carboxylic acid $^1$H NMR (500 MHz, DMSO-d$_6$): δ 11.29 (s, 1H), 8.81 (d, J=5.52 Hz, 1H), 8.24-8.26 (m, 1H), 7.85-7.90 (m, 2H), 7.64-7.66 (m, 1H), 7.31-7.39 (m, 3H), 7.35-7.45 (m, 4H), 7.15-7.28 (m, 5H), 6.92-6.97 (m, 2H), 6.84 (d, J=7.67 Hz, 1H), 4.12 (t, J=6.14 Hz, 2H), 3.28-3.34 (m, 2H), 2.17-2.21 (m, 2H), 2.15 (s, 3H).

EXAMPLE 280

7-(4-methyl-2-vinylpyridin-3-yl)-3-(3-(1-naphthyloxy)propyl)-1H-indole-2-carboxylic acid $^1$H NMR (500 MHz, DMSO-d$_6$): δ 11.22 (s, 1H), 8.65 (d, J=5.83 Hz, 1H), 8.25-8.27 (m, 1H), 7.86-7.88 (m, 1H), 7.81 (d, J=7.98 Hz, 1H), 7.62-7.64 (m, 1H), 7.45-7.54 (m, 3H), 7.39 (t, J=7.98 Hz, 1H), 7.04 (d, J=6.44 Hz, 1H), 6.91 (d, J=7.67 Hz, 1H), 6.16-6.29 (m, 2H), 5.47-5.49 (m, 1H), 4.22 (t, J=6.14 Hz, 2H), 3.28-3.34 (m, 2H), 2.21-2.28 (m, 2H), 2.04 (s, 3H).

EXAMPLE 281

7-(4-methyl-2-((1E)-prop-1-enyl)pyridin-3-yl)-3-(3-(1-naphthyloxy)propyl)-1H-indole-2-carboxylic acid $^1$H NMR (500 MHz, DMSO-d$_6$): δ 11.24 (s, 1H), 8.65 (d, J=5.83 Hz, 1H), 8.25-8.28 (m, 1H), 7.82-7.88 (m, 2H), 7.70 (d, J=5.83 Hz, 1H), 7.45-7.55 (m, 3H), 7.39 (t, J=7.98 Hz, 1H), 7.14-7.18 (m, 1H), 7.05 (d, J=7.14 Hz, 1H), 6.90 (d, J=7.36 Hz, 1H), 6.16-6.29 (m, 2H), 6.82 (dd, J=15.65, 6.75 Hz, 1H), 5.92 (dd, J=15.65, 1.53 Hz, 1H), 4.22 (t, J=6.14 Hz, 2H), 3.36-3.40 (m, 2H), 2.22-2.28 (m, 2H), 2.04 (s, 3H), 1.69-1.71 (m, 3H).

EXAMPLE 282

7-(2-ethyl-4-methylpyridin-3-yl)-3-(3-(1-naphthyloxy)propyl)-1H-indole-2-carboxylic acid $^1$H NMR (500 MHz, DMSO-d$_6$): δ 11.30 (s, 1H), 8.76 (d, J=5.83 Hz, 1H), 8.25-8.27 (m, 1H), 7.84-7.88 (m, 2H), 7.45-7.56 (m, 3H), 7.39 (t, J=7.83 Hz, 1H), 7.12-7.20 (m, 2H), 6.90 (d, J=7.67 Hz, 1H), 4.22 (t, J=6.14 Hz, 2H), 3.36-3.40 (m, 2H), 2.59-2.65 (m, 1H), 2.42-2.48 (m, 1H), 2.21-2.27 (m, 2H), 2.10 (s, 3H).

EXAMPLE 283

7-(3,5-dimethyl-1-(pyridin-3-ylmethyl)-1H-pyrazol-4-yl)-3-(3-(1-naphthyloxy)propyl)-1H-indole-2-carboxylic acid $^1$H NMR (500 MHz, DMSO-$d_6$): δ 10.95 (s, 1H), 8.60-8.65 (m, 2H), 8.24-8.26 (m, 1H), 7.94 (d, J=7.98 Hz, 1H), 7.85-7.87 (m, 1H), 7.62-7.67 (m, 2H), 7.44-7.53 (m, 3H), 7.39 (t, J=7.98 Hz, 1H), 7.03-7.08 (m, 2H), 6.91 (d, J=7.36 Hz, 1H), 5.41 (s, 2H), 4.21 (t, J=5.98 Hz, 2H), 3.34-3.38 (m, 2H), 2.21-2.26 (m, 2H), 2.08 (s, 3H), 2.02 (s, 3H).

EXAMPLE 284

7-(2-isopropenyl-4-methylpyridin-3-yl)-3-(3-(1-naphthyloxy)propyl)-1H-indole-2-carboxylic acid $^1$H NMR (500 MHz, DMSO-$d_6$): δ 11.26 (s, 1H), 8.71 (d, J=5.52 Hz, 1H), 8.26-8.28 (m, 1H), 7.80-7.88 (m, 2H), 7.77 (d, J=7.67 Hz, 1H), 7.45-7.55 (m, 3H), 7.38 (t, J=7.83 Hz, 1H), 7.04-7.11 (m, 2H), 6.88 (d, J=7.37 Hz, 1H), 5.15 (s, 1H), 5.13 (s, 1H), 4.20 (t, J=6.14 Hz, 2H), 3.33-3.37 (m, 2H), 2.21-2.26 (m, 2H), 2.10 (s, 3H), 1.67 (s, 3H).

EXAMPLE 285

7-(4-methyl-2-pentylpyridin-3-yl)-3-(3-(1-naphthyloxy)propyl)-1H-indole-2-carboxylic acid $^1$H NMR (500 MHz, DMSO-$d_6$): δ 11.23 (s, 1H), 8.74 (d, J=5.83 Hz, 1H), 8.25-8.28 (m, 1H), 7.83-7.88 (m, 3H), 7.45-7.55 (m, 3H), 7.38 (t, J=7.83 Hz, 1H), 7.11-7.18 (m, 2H), 6.87 (d, J=7.67 Hz, 1H), 4.20 (t, J=6.19 Hz, 2H), 3.33-3.37 (m, 2H), 2.54-2.62 (m, 1H), 2.29-2.46 (m, 1H), 2.22-2.28 (m, 2H), 2.12 (s, 3H), 1.35-1.40 (m, 2H), 0.88-0.99 (m, 4H), 0.58 (t, J=7.06 Hz, 3H).

EXAMPLE 286

7-(4-methyl-2-propylpyridin-3-yl)-3-(3-(1-naphthyloxy)propyl)-1H-indole-2-carboxylic acid $^1$H NMR (500 MHz, DMSO-$d_6$): δ 11.30 (s, 1H), 8.73 (d, J=5.83 Hz, 1H), 8.26-8.28 (m, 1H), 7.82-7.88 (m, 2H), 7.79 (d, J=5.83 Hz, 1H), 7.45-7.55 (m, 3H), 7.38 (t, J=7.83 Hz, 1H), 7.10-7.18 (m, 2H), 6.89 (d, J=7.36 Hz, 1H), 4.21 (t, J=5.98 Hz, 2H), 3.37-3.40 (m, 2H), 2.54-2.64 (m, 1H), 2.34-2.42 (m, 1H), 2.22-2.28 (m, 2H), 2.09 (s, 3H), 1.39-1.49 (m, 2H), 0.65 (t, J=7.36 Hz, 3H).

EXAMPLE 287

7-(2-isopropyl-4-methylpyridin-3-yl)-3-(3-(1-naphthyloxyl)propyl)-1H-indole-2-carboxylic acid $^1$H NMR (500 MHz, DMSO-$d_6$): δ 11.26 (s, 1H), 8.65 (d, J=5.83 Hz, 1H), 8.22-8.24 (m, 1H), 7.84-7.86 (m, 1H), 7.80 (d, J=7.98 Hz, 1H), 7.72 (d, J=6.14 Hz, 1H), 7.35-7.45 (m, 3H), 7.37 (t, J=7.98 Hz, 1H), 7.15 (t, J=7.52 Hz, 1H), 7.07-7.08 (m, 1H), 6.88 (d, J=7.36 Hz, 1H), 4.20 (t, J=5.98 Hz, 2H), 3.36 (m, 2H), 2.67-2.70 (m, 2H), 2.22-2.28 (m, 2H), 2.02 (s, 3H), 1.12 (dd, J=6.75, 5.22 Hz, 6H).

EXAMPLE 288

7-(3,5-diisopropyl-1-methyl-1H-pyrazol-4-yl)-3-(3-(1-naphthyloxy)propyl)-1H-indole-2-carboxylic acid $^1$H NMR (500 MHz, DMSO-$d_6$): δ 10.43 (s, 1H), 8.27-8.29 (m, 1H), 7.86-7.88 (m, 1H), 7.66 (d, J=7.06 Hz, 1H), 7.45-7.55 (m, 3H), 7.36-7.40 (m, 1H), 6.99-7.06 (m, 2H), 6.89 (d, J=7.06 Hz, 1H), 4.20 (t, J=6.14 Hz, 2H), 3.82 (s, 3H), 3.32-3.36 (m, 2H), 2.89-2.94 (m, 1H), 2.43-2.50 (m, 1H), 2.19-2.26 (m, 2H), 1.03-1.06 (m, 6H), 0.96 (d, J=6.75, Hz, 3H), 0.91 (d, J=7.06 Hz, 3H).

EXAMPLE 289

7-(5-carboxy-1,3-dimethyl-1H-pyrazol-4-yl)-3-(3-(1-naphthyloxyl)propyl)-1H-indole-2-carboxylic acid $^1$H NMR (500 MHz, DMSO-$d_6$): δ 10.61 (s, 1H), 8.28-8.30 (m, 1H), 7.86-7.88 (m, 1H), 7.64 (d, J=7.06, 2.15 Hz, 1H), 7.45-7.55 (m, 3H), 7.40 (t, J=7.83 Hz, 1H), 7.00-7.05 (m, 2H), 6.92 (d, J=7.36 Hz, 1H), 4.22 (t, J=6.14 Hz, 2H), 4.09 (s, 3H), 3.33-3.36 (m, 2H), 2.21-2.26 (m, 2H), 1.92 (s, 3H).

EXAMPLE 290

7-(4-methyl-2-(2-methylprop-1-enyl)pyridin-3-yl)-3-(3-(1-naphthyloxyl)propyl)-1H-indole-2-carboxylic acid $^1$H NMR (500 MHz, DMSO-$d_6$): δ 11.20 (s, 1H), 8.70 (d, J=5.83 Hz, 1H), 8.25-8.27 (m, 1H), 7.86-7.88 (m, 1H), 7.80 (d, J=7.67 Hz, 1H), 7.45-7.55 (m, 3H), 7.38 (t, J=7.83 Hz, 1H), 7.11-7.14 (m, 1H), 7.04-7.06 (m 1H), 6.88 (d, J=7.67 Hz, 1H), 5.78 (s, 1H), 4.20 (t, J=5.98 Hz, 2H), 3.33-3.36 (m, 2H), 2.20-2.28 (m, 2H), 2.11 (s, 3H), 1.78 (s, 3H), 1.60 (s, 3H).

EXAMPLE 291

7-(4-carboxy-1-phenyl-1H-pyrazol-5-yl)-3-(3-(1-naphthyloxy)propyl)-1H-indole-2-carboxylic acid $^1$H NMR (500 MHz, DMSO-$d_6$): δ 11.40 (s, 1H), 8.27-8.29 (m, 1H), 8.16 (s, 1H), 7.85-7.88 (m, 1H), 7.69 (d, J=7.98 Hz, 1H), 7.44-7.55 (m, 3H), 7.38 (t, J=7.98 Hz, 1H), 7.19-7.23 (m, 5H), 7.02 (d, J=6.75 Hz, 1H), 6.93 (t, J=7.67 Hz, 1H), 6.87 (d, J=7.36 Hz, 1H), 5.78 (s, 1H), 4.16 (t, J=6.14 Hz, 2H), 3.28-3.34 (m, 2H), 2.16-2.24 (m, 2H).

EXAMPLE 292

7-(2-isobutyl-4-methylpyridin-3-yl)-3-(3-(1-naphthyloxyl)propyl)-1H-indole-2-carboxylic acid $^1$H NMR (500 MHz, DMSO-$d_6$): δ 11.31 (s, 1H), 8.75 (d, J=6.14 Hz, 1H), 8.26-8.28 (m, 1H), 7.83-7.88 (m, 1H), 7.44-7.56 (m, 3H), 7.37 (t, J=7.98 Hz, 1H), 7.12-7.17 (m, 2H), 6.87 (d, J=7.36 Hz, 1H), 4.19 (t, J=6.14 Hz, 2H), 3.28-3.34 (m, 2H), 2.54-2.61 (m, 1H), 2.22-2.32 (m, 3H), 2.12 (m, 3H), 1.72-1.78 (m, 1H), 0.66 (d, J=6.44 Hz, 3H), 0.62 (d, J=6.75 Hz, 3H).

EXAMPLE 293

7-(4-methyl-2,3'-bipyridin-3-yl)-3-(3-(1-naphthyloxy)propyl)-1H-indole-2-carboxylic acid $^1$H NMR (500 MHz, DMSO-d$_6$): δ 11.32 (s, 1H), 8.71 (d, J=5.22 Hz, 1H), 8.43 (s, 1H), 8.36 (d, J=6.1 Hz, 1H), 8.25-8.27 (m, 1H), 7.85-7.88 (m, 1H), 7.71 (d, J=7.98 Hz, 1H), 7.61-7.65 (m, 2H), 7.44-7.55 (m, 3H), 7.38 (t, J=7.98 Hz, 1H), 7.26 (dd, J=7.98, 5.22 Hz, 1H), 6.93-6.96 (m, 2H), 6.86 (d, J=7.36 Hz, 1H), 4.14 (t, J=6.14 Hz, 2H), 3.30-3.34 (m, 2H), 2.16-2.20 (m, 2H), 2.06 (s, 3H).

EXAMPLE 294

7-(2-(4-methoxyphenyl)-4-methylpyridin-3-yl)-3-(3-(1-naphthyloxyl)propyl)-1H-indole-2-carboxylic acid $^1$H NMR (500 MHz, DMSO-d$_6$): δ 11.28 (s, 1H), 8.75 (d, J=5.83 Hz, 1H), 8.25-8.27 (m, 1H), 7.83-7.88 (m, 2H), 7.68 (dd, J=7.06, 2.15 Hz, 1H), 7.44-7.55 (m, 3H), 7.37 (t, J=7.83 Hz, 1H), 7.20 (d, J=8.59 Hz, 1H), 6.94-6.99 (m, 2H), 6.85 (d, J=7.67 Hz, 1H), 6.74 (d, J=8.59 Hz, 1H), 4.14 (t, J=6.29 Hz, 2H), 3.63 (s, 3H), 3.31-3.35 (m, 2H), 2.18-2.24 (m, 2H), 2.11 (s, 3H).

EXAMPLE 295

7-(4-methyl-2-(1-methyl-H-pyrazol-4-yl)pyridin-3-yl)-3-(3-(1-naphthyloxy)propyl)-1H-indole-2-carboxylic acid $^1$H NMR (500 MHz, DMSO-d$_6$): δ 11.28 (s, 1H), 8.66 (d, J=5.19 Hz, 1H), 8.27-8.29 (m, 1H), 7.84-7.88 (m, 2H), 7.86 (s, 1H), 7.45-7.55 (m, 3H), 7.37 (t, J=7.83 Hz, 1H), 7.37-7.40 (m, 1H), 7.07-7.15 (m, 2H), 6.88 (d, J=7.63 Hz, 1H), 6.78 (s, 1H), 4.18 (t, J=6.26 Hz, 2H), 3.63 (s, 3H), 3.29-3.33 (m, 2H), 2.21-2.27 (m, 2H), 2.08 (s, 3H).

EXAMPLE 296

7-(3-(hydroxymethyl)-1,5-dimethyl-1H-pyrazol-4-yl)-3-(3-(1-naphthyloxy)propyl)-1H-indole-2-carboxylic acid

EXAMPLE 296A

Ethyl 4-bromo-5-methyl-1H-pyrazole-3-carboxylate

Ethyl 5-methyl-1H-pyrazole-3-carboxylate (3.24 g) in CH$_3$CN (25 mL) was treated with N-bromosuccinimide (3.92 g) at 0° C. The solution was stirred at room temperature for 2 hours. The solvent was removed, and the residue was purified by flash chromatography on silica gel (ethyl acetate in hexanes) to give the title compound. $^1$H NMR (500 MHz, DMSO-d6): 13.61 (s, 1H), 4.27 (q, J=6.75 Hz, 2H), 2.21 (s, 3H), 1.28 (t, J=7.06 Hz, 3H).

EXAMPLE 296B

Ethyl 4-bromo-1,5-dimethyl-1H-pyrazole-3-carboxylate

EXAMPLE 296A (2.33 g) in N,N-dimethylformamide was treated with 60% NaH (0.8 g) at 0° C. After 10 minutes, to this solution was added iodomethane (1.703 g). The solution was stirred at room temperature for 3 hours. Aqueous workup followed by drying, filtering, and flash chromatography (ethyl acetate in hexanes) afforded the title compound. $^1$H NMR (500 MHz, DMSO-d$_6$): 4.26 (q, J=7.06 Hz, 2H), 3.86 (s, 3H), 2.27 (s, 3H), 1.28 (t, J=7.06 Hz, 3H).

EXAMPLE 296C (4-Bromo-1,5-dimethyl-1H-pyrazol-3-yl)methanol

EXAMPLE 296B (1.43 g) in tetrahydrofuran (10 ml) was treated with 1N LiAlH$_4$ in tetrahydrofuran (5.79 mL) at 0° C. The solution was stirred for 10 minutes. Aqueous workup followed by flash chromatography (ethyl acetate in hexanes) afforded the title compound. $^1$H NMR (500 MHz, DMSO-d6): 4.91 (t, J=5.68 Hz, 1H), 4.30 (d, J=5.52 Hz, 2H), 3.73 (s, 3H), 2.21 (s, 3H).

EXAMPLE 296D

Methyl 7-(3-(hydroxymethyl)-1,5-dimethyl-1H-pyrazol-4-yl)-3-(3-(naphthalen-1-yloxy)propyl)-1H-indole-2-carboxylate The title compound was synthesized according to the procedure for EXAMPLE 192A by substituting 2-fluoro-4-iodo-5-methylpyridine with EXAMPLE 296C. $^1$H NMR (500 MHz, DMSO-d$_6$): δ 11.06 (s, 1H), 8.25-8.26 (m, 1H), 7.86-7.88 (m, 1H), 7.65 (dd, J=7.02, 1.83 Hz, 1H), 7.45-7.55 (m, 3H), 7.39 (t, J=7.93 Hz, 1H), 7.05-7.09 (m, 2H), 6.91 (d, J=7.63 Hz, 1H), 6.78 (s, 1H), 4.24 (s, 2H), 4.21 (t, J=6.1 Hz, 2H), 3.83 (s, 3H), 3.34-3.37 (m, 2H), 2.21-2.26 (m, 2H), 2.15 (s, 3H).

EXAMPLE 296E 7-(3-(hydroxymethyl)-1,5-dimethyl-1H-pyrazol-4-yl)-3-(3-(1-naphthyloxy)propyl)-1H-indole-2-carboxylic acid The title compound was synthesized according to the procedure for EXAMPLE 175B by substituting EXAMPLE 175A with EXAMPLE 296D. $^1$H NMR (500 MHz, DMSO-d6): 11.06 (s, 1H), 8.25-8.26 (m, 1H), 7.86-7.88 (m, 1H), 7.65 (dd, J=7.02, 1.83 Hz, 1H), 7.45-7.55 (m, 3H), 7.39 (t, J=7.93 Hz, 1H), 7.05-7.09 (m, 2H), 6.91 (d, J=7.63 Hz, 1H), 6.78 (s, 1H), 4.24 (s, 2H), 4.21 (t, J=6.1 Hz, 2H), 3.83 (s, 3H), 3.34-3.37 (m, 2H), 2.21-2.26 (m, 2H), 2.15 (s, 3H).

EXAMPLE 297

3-Bromo-7-(1,3-dimethyl-5-phenyl-1H-pyrazol-4-yl)-1H-indole-2-carboxylic acid

EXAMPLE 297A

4-Bromo-1,3-dimethyl-5-phenyl-1H-pyrazole

The title compound was synthesized according to the procedure for EXAMPLE 296B by substituting ethyl 5-methyl-1H-pyrazole-3-carboxylate with 5-methyl-3-phenyl-1H- pyrazole. ¹H NMR (500 MHz, DMSO-d6): 7.46-7.56 (m, 5H), 3.70 (s, 3H), 2.18 (s, 3H).

EXAMPLE 297B 7-(4,4,5,5-Tetramethyl-(1,3,2)dioxaborolan-2-yl)-1H-indole-2-carboxylic acid ethyl ester A mixture of ethyl 1H-indole-2-carboxylate (1.89 g), 5,5'-di-tert-butyl-2,2'-bipyridine (0.081 g), and (Ir(OMe)(COD))$_2$ (0.152 g) in hexanes (30 mL) was treated with 4,4,5,5-tetramethyl-1,3,2-dioxaborolane (1.66 g) via a syringe. The reaction mixture was degassed via vacuum/nitrogen cycle three times. The reaction mixture was heated at 62° C. for 12 hours. After this time, the solvent was removed and the residue was purified by flash chromatography on silica gel eluting with 1:9 ethyl acetate/hexane to give the title compound. ¹H NMR (500 MHz, DMSO-d$_6$): 9.75 (s, 1H), 7.87 (d, J=7.93 Hz, 1H), 7.64-7.65 (m, 1H), 7.24 (s, 1H), 7.16-7.17 (m, 1H), 4.36 (q, J=7.02 Hz, 2H), 1.38 (s, 12H), 1.35 (q, J=7.02 Hz, 3H).

EXAMPLE 297C 7-(1,3-Dimethyl-5-phenyl-1H-pyrazol-4-yl)-1H-indole-2-carboxylic acid methyl ester The title compound was synthesized according to the procedure for EXAMPLE 192 by substituting EXAMPLE 43A and 2-fluoro-4-iodo-5-methylpyridine with EXAMPLE 297B and EXAMPLE 297A, respectively.

EXAMPLE 297D

3-Bromo-7-(1,3-dimethyl-5-phenyl-1H-pyrazol-4-yl)-1H-indole-2-carboxylic acid

A mixture of EXAMPLE 279C (60 mg) and N-bromosuccinimide (32 mg) in acetonitrile (2 mL) was stirred for 3 hours at room temperature. The desired product was purified by flash chromatography on silica gel. It was then hydrolyzed with 1.0 N LiOH, and purified by Prep HPLC to give the title compound. ¹H NMR (500 MHz, DMSO-d$_6$): 13.22 (s, 1H), 11.44 (s, 1H), 7.41 (d, J=7.93 Hz, 1H), 7.24-7.30 (m, 5H), 7.11-7.14 (m, 2H), 7.04 (d, J=7.02 Hz, 1H), 3.73 (s, 3H), 1.98 (s, 3H).

EXAMPLE 298

7-(1,3-dimethyl-5-(phenoxymethyl)-1H-pyrazol-4-yl)-3-(3-(1-naphthyloxy)propyl)-1H-indole-2-carboxylic acid ¹H NMR (500 MHz, DMSO-d$_6$): δ 12.96 (s, 1H), 10.45 (s, 1H), 8.23-8.25 (m, 2H), 7.85-7.87 (m, 2H), 7.65 (d, J=7.93 Hz, 1H), 7.44-7.54 (m, 3H), 7.38 (t, J=7.93 Hz, 1H), 7.17-7.20 (m, 3H), 7.10 (d, J=7.02 Hz, 1H), 7.01-7.04 (m, 1H), 6.85-6.90 (m, 4H), 4.78 (s, 2H), 4.19 (t, J=6.1 Hz, 2H), 3.82 (s, 3H), 3.32-3.35 (m, 2H), 2.19-2.24 (m 2H), 2.09 (s, 3H).

EXAMPLE 299

7-(1-methyl-1H-pyrazol-4-yl)-3-(3-(1-naphthyloxyl)propyl)-1H-indole-2-carboxylic acid ¹H NMR (500 MHz, DMSO-d$_6$): δ 10.21 (s, 1H), 8.29 (s, 1H), 8.22-8.24 (m, 1H), 7.84-7.87 (m, 2H), 7.59 (d, J=7.98 Hz, 1H), 7.44-7.54 (m, 3H), 7.39 (t, J=7.67 Hz, 1H), 7.33-7.35 (m, 1H), 7.01-7.04 (m, 1H), 6.88 (d, J=7.67 Hz, 1H), 4.18 (t, J=5.98 Hz, 2H), 3.93 (s, 3H), 3.35 (t, J=7.36 Hz, 2H), 2.19-2.26 (m 2H).

EXAMPLE 300

3-bromo-7-(2-((E)-2-cyclohexylvinyl)-4-methylpyridin-3-yl)-1H-indole-2-carboxylic acid ¹H NMR (500 MHz, DMSO-d$_6$): δ 11.90 (s, 1H), 8.61 (d, J=5.52 Hz, 1H), 7.67 (d, J=7.98 Hz, 1H), 7.62 (s, 1H), 7.33-7.36 (m, 1H), 7.17 (d, J=7.06 Hz, 1H), 6.70 (dd, J=15.8, 7.21 Hz, 1H), 5.81 (d, J=15.65 Hz, 1H), 2.04 (s, 3H), 1.95 (m, 2H), 1.43-1.54 (m 5H), 0.99-1.16 (m, 5H).

EXAMPLE 301

7-(3-isopropyl-1-methyl-5-(phenoxymethyl)-1H-pyrazol-4-yl)-3-(3-(1-naphthyloxyl)propyl)-1H-indole-2-carboxylic acid ¹H NMR (500 MHz, DMSO-d$_6$): δ 10.33 (s, 1H), 8.23-8.25 (m, 1H), 7.85-7.87 (m, 1H), 7.69 (dd, J=7.32, 1.53 Hz, 1H), 7.44-7.54 (m, 3H), 7.37 (t, J=7.98 Hz, 1H), 7.18 (t, J=7.93 Hz, 1H), 7.05-7.09 (m, 2H), 6.89 (t, J=8.09 Hz, 1H), 6.83 (t, J=7.93 Hz, 1H), 4.85-4.87 (m, 1H), 4.75-4.77 (m 1H), 4.19 (t, J=6.26 Hz, 2H), 3.87 (s, 3H), 3.32-3.35 (m, 2H), 2.73-2.79 (m, 1H), 2.19-2.26 (m 2H), 1.09 (d J=6.71 Hz, 3H), 1.06 (d, J=7.02 Hz, 3H).

EXAMPLE 302

7-(1,5-dimethyl-3-(phenoxymethyl)-1H-pyrazol-4-yl)-3-(3-(1-naphthyloxy)propyl)-1H-indole-2-carboxylic acid A mixture of EXAMPLE 296 (0.060 g), phenol (13 mg), and triphenylphosphine (48.8 mg) in tetrahydrofuran (2 mL) was cooled to 0° C. To this solution was added (E)-di-tert-butyl diazene-1,2-dicarboxylate (34.3 mg). The solution was stirred at room temperature for 15 hours. The solvent was removed and the residue was hydrolyzed in 1.0 N LiOH/dioxane. The crude acid was purified by RP HPLC to give the title compound. ¹H NMR (500 MHz, DMSO-d$_6$): δ 10.40 (s, 1H), 8.22-8.24 (m, 1H), 7.85-7.87 (m, 1H), 7.65 (d, J=7.67 Hz, 1H), 7.44-7.54 (m, 3H), 7.37 (t, J=7.98 Hz, 1H), 7.16-7.20 (m, 2H), 7.09-7.11 (m, 1H), 7.01-7.05 (m, 1H), 6.84-6.90 (m, 4H), 4.48 (s, 2H), 4.19 (t, J=6.41 Hz, 2H), 3.82 (s, 3H), 3.31-3.35 (m, 2H), 2.73-2.79 (m, 1H), 2.18-2.25 (m 2H), 2.09 (s, 3H).

EXAMPLE 303

7-(4-(anilinocarbonyl)-1-phenyl-1H-pyrazol-5-yl)-3-(3-(1-naphthyloxy)propyl)-1H-indole-2-carboxylic acid ¹H NMR (500 MHz, DMSO-d$_6$): δ 13.01 (s, 1H), 11.37 (s, 1H), 9.45 (s, 1H), 8.49 (s, 1H), 8.27-8.29 (m, 1H), 7.86-7.88 (m, 1H), 7.73 (d, J=7.93 Hz, 1H), 7.44-7.54 (m, 5H), 7.21-7.24 (m, 7H), 7.07 (d, J=7.32 Hz, 1H), 6.94-7.00 (m, 2H), 6.87 (d, J=7.63 Hz, 1H), 4.16 (t, J=6.1 Hz, 2H), 3.31-3.35 (m, 2H), 2.18-2.23 (m 2H).

EXAMPLE 304

7-(3-((3-chlorophenoxy)methyl)-1,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.41 (s, 1H), 8.22-8.24 (m, 1H), 7.85-7.87 (m, 1H), 7.65 (d, J=7.67 Hz, 1H), 7.44-7.54 (m, 3H), 7.37 (t, J=7.98 Hz, 1H), 7.19 (t, J=8.13 Hz, 1H), 7.07-7.09 (m, 1H), 7.01-7.05 (m, 1H), 6.84-6.95 (m, 4H), 4.82 (s, 2H), 4.19 (t, J=6.14 Hz, 2H), 3.82 (s, 3H), 3.32-3.36 (m, 2H), 2.19-2.25 (m 2H), 2.09 (s, 3H).

EXAMPLE 305

7-(1,5-dimethyl-3-((3-phenoxyphenoxy)methyl)-1H-pyrazol-4-yl)-3-(3-(1-naphthyloxyl)propyl)-1H-indole-2-carboxylic acid $^1$H NMR (500 MHz, DMSO-d$_6$): δ 10.43 (s, 1H), 8.23-8.25 (m, 1H), 7.85-7.87 (m, 1H), 7.64 (d, J=7.98 Hz, 1H), 7.34-7.54 (m, 6H), 6.95-7.18 (m, 6H), 6.89 (d, J=7.36 Hz, 1H), 6.67 (dd, J=8.29, 2.46 Hz, 1H), 6.57 (t, J=2.3 Hz, 1H), 6.46 (dd, J=8.13, 2.3 Hz, 1H), 4.78 (s, 2H), 4.19 (t, J=6.14 Hz, 2H), 3.80 (s, 3H), 3.31-3.35 (m, 2H), 2.17-2.25 (m 2H), 2.08 (s, 3H).

EXAMPLE 306

3-bromo-4-(2-((4-bromo-1-naphthyl)oxy)ethyl)-7-(2-methylphenyl)-1H-indole-2-carboxylic acid $^1$H NMR (500 MHz, DMSO-d$_6$): δ 13.29 (s, 1H), 11.32 (s, 1H), 8.22 (d, J=8.29 Hz, 1H), 8.05 (d, J=8.59 Hz, 1H), 7.73 (d, J=8.29 Hz, 1H), 7.67-7.70 (m, 1H), 7.56-7.60 (m, 1H), 7.26-7.33 (m, 3H), 7.23 (d, J=7.06 Hz, 1H), 7.19 (d, J=7.36 Hz, 1H), 7.06 (d, J=7.36 Hz, 1H), 7.00 (d, J=8.29 Hz, 1H), 4.53 (t, J=6.9 Hz, 2H), 3.89 (br, 2H), 3.12 (s, 3H).

EXAMPLE 307

7-(1,5-dimethyl-3-((4-morpholin-4-ylphenoxy)methyl)-1H-pyrazol-4-yl)-3-(3-(1-naphthyloxyl)propyl)-1H-indole-2-carboxylic acid $^1$H NMR (500 MHz, DMSO-d$_6$): δ 10.39 (s, 1H), 8.22-8.24 (m, 1H), 7.85-7.87 (m, 1H), 7.66 (d, J=7.67 Hz, 1H), 7.44-7.54 (m, 3H), 7.37 (t, J=7.98 Hz, 1H), 7.02-7.11 (m, 2H), 6.79-6.89 (m, 5H), 4.73 (s, 2H), 4.19 (t, J=6.14 Hz, 2H), 3.81 (s, 3H), 3.71-3.73 (m, 4H), 3.34 (t, J=7.52 Hz, 2H), 3.01-3.02 (m, 4H), 2.18-2.26 (m 2H), 2.09 (s, 3H).

EXAMPLE 308

7-(3-(((5-chloropyridin-3-yl)oxy)methyl)-1,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.38 (s, 1H), 8.16-8.18 (m, 1H), 8.10 (d, J=2.4 Hz, 1H), 8.06 (d, J=2.15 Hz, 1H), 7.78-7.80 (m, 1H), 7.58 (d, J=7.36 Hz, 1H), 7.37-7.47 (m, 4H), 7.29-7.33 (m, 1H), 6.94-7.02 (m, 2H), 6.82 (d, J=7.06 Hz, 1H), 4.86 (s, 2H), 4.12 (t, J=6.14 Hz, 2H), 3.75 (s, 3H), 3.25-3.28 (m, 2H), 2.11-2.17 (m 2H), 2.02 (s, 3H).

EXAMPLE 309

7-(3,5-dimethyl-1-(2-nitrophenyl)-1H-pyrazol-4-yl)-3-(3-(1-naphthyloxy)propyl)-1H-indole-2-carboxylic acid $^1$H NMR (500 MHz, DMSO-d$_6$): δ 13.00 (s, 1H), 10.77 (s, 1H), 8.25-8.27 (m, 1H), 8.11 (d, J=7.63 Hz, 1H), 7.86-7.95 (m, 3H), 7.71-7.76 (m, 2H), 7.45-7.55 (m, 3H), 7.40 (t, J=7.78 Hz, 1H), 7.10-7.16 (m, 2H), 6.92 (d, J=7.63 Hz, 1H), 4.23 (t, J=6.1 Hz, 2H), 3.36-3.39 (m, 2H), 2.23-2.28 (m 2H), 2.06 (s, 3H), 2.05 (s, 3H).

EXAMPLE 310

3-(3-(1-naphthyloxy)propyl)-7-((2-(phenylthio)ethyl)amino)-1H-indole-2-carboxylic acid $^1$H NMR (500 MHz, DMSO-d$_6$): δ 11.15 (s, 1H), 8.21-8.23 (m, 1H), 7.85-7.87 (m, 1H), 7.43-7.53 (m, 3H), 7.32-7.40 (m, 5H), 7.21 (t, J=7.32 Hz, 1H), 6.91 (d, J=7.93 Hz, 1H), 6.86 (d, J=7.32 Hz, 1H), 6.77 (t, J=7.63 Hz, 1H), 6.24 (d, J=7.32 Hz, 1H), 4.14 (t, J=6.1 Hz, 2H), 3.42 ((t, J=6.87 Hz, 2H), 3.23-3.29 (m, 4H), 2.15-2.21 (m 2H), 2.06 (s, 3H), 2.05 (s, 3H).

EXAMPLE 311

7-(3-((2-cyanophenoxy)methyl)-1,5-dimethyl-1H-pyrazol-4-yl)-3-(3-(1-naphthyloxyl)propyl)-1H-indole-2-carboxylic acid $^1$H NMR (500 MHz, DMSO-d$_6$): δ 12.94 (s, 1H), 10.62 (s, 1H), 8.23-8.24 (m, 1H), 7.86 (d, J=8.63 Hz, 1H), 7.64-7.66 (m, 2H), 7.44-7.54 (m, 4H), 7.39 (t, J=7.93 Hz, 1H), 7.22 (d, J=8.54 Hz, 1H), 7.18 (d, J=7.02 Hz, 1H), 6.99-7.03 (m, 2H), 6.89 (d, J=7.32 Hz, 1H), 5.07 (br, 1H), 4.83 (br, 1H), 4.19 (t, J=6.1 Hz, 2H), 3.83 (s, 3H), 3.35 (t, J=7.48 Hz, 2H), 2.19-2.14 (m 2H), 2.08 (s, 3H).

EXAMPLE 312

7-(3-((4-(4-acetylpiperazin-1-yl)phenoxy)methyl)-1,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.39 (s, 1H), 8.22-8.24 (m, 1H), 7.85-7.87 (m, 2H), 7.65 (d, J=7.98 Hz, 1H), 7.44-7.54 (m, 3H), 7.38 (t, J=7.83 Hz, 1H), 7.09-7.10 (m, 1H), 7.03 (t, J=7.52 Hz, 1H), 6.80-7.91 (m, 5H), 4.73 (s, 2H), 4.19 (t, J=6.14 Hz, 2H), 3.81 (s, 3H), 3.56-3.57 (m 2H), 3.34 (t, J=7.52 Hz, 2H), 2.99-3.05 (m, 4H), 2.18-2.15 (m 2H), 2.09 (s, 3H), 2.02 (s, 3H).

EXAMPLE 313

3-bromo-7-(2-methylphenyl)-4-(2-(1-naphthyloxyl)ethyl)-1H-indole-2-carboxylic acid $^1$H NMR (500 MHz, DMSO-d$_6$): δ 11.36 (s, 1H), 8.15 (d, J=8.24 Hz, 1H), 7.85 (d, J=7.93 Hz, 1H), 7.45-7.53 (m, 3H), 7.39 (t, J=7.83 Hz, 1H), 7.28-7.35 (m, 2H), 7.24-7.28 (m 2H), 7.20 (d, J=7.32 Hz, 1H), 7.07 (d, J=7.32 Hz, 1H), 7.01 (d, J=7.63 Hz, 1H), 4.52 (t, J=6.87 Hz, 2H), 3.92 (br, 1H), 3.85 (br, 1H), 3.34 (t, J=7.52 Hz, 2H), 2.03 (s, 3H).

EXAMPLE 314

7-(1-(2-aminophenyl)-3,5-dimethyl-1H-pyrazol-4-yl)-3-(3-(1-naphthyloxyl)propyl)-1H-indole-2-carboxylic acid $^1$H NMR (500 MHz, DMSO-d$_6$): δ 11.01 (s, 1H), 8.25-8.27 (m, 1H), 7.86-7.88 (m, 3H), 7.68 (d, J=7.63 Hz, 1H), 7.45-7.55 (m, 3H), 7.39 (t, J=7.93 Hz, 1H), 7.07-7.20 (m, 4H), 6.91 (d, J=7.32 Hz, 1H), 6.96 (d, J=7.93 Hz, 1H), 6.67 (t, J=7.48 Hz, 1H), 4.22 (t, J=6.1 Hz, 2H), 3.37 (t, J=7.48 Hz, 2H), 2.22-2.29 (m, 2H), 2.09 (s, 3H), 1.88 (s, 3H).

EXAMPLE 315

7-(3-(1H-imidazol-1-ylmethyl)-1,5-dimethyl-1H-pyrazol-4-yl)-3-(3-(1-naphthyloxyl)propyl)-1H-indole-2-carboxylic acid $^1$H NMR (500 MHz, DMSO-d$_6$): δ 13.01 (s, 1H), 10.88 (s, 1H), 8.45 (s, 1H), 8.25-8.27 (m, 1H), 7.86-7.88 (m, 1H), 7.68 (d, J=7.93 Hz, 1H), 7.37-7.55 (m, 6H), 7.96-7.05 (m, 2H), 5.18-5.27 (m, 2H), 4.20 (t, J=6.1 Hz, 2H), 3.81 (s, 3H), 3.34-3.37 (m, 2H), 2.19-2.26 (m, 2H), 2.05 (s, 3H).

EXAMPLE 316

7-(2-methylphenyl)-4-(2-(1-naphthyloxy)ethyl)-3-vinyl-1H-indole-2-carboxylic acid $^1$H NMR (500 MHz, DMSO-d$_6$): δ 12.92 (s, 1H), 10.66 (s, 1H), 8.04 (d, J=8.24 Hz, 1H), 7.84 (d, J=7.93 Hz, 1H), 7.43-7.51 (m, 3H), 7.38 (t, J=7.78 Hz, 1H), 7.26-7.33 (m, 4H), 7.22 (t, J=7.48 Hz, 1H), 7.18 (d, J=7.32 Hz, 1H), 7.03 (d, J=7.32 Hz, 1H), 6.99 (d, J=7.32 Hz, 1H), 5.47-5.53 (m, 2H), 4.41 (t, J=6.87 Hz, 2H), 3.86 (br, 2H), 2.05 (s, 3H).

EXAMPLE 317

7-(4-((benzylamino)carbonyl)-1-phenyl-1H-pyrazol-5-yl)-3-(3-(1-naphthyloxy)propyl)-1H-indole-2-carboxylic acid $^1$H NMR (500 MHz, DMSO-d$_6$): δ 11.22 (s, 1H), 8.22 (s, 1H), 8.20 (d, J=4.3 Hz, 1H), 7.88 (t, J=6.14 Hz, 1H), 7.78-7.81 (m, 1H), 7.61 (d, J=7.98 Hz, 1H), 7.37-7.48 (m, 3H), 7.30 (t, J=7.83 Hz, 1H), 7.09-7.17 (m, 8H), 7.00 (d, J=7.06 Hz, 1H), 6.96 (d, J=7.36 Hz, 1H), 6.92-6.96 (m, 1H), 6.78 (d, J=7.67 Hz, 1H), 4.21-4.23 (m, 2H), 4.07 (t, J=6.14 Hz, 2H), 3.24 (m, 2H), 2.18-2.25 (m, 2H).

EXAMPLE 318

3-(3-(1-naphthyloxy)propyl)-7-(1-phenyl-4-(((3-pyrrolidin-1-ylpropyl)amino)carbonyl)-1H-pyrazol-5-yl)-1H-indole-2-carboxylic acid $^1$H NMR (500 MHz, DMSO-d$_6$): δ 11.26 (s, 1H), 9.24 (s, 1H), 8.27-8.29 (m, 1H), 8.10 (t, J=5.98 Hz, 1H), 7.86-7.88 (m, 5H), 7.70 (d, J=7.36 Hz, 1H), 7.45-7.56 (m, 3H), 7.39 (t, J=7.98 Hz, 1H), 7.16-7.25 (m, 8H), 6.87-6.99 (m, 3H), 4.18 (t, J=5.98 Hz, 2H), 3.17-3.19 (m, 2H), 3.00 (t, J=6.9 Hz, 2H), 2.82 (br, 1H), 2.17-2.23 (m, 2H), 1.72-2.08 (m, 6H).

EXAMPLE 319

7-(4,6-dimethylpyrimidin-5-yl)-3-(3-(1-naphthyloxy)propyl)-1H-indole-2-carboxylic acid $^1$H NMR (500 MHz, DMSO-d$_6$): δ 11.37 (s, 1H), 8.95 (s, 1H), 8.26-8.28 (m, 1H), 7.86-7.88 (m, 1H), 7.77 (d, J=7.67 Hz, 1H), 7.45-7.56 (m, 3H), 7.39 (t, J=7.98 Hz, 1H), 7.06-7.14 (m, 2H), 6.90 (d, J=7.67 Hz, 1H), 4.22 (t, J=6.14 Hz, 2H), 3.35-3.39 (m, 2H), 2.22-2.28 (m, 2H), 2.08 (s, 6H).

EXAMPLE 320

7-(4,6-dimethylpyrimidin-5-yl)-3-(3-(1-naphthyloxyl)propyl)-1-(pyridin-3-ylmethyl)-1H-indole-2-carboxylic acid $^1$H NMR (500 MHz, DMSO-d$_6$): δ 8.86 (s, 1H), 8.48 (d, J=4.6 Hz, 1H), 8.26-8.28 (m, 1H), 7.94 (d, J=7.98 Hz, 1H), 7.87-7.89 (m, 1H), 7.67 (s, 1H), 7.46-7.56 (m, 3H), 7.42 (t, J=7.67 Hz, 1H), 7.35-7.39 (m, 1H), 7.19-7.23 (m, 1H), 7.02 (d, J=7.36 Hz, 1H), 6.97 (d, J=7.67 Hz, 1H), 6.94 (d, J=7.36 Hz, 1H), 5.31 (s, 2H), 4.29 (t, J=5.98 Hz, 2H), 3.42-3.46 (m, 2H), 2.28-2.35 (m, 2H), 1.78 (s, 6H).

EXAMPLE 321

7-(2-ethyl-4-methylpyridin-3-yl)-3-(3-(1-naphthyloxyl)propyl)-1-(pyridin-3-ylmethyl)-1H-indole-2-carboxylic acid $^1$H NMR (500 MHz, DMSO-d$_6$): δ 8.61 (d, J=4.6 Hz, 1H), 8.43 (s, 1H), 8.25-8.27 (m, 1H), 7.96 (d, J=7.98 Hz, 1H), 7.87-7.89 (m, 1H), 7.61 (s, 1H), 7.46-7.56 (m, 4H), 7.41 (t, J=7.83 Hz, 1H), 7.20-7.26 (m, 1H), 7.02 (d, J=6.44 Hz, 1H), 6.93 (d, J=7.36 Hz, 1H), 6.86 (d, J=8.29 Hz, 1H), 5.13-5.37 (m, 2H), 4.28 (t, J=6.14 Hz, 2H), 3.42-3.46 (m, 2H), 2.19-2.25 (m, 2H), 1.92-2.08 (m, 2H), 1.81 (s, 3H), 0.87 (t, J=7.52 Hz, 3H).

EXAMPLE 322

7-(2-ethyl-4-methylpyridin-3-yl)-3-(3-(1-naphthyloxyl)propyl)-1-(1,3-thiazol-4-ylmethyl)-1H-indole-2-carboxylic acid $^1$H NMR (500 MHz, DMSO-d$_6$): δ 8.82 (d, J=1.84 Hz, 1H), 8.61 (d, J=5.52 Hz, 1H), 8.22-8.25 (m, 1H), 7.93 (d, J=7.67 Hz, 1H), 7.86-7.88 (m, 1H), 7.46-7.56 (m, 4H), 7.40 (t, J=7.83 Hz, 1H), 7.21 (t, J=7.52 Hz, 1H), 7.02 (d, J=6.75 Hz, 1H), 6.91 (d, J=7.36 Hz, 1H), 6.47 (s, 1H), 5.21-5.36 (m, 2H), 4.27 (t, J=5.98 Hz, 2H), 3.39-3.43 (m, 2H), 2.25-2.33 (m, 2H), 2.15-2.21 (m, 2H), 1.87 (s, 3H), 0.94 (t, J=7.52 Hz, 3H).

EXAMPLE 323

7-(2-chloro-4-((4-morpholin-4-ylphenoxy)methyl) pyridin-3-yl)-3-(3-(1-naphthyloxyl)propyl)-1H-indole-2-carboxylic acid $^1$H NMR (500 MHz, DMSO-d$_6$): δ 11.50 (s, 1H), 8.47 (d, J=4.91 Hz, 1H), 8.26-8.29 (m, 1H), 7.85-7.88 (m, 1H), 7.77 (dd, J=7.06, 1.84 Hz, 1H), 7.57 (d, J=7.22 Hz, 1H), 7.44-7.55 (m, 3H), 7.37 (t, J=7.83 Hz, 1H), 7.07-7.12 (m, 2H), 6.87 (d, J=7.36 Hz, 1H), 6.77 (d, J=8.9 Hz, 2H), 6.63 (d, J=8.9 Hz, 2H), 4.72 (d, J=14.12 Hz, 1H), 4.50 (d, J=13.81 Hz, 1H), 4.20

(t, J=6.29 Hz, 2H), 3.65-3.68 (m, 4H), 3.35-3.39 (m, 2H), 2.90-2.92 (m, 4H), 2.21-2.27 (m, 2H).

EXAMPLE 324

7-(5-isopropyl-1-methyl-3-((4-morpholin-4-ylphenoxy)methyl)-1H-pyrazol-4-yl)-3-(1-naphthyloxy)propyl)-1H-indole-2-carboxylic acid $^1$H NMR (500 MHz, DMSO-$d_6$): δ10.20 (s, 1H), 8.25-8.27 (m, 1H), 7.85-7.87 (m, 1H), 7.65 (dd, J=7.06, 2.15, Hz, 1H), 7.44-7.55 (m, 3H), 7.36 (t, J=7.98 Hz, 1H), 7.00-7.05 (m, 2H), 6.85 (d, J=7.67 Hz, 1H), 6.81 (d, J=8.59 Hz, 2H), 6.65 (d, J=8.9 Hz, 2H), 4.54-4.60 (m, 2H), 4.17 (t, J=6.29 Hz, 1H), 3.89 (s, 3H), 3.66-3.69 (m, 4H), 3.28-3.37 (m, 2H), 2.96-3.04 (m, 5H), 2.18-2.25 (m, 2H), 1.12 (d, J=7.06 Hz, 3H), 0.96 (d, J=7.06 Hz, 3H).

EXAMPLE 325

7-(3-isopropyl-1-methyl-5-((4-morpholin-4-ylphenoxy)methyl)-1H-pyrazol-4-yl)-3-(3-(1-naphthyloxy)propyl)-1H-indole-2-carboxylic acid $^1$H NMR (500 MHz, DMSO-$d_6$): δ10.20 (s, 1H), 8.23-8.25 (m, 1H), 7.85-7.87 (m, 1H), 7.69 (d, J=6.44, Hz, 1H), 7.44-7.55 (m, 3H), 7.37 (t, J=7.83 Hz, 1H), 7.03-7.10 (m, 2H), 6.88 (d, J=7.36 Hz, 1H), 6.81-6.83 (m, 2H), 6.72-6.75 (m, 2H), 4.69-4.82 (m, 2H), 4.19 (t, J=6.29 Hz, 1H), 3.87 (s, 3H), 3.69-3.72 (m, 4H), 3.32-3.36 (m, 2H), 2.97-2.99 (m, 4H), 2.72-2.79 (m, 1H), 2.18-2.25 (m, 2H), 1.08 (d, J=6.75 Hz, 3H), 1.06 (d, J=7.06 Hz, 3H).

EXAMPLE 326

7-(2-isopropenyl-4-methylpyridin-3-yl)-3-(3-(1-naphthyloxy)propyl)-1-(pyridin-2-ylmethyl)-1H-indole-2-carboxylic acid $^1$H NMR (500 MHz, DMSO-$d_6$): δ 8.56 (d, J=5.22 Hz, 1H), 8.25-8.28 (m, 2H), 7.86-7.88 (m, 2H), 7.44-7.55 (m, 3H), 7.39 (t, J=7.98 Hz, 1H), 7.33 (d, J=4.6 Hz, 2H), 7.12-7.16 (m, 2H), 7.00 (d, J=7.06 Hz, 1H), 6.89 (d, J=7.36 Hz, 1H), 6.27 (d, J=7.98 Hz, 1H), 5.75 (d, J=17.8 Hz, 1H), 4.83-5.05 (m, 3H), 4.23 (t, J=6.29 Hz, 2H), 3.40 (t, J=7.52 Hz, 2H), 2.25-2.34 (m, 2H), 1.64 (s, 3H), 1.58 (s, 3H).

EXAMPLE 327

7-(1,5-dimethyl-3-((4-morpholin-4-ylphenoxy)methyl)-1H-pyrazol-4-yl)-3-(3-(1-naphthyloxy)propyl)-1-(pyridin-3-ylmethyl)-1H-indole-2-carboxylic acid $^1$H NMR (500 MHz, DMSO-$d_6$): δ 8.50 (d, J=4.6 Hz, 1H), 8.24-8.27 (m, 1H), 7.86-7.88 (m, 1H), 7.79-7.84 (m, 2H), 7.44-7.54 (m, 4H), 7.38-7.40 (m, 1H), 7.06-7.10 (m, 2H), 6.93-6.94 (m, 1H), 6.88 (d, J=7.36 Hz, 1H), 6.77 (d, J=9.21 Hz, 2H), 6.60 (d, J=9.21 Hz, 2H), 5.50-5.69 (m, 2H), 4.51 (s 2H), 4.22 (t, J=6.44 Hz, 2H), 3.64-3.66 (m, 7H), 3.35-3.43 (m, 2H), 2.90-2.92 (m, 4H), 2.23-2.29 (m, 2H), 1.47 (s, 3H).

EXAMPLE 328

7-(2-ethyl-4-((4-morpholin-4-ylphenoxy)methyl)pyridin-3-yl)-3-(3-(1-naphthyloxyl)propyl)-1H-indole-2-carboxylic acid $^1$H NMR (500 MHz, DMSO-$d_6$): δ 11.40 (s, 1H), 8.84 (d, J=5.83 Hz, 1H), 8.25-8.27 (m, 1H), 7.84-7.89 (m, 4H), 7.44-7.55 (m, 3H), 7.37 (t, J=7.98 Hz, 1H), 7.14-7.21 (m, 2H), 6.87 (d, J=7.67 Hz, 1H), 6.77 (d, J=8.9 Hz, 2H), 6.64 (d, J=9.21 Hz, 2H), 4.87 (d, J=15.65 Hz, 1H), 4.52 (d, J=15.34 Hz, 1H), 4.20 (t, J=6.14 Hz, 2H), 3.66-3.68 (m, 7H), 3.36-3.39 (m, 2H), 2.89-2.92 (m, 4H), 2.59-2.62 (m 1H), 2.24-2.48 (m, 1H), 2.21-2.28 (m, 2H), 1.03 (t, J=7.52 Hz, 3H).

EXAMPLE 329

7-(4-methyl-2-pyrimidin-5-ylpyridin-3-yl)-3-(3-(1-naphthyloxyl)propyl)-1H-indole-2-carboxylic acid $^1$H NMR (500 MHz, DMSO-$d_6$): δ 11.36 (s, 1H), 8.99 (s, 1H), 8.72 (d, J=5.19 Hz, 1H), 8.54 (s, 2H), 8.26-8.28 (m, 1H), 7.86-7.88 (m, 1H), 7.68 (dd, J=7.32, 1.53 Hz, 1H), 7.60 (d, J=5.19 Hz, 1H), 7.45-7.55 (m, 3H), 7.38 (t, J=7.93 Hz, 1H), 6.96-7.01 (m, 2H), 6.86 (d, J=7.32 Hz, 1H), 4.14 (t, J=6.26 Hz, 2H), 3.26-3.37 (m, 2H), 2.16-2.22 (m, 2H), 2.06 (s, 3H).

EXAMPLE 330

7-(4-methyl-6'-morpholin-4-yl-2,3'-bipyridin-3-yl)-3-(3-(1-naphthyloxy)propyl)-1H-indole-2-carboxylic acid $^1$H NMR (500 MHz, DMSO-$d_6$): δ 13.11 (s, 1H), 11.33 (s, 1H), 8.78 (d, J=5.8 Hz, 1H), 8.25-8.27 (m, 1H), 8.01 (d, J=2.14 Hz, 1H), 7.82-7.86 (m, 2H), 7.72-7.75 (m, 1H), 7.45-7.55 (m, 3H), 7.34-7.39 (m, 2H), 7.03 (d, J=4.88 Hz, 2H), 6.86 (d, J=7.32 Hz, 1H), 6.61 (d, J=9.15 Hz, 1H), 4.16 (t, J=6.41 Hz, 2H), 3.32-3.39 (m, 10H), 2.18-2.24 (m, 2H), 2.10 (s, 3H).

EXAMPLE 331

7-(4,6-dimethylpyrimidin-5-yl)-3-(3-(1-naphthyloxyl)propyl)-1-(pyridin-2-ylmethyl)-1H-indole-2-carboxylic acid $^1$H NMR (500 MHz, DMSO-$d_6$): δ 8.84 (s, 1H), 8.26-8.30 (m, 2H), 7.87-7.92 (m, 2H), 7.46-7.62 (m, 4H), 7.40 (t, J=7.93 Hz, 1H), 7.17-7.24 (m, 2H), 6.99 (d, J=6.1 Hz, 1H), 6.93 (d, J=7.63 Hz, 1H), 6.34 (d, J=7.93 Hz, 1H), 5.36 (s, 2H), 4.27 (t, J=6.1 Hz, 2H), 3.42-3.45 (m, 10H), 2.29-2.33 (m, 2H), 1.79 (s, 6H).

EXAMPLE 332

7-(4,6-dimethylpyrimidin-5-yl)-1-(2-(4-methylpiperazin-1-yl)-2-oxoethyl)-3-(3-(1-naphthyloxyl)propyl)-1H-indole-2-carboxylic acid $^1$H NMR (500 MHz, DMSO-$d_6$): δ 13.27 (s, 1H), 9.94 (s, 1H), 9.02 (s, 1H), 8.26-8.28 (m, 1H), 7.86-7.89 (m, 2H), 7.46-7.56 (m, 3H), 7.40 (t, J=7.78 Hz, 1H), 7.16-7.19 (m, 1H), 7.03 (d, J=6.41 Hz, 1H), 6.92 (d, J=7.63 Hz, 1H), 6.34 (d, J=7.93 Hz, 1H), 4.24 (t, J=6.26 Hz, 2H), 3.42-3.45 (m, 2H), 2.64-2.81 (m, 7H), 2.07-2.11 (m, 6H).

EXAMPLE 333

1-(2-(dimethylamino)-2-oxoethyl)-7-(4,6-dimethylpyrimidin-5-yl)-3-(3-(1-naphthyloxyl)propyl)-1H-indole-2-carboxylic acid $^1$H NMR (500 MHz, DMSO-$d_6$): δ 8.98 (s, 1H), 8.27-8.29 (m, 1H), 7.84-7.89 (m, 2H), 7.46-7.55 (m, 3H), 7.40 (t, J=7.93

Hz, 1H), 7.14-7.17 (m, 1H), 7.01 (d, J=7.02 Hz, 1H), 6.92 (d, J=7.32 Hz, 1H), 4.92 (s, 2H), 4.24 (t, J=6.1 Hz, 2H), 3.36-3.39 (m, 2H), 2.63 (s, 3H), 2.41 (s, 3H), 2.21-2.27 (m, 2H), 2.08 (s, 6H).

EXAMPLE 334

7-(3-((4-(1,1-dioxidothiomorpholin-4-yl)phenoxy)methyl)-1,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.43 (s, 1H), 8.98 (s, 1H), 8.24 (d, J=7.93 Hz, 1H), 7.85-7.87 (m, 2H), 7.65 (d, J=7.93 Hz, 1H), 7.44-7.54 (m, 3H), 7.38 (t, J=7.93 Hz, 1H), 7.02-7.11 (m, 2H), 6.85-6.90 (m, 3H), 6.87-6.90 (m, 2H), 4.72 (s, 2H), 4.19 (t, J=6.1 Hz, 2H), 3.81 (s, 3H), 3.54-3.56 (m, 2H), 3.32-3.35 (m, 2H), 3.38-3.10 (m, 4H), 2.18-2.25 (m, 2H), 2.09 (s, 3H).

EXAMPLE 335

7-(4,6-dimethylpyrimidin-5-yl)-1-(2-morpholin-4-ylethyl)-3-(3-(1-naphthyloxy)propyl)-1H-indole-2-carboxylic acid $^1$H NMR (500 MHz, DMSO-d$_6$): δ 9.04 (s, 1H), 8.23-8.25 (m, 1H), 7.86-7.91 (m, 2H), 7.45-7.56 (m, 3H), 7.40 (t, J=7.83 Hz, 1H), 7.22 (t, J=7.67 Hz, 1H), 7.11 (d, J=7.37 Hz, 1H), 6.92 (d, J=7.36 Hz, 1H), 4.23-4.33 (m, 4H), 3.36-3.40 (m, 2H), 2.84 (br, 4H), 2.18-2.25 (m, 2H), 2.20-2.26 (m, 8H).

EXAMPLE 336

7-(1,5-dimethyl-3-((4-piperazin-1-ylphenoxy)methyl)-1H-pyrazol-4-yl)-3-(3-(1-naphthyloxy)propyl)-1H-indole-2-carboxylic acid $^1$H NMR (500 MHz, DMSO-d$_6$): δ 10.40 (s, 1H), 8.69 (s, 2H), 8.22-8.24 (m, 1H), 7.85-7.87 (m, 1H), 7.65 (d, J=7.98 Hz, 1H), 7.44-7.55 (m, 3H), 7.38 (t, J=7.83 Hz, 1H), 7.01-7.11 (m, 2H), 6.89 (d, J=7.06 Hz, 1H), 6.79-6.85 (m, 4H), 4.72 (s, 2H), 4.20 (t, J=6.14 Hz, 2H), 3.81 (s, 3H), 3.34 (t, J=7.52 Hz, 2H), 3.15-3.19 (m, 8H), 2.19-2.25 (m, 2H), 2.09 (s, 3H).

EXAMPLE 337

7-(3-((4-(4-acetylpiperazin-1-yl)phenoxy)methyl)-1,5-dimethyl-1H-pyrazol-4-yl)-3-(3-(1-naphthyloxyl)propyl)-1-(pyridin-3-ylmethyl)-1H-indole-2-carboxylic acid $^1$H NMR (500 MHz, DMSO-d$_6$): δ 8.51 (d, J=4.91 Hz, 1H), 8.24-8.27 (m, 1H), 7.79-7.89 (m, 3H), 7.45-7.55 (m, 4H), 7.38 (t, J=7.83 Hz, 1H), 7.06-7.12 (m, 2H), 6.93 (d, J=6.75 Hz, 1H), 6.88 (d, J=7.36 Hz, 1H), 6.80 (d, J=9.21 Hz, 2H), 6.61 (d, J=9.21 Hz, 2H), 5.50-5.65 (m, 2H), 4.52 (s, 2H), 4.22 (t, J=6.44 Hz, 2H), 3.66 (s, 3H), 3.37-3.53 (m, 6H), 2.86-2.95 (m, 4H), 2.23-2.30 (m, 2H), 1.99 (s, 3H), 1.47 (s, 3H).

EXAMPLE 338

7-(4,6-dimethylpyrimidin-5-yl)-1-(2-(4-methylpiperazin-1-yl)ethyl)-3-(3-(1-naphthyloxyl)propyl)-1H-indole-2-carboxylic acid $^1$H NMR (500 MHz, DMSO-d$_6$): δ 10.06 (s, 1H), 9.00 (s, 1H), 8.23-8.25 (m, 1H), 7.84-7.88 (m, 2H), 7.45-7.56 (m, 3H), 7.40 (t, J=7.83 Hz, 1H), 7.17-7.21 (m, 1H), 7.08 (d, J=7.06 Hz, 1H), 6.91 (d, J=7.67 Hz, 1H), 4.23 (t, J=5.98 Hz, 2H), 4.00-4.04 (m, 2H), 3.25-3.36 (m, 4H), 2.85 (br, 2H), 2.70 (s, 3H), 2.18-2.25 (m, 10H).

EXAMPLE 339

7-(3-((4-(4-(tert-butoxycarbonyl)piperazin-1-yl)phenoxy)methyl)-1,5-dimethyl-1H-pyrazol-4-yl)-3-(3-(1-naphthyloxy)propyl)-1H-indole-2-carboxylic acid $^1$H NMR (500 MHz, DMSO-d$_6$): δ 10.38 (s, 1H), 9.00 (s, 1H), 8.22-8.24 (m, 1H), 7.85-7.87 (m, 1H), 7.65 (d, J=7.98 Hz, 1H), 7.45-7.56 (m, 3H), 7.37 (t, J=7.98 Hz, 1H), 7.01-7.10 (m, 2H), 6.78-6.89 (m, 5H), 4.72 (s, 2H), 4.19 (t, J=6.14 Hz, 2H), 3.81 (s, 3H), 3.42-3.45 (m, 4H), 3.34 (t, J=7.36 Hz, 2H), 2.94-2.97 (m, 2H), 2.18-2.26 (m, 2H), 2.09 (s, 3H), 1.41 (s, 9H).

EXAMPLE 340

1-(2-(dimethylamino)ethyl)-7-(4,6-dimethylpyrimidin-5-yl)-3-(3-(1-naphthyloxy)propyl)-1H-indole-2-carboxylic acid $^1$H NMR (500 MHz, DMSO-d$_6$): δ 8.96 (s, 1H), 8.16-8.18 (m, 1H), 7.79-7.84 (m, 2H), 7.38-7.49 (m, 3H), 7.33 (t, J=7.83 Hz, 1H), 7.16 (t, J=7.52 Hz, 1H), 7.04 (d, J=7.06 Hz, 1H), 6.85 (d, J=7.67 Hz, 1H), 4.16-4.23 (m, 4H), 3.51 (br, 6H), 3.30-3.34 (m, 2H), 2.77-2.81 (m, 2H), 2.43 (m, 2H), 2.13-2.26 (m, 8H).

EXAMPLE 341

3-(3-(1-naphthyloxyl)propyl)-7-(4-(1H-pyrazol-1-yl)phenyl)-1H-indole-2-carboxylic acid $^1$H NMR (300 MHz, DMSO-d$_6$) δ 13.03 (s, 1H), 10.59 (s, 1H), 8.58 (d, 1H), 8.23 (m, 1H), 7.98 (ddd, 2H), 7.86 (m, 1H), 7.75 (m, 4H), 7.51 (m, 3H), 7.39 (m, 1H), 7.28 (m, 1H), 7.11 (m, 1H), 6.89 (m, 1H), 6.58 (m, 1H), 4.20 (t, 2H), 3.38 (t, 2H), 2.24 (m, 2H).

EXAMPLE 342

3-(3-(1-naphthyloxy)propyl)-7-(2,3,4-trifluorophenyl)-1H-indole-2-carboxylic acid $^1$H NMR (300 MHz, DMSO-d$_6$) δ 13.05 (s, 1H), 11.23 (s, 1H), 8.25 (m, 1H), 7.86 (m, 1H), 7.77 (d, 1H), 7.51 (m, 2H), 7.38 (m, 3H), 7.28 (m, 1H), 7.18 (m, 1H), 7.08 (m, 1H), 6.89 (m, 1H), 4.19 (t, 2H), 3.37 (t, 2H), 2.24 (m, 2H).

EXAMPLE 343

7-(4-hydroxy-3-methoxyphenyl)-3-(3-(1-naphthyloxy)propyl)-1H-indole-2-carboxylic acid $^1$H NMR (300 MHz, DMSO-d$_6$) δ 13.01 (s, 1H), 10.23 (s, 1H), 9.10 (s, 1H), 8.23 (td, 7.87 (m, 1H), 7.63 (d, 1H), 7.51

(m, 3H), 7.38 (m, 1H), 7.21 (dd, 1H), 7.12 (d, 1H), 7.05 (m, 2H), 6.90 (m, 2H), 4.18 (t, 2H), 3.83 (s, 3H), 3.36 (m, 2H), 2.23 (m, 2H).

EXAMPLE 344

3-(3-(1-naphthyloxyl)propyl)-7-(3,4,5-trimethoxyphenyl)-1H-indole-2-carboxylic acid $^1$H NMR (300 MHz, DMSO-d$_6$) δ 13.00 (s, 1H), 10.58 (s, 1H), 8.24 (m, 1H), 7.87 (m, 1H), 7.67 (d, 1H), 7.52 (m, 2H), 7.41 (m, 2H), 7.26 (dd, 1H), 7.07 (dd, 1H), 6.89 (dd, 1H), 6.85 (s, 2H), 4.19 (t, 2H), 3.84 (s, 6H), 3.73 (s, 3H), 3.37 (m, 2H), 2.24 (m, 2H).

EXAMPLE 345

3-(3-(1-naphthyloxy)propyl)-7-(4-(trifluoromethoxy)phenyl)-1H-indole-2-carboxylic acid $^1$H NMR (300 MHz, DMSO-d$_6$) δ 13.05 (s, 1H), 10.78 (s, 1H), 8.23 (m, 1H), 7.87 (m, 1H), 7.72 (m, 3H), 7.51 (m, 5H), 7.38 (m, 1H), 7.24 (dd, 1H), 7.09 (m, 1H), 6.89 (m, 1H), 4.19 (t, 2H), 3.37 (m, 2H), 2.24 (m, 2H).

EXAMPLE 346

7-(2-methoxy-5-methylphenyl)-3-(3-(1-naphthyloxy)propyl)-1H-indole-2-carboxylic acid $^1$H NMR (300 MHz, DMSO-d$_6$) δ 12.97 (s, 1H), 9.97 (s, 1H), 8.25 (m, 1H), 7.87 (m, 1H), 7.67 (d, 1H), 7.51 (m, 3H), 7.40 (d, 1H), 7.21 (m, 1H), 7.12 (m, 2H), 7.04 (m, 2H), 6.90 (dd, 1H), 4.20 (t, 2H), 3.70 (s, 3H), 3.35 (m, 2H), 2.30 (s, 3H), 2.24 (m, 2H).

EXAMPLE 347

7-(3-fluoro-4-methoxyphenyl)-3-(3-(1-naphthyloxy)propyl)-1H-indole-2-carboxylic acid $^1$H NMR (300 MHz, DMSO-d$_6$) δ 13.05 (s, 1H), 10.61 (s, 1H), 8.23 (m, 1H), 7.87 (m, 1H), 7.67 (d, 1H), 7.51 (m, 2H), 7.40 (m, 4H), 7.29 (t, 1H), 7.21 (dd, 1H), 7.06 (m, 1H), 6.89 (dd, 1H), 4.18 (t, 2H), 3.91 (s, 3H), 3.36 (m, 2H), 2.24 (m, 2H).

EXAMPLE 348

3-(3-(1-naphthyloxyl)propyl)-7-(4-(5-oxo-2,5-dihydro-1H-pyrazol-3-yl)phenyl)-1H-indole-2-carboxylic acid $^1$H NMR (500 MHz, DMSO-da) δ 12.94 (s, 1H), 12.22 (s, 1H), 10.55 (s, 1H), 9.74 (s, 1H), 8.23 (m, 1H), 7.87 (m, 1H), 7.81 (d, 2H), 7.70 (d, 1H), 7.66 (d, 2H), 7.52 (m, 2H), 7.45 (m, 1H), 7.39 (t, 1H), 7.28 (dd, 1H), 7.10 (m, 1H), 6.90 (d, 1H), 5.96 (s, 1H), 4.19 (t, 2H), 3.39 (m, 2H), 2.24 (m, 2H).

EXAMPLE 349

7-(3-(morpholin-4-ylmethyl)phenyl)-3-(3-(1-naphthyloxyl)propyl)-1H-indole-2-carboxylic acid $^1$H NMR (300 MHz, DMSO-d$_6$) δ 10.58 (s, 1H), 8.24 (m, 1H), 7.87 (m, 1H), 7.73 (m, 3H), 7.62 (t, 1H), 7.51 (m, 4H), 7.39 (m, 1H), 7.27 (dd, 1H), 7.12 (m, 1H), 6.89 (dd, 1H), 4.45 (s, 2H), 4.19 (t, 2H), 3.97 (m, 2H), 3.63 (t, 2H), 3.41 (m, 2H), 3.38 (m, 3H), 3.17 (m, 3H), 2.24 (m, 2H).

EXAMPLE 350

7-(4-(morpholin-4-ylmethyl)phenyl)-3-(3-(1-naphthyloxyl)propyl)-1H-indole-2-carboxylic acid $^1$H NMR (300 MHz, DMSO-d$_6$) δ 13.12 (s, 1H), 10.39 (s, 1H), 8.22 (m, 1H), 7.87 (m, 1H), 7.74 (d, 3H), 7.62 (d, 2H), 7.51 (m, 2H), 7.46 (m, 1H), 7.38 (m, 1H), 7.27 (dd, 1H), 7.12 (m, 1H), 6.89 (dd, 1H), 4.44 (s, 2H), 4.20 (t, 2H), 4.00 (m, 2H), 3.66 (t, 2H), 3.38 (m, 3H), 3.21 (m, 3H), 2.24 (m, 2H).

EXAMPLE 351

7-(4-isopropoxy-2-methylphenyl)-3-(3-(1-naphthyloxyl)propyl)-1H-indole-2-carboxylic acid $^1$H NMR (300 MHz, DMSO-d$_6$) δ 12.92 (s, 1H), 10.37 (s, 1H), 8.25 (m, 1H), 7.87 (m, 1H), 7.66 (dd, 1H), 7.52 (m, 2H), 7.42 (m, 2H), 7.04 (m, 3H), 6.88 (m, 2H), 6.81 (dd, 1H), 4.65 (septet, 1H), 4.20 (t, 2H), 3.36 (m, 2H), 2.23 (m, 2H), 2.02 (s, 3H), 1.31 (d, 6H).

EXAMPLE 352

3-(3-(1-naphthyloxy)propyl)-7-(4-(1H-pyrazol-5-yl)phenyl)-1H-indole-2-carboxylic acid $^1$H NMR (300 MHz, DMSO-d$_6$) δ 13.01 (s, 1H), 10.46 (s, 1H), 8.24 (m, 1H), 7.94 (d, 2H), 7.87 (m, 1H), 7.71 (m, 4H), 7.50 (m, 3H), 7.39 (m, 1H), 7.28 (m, 1H), 7.10 (m, 1H), 6.89 (m, 1H), 6.78 (d, 1H), 4.20 (t, 2H), 3.38 (t, 2H), 2.25 (m, 2H).

EXAMPLE 354

7-(2,5-dimethylphenyl)-3-(3-(1-naphthyloxy)propyl)-1H-indole-2-carboxylic acid $^1$H NMR (300 MHz, DMSO-d$_5$) δ 12.93 (s, 1H), 10.36 (s, 1H), 8.24 (m, 1H), 7.87 (m, 1H), 7.68 (dd, 1H), 7.50 (m, 3H), 7.40 (d, 1H), 7.16 (m, 2H), 7.04 (m, 3H), 6.90 (d, 1H), 4.20 (t, 2H), 3.36 (m, 2H), 2.31 (s, 3H), 2.23 (m, 2H), 2.01 (s, 3H).

EXAMPLE 355

3-(3-(1-naphthyloxyl)propyl)-7-(2,4,5-trimethylphenyl)-1H-indole-2-carboxylic acid $^1$H NMR (300 MHz, DMSO-d$_5$) δ 12.91 (s, 1H), 10.25 (s, 1H), 8.24 (m, 1H), 7.87 (m, 1H), 7.66 (dd, 1H), 7.52 (m, 2H), 7.41 (m, 2H), 7.04 (m, 4H), 6.90 (m, 1H), 4.20 (t, 2H), 3.36 (m, 2H), 2.26 (s, 3H), 2.24 (m, 2H), 2.22 (s, 3H), 1.99 (s, 3H).

EXAMPLE 356

3-(3-(1-naphthyloxy)propyl)-7-(3-(trifluoromethoxy)phenyl)-1H-indole-2-carboxylic acid $^1$H NMR (300 MHz, DMSO-d$_6$) δ 13.05 (s, 1H), 10.80 (s, 1H), 8.21 (m, 1H), 7.86 (m, 1H), 7.73 (d, 1H), 7.62 (m, 2H), 7.47 (m, 6H), 7.26 (d, 1H), 7.10 (t, 1H), 6.89 (d, 1H), 4.19 (t, 2H), 3.37 (m, 2H), 2.22 (m, 2H).

EXAMPLE 357

7-(2-methyl-4-propoxyphenyl)-3-(3-(1-naphthyloxy)propyl)-1H-indole-2-carboxylic acid $^1$H NMR (300 MHz, DMSO-$d_6$) δ 12.92 (s, 1H), 10.38 (s, 1H), 8.25 (m, 1H), 7.87 (m, 1H), 7.66 (dd, 1H), 7.52 (m, 2H), 7.41 (m, 2H), 7.04 (m, 3H), 6.91 (m, 2H), 6.82 (dd, 1H), 4.20 (t, 2H), 3.98 (t, 2H), 3.36 (m, 2H), 2.23 (m, 2H), 2.03 (s, 3H), 1.76 (m, 2H), 1.01 (t, 3H).

EXAMPLE 358

7-(3-cyanophenyl)-3-(3-(1-naphthyloxy)propyl)-1H-indole-2-carboxylic acid $^1$H NMR (300 MHz, DMSO-$d_6$) δ 11.07 (s, 1H), 8.22 (m, 1H), 8.02 (t, 1H), 7.87 (m, 3H), 7.71 (ddd, 2H), 7.51 (m, 3H), 7.40 (d, 1H), 7.26 (dd, 1H), 7.10 (m, 1H), 6.89 (dd, 1H), 4.19 (t, 2H), 3.37 (m, 2H), 2.24 (m, 2H).

EXAMPLE 359

3-(3-(1-naphthyloxy)propyl)-7-(2,3,5,6-tetramethylphenyl)-1H-indole-2-carboxylic acid $^1$H NMR (300 MHz, DMSO-$d_6$) δ 10.22 (s, 1H), 8.28 (m, 1H), 7.87 (m, 1H), 7.68 (d, 1H), 7.53 (m, 2H), 7.42 (m, 2H), 7.08 (dd, 1H), 7.03 (s, 1H), 6.89 (ddd, 2H), 4.22 (t, 2H), 3.39 (m, 2H), 2.25 (m, 2H), 2.22 (s, 6H), 1.73 (s, 6H).

EXAMPLE 360

7-(3-cyano-2-methylphenyl)-3-(3-(1-naphthyloxy)propyl)-1H-indole-2-carboxylic acid $^1$H NMR (300 MHz, DMSO-$d_6$) δ 11.04 (s, 1H), 8.24 (m, 1H), 7.85 (m, 2H), 7.74 (m, 1H), 7.47 (m, 6H), 7.06 (m, 2H), 6.90 (d, 1H), 4.20 (t, 2H), 3.38 (m, 2H), 2.23 (m, 2H), 2.19 (s, 3H).

EXAMPLE 361

7-(3-ethynyl-2-methylphenyl)-3-(3-(1-naphthyloxy)propyl)-1H-indole-2-carboxylic acid $^1$H NMR (300 MHz, DMSO-$d_6$) δ 12.93 (s, 1H), 10.87 (s, 1H), 8.26 (m, 1H), 7.87 (m, 1H), 7.70 (dd, 1H), 7.51 (m, 4H), 7.40 (d, 1H), 7.24 (m, 2H), 7.04 (m, 2H), 6.90 (dd, 1H), 4.38 (s, 1H), 4.20 (t, 2H), 3.37 (m, 2H), 2.23 (m, 2H), 2.12 (s, 3H).

EXAMPLE 362

7-(5-(((3-(dimethylamino)propyl)amino)carbonyl)-2-methylphenyl)-3-(3-(1-naphthyloxyl)propyl)-1H-indole-2-carboxylic acid $^1$H NMR (300 MHz, DMSO-$d_6$) δ 10.79 (s, 1H), 9.21 (s, 1H), 8.53 (t, 1H), 8.27 (m, 1H), 7.86 (m, 2H), 7.73 (m, 2H), 7.49 (m, 4H), 7.07 (m, 2H), 6.90 (m, 1H), 4.21 (t, 2H), 3.30 (m, 4H), 3.06 (m, 2H), 2.76 (d, 6H), 2.24 (m, 2H), 2.11 (s, 3H), 1.85 (m, 2H).

EXAMPLE 363

7-(2-isopropylphenyl)-3-(3-(1-naphthyloxyl)propyl)-1H-indole-2-carboxylic acid $^1$H NMR (300 MHz, DMSO-$d_6$) δ 12.93 (s, 1H), 10.35 (s, 1H), 8.26 (m, 1H), 7.87 (m, 1H), 7.69 (d, 1H), 7.53 (m, 2H), 7.41 (m, 4H), 7.25 (td, 1H), 7.15 (m, 1H), 7.04 (m, 2H), 6.91 (dd, 1H), 4.22 (t, 2H), 3.39 (m, 2H), 2.69 (m, 1H), 2.26 (m, 2H), 1.06 (dd, 6H).

EXAMPLE 364

7-(5-(((2-(dimethylamino)ethyl)amino)carbonyl)-2-methylphenyl)-3-(3-(1-naphthyloxyl)propyl)-1H-indole-2-carboxylic acid $^1$H NMR (300 MHz, DMSO-$d_6$) δ 12.97 (s, 1H), 10.77 (s, 1H), 9.24 (s, 1H), 8.59 (m, 1H), 8.27 (m, 1H), 7.87 (m, 2H), 7.74 (m, 2H), 7.50 (m, 4H), 7.07 (m, 2H), 6.90 (m, 1H), 4.20 (t, 2H), 3.58 (m, 2H), 3.38 (m, 2H), 3.23 (m, 2H), 2.82 (d, 6H), 2.25 (m, 2H), 2.12 (s, 3H).

EXAMPLE 365

7-(2-methyl-5-(((2-morpholin-4-ylethyl)amino)carbonyl)phenyl)-3-(3-(1-naphthyloxyl)propyl)-1H-indole-2-carboxylic acid $^1$H NMR (300 MHz, DMSO-$d_6$) δ 12.98 (s, 1H), 10.77 (s, 1H), 9.54 (s, 1H), 8.61 (m, 1H), 8.27 (m, 1H), 7.87 (m, 2H), 7.74 (m, 2H), 7.53 (m, 2H), 7.43 (m, 2H), 7.08 (m, 2H), 6.91 (dd, 1H), 4.21 (t, 2H), 3.98 (m, 2H), 3.55 (m, 5H), 3.39 (m, 7H), 2.26 (m, 2H), 2.12 (s, 3H).

EXAMPLE 366

7-(2-methyl-5-(((3-morpholin-4-ylpropyl)amino)carbonyl)phenyl)-3-(3-(1-naphthyloxyl)propyl)-1H-indole-2-carboxylic acid $^1$H NMR (300 MHz, DMSO-$d_6$) δ 12.97 (s, 1H), 10.79 (s, 1H), 9.50 (s, 1H), 8.55 (t, 1H), 8.27 (m, 1H), 7.86 (m, 2H), 7.73 (m, 2H), 7.53 (m, 2H), 7.42 (m, 2H), 7.07 (m, 2H), 6.91 (dd, 1H), 4.20 (t, 2H), 3.95 (m, 2H), 3.61 (td, 2H), 3.38 (m, 2H), 3.32 (m, 4H), 3.09 (m, 4H), 2.23 (m, 2H), 2.11 (s, 3H), 1.88 (m, 2H).

EXAMPLE 367

7-(2-methyl-5-(((2-phenylethyl)amino)carbonyl)phenyl)-3-(3-(1-naphthyloxy)propyl)-1H-indole-2-carboxylic acid $^1$H NMR (300 MHz, DMSO-$d_6$) δ 12.94 (s, 1H), 10.83 (s, 1H), 8.49 (t, 1H), 8.28 (m, 1H), 7.87 (m, 1H), 7.81 (dd, 1H), 7.71 (m, 2H), 7.53 (m, 2H), 7.46 (m, 1H), 7.39 (ddd, 2H), 7.22 (m, 5H), 7.08 (m, 2H), 6.91 (dd, 1H), 4.20 (t, 2H), 3.46 (m, 2H), 3.37 (m, 2H), 2.82 (t, 2H), 2.24 (m, 2H), 2.09 (s, 3H).

EXAMPLE 368

7-(1H-indazol-5-yl)-3-(3-(1-naphthyloxy)propyl)-1H-indole-2-carboxylic acid $^1$H NMR (300 MHz, DMSO-$d_6$) δ 13.11 (s, 1H), 13.02 (s, 1H), 10.44 (s, 1H), 8.24 (m, 1H), 8.15 (d, 1H), 8.00 (dd, 1H), 7.87 (m, 1H), 7.67 (m, 2H), 7.58 (dd, 1H), 7.52 (m, 2H), 7.39 (m, 1H), 7.27 (dd, 1H), 7.10 (dd, 1H), 6.90 (dd, 1H), 4.20 (t, 2H), 3.38 (m, 2H), 2.25 (m, 2H).

EXAMPLE 369

7-(5-(((((1S,4R)-bicyclo(2.2.1)hept-2-ylmethyl)amino)carbonyl)-2-methylphenyl)-3-(3-(1-naphthyloxyl)propyl)-1H-indole-2-carboxylic acid $^1$H NMR (300 MHz, DMSO-da) δ 12.92 (s, 1H), 10.82 (s, 1H), 8.34 (m, 2H), 7.85 (m, 2H), 7.72 (m, 2H), 7.53 (m, 2H), 7.41 (m, 3H), 7.06 (m, 2H), 6.91 (d, 1H), 4.21 (t, 2H), 3.39 (m, 2H), 3.23 (m, 2H), 3.02 (m, 1H), 2.26 (m, 2H), 2.14 (m, 2H), 2.09 (m, 3H), 2.04 (m, 1H), 1.65 (m, 3H), 1.27 (m, 2H), 1.07 (m, 2H).

EXAMPLE 370

7-(2-methyl-5-(((3-phenylpropyl)amino)carbonyl)phenyl)-3-(3-(1-naphthyloxyl)propyl)-1H-indole-2-carboxylic acid $^1$H NMR (300 MHz, DMSO-da) δ 12.93 (s, 1H), 10.83 (s, 1H), 8.41 (t, 1H), 8.27 (m, 1H), 7.85 (m, 2H), 7.73 (td, 2H), 7.53 (m, 2H), 7.41 (m, 3H), 7.21 (m, 5H), 7.07 (m, 2H), 6.90 (dd, 1H), 4.21 (m, 2H), 3.43 (m, 2H), 3.27 (m, 2H), 2.60 (m, 2H), 2.24 (m, 2H), 2.09 (s, 3H), 1.81 (m, 2H).

EXAMPLE 371

7-(2-((2-isopropyl-5-methylphenoxy)methyl)phenyl)-3-(3-(1-naphthyloxyl)propyl)-1H-indole-2-carboxylic acid $^1$H NMR (300 MHz, DMSO-da) δ 12.97 (s, 1H), 10.56 (s, 1H), 8.24 (m, 1H), 7.86 (m, 1H), 7.71 (d, 1H), 7.65 (dd, 1H), 7.49 (m, 5H), 7.37 (m, 2H), 7.14 (m, 1H), 7.06 (m, 1H), 6.97 (d, 1H), 6.88 (dd, 1H), 6.61 (d, 1H), 6.38 (d, 1H), 4.82 (m, 2H), 4.19 (t, 2H), 3.37 (m, 2H), 3.07 (septet, 1H), 2.23 (m, 2H), 2.07 (s, 3H), 1.04 (d, 6H).

EXAMPLE 372

7-(2-chloro-6-methylphenyl)-3-(3-(1-naphthyloxy)propyl)-1H-indole-2-carboxylic acid $^1$H NMR (300 MHz, DMSO-$d_6$) δ 12.92 (s, 1H), 11.00 (s, 1H), 8.29 (m, 1H), 7.87 (m, 1H), 7.71 (d, 1H), 7.53 (m, 2H), 7.37 (m, 5H), 7.09 (dd, 1H), 6.96 (dd, 1H), 6.91 (dd, 1H), 4.22 (t, 2H), 3.37 (m, 2H), 2.25 (m, 2H), 1.94 (s, 3H).

EXAMPLE 373

7-(2-benzylphenyl)-3-(3-(1-naphthyloxy)propyl)-1H-indole-2-carboxylic acid $^1$H NMR (300 MHz, DMSO-$d_6$) δ 12.94 (s, 1H), 10.41 (s, 1H), 8.26 (m, 1H), 7.87 (m, 1H), 7.69 (dd, 1H), 7.52 (m, 2H), 7.38 (m, 4H), 7.24 (m, 2H), 7.05 (m, 5H), 6.90 (dd, 1H), 6.83 (m, 2H), 4.20 (t, 2H), 3.81 (m, 1H), 3.66 (m, 1H), 3.37 (m, 2H), 2.25 (m, 2H).

EXAMPLE 374

3-(3-(1-naphthyloxyl)propyl)-7-(2,4,6-triisopropylphenyl)-1H-indole-2-carboxylic acid $^1$H NMR (300 MHz, DMSO-$d_6$) δ 12.92 (s, 1H), 10.23 (s, 1H), 8.28 (m, 1H), 7.87 (m, 1H), 7.67 (d, 1H), 7.51 (m, 3H), 7.39 (m, 1H), 7.08 (m, 3H), 6.93 (m, 2H), 4.23 (t, 2H), 3.37 (m, 2H), 2.95 (m, 1H), 2.33 (m, 2H), 2.25 (m, 2H), 1.29 (d, 6H), 0.99 (dd, 12H).

EXAMPLE 375

3-(3-(1-naphthyloxy)propyl)-7-(1-oxo-2,3-dihydro-1H-inden-4-yl)-1H-indole-2-carboxylic acid $^1$H NMR (300 MHz, DMSO-$d_6$) δ 12.98 (s, 1H), 10.99 (s, 1H), 8.25 (m, 1H), 7.87 (m, 1H), 7.75 (dd, 1H), 7.71 (dd, 1H), 7.63 (m, 1H), 7.50 (m, 5H), 7.14 (m, 2H), 6.91 (dd, 1H), 4.21 (t, 2H), 3.38 (m, 2H), 2.82 (m, 2H), 2.58 (m, 2H), 2.24 (m, 2H).

EXAMPLE 376

7-(2-cyclopentylphenyl)-3-(3-(1-naphthyloxy)propyl)-1H-indole-2-carboxylic acid $^1$H NMR (300 MHz, DMSO-$d_6$) δ 12.95 (s, 1H), 10.24 (s, 1H), 8.25 (m, 1H), 7.87 (m, 1H), 7.69 (d, 1H), 7.52 (m, 2H), 7.40 (m, 4H), 7.24 (td, 1H), 7.16 (m, 1H), 7.05 (m, 2H), 6.90 (d, 1H), 4.21 (m, 2H), 3.38 (m, 2H), 2.74 (m, 1H), 2.25 (m, 2H), 1.72 (m, 4H), 1.37 (m, 4H).

EXAMPLE 377

7-(2',6'-dimethoxy-1,1'-biphenyl-2-yl)-3-(3-(1-naphthyloxy)propyl)-1H-indole-2-carboxylic acid $^1$H NMR (300 MHz, DMSO-$d_5$) δ 13.07 (s, 1H), 8.93 (s, 1H), 8.22 (m, 1H), 7.86 (m, 1H), 7.45 (m, 8H), 7.25 (m, 1H), 6.94 (m, 3H), 6.82 (m, 1H), 6.41 (d, 2H), 4.07 (t, 2H), 3.42 (s, 6H), 3.24 (m, 2H), 2.14 (m, 2H).

EXAMPLE 378

3-(3-(1-naphthyloxy)propyl)-7-(5,6,7,8-tetrahydronaphthalen-1-yl)-1H-indole-2-carboxylic acid $^1$H NMR (300 MHz, DMSO-$d_6$) δ 12.91 (s, 1H), 10.43 (s, 1H), 8.25 (m, 1H), 7.87 (m, 1H), 7.67 (m, 1H), 7.52 (m, 2H), 7.42 (m, 2H), 7.14 (m, 2H), 7.02 (m, 3H), 6.91 (dd, 1H), 4.21 (t, 2H), 3.38 (td, 2H), 2.82 (t, 2H), 2.29 (m, 4H), 1.73 (m, 2H), 1.60 (m, 2H).

EXAMPLE 379

7-(4'-tert-butyl-1,1'-biphenyl-2-yl)-3-(3-(1-naphthyloxy)propyl)-1H-indole-2-carboxylic acid $^1$H NMR (300 MHz, DMSO-$d_6$) δ 12.85 (s, 1H), 9.87 (s, 1H), 8.23 (m, 1H), 7.86 (m, 1H), 7.50 (m, 9H), 7.06 (ddd, 4H), 6.91 (m, 2H), 6.85 (m, 1H), 4.13 (t, 2H), 3.25 (m, 2H), 2.18 (m, 2H), 1.12 (s, 9H).

EXAMPLE 380

7-(5-fluoro-2-methyl-3-((methylsulfonyl)methyl)phenyl)-3-(3-(1-naphthyloxyl)propyl)-1H-indole-2-carboxylic acid $^1$H NMR (300 MHz, DMSO-$d_6$) δ 12.95 (s, 1H), 10.76 (s, 1H), 8.24 (m, 1H), 7.87 (m, 1H), 7.71 (dd, 1H), 7.52 (m, 2H), 7.41 (m, 2H), 7.28 (dd, 1H), 7.05 (m, 3H), 6.90 (dd, 1H), 4.64 (s, 2H), 4.21 (t, 2H), 3.40 (m, 2H), 3.06 (s, 3H), 2.24 (m, 2H), 2.04 (s, 3H).

EXAMPLE 381

7-(5-(((2-hydroxy-1,1-dimethylethyl)amino)carbonyl)-2,3,4-trimethylphenyl)-3-(3-(1-naphthyloxyl)propyl)-1H-indole-2-carboxylic acid $^1$H NMR (300 MHz, DMSO-d$_6$) δ 8.24 (m, 1H), 7.86 (m, 1H), 7.63 (d, 1H), 7.51 (m, 4H), 7.38 (m, 1H), 7.03 (m, 1H), 6.95 (m, 2H), 6.89 (d, 1H), 4.87 (s, 1H), 4.20 (t, 2H), 3.46 (s, 2H), 3.39 (m, 2H), 2.29 (s, 3H), 2.26 (m, 2H), 2.24 (s, 3H), 1.99 (s, 3H), 1.26 (s, 6H).

EXAMPLE 382

7-(2-(4-(ethoxycarbonyl)piperazin-1-yl)phenyl)-3-(3-(1-naphthyloxy)propyl)-1H-indole-2-carboxylic acid $^1$H NMR (300 MHz, DMSO-d$_6$) δ 13.08 (s, 1H), 10.05 (s, 1H), 8.25 (m, 1H), 7.86 (m, 1H), 7.74 (d, 1H), 7.43 (m, 7H), 7.15 (m, 3H), 6.84 (m, 1H), 4.16 (t, 2H), 3.93 (q, 2H), 3.39 (m, 2H), 2.97 (m, 4H), 2.76 (m, 4H), 2.24 (m, 2H), 1.08 (t, 3H).

EXAMPLE 383

7-(2-methyl-6-nitrophenyl)-3-(3-(1-naphthyloxy)propyl)-1H-indole-2-carboxylic acid $^1$H NMR (300 MHz, DMSO-d$_6$) δ 13.01 (s, 1H), 11.04 (s, 1H), 8.28 (m, 1H), 7.86 (m, 2H), 7.65 (m, 2H), 7.54 (m, 3H), 7.41 (m, 2H), 7.02 (m, 1H), 6.89 (ddd, 2H), 4.22 (t, 2H), 3.38 (m, 2H), 2.24 (m, 2H), 1.94 (s, 3H).

EXAMPLE 384

3-(3-(1-naphthyloxy)propyl)-7-(2-(4-propionylpiperazin-1-yl)phenyl)-1H-indole-2-carboxylic acid $^1$H NMR (300 MHz, DMSO-d$_6$) δ 13.10 (s, 1H), 10.09 (s, 1H), 8.24 (m, 1H), 7.86 (m, 1H), 7.75 (d, 1H), 7.51 (m, 2H), 7.39 (m, 5H), 7.15 (td, 3H), 6.85 (dd, 1H), 4.16 (t, 2H), 3.39 (m, 2H), 3.17 (m, 2H), 2.94 (m, 2H), 2.75 (m, 4H), 2.24 (m, 2H), 2.12 (q, 2H), 0.85 (t, 3H).

EXAMPLE 385

7-(2-methyl-6-thien-2-ylphenyl)-3-(3-(1-naphthyloxy)propyl)-1H-indole-2-carboxylic acid $^1$H NMR (300 MHz, DMSO-d$_5$) δ 12.89 (s, 1H), 10.76 (s, 1H), 8.29 (m, 1H), 7.86 (m, 1H), 7.66 (d, 1H), 7.51 (m, 4H), 7.35 (m, 3H), 7.16 (dd, 1H), 6.96 (dd, 1H), 6.86 (ddd, 2H), 6.72 (m, 1H), 6.67 (m, 1H), 4.17 (t, 2H), 3.38 (m, 2H), 2.23 (m, 2H), 1.93 (s, 3H).

EXAMPLE 386

3-(3-(1-naphthyloxyl)propyl)-7-(2-(4-(1,3-thiazol-4-ylmethyl)piperazin-1-yl)phenyl)-1H-indole-2-carboxylic acid $^1$H NMR (300 MHz, DMSO-d$_6$) δ 13.00 (s, 1H), 10.21 (s, 1H), 9.12 (d, 1H), 8.27 (m, 1H), 7.87 (m, 1H), 7.79 (s, 1H), 7.72 (d, 1H), 7.53 (m, 2H), 7.40 (m, 4H), 7.28 (dd, 1H), 7.17 (t, 2H), 7.10 (dd, 1H), 6.90 (dd, 1H), 4.29 (s, 2H), 4.21 (t, 2H), 3.39 (m, 6H), 3.16 (m, 2H), 2.90 (m, 2H), 2.25 (m, 2H).

EXAMPLE 387

7-(2-(4-(2-hydroxyethyl)piperazin-1-yl)phenyl)-3-(3-(1-naphthyloxyl)propyl)-1H-indole-2-carboxylic acid $^1$H NMR (300 MHz, DMSO-d$_5$) δ 13.02 (s, 1H), 9.91 (s, 1H), 8.24 (d, 1H), 7.86 (m, 1H), 7.73 (d, 1H), 7.51 (m, 2H), 7.38 (m, 5H), 7.14 (m, 3H), 6.85 (dd, 1H), 4.30 (s, 1H), 4.17 (t, 2H), 3.40 (m, 6H), 2.76 (m, 4H), 2.21 (m, 6H).

EXAMPLE 388

7-(2-(4-(methylsulfonyl)piperazin-1-yl)phenyl)-3-(3-(1-naphthyloxyl)propyl)-1H-indole-2-carboxylic acid $^1$H NMR (300 MHz, DMSO-d$_6$) δ 13.21 (s, 1H), 10.13 (s, 1H), 8.24 (m, 1H), 7.86 (m, 1H), 7.73 (d, 1H), 7.52 (m, 2H), 7.41 (m, 4H), 7.33 (m, 1H), 7.14 (m, 3H), 6.87 (dd, 1H), 4.18 (t, 2H), 3.39 (m, 3H), 2.85 (m, 4H), 2.72 (m, 3H), 2.64 (s, 3H), 2.23 (m, 2H).

EXAMPLE 389

7-(2-((4-(tert-butoxycarbonyl)piperazin-1-yl)sulfonyl)phenyl)-3-(3-(1-naphthyloxyl)propyl)-1H-indole-2-carboxylic acid $^1$H NMR (300 MHz, DMSO-d$_6$) δ 10.33 (s, 1H), 8.28 (m, 1H), 8.07 (dd, 1H), 7.87 (m, 1H), 7.73 (td, 1H), 7.65 (td, 2H), 7.53 (m, 2H), 7.42 (m, 3H), 7.09 (dd, 1H), 6.97 (m, 1H), 6.89 (d, 1H), 4.17 (m, 2H), 3.42 (m, 2H), 3.18 (m, 2H), 2.82 (m, 2H), 2.58 (m, 2H), 2.42 (m, 2H), 2.20 (m, 2H), 1.28 (s, 9H).

EXAMPLE 390

7-(2-((4-ethylpiperazin-1-yl)sulfonyl)phenyl)-3-(3-(1-naphthyloxy)propyl)-1H-indole-2-carboxylic acid $^1$H NMR (300 MHz, DMSO-d$_6$) δ 13.04 (s, 1H), 11.19 (s, 1H), 8.27 (m, 1H), 8.08 (m, 1H), 7.89 (m, 1H), 7.75 (m, 3H), 7.54 (m, 2H), 7.45 (m, 3H), 7.11 (m, 2H), 6.93 (d, 1H), 4.23 (t, 2H), 3.47 (m, 3H), 3.18 (m, 3H), 2.72 (m, 4H), 2.36 (m, 2H), 2.23 (m, 2H), 1.49 (m, 1H), 1.00 (t, 3H).

EXAMPLE 391

3-(3-(1-naphthyloxyl)propyl)-7-(2-((4-(2-oxopyrrolidin-1-yl)piperidin-1-yl)sulfonyl)phenyl)-1H-indole-2-carboxylic acid $^1$H NMR (300 MHz, DMSO-d$_6$) δ 12.95 (s, 1H), 11.08 (s, 1H), 8.27 (m, 1H), 8.07 (dd, 1H), 7.87 (m, 1H), 7.67 (m, 3H), 7.53 (m, 2H), 7.41 (m, 3H), 7.17 (dd, 1H), 7.03 (dd, 1H), 6.89 (dd, 1H), 4.19 (m, 2H), 3.45 (m, 3H), 2.95 (m, 4H), 2.25 (m, 4H), 2.09 (m, 2H), 1.77 (dq, 2H), 1.10 (m, 3H), 0.31 (m, 1H).

EXAMPLE 392

7-(3-((1S,4R)-2-hydroxybicyclo(2.2.1)hept-2-yl)-2-methylphenyl)-3-(3-(1-naphthyloxy)propyl)-1H-indole-2-carboxylic acid $^1$H NMR (500 MHz, DMSO-d$_6$) δ 12.97 (m, 1H), 10.55 (s, 0.5H), 9.78 (s, 0.5H), 8.24 (m, 1H), 7.87 (d, 1H), 7.69 (m, 1H), 7.48 (m, 4H), 7.39 (t, 1H), 7.19 (m, 1H), 7.07 (m, 2.5H), 6.92 (m, 1.5H), 4.75 (d, 1H), 4.21 (t, 2H), 3.38 (m, 2H), 2.83 (m, 1H), 2.24 (m, 4H), 2.15 (d, 3H), 1.98 (m, 1H), 1.50 (m, 6H).

EXAMPLE 393

7-((1E)-1-ethylbut-1-enyl)-3-(3-(1-naphthyloxy) propyl)-1H-indole-2-carboxylic acid $^1$H NMR (300 MHz, DMSO-d$_6$) δ 13.01 (s, 1H), 10.41 (s, 1H), 8.23 (m, 1H), 7.86 (m, 1H), 7.51 (m, 4H), 7.39 (d, 1H), 6.98 (m, 2H), 6.89 (dd, 1H), 5.50 (t, 1H), 4.18 (t, 2H), 3.39 (m, 2H), 2.53 (m, 2H), 2.22 (m, 4H), 1.05 (t, 3H), 0.83 (t, 3H).

EXAMPLE 394

7-((Z)-2-carboxy-1-pentylvinyl)-3-(3-(1-naphthyloxy)propyl)-1H-indole-2-carboxylic acid $^1$H NMR (300 MHz, DMSO-d$_6$) δ 12.97 (s, 1H), 12.13 (s, 1H), 11.07 (s, 1H), 8.23 (m, 1H), 7.86 (m, 1H), 7.66 (d, 1H), 7.51 (m, 2H), 7.41 (m, 2H), 7.12 (m, 1H), 6.99 (m, 1H), 6.89 (m, 1H), 5.90 (s, 1H), 4.18 (t, 2H), 3.40 (m, 2H), 3.07 (m, 2H), 2.21 (m, 2H), 1.23 (m, 6H), 0.76 (m, 3H).

EXAMPLE 395

7-(5,7-dimethylpyrazolo(1,5-a)pyrimidin-3-yl)-3-(3-(1-naphthyloxy)propyl)-1H-indole-2-carboxylic acid $^1$H NMR (300 MHz, DMSO-d$_6$) δ 13.56 (s, 1H), 13.08 (s, 1H), 8.92 (s, 1H), 8.25 (m, 1H), 7.86 (m, 2H), 7.59 (d, 1H), 7.52 (m, 2H), 7.41 (m, 2H), 7.03 (m, 2H), 6.89 (dd, 1H), 4.19 (t, 2H), 3.39 (m, 2H), 2.75 (s, 3H), 2.72 (s, 3H), 2.25 (m, 2H).

EXAMPLE 396

7-(4-(4-fluorophenyl)-5-(4-(methylsulfonyl)phenyl) thien-2-yl)-3-(3-(1-naphthyloxyl)propyl)-1H-indole-2-carboxylic acid $^1$H NMR (300 MHz, DMSO-d$_6$) δ 13.17 (s, 1H), 10.87 (s, 1H), 8.22 (m, 1H), 7.89 (m, 3H), 7.76 (d, 1H), 7.71 (s, 1H), 7.48 (m, 8H), 7.26 (ddd, 2H), 7.11 (m, 1H), 6.90 (dd, 1H), 4.20 (t, 2H), 3.40 (m, 2H), 3.24 (s, 3H), 2.24 (m, 2H).

EXAMPLE 397

3-(3-(1-naphthyloxyl)propyl)-1-(pyridin-4-ylmethyl)-7-(2-(trifluommethyl)phenyl)-1H-indole-2-carboxylic acid $^1$H NMR (300 MHz, DMSO-da) δ 13.29 (s, 1H), 8.40 (d, 2H), 8.23 (m, 1H), 7.90 (m, 2H), 7.77 (d, 1H), 7.53 (m, 5H), 7.31 (t, 1H), 7.16 (dd, 1H), 7.03 (t, 2H), 6.93 (dd, 1H), 6.63 (d, 2H), 5.61 (d, 1H), 5.01 (d, 1H), 4.26 (t, 2H), 3.42 (m, 2H), 2.29 (m, 2H).

EXAMPLE 398

7-(5-(((2-(dimethylamino)ethyl)(pyridin-2-yl)amino) methyl)thien-2-yl)-3-(3-(1-naphthyloxyl)propyl)-1H-indole-2-carboxylic acid $^1$H NMR (500 MHz, DMSO-d$_6$) δ 9.77 (s, 1H), 8.16 (m, 2H), 7.82 (d, 1H), 7.68 (m, 1H), 7.59 (m, 1H), 7.44 (m, 4H), 7.35 (dd, 2H), 7.14 (t, 1H), 7.07 (td, 1H), 6.91 (d, 1H), 6.87 (m, 1H), 6.72 (m, 1H), 4.94 (s, 1H), 4.77 (s, 1H), 4.21 (m, 2H), 3.94 (t, 1H), 3.36 (m, 4H), 2.89 (s, 6H), 2.24 (m, 3H).

EXAMPLE 399

7-(2-morpholin-4-yl-6-(trifluoromethyl)phenyl)-3-(3-(1-naphthyloxyl)propyl)-1H-indole-2-carboxylic acid $^1$H NMR (300 MHz, DMSO-d$_6$) δ 12.81 (s, 1H), 10.77 (s, 1H), 8.31 (m, 1H), 7.87 (m, 1H), 7.69 (dd, 1H), 7.55 (m, 4H), 7.40 (m, 3H), 7.00 (m, 2H), 6.83 (d, 1H), 4.16 (m, 2H), 3.40 (d, 2H), 2.92 (m, 2H), 2.75 (m, 2H), 2.62 (m, 4H), 2.24 (m, 2H).

EXAMPLE 400

7-(4-methoxy-2-phenyl-1-benzofuran-3-yl)-3-(3-(1-naphthyloxyl)propyl)-1H-indole-2-carboxylic acid $^1$H NMR (300 MHz, DMSO-d$_6$) δ 12.81 (s, 1H), 10.99 (s, 1H), 8.31 (m, 1H), 7.87 (m, 1H), 7.75 (d, 1H), 7.53 (m, 2H), 7.46 (m, 1H), 7.34 (m, 5H), 7.21 (m, 4H), 7.06 (m, 1H), 6.88 (d, 1H), 6.73 (m, 1H), 4.19 (t, 2H), 3.42 (s, 3H), 3.38 (d, 2H), 2.26 (m, 2H).

EXAMPLE 401

4-fluoro-7-(2-morpholin-4-ylphenyl)-3-(3-(1-naphthyloxyl)propyl)-1H-indole-2-carboxylic acid $^1$H NMR (300 MHz, DMSO-d$_6$) δ 13.29 (s, 1H), 10.36 (s, 1H), 8.17 (dd, 1H), 7.85 (m, 1H), 7.43 (m, 6H), 7.30 (dd, 1H), 7.14 (m, 2H), 6.96 (dd, 1H), 6.89 (dd, 1H), 4.22 (t, 2H), 3.48 (m, 2H), 3.23 (m, 4H), 2.75 (m, 4H), 2.25 (m, 2H).

EXAMPLE 402

4-fluoro-7-(2-methylphenyl)-3-(3-(1-naphthyloxyl) propyl)-1H-indole-2-carboxylic acid

EXAMPLE 402A ethyl 7-bromo-3-(3-ethoxy-3-oxopropyl)-4-fluoro-1H-indole-2-carboxylate A mixture of 2-bromo-5-fluoroaniline (5 g) in ethanol (17.5 ml) and 1.6M HCl (50 mL) at −5° C. was treated with 2.5M NaNO$_2$ (10.5 ml). 4.5M potassium acetate (29.2 ml) was then added, followed by ethyl 2-oxocyclopentanecarboxylate (3.8 ml). The reaction mixture was stirred at 0° C. for 15 minutes, warmed to 20° C. over 1.5 hours, extracted with dichloromethane, concentrated and dried in vacuo. The residue was dissolved in 67 ml of (H$_2$SO$_4$/ethanol, 17:50), refluxed for 2 days, cooled to room temperature, quenched with water and extracted with dichloromethane. The combined extracts were washed with brine, dried (MgSO$_4$), filtered and concentrated. The concentrate was purified by column chromatography on silica gel with 5-20% ethyl acetate in hexanes. The product was purified further by trituration with ethanol.

EXAMPLE 402B 3-(7-bromo-2-(ethoxycarbonyl)-4-fluoro-1H-indol-3-yl)propanoic acid To a mixture of EXAMPLE 402A (2.3 g) in acetic acid (40 ml) was added concentrated hydrochloric acid (3 ml). The mixture was heated at 80° C. for 4 hours. After cooling to room temperature, precipitation of the product occurred. Water (50 mL) was added to further induce precipitation. The solid was filtered, rinsed with water and dried in vacuo.

EXAMPLE 402C 7-bromo-4-fluoro-3-(3-hydroxypropyl)-1H-indole-2-carboxylate

To a suspension of EXAMPLE 402B (1.9 g) in tetrahydrofuran (10 ml) was added 1M borane.tetrahydrofuran (5.8 ml). The reaction mixture was stirred at ambient temperature overnight. Additional 1M borane.tetrahydrofuran (2.0 ml) was added and stirring was continued for 3 hours. The reaction was quenched with methanol and concentrated. The concentrate was dissolved in hot ethanol (30 ml) and 1 ml of concentrated HCl, and was stirred for 1 hour. Precipitation of the product occurred. Water (20 ml) was added to further induce precipitation. The solid was filtered, rinsed with water and dried.

EXAMPLE 402D ethyl 7-bromo-4-fluoro-3-(3-(naphthalen-1-yloxy)propyl)-1H-indole-2-carboxylate To a mixture of EXAMPLE 402C (1.03 g), naphthalen-1-ol (519 mg), and triphenylphosphine (905 mg) in tetrahydrofuran (15 ml) at −10° C. was added di-tert-butyl azodicarboxylate (794 mg) slowly. After one hour, the reaction was allowed to warm to room temperature. Stirring was continued for two hours at room temperature. The reaction mixture was concentrated. The concentrate was purified by column chromatography on silica gel with 0-4% ethyl acetate in hexanes.

EXAMPLE 402E 4-fluoro-7-(2-methylphenyl)-3-(3-(1-naphthyloxy)propyl)-1H-indole-2-carboxylic acid A mixture of EXAMPLE 402D (47 mg), o-tolylboronic acid (19 mg), tris(dibenzylidineacetone)dipalladium(0) (4.6 mg), tri-t-butyl-phosphonium tetrafluoroborate (3.5 mg), cesium fluoride (45.6 mg) and tetrahydrofuran (1.5 ml) was stirred at ambient temperature under a nitrogen atmosphere overnight. Additional o-tolylboronic acid (9.5 mg), tris(dibenzylidineacetone)dipalladium(0) (2.3 mg), tri-t-butyl-phosphonium tetrafluoroborate (1.8 mg) and cesium fluoride (23 mg) were added and stirring was continued at ambient temperature overnight. LiOH—$H_2O$ (42 mg) and water (0.5 ml) were added and the mixture was heated overnight at 60° C. The reaction mixture was acidified with 1 M HCl (aq), extracted (3×5 ml) with ethyl acetate, dried ($MgSO_4$), filtered and concentrated. The concentrate was slurried in methanol and filtered through a syringe filter. The filtrate was concentrated. The concentrate was purified by reverse phase HPLC (50-95% acetonitrile/water/0.1% trifluoroacetic acid). $^1$H NMR (300 MHz, DMSO-$d_6$) δ 13.10 (s, 1H), 10.86 (s, 1H), 8.20 (m, 1H), 7.86 (m, 1H), 7.48 (m, 4H), 7.28 (m, 4H), 6.99 (m, 1H), 6.90 (m, 2H), 4.23 (t, 2H), 3.45 (t, 2H), 2.25 (m, 2H), 2.05 (s, 3H).

EXAMPLE 403

7-(2-((2-adamantylamino)carbonyl)-6-methylimidazo(1,2-a)pyridin-8-yl)-3-(3-(1-naphthyloxyl)propyl)-1H-indole-2-carboxylic acid $^1$H NMR (300 MHz, DMSO-$d_6$) δ 13.03 (s, 1H), 10.76 (s, 1H), 8.48 (d, 2H), 8.22 (m, 1H), 7.85 (m, 2H), 7.59 (m, 1H), 7.49 (m, 5H), 7.37 (m, 1H), 7.16 (dd, 1H), 6.87 (dd, 1H), 4.19 (t, 2H), 3.95 (m, 1H), 3.41 (m, 2H), 2.39 (d, 3H), 2.26 (m, 2H), 1.86 (m, 2H), 1.78 (m, 6H), 1.62 (m, 4H), 1.43 (m, 2H).

EXAMPLE 404

7-(1-(1-adamantyl)-3-carboxy-1H-pyrazol-4-yl)-3-(3-(1-naphthyloxyl)propyl)-1H-indole-2-carboxylic acid $^1$H NMR (300 MHz, DMSO-$d_6$) δ 12.86 (s, 1H), 12.22 (s, 1H), 10.59 (s, 1H), 8.26 (m, 1H), 7.99 (s, 1H), 7.87 (m, 1H), 7.62 (d, 1H), 7.51 (m, 3H), 7.40 (d, 1H), 7.10 (d, 1H), 6.98 (t, 1H), 6.90 (d, 1H), 4.19 (t, 2H), 3.37 (m, 2H), 2.24 (m, 2H), 2.20 (s, 9H), 1.75 (s, 6H).

EXAMPLE 405

7-(2-(1-hydroxy-4-methoxycyclohexyl)-1-benzothien-3-yl)-3-(3-(1-naphthyloxyl)propyl)-1H-indole-2-carboxylic acid $^1$H NMR (300 MHz, DMSO-$d_6$) δ 12.93 (s, 1H), 10.63 (s, 1H), 8.29 (m, 1H), 7.91 (m, 2H), 7.76 (m, 1H), 7.51 (m, 2H), 7.42 (m, 2H), 7.28 (ddd, 1H), 7.11 (m, 2H), 6.88 (m, 1H), 6.64 (d, 1H), 6.07 (s, 1H), 5.57 (s, 1H), 4.21 (m, 2H), 3.40 (s, 2H), 3.06 (s, 3H), 2.64 (m, 1H), 2.26 (m, 2H), 1.62 (m, 6H).

EXAMPLE 406

7-(5-chloro-3-methyl-1-tetrahydro-2H-pyran-2-yl-1H-pyrazol-4-yl)-3-(3-(1-naphthyloxy)propyl)-1H-indole-2-carboxylic acid $^1$H NMR (300 MHz, DMSO-$d_6$) δ 10.71 (s, 1H), 8.25 (m, 1H), 7.87 (m, 1H), 7.69 (dt, 1H), 7.52 (m, 2H), 7.41 (dt, 2H), 7.05 (m, 2H), 6.91 (d, 1H), 5.44 (dd, 1H), 4.20 (t, 2H), 3.94 (d, 1H), 3.69 (m, 1H), 3.46 (m, 2H), 2.25 (m, 3H), 2.13 (s, 3H), 1.99 (m, 2H), 1.73 (m, 1H), 1.55 (m, 2H).

EXAMPLE 407

3-(3-(1-naphthyloxy)propyl)-7-(2,2,4-trimethyl-1-(phenylsulfonyl)-1,2-dihydroquinolin-3-yl)-1H-indole-2-carboxylic acid $^1$H NMR (300 MHz, DMSO-$d_6$) δ 13.01 (s, 1H), 11.27 (s, 1H), 8.23 (m, 1H), 7.86 (m, 1H), 7.67 (m, 1H), 7.52 (m, 7H), 7.34 (m, 6H), 6.85 (m, 2H), 6.43 (m, 1H), 4.95 (s, 1H), 4.17 (t, 2H), 3.76 (s, 2H), 3.37 (m, 2H), 2.20 (m, 2H), 1.33 (s, 6H).

EXAMPLE 408

7-(7,8-dimethyl-2-(1-methyl-1-phenylethyl)imidazo(1,2-a)pyridin-6-yl)-3-(3-(1-naphthyloxy)propyl)-1H-indole-2-carboxylic acid $^1$H NMR (300 MHz, DMSO-$d_6$) δ 13.50 (s, 1H), 11.16 (s, 1H), 8.67 (s, 1H), 8.26 (m, 1H), 8.16 (s, 1H), 7.85 (m, 2H), 7.53 (m, 2H), 7.38 (m, 7H), 7.16 (m, 2H), 6.91 (dd, 1H), 4.21 (t, 2H), 3.42 (m, 2H), 2.56 (s, 3H), 2.25 (m, 2H), 2.07 (s, 3H), 1.81 (s, 6H).

EXAMPLE 409

7-(1-(4-((2-fluorobenzoyl)amino)phenyl)-3-(trifluoromethyl)-1H-pyrazol-5-yl)-3-(3-(1-naphthyloxy)propyl)-1H-indole-2-carboxylic acid $^1$H NMR (400 MHz, DMSO-d$_6$) δ 11.33 (s, 1H), 10.48 (s, 1H), 8.23 (d, 1H), 7.85 (d, 1H), 7.74 (d, 1H), 7.62 (m, 3H), 7.53 (m, 3H), 7.44 (m, 1H), 7.33 (m, 5H), 7.09 (m, 2H), 6.98 (t, 1H), 6.87 (d, 1H), 4.16 (t, 2H), 3.38 (m, 2H), 2.20 (m, 2H).

EXAMPLE 410

7-(5-amino-3-(piperidin-1-ylcarbonyl)-1H-pyrazol-4-yl)-3-(3-(1-naphthyloxy)propyl)-1H-indole-2-carboxylic acid $^1$H NMR (500 MHz, DMSO-d$_5$) δ 13.03 (s, 1H), 10.30 (s, 1H), 8.27 (m, 1H), 7.86 (m, 1H), 7.61 (d, 1H), 7.53 (m, 2H), 7.45 (d, 1H), 7.38 (t, 1H), 7.10 (m, 1H), 7.00 (m, 1H), 6.86 (d, 1H), 5.17 (s, 2H), 4.16 (t, 2H), 3.59 (m, 4H), 3.01 (m, 2H), 2.22 (ddd, 2H), 1.28 (m, 4H), 0.76 (m, 2H).

EXAMPLE 411

7-(3-methyl-1-(2-nitrophenyl)-5-phenyl-1H-pyrazol-4-yl)-3-(3-(1-naphthyloxy)propyl)-1H-indole-2-carboxylic acid $^1$H NMR (300 MHz, DMSO-d$_6$) δ 12.99 (s, 1H), 10.72 (s, 1H), 8.26 (m, 1H), 8.04 (dd, 1H), 7.87 (m, 1H), 7.65 (s, 3H), 7.50 (m, 3H), 7.37 (m, 2H), 7.13 (m, 3H), 7.04 (m, 2H), 6.98 (m, 2H), 6.90 (dd, 1H), 4.20 (t, 2H), 3.41 (m, 2H), 2.22 (m, 2H), 2.03 (s, 3H).

EXAMPLE 412

7-(5-methyl-1-(2-oxo-2-((2-phenylethyl)amino)ethyl)-3-(trifluoromethyl)-1H-pyrazol-4-yl)-3-(3-(1-naphthyloxy)propyl)-1H-indole-2-carboxylic acid $^1$H NMR (400 MHz, DMSO-d$_5$) δ 10.80 (s, 1H), 8.26 (m, 1H), 8.22 (t, 1H), 7.87 (td, 1H), 7.73 (m, 1H), 7.52 (m, 2H), 7.46 (m, 1H), 7.39 (t, 1H), 7.24 (m, 4H), 7.16 (m, 1H), 7.08 (m, 2H), 6.91 (d, 1H), 4.89 (s, 2H), 4.22 (t, 2H), 3.49 (m, 4H), 2.79 (m, 2H), 2.23 (m, 2H), 1.84 (s, 3H).

EXAMPLE 413

7-(2-(1-adamantyl)imidazo(1,2-a)pyridin-5-yl)-3-(3-(1-naphthyloxy)propyl)-1H-indole-2-carboxylic acid $^1$H NMR (400 MHz, DMSO-d$_6$) δ 11.30 (s, 1H), 8.17 (dd, 1H), 8.01 (d, 1H), 7.94 (m, 2H), 7.87 (m, 1H), 7.49 (m, 5H), 7.39 (m, 1H), 7.25 (dd, 1H), 7.02 (s, 1H), 6.90 (d, 1H), 4.22 (t, 2H), 3.80 (m, 2H), 2.27 (qd, 2H), 2.01 (m, 3H), 1.88 (m, 6H), 1.70 (m, 6H).

EXAMPLE 414

7-(1,1-dioxido-1-benzothien-3-yl)-3-(3-(1-naphthyloxyl)propyl)-1H-indole-2-carboxylic acid $^1$H NMR (400 MHz, DMSO-d$_6$) δ 11.54 (s, 1H), 8.24 (m, 1H), 7.92 (d, 1H), 7.87 (m, 2H), 7.61 (m, 2H), 7.52 (m, 2H), 7.46 (m, 2H), 7.39 (m, 1H), 7.32 (d, 1H), 7.11 (m, 2H), 6.90 (d, 1H), 4.20 (t, 2H), 3.40 (m, 2H), 2.25 (m, 2H).

EXAMPLE 415

7-(2-cyclohexyl-6-methylphenyl)-3-(3-(1-naphthyloxy)propyl)-1H-indole-2-carboxylic acid $^1$H NMR (300 MHz, DMSO-d$_6$) δ 12.87 (s, 1H), 10.39 (s, 1H), 8.29 (m, 1H), 7.87 (m, 1H), 7.69 (d, 1H), 7.53 (m, 2H), 7.45 (m, 1H), 7.37 (m, 1H), 7.25 (m, 2H), 7.09 (m, 2H), 6.88 (m, 2H), 4.19 (t, 2H), 3.38 (m, 2H), 2.25 (m, 2H), 2.02 (m, 1H), 1.83 (s, 3H), 1.54 (m, 5H), 1.33 (m, 2H), 1.09 (m, 1H), 0.82 (m, 1H), 0.71 (m, 1H).

EXAMPLE 416

7-(4-(((2-(2-(2-aminoethoxy)ethoxy)ethyl)amino)carbonyl)-2-methylphenyl)-3-(3-(1-naphthyloxy)propyl)-1H-indole-2-carboxylic acid $^1$H NMR (300 MHz, DMSO-d$_6$) δ 12.94 (s, 1H), 10.71 (s, 1H), 8.51 (t, 1H), 8.24 (m, 1H), 7.87 (ddd, 1H), 7.74 (m, 5H), 7.52 (m, 3H), 7.40 (d, 1H), 7.30 (d, 1H), 7.06 (m, 2H), 6.90 (m, 1H), 4.21 (t, 2H), 3.59 (m, 8H), 3.47 (m, 2H), 3.39 (m, 2H), 2.98 (m, 2H), 2.24 (m, 2H), 2.10 (s, 3H).

EXAMPLE 417

7-(1-methyl-3,5-diphenyl-1H-pyrazol-4-yl)-3-(3-(1-naphthyloxy)propyl)-1H-indole-2-carboxylic acid $^1$H NMR (300 MHz, DMSO-d$_6$) δ 12.85 (s, 1H), 10.75 (s, 1H), 8.26 (m, 1H), 7.86 (m, 1H), 7.60 (d, 1H), 7.50 (m, 3H), 7.31 (m, 8H), 7.11 (m, 3H), 7.05 (dd, 1H), 6.93 (dd, 1H), 6.84 (m, 1H), 4.13 (t, 2H), 3.82 (s, 3H), 3.25 (m, 2H), 2.18 (m, 2H).

EXAMPLE 418

7-((Z)-2-(1H-imidazol-1-yl)-1-phenylvinyl)-3-(3-(1-naphthyloxy)propyl)-1H-indole-2-carboxylic acid $^1$H NMR (300 MHz, DMSO-d$_6$) δ 13.20 (m, 1H), 11.04 (m, 1H), 8.25 (m, 1H), 7.87 (m, 1H), 7.76 (m, 1H), 7.52 (m, 4H), 7.35 (m, 6H), 7.22 (m, 2H), 7.11 (m, 1H), 7.00 (m, 2H), 6.89 (d, 1H), 4.19 (t, 2H), 3.54 (m, 2H), 2.23 (m, 2H).

EXAMPLE 419

7-(1-benzyl-2-methyl-4-nitro-1H-imidazol-5-yl)-3-(3-(1-naphthyloxy)propyl)-1H-indole-2-carboxylic acid $^1$H NMR (300 MHz, DMSO-d$_6$) δ 13.05 (s, 1H), 11.61 (s, 1H), 8.26 (m, 1H), 7.87 (m, 1H), 7.80 (d, 1H), 7.51 (m, 2H), 7.41 (m, 2H), 7.20 (m, 4H), 7.03 (m, 1H), 6.92 (m, 3H), 5.07 (d, 1H), 4.75 (d, 1H), 4.19 (t, 2H), 3.39 (m, 2H), 2.30 (s, 3H), 2.20 (m, 2H).

EXAMPLE 420

3-(3-(1-naphthyloxy)propyl)-7-(2-prop-1-ynylphenyl)-1H-indole-2-carboxylic acid

EXAMPLE 420A 1-bromo-2-(prop-1-ynyl)benzene

1M Lithium hexamethyldisilazide solution (6 mL) was added to 1-bromo-2-ethynylbenzene (1 g) in 20 mL tetrahydrofuran at room temperature, and the reaction was stirred 30 minutes. $(CH_3)_2SO_4$ (0.58 mL) was added and the reaction was stirred 30 minutes. The reaction was poured into 20 mL water, extracted with 2×50 mL ether, and the combined organic layers were dried over $Na_2SO_4$, filtered, and the filtrate was concentrated.

EXAMPLE 420B 2-(prop-1-ynyl)phenylboronic acid 2.5M n-butyllithium (1.92 mL) was added to EXAMPLE 420A (850 mg) in 15 mL tetrahydrofuran at −78° C. The reaction was stirred 1 minute, trimethylborate (0.974 mL) was added, and the reaction was allowed to warm to room temperature. The reaction was poured into 20 mL 1M HCl, extracted with 3×50 mL ether, and the organic layers were concentrated. The crude material was taken up in 50 mL 1M NaOH, and rinsed with 2×50 mL ether. The aqueous layer was acidified with concentrated HCl, extracted with 3×50 mL ether, and the combined extracts were washed with brine, dried over $Na_2SO_4$, and concentrated. The crude product was triturated from ether/hexane.

EXAMPLE 420C 3-(3-(1-naphthyloxy)propyl)-7-(2-prop-1-ynylphenyl)-1H-indole-2-carboxylic acid A suspension of EXAMPLE 1C (0.034 g, 0.075 mmol), EXAMPLE 420B (0.1 g, 0.68 mmol), tetrakis(triphenylphosphine)palladium (0.004 g, 0.006 mmol), and solution of $Na_2CO_3$ (2M, 0.5 ml, 1 mmol) in dimethoxyethane/EtOH/$H_2O$ (7/2/3) 3 mL was heated under microwave conditions at 150 C for 30 min. The reaction mixture was quenched with aq. HCl (1 M, 0.4 mL) and product extracted with ethyl acetate (3×7 mL). The organic phases were filtered through a drying cartridge (MgSO₄, Alltech Asoc., 2 g) and concentrated under reduced pressure. The crude product was purified by chromatography on SiO2 using 1% AcOH in EtOAc as eluent. $^1$H NMR (300 MHz, DMSO-$d_6$) δ12.39 (br s, 1H), 10.28 (s, 1H), 8.25 (dd, 1H), 7.87 (d, 1H), 7.71 (d, 1H), 7.38-7.56 (m, 8H), 7.21 (d, 1H), 7.09 (dd, 1H), 6.89 (d, 1H), 4.20 (m, 2H), 3.38 (m, 2H), 2.24 (m, 2H), 1.91 (s, 3H).

EXAMPLE 421

3-(3-(1-naphthyloxy)propyl)-7-(2-(phenylethynyl)phenyl)-1H-indole-2-carboxylic acid $^1$H NMR (300 MHz, DMSO-$d_6$) δ 12.85 (br s, 1H), 10.66 (s, 1H), 8.28 (dd, 1H), 7.87 (d, 1H), 7.78 (d, 1H), 7.68 (d, 1H), 7.40-7.58 (m, 8H), 7.18-7.26 (m, 3H), 7.08 (dd, 1H), 6.89 (m, 3H), 4.21 (t, 2H), 3.40 (t, 2H), 2.26 (m, 2H).

EXAMPLE 422

3,7-bis(3-(1-naphthyloxy)propyl)-1H-indole-2-carboxylic acid $^1$H NMR (300 MHz, DMSO-$d_6$) δ 12.80 (br s, 1H), 11.35 (s, 1H), 8.21 (dd, 2H), 7.86 (d, 2H), 7.35-7.55 (m, 8H), 7.08 (d, 1H), 6.86-6.96 (m, 4H), 4.18 (m, 4H), 3.37 (m, 4H), 2.21 (m, 4H).

EXAMPLE 423

1-(2-(dimethylamino)-2-oxoethyl)-7-(2-methylphenyl)-3-(3-(1-naphthyloxy)propyl)-1H-indole-2-carboxylic acid $^1$H NMR (300 MHz, DMSO-$d_6$) 13.02 (s, 1H), 8.24-8.31 (m, 1H), 7.84-7.91 (m, 1H), 7.75 (dd, J=8.1, 1.4 Hz, 1H), 7.50-7.56 (m, 2H), 7.46 (d, J=8.1, 1H), 7.41 (d, J=7.1 Hz, 1H), 7.31-7.39 (m, 2H), 7.20-7.28 (m, 1H), 7.02-7.12 (m, 2H), 6.91 (dd, J=6.8, 4.4 Hz, 2H), 5.05 (d, J=17.3 Hz, 1H), 4.70 (d, J=17.6 Hz, 1H), 4.23 (t, J=6.1 Hz, 2H), 3.32-3.40 (m, 2H), 2.63 (s, 3H), 2.28 (s, 3H), 2.18-2.27 (m, 2H), 1.95 (s, 3H).

EXAMPLE 424

1-(2-methylbenzyl)-7-(2-methylphenyl)-3-(3-(1-naphthyloxyl)propyl)-1H-indole-2-carboxylic acid $^1$H NMR (300 MHz, DMSO-$d_6$) 13.13 (s, 1H), 8.22-8.30 (m, 1H), 7.81-7.91 (m, 2H), 7.49-7.56 (m, 1H), 7.44-7.49 (m, 1H), 7.36-7.44 (m, 1H), 7.23-7.31 (m, 1H), 7.07-7.19 (m, 2H), 6.99-7.04 (m, 1H), 6.92-6.99 (m, 3H), 6.84-6.92 (m, 2H), 6.74-6.82 (m, 2H), 5.50 (d, J=7.8 Hz, 1H), 5.34 (d, J=17.6 Hz, 1H), 5.17 (d, J=17.6 Hz, 1H), 4.26 (t, J=6.1 Hz, 2H), 3.37-3.49 (m, 2H), 2.22-2.36 (m, 2H), 1.61 (s, 3H), 1.57 (s, 3H).

EXAMPLE 425

1-(3-methylbenzyl)-7-(2-methylphenyl)-3-(3-(1-naphthyloxyl)propyl)-1H-indole-2-carboxylic acid $^1$H NMR (300 MHz, DMSO-$d_6$) 13.18 (s, 1H), 8.20-8.29 (m, 1H), 7.83-7.91 (m, 1H), 7.80 (d, J=8.3 Hz, 1H), 7.48-7.58 (m, 2H), 7.43-7.48 (m, 1H), 7.34-7.42 (m, 1H), 7.30 (t, J=7.3 Hz, 1H), 7.21 (d, J=7.1 Hz, 1H), 7.06-7.17 (m, 2H), 7.00 (d, J=7.5 Hz, 1H), 6.82-6.96 (m, 4H), 6.04 (s, 1H), 5.98 (d, J=6.7 Hz, 1H), 5.29 (d, J=16.6 Hz, 1H), 5.19 (d, J=16.6 Hz, 1H), 4.22 (t, J=6.1 Hz, 2H), 3.34-3.43 (m, 2H), 2.19-2.33 (m, 2H), 2.06 (s, 3H), 1.70 (s, 3H).

EXAMPLE 426

1-(4-methylbenzyl)-7-(2-methylphenyl)-3-(3-(1-naphthyloxyl)propyl)-1H-indole-2-carboxylic acid $^1$H NMR (300 MHz, DMSO-$d_6$) 13.13 (s, 1H), 8.21-8.29 (m, 1H), 7.84-7.92 (m, 2H), 7.80 (d, J=6.7 Hz, 1H), 7.50-7.58 (m, 2H), 7.47 (d, J=8.7 Hz, 2H), 7.35-7.42 (m, 1H), 7.26-7.33 (m, 1H), 7.23 (d, J=7.1 Hz, 1H), 7.08-7.16 (m, 2H), 7.03 (d, J=6.7 Hz, 1H), 6.95 (d, J=5.9 Hz, 1H), 6.89 (d, J=6.7 Hz, 1H), 6.83 (d, J=7.9 Hz, 2H), 6.14 (d, J=8.3 Hz, 2H), 5.29 (d, J=16.7 Hz, 1H), 5.11 (d, J=16.7 Hz, 1H), 4.21 (t, J=6.1 Hz, 2H), 3.34-3.42 (m, 2H), 2.18-2.32 (m, 2H), 2.14 (s, 3H), 1.76 (s, 3H).

EXAMPLE 427

7-(2-methylphenyl)-1-(3-morpholin-4-ylpropyl)-3-(3-(1-naphthyloxy)propyl)-1H-indole-2-carboxylic acid $^1$H NMR (300 MHz, DMSO-$d_6$) 13.31 (s, 1H), 9.43 (s, 1H), 8.19-8.27 (m, 1H), 7.83-7.91 (m, 1H), 7.79 (dd, J=8.1, 1.4 Hz, 1H), 7.49-7.58 (m, 2H), 7.47 (d, J=8.4 Hz, 1H), 7.34-7.44 (m, 5H), 7.10-7.18 (m, 1H), 7.00 (d, J=5.8 Hz, 1H), 6.92 (d, J=6.4 Hz, 1H), 4.26-4.40 (m, 1H), 4.23 (t, J=5.9 Hz, 2H), 3.88 (bs, 2H), 3.48-3.65 (m, 4H), 3.29-3.39 (m, 4H), 2.85 (bs, 2H), 1.99 (s, 3H), 1.60 (bs, 2H).

EXAMPLE 428

7-(2-methylphenyl)-1-(2-(4-methylpiperazin-1-yl)-2-oxoethyl)-3-(3-(1-naphthyloxyl)propyl)-1H-indole-2-carboxylic acid $^1$H NMR (300 MHz, DMSO-$d_6$) 13.07 (s, 1H), 9.69 (s, 1H), 8.22-8.32 (m, 1H), 7.84-7.92 (m, 1H), 7.77 (dd, J=8.1, 1.4 Hz, 1H), 7.50-7.58 (m, 2H), 7.47 (d, J=8.1 Hz, 1H), 7.33-7.43 (m, 4H), 7.23-7.32 (m, 1H), 7.05-7.13 (m, 1H), 6.92 (d, J=7.5 Hz, 2H), 5.39 (bs, 1H), 4.93 (bs, 1H), 4.23 (t, J=6.1 Hz, 2H), 3.36-3.44 (m, 4H), 2.72-2.86 (m, 4H), 2.17-2.30 (m, 2H), 1.93 (s, 3H).

EXAMPLE 429

7-(2-methylphenyl)-1-(2-(4-methylpiperazin-1-yl)ethyl)-3-(3-(1-naphthyloxyl)propyl)-1H-indole-2-carboxylic acid $^1$H NMR (300 MHz, DMSO-$d_6$) 13.17 (s, 1H), 9.20 (s, 1H), 8.17-8.25 (m, 1H), 7.84-7.90 (m, 1H), 7.76 (dd, J=8.1, 1.4 Hz, 1H), 7.49-7.58 (m, 1H), 7.46 (d, J=8.4 Hz, 1H), 7.37-7.43 (m, 1H), 7.25-7.36 (m, 4H), 7.07-7.16 (m, 1H), 6.96 (dd, J=7.1, 1.4 Hz, 1H), 4.27-4.40 (m, 1H), 4.22 (t, J=5.9 Hz, 2H), 3.70-3.85 (m, 1H), 3.27-3.40 (m, 2H), 3.21 (d, J=12.5 Hz, 2H), 2.70-2.88 (m, 2H), 2.69 (s, 3H), 2.39 (d, J=14.6 Hz, 2H), 2.14-2.30 (m, 2H), 2.06 (m, 4H), 2.00 (s, 3H).

EXAMPLE 430

1-(1,1'-biphenyl-2-ylmethyl)-7-(2-methylphenyl)-3-(3-(1-naphthyloxyl)propyl)-1H-indole-2-carboxylic acid $^1$H NMR (300 MHz, DMSO-$d_6$) 12.97 (s, 1H), 8.18-8.26 (m, 1H), 7.82-7.91 (m, 2H), 7.43-7.58 (m, 3H), 7.35-7.43 (m, 1H), 7.29-7.36 (m, 4H), 7.26 (d, J=7.1 Hz, 1H), 7.03-7.19 (m, 3H), 6.87-7.02 (m, 5H), 6.65-6.75 (m, 2H), 5.52 (d, J=7.5 Hz, 1H), 5.29 (d, J=17.8 Hz, 1H), 5.10 (d, J=17.8 Hz, 1H), 4.23 (t, J=6.1 Hz, 2H), 3.36-3.45 (m, 2H), 2.27 (qt, J=7.3 Hz, 2H), 1.76 (s, 3H).

EXAMPLE 431

1-(1,1'-biphenyl-3-ylmethyl)-7-(2-methylphenyl)-3-(3-(1-naphthyloxyl)propyl)-1H-indole-2-carboxylic acid $^1$H NMR (300 MHz, DMSO-$d_6$) 13.23 (s, 1H), 8.20-8.30 (m, 1H), 7.84-7.91 (m, 1H), 7.81 (d, J=7.8 Hz, 1H), 7.48-7.59 (m, 2H), 7.46 (d, J=8.1 Hz, 1H), 7.32-7.41 (m, 6H), 7.22-7.32 (m, 2H), 7.06-7.20 (m, 4H), 7.01 (d, J=6.8 Hz, 1H), 6.94 (d, J=7.1 Hz, 1H), 6.87 (d, J=7.5 Hz, 1H), 6.44 (s, 1H), 6.22 (d, J=8.1 Hz, 1H), 5.39 (d, J=16.6 Hz, 1H), 5.27 (d, J=16.6 Hz, 1H), 4.23 (t, J=6.3 Hz, 2H), 3.39 (t, J=7.5 Hz, 2H), 2.21-2.36 (m, 2H), 1.70 (s, 3H).

EXAMPLE 432

1-(1,1'-biphenyl-4-ylmethyl)-7-(2-methylphenyl)-3-(3-(1-naphthyloxyl)propyl)-1H-indole-2-carboxylic acid $^1$H NMR (300 MHz, DMSO-$d_6$) 13.20 (s, 1H), 8.17-8.27 (m, 1H), 7.80-7.90 (m, 2H), 7.48-7.57 (m, 4H), 7.46 (d, J=8.1 Hz, 1H), 7.34-7.43 (m, 3H), 7.26-7.34 (m, 4H), 7.23 (d, J=7.1 Hz, 1H), 7.08-7.18 (m, 2H), 7.03 (d, J=6.8 Hz, 1H), 6.96 (d, J=6.1 Hz, 1H), 6.90 (d, J=6.8 Hz, 1H), 6.31 (d, J=8.1 Hz, 2H), 5.38 (d, J=17.3 Hz, 1H), 5.25 (d, J=17.3 Hz, 1H), 4.23 (t, J=6.1 Hz, 2H), 3.35-3.45 (m, 2H), 2.21-2.35 (m, 2H), 1.75 (s, 3H).

EXAMPLE 433

1-(2,4-dimethylbenzyl)-7-(2-methylphenyl)-3-(3-(1-naphthyloxyl)propyl)-1H-indole-2-carboxylic acid $^1$H NMR (300 MHz, DMSO-$d_6$) 13.07 (s, 1H), 8.21-8.30 (m, 1H), 7.85-7.91 (m, 1H), 7.83 (d, J=7.9 Hz, 1H), 7.49-7.57 (m, 2H), 7.48 (d, J=8.1 Hz, 1H), 7.36-7.44 (m, 1H), 7.27 (t, J=7.3 Hz, 1H), 7.17 (d, J=7.1 Hz, 1H), 7.07-7.14 (m, 1H), 7.02 (t, J=7.3 Hz, 1H), 6.91 (d, J=7.5 Hz, 1H), 6.88 (d, J=7.1 Hz, 1H), 6.81 (d, J=7.5 Hz, 1H), 6.76 (s, 1H), 6.56 (d, J=−7.9 Hz, 1H), 5.38 (d, J=7.9 Hz, 1H), 5.28 (d, J=17.4 Hz, 1H), 5.09 (d, J=17.4 Hz, 1H), 4.25 (t, J=6.1 Hz, 2H), 3.41 (t, J=7.3 Hz, 2H), 2.22-2.36 (m, 2H), 2.11 (s, 3H), 1.64 (s, 3H), 1.54 (s, 3H).

EXAMPLE 434

1-(4-carboxybenzyl)-7-(2-methylphenyl)-3-(3-(1-naphthyloxyl)propyl)-1H-indole-2-carboxylic acid $^1$H NMR (300 MHz, DMSO-$d_6$) 13.09 (s, 1H), 12.79 (s, 1H), 8.19-8.30 (m, 1H), 7.85-7.91 (m, 1H), 7.83 (d, J=7.9 Hz, 1H), 7.62 (d, J=8.3 Hz, 2H), 7.49-7.58 (m, 2H), 7.46 (d, J=8.3 Hz, 1H), 7.35-7.43 (m, 1H), 7.28 (t, J=7.5 Hz, 1H), 7.19 (d, J=7.5 Hz, 1H), 7.09-7.16 (m, 1H), 7.06 (t, J=7.5 Hz, 1H), 6.89-7.01 (m, 3H), 6.33 (d, J=8.3 Hz, 2H), 5.43 (d, J=17.1 Hz, 1H), 5.25 (d, J=17.1 Hz, 1H), 4.23 (t, J=6.1 Hz, 2H), 3.36-3.46 (m, 2H), 2.19-2.35 (m, 2H), 1.71 (s, 3H).

EXAMPLE 435

1-(1,1'-biphenyl-2-ylmethyl)-7-(2-morpholin-4-ylphenyl)-3-(3-(1-naphthyloxyl)propyl)-1H-indole-2-carboxylic acid $^1$H NMR (300 MHz, DMSO-$d_6$) 12.90 (s, 1H), 8.23-8.31 (m, 1H), 7.85-7.89 (m, 1H), 7.82 (dd, J=7.5, 2.0 Hz, 1H), 7.48-7.58 (m, 2H), 7.42-7.48 (m, 2H), 7.32-7.42 (m, 5H), 7.04-7.15 (m, 4H), 6.96-7.04 (m, 2H), 6.88-6.96 (m, 1H), 6.86 (d, J=7.5 Hz, 1H), 6.62-6.72 (m, 2H), 5.55 (d, J=18.0 Hz, 1H), 5.47 (d, J=7.8 Hz, 1H), 5.16 (d, J=18.0 Hz, 1H), 4.19 (t, J=6.1 Hz, 2H), 3.31-3.51 (m, 4H), 3.00-3.10 (m, 2H), 2.73-2.84 (m, 2H), 2.20-2.31 (m, 4H).

EXAMPLE 436

1-(1,1'-biphenyl-3-ylmethyl)-7-(2-morpholin-4-ylphenyl)-3-(3-(1-naphthyloxy)propyl)-1H-indole-2-carboxylic acid $^1$H NMR (300 MHz, DMSO-$d_6$) 13.23 (s, 1H), 8.21-8.33 (m, 1H), 7.83-7.91 (m, 1H), 7.77 (dd, J=7.1, 2.4 Hz, 1H), 7.49-7.57 (m, 2H), 7.45 (d, J=8.3 Hz, 1H), 7.26-7.41 (m, 8H), 7.18 (dd, J=7.5, 1.6 Hz, 1H), 7.05-7.14 (m, 4H), 7.00 (t, J=7.3 Hz, 1H), 6.81 (d, J=7.5 Hz, 1H), 6.60 (s, 1H), 6.30 (d, J=7.9 Hz, 1H), 5.82 (d, J=16.7 Hz, 1H), 5.02 (d, J=16.7 Hz, 1H), 4.16 (t, J=5.9 Hz, 2H), 3.33-3.45 (m, 2H), 3.15-3.26 (m, 4H), 2.89 (s, 2H), 2.53-2.70 (m, 2H), 2.13-2.31 (m, 2H).

EXAMPLE 437

1-(1,1'-biphenyl-4-ylmethyl)-7-(2-morpholin-4-ylphenyl)-3-(3-(1-naphthyloxy)propyl)-1H-indole-2-carboxylic acid $^1$H NMR (300 MHz, DMSO-d$_6$) 13.20 (s, 1H), 8.22-8.31 (m, 1H), 7.83-7.91 (m, 1H), 7.75-7.82 (m, 1H), 7.50-7.57 (m, 2H), 7.33-7.50 (m, 6H), 7.24-7.33 (m, 3H), 7.21 (dd, J=7.5, 1.7 Hz, 1H), 6.97-7.15 (m, 4H), 6.83 (d, J=6.8 Hz, 1H), 6.40 (d, J=8.1 Hz, 2H), 5.79 (d, J=16.3 Hz, 1H), 4.99 (d, J=16.3 Hz, 1H), 4.17 (t, J=6.1 Hz, 2H), 3.29-3.52 (m, 2H), 3.15-3.28 (m, 2H), 2.90 (s, 2H), 2.53-2.71 (m, 4H), 2.18-2.30 (m, 2H).

EXAMPLE 438

1-(2,4-dimethylbenzyl)-7-(2-morpholin-4-ylphenyl)-3-(3-(1-naphthyloxy)propyl)-1H-indole-2-carboxylic acid $^1$H NMR (300 MHz, DMSO-d$_6$) 13.05 (s, 1H), 8.23-8.34 (m, 1H), 7.84-7.92 (m, 1H), 7.80 (dd, J=7.5, 1.7 Hz, 1H), 7.49-7.59 (m, 2H), 7.46 (d, J=8.5 Hz, 1H), 7.30-7.41 (m, 2H), 7.00-7.13 (m, 3H), 6.88-6.98 (m, 2H), 6.86 (d, J=6.4 Hz, 1H), 6.52 (d, J=8.1 Hz, 1H), 5.65 (d, J=17.0 Hz, 1H), 5.41 (d, J=8.1 Hz, 1H), 4.99 (d, J=17.0 Hz, 1H), 4.20 (t, J=6.3 Hz, 2H), 3.38-3.53 (m, 2H), 3.12-3.25 (m, 2H), 2.79-3.01 (m, 2H), 2.51-2.60 (m, 4H), 2.17-2.35 (m, 2H), 2.02-2.10 (m, 3H), 1.59 (s, 3H).

EXAMPLE 439

1-(2,6-dichlorobenzyl)-7-(2-morpholin-4-ylphenyl)-3-(3-(1-naphthyloxyl)propyl)-1H-indole-2-carboxylic acid $^1$H NMR (300 MHz, DMSO-d$_6$) 12.90 (s, 1H), 8.23-8.31 (m, 1H), 7.83-7.90 (m, 1H), 7.74 (dd, J=7.5, 1.7 Hz, 1H), 7.48-7.57 (m, 2H), 7.45 (d, J=8.5 Hz, 1H), 7.30-7.42 (m, 2H), 7.27 (dd, J=7.6, 1.5 Hz, 1H), 7.15-7.23 (m, 3H), 6.98-7.14 (m, 4H), 6.80 (d, J=6.8 Hz, 1H), 5.80 (d, J=16.3 Hz, 1H), 4.97 (d, J=15.9 Hz, 1H), 4.06-4.18 (m, 2H), 3.19-3.34 (m, 4H), 2.95 (bs, 2H), 2.60-2.70 (m, 4H), 2.10-2.24 (m, 2H).

EXAMPLE 440

1-(4-carboxybenzyl)-7-(2-morpholin-4-ylphenyl)-3-(3-(1-naphthyloxyl)propyl)-1H-indole-2-carboxylic acid $^1$H NMR (300 MHz, DMSO-d$_6$) 13.14 (s, 1H), 12.79 (s, 1H), 8.23-8.32 (m, 1H), 7.83-7.91 (m, 1H), 7.79 (dd, J=5.8, 3.4 Hz, 1H), 7.55-7.61 (m, 2H), 7.49-7.55 (m, 2H), 7.45 (d, J=8.5 Hz, 2H), 7.32-7.41 (m, 2H), 7.01-7.14 (m, 4H), 6.95 (t, J=8.0 Hz, 1H), 6.84 (d, J=6.8 Hz, 1H), 6.37 (d, J=8.5 Hz, 2H), 5.86 (d, J=17.3 Hz, 1H), 5.02 (d, J=17.0 Hz, 1H), 4.16 (t, J=6.1 Hz, 2H), 3.38-3.50 (m, 2H), 3.13-3.27 (m, 2H), 2.81-2.97 (m, 2H), 2.52-2.70 (m, 4H), 2.16-2.31 (m, 2H).

EXAMPLE 441

7-(6,6-dimethylcyclohex-1-en-1-yl)-3-(3-(1-naphthyloxyl)propyl)-1H-indole-2-carboxylic acid $^1$H NMR (300 MHz, DMSO-d$_6$) 12.98 (s, 1H), 10.41 (s, 1H), 8.15-8.33 (m, 1H), 7.78-7.95 (m, 1H), 7.34-7.58 (m, 5H), 6.86-6.99 (m, 3H), 5.46 (t, J=3.6 Hz, 1H), 4.19 (t, J=6.1 Hz, 2H), 3.33-3.38 (m, 2H), 2.10-2.28 (m, 4H), 1.62-1.82 (m, 4H), 0.97 (s, 6H).

EXAMPLE 442

7-(5,5-dimethylcyclopent-1-en-1-yl)-3-(3-(1-naphthyloxyl)propyl)-1H-indole-2-carboxylic acid $^1$H NMR (300 MHz, DMSO-d$_6$) 13.04 (s, 1H), 10.19 (s, 1H), 8.16-8.30 (m, 1H), 7.79-7.92 (m, 1H), 7.42-7.63 (m, 4H), 7.34-7.42 (m, 1H), 6.93-7.08 (m, 2H), 6.90 (d, J=6.4 Hz, 1H), 5.78 (t, J=2.4 Hz, 1H), 4.19 (t, J=6.1 Hz, 2H), 3.33-3.42 (m, 2H), 2.42-2.49 (m, 2H), 2.13-2.29 (m, 2H), 1.90 (t, J=7.0 Hz, 2H), 1.11 (s, 6H).

EXAMPLE 443

3-(3-(1-naphthyloxyl)propyl)-7-(7-phenylcyclohept-1-en-1-yl)-1H-indole-2-carboxylic acid $^1$H NMR (300 MHz, DMSO-d$_6$) 13.02 (s, 1H), 10.25 (s, 1H), 8.13-8.24 (m, 1H), 7.80-7.90 (m, 1H), 7.32-7.58 (m, 7H), 7.24 (t, J=7.6 Hz, 2H), 7.10 (t, J=7.1 Hz, 1H), 6.97 (d, =6.1 Hz, 1H), 6.80-6.90 (m, 2H), 6.29 (t, J=6.3 Hz, 1H), 4.21 (t, J=4.7 Hz, 2H), 4.14 (t, J=5.9 Hz, 2H), 3.21-3.32 (m, 2H), 2.31-2.45 (m, 2H), 2.10-2.24 (m, 4H), 1.50-1.85 (m, 3H), 1.30-1.49 (m, 1H).

EXAMPLE 444

3-(3-(1-naphthyloxy)propyl)-7-tricyclo(4.3.1.1$^{3,8}$)undec-4-en-4-yl-1H-indole-2-carboxylic acid $^1$H NMR (300 MHz, DMSO-d$_6$) 13.15 (s, 1H), 9.53 (s, 1H), 8.12-8.32 (m, 1H), 7.72-7.93 (m, 1H), 7.27-7.62 (m, 5H), 7.01-7.07 (m, 1H), 6.93-7.01 (m, 1H), 6.87 (d, J=6.4 Hz, 1H), 6.30-6.42 (m, 1H), 4.17 (t, J=6.1 Hz, 2H), 3.33-3.41 (m, 2H), 2.63-2.71 (m, 1H), 2.11-2.26 (m, 4H), 1.70-2.06 (m, 11H).

EXAMPLE 445

3-(3-(1-naphthyloxy)propyl)-7-(2-phenylcyclohept-1-en-1-yl)-1H-indole-2-carboxylic acid $^1$H NMR (300 MHz, DMSO-d$_6$) 12.94 (s, 1H), 10.53 (s, 1H), 8.17-8.26 (m, 1H), 7.81-7.89 (m, 1H), 7.47-7.56 (m, 2H), 7.32-7.47 (m, 3H), 6.87-6.98 (m, 5H), 6.85 (d, J=6.4 Hz, 1H), 6.65-6.77 (m, 2H), 4.13 (t, J=6.1 Hz, 2H), 3.18-3.30 (m, 2H), 2.73-3.07 (m, 2H), 2.24-2.44 (m, 2H), 2.16 (t, J=6.6 Hz, 2H), 1.38-2.05 (m, 6H).

EXAMPLE 446

3-(3-(1-naphthyloxy)propyl)-7-(2,6,6-trimethylcyclohex-1-en-1-yl)-1H-indole-2-carboxylic acid $^1$H NMR (300 MHz, DMSO-d$_6$) 12.96 (s, 1H), 10.46 (s, 1H), 8.19-8.36 (m, 1H), 7.77-7.97 (m, 1H), 7.48-7.60 (m, 3H), 7.46 (d, J=8.1 Hz, 1H), 7.34-7.42 (m, 1H), 6.94-7.01 (m, 1H), 6.89 (d, J=6.8 Hz, 1H), 6.83 (d, J=6.1 Hz, 1H), 4.20 (t, J=6.1 Hz, 2H), 3.22-3.33 (m, 2H), 2.12-2.31 (m, 3H), 1.91-2.05 (m, 1H), 1.69-1.84 (m, 3H), 1.45-1.59 (m, 1H), 1.17 (s, 3H), 1.05 (s, 3H), 0.74 (s, 3H).

EXAMPLE 447

3-(3-(1-naphthyloxy)propyl)-7-((1R,4R)-1,7,7-trimethylbicyclo(2.2.1)hept-2-en-2-yl)-1H-indole-2-carboxylic acid $^1$H NMR (300 MHz, DMSO-$d_6$) 13.18 (s, 1H), 9.34 (s, 1H), 8.16-8.27 (m, 1H), 7.81-7.90 (m, 1H), 7.47-7.59 (m, 3H), 7.45 (d, J=8.1 Hz, 1H), 7.33-7.41 (m, 1H), 7.07 (d, J=7.3 Hz, 1H), 7.00 (t, J=7.5 Hz, 1H), 6.89 (d, J=7.5 Hz, 1H), 6.38 (d, J=3.6 Hz, 1H), 4.18 (t, J=5.9 Hz, 2H), 3.32-3.39 (m, 2H), 2.54 (t, J=3.4 Hz, 1H), 2.15-2.28 (m, 2H), 1.89-2.04 (m, 1H), 1.64-1.78 (m, 1H), 1.30-1.45 (m, 1H), 1.07-1.19 (m, 1H), 1.04 (s, 3H), 0.98 (s, 3H), 0.86 (s, 3H).

EXAMPLE 448

7-(2-methylphenyl)-3-(3-(1-naphthyloxyl)propyl)-4-(trifluoromethyl)-1H-indole-2-carboxylic acid $^1$H NMR (300 MHz, DMSO-$d_6$) 13.23 (s, 1H), 11.20 (s, 1H), 8.21-8.37 (m, 1H), 7.83-7.90 (m, 1H), 7.62 (d, J=7.8 Hz, 1H), 7.22-7.58 (m, 8H), 7.20 (d, J=7.5 Hz, 1H), 6.99 (d, J=7.1 Hz, 1H), 4.25 (t, J=5.8 Hz, 2H), 3.35-3.48 (m, 2H), 2.09-2.23 (m, 2H), 2.05 (s, 3H).

EXAMPLE 449

7-(2-morpholin-4-ylphenyl)-3-(3-(1-naphthyloxyl)propyl)-4-(trifluoromethyl)-1H-indole-2-carboxylic acid $^1$H NMR (300 MHz, DMSO-$d_6$) 13.51 (s, 1H), 10.79 (s, 1H), 8.23-8.38 (m, 1H), 7.82-7.91 (m, 1H), 7.67 (d, J=7.8 Hz, 1H), 7.35-7.57 (m, 7H), 7.15-7.27 (m, 2H), 6.94-7.04 (m, 1H), 4.25 (t, J=5.9 Hz, 2H), 3.37-3.51 (m, 2H), 3.07-3.36 (m, 4H), 2.71-2.87 (m, 4H), 2.17 (s, 2H).

EXAMPLE 450

1-(2-(dimethylamino)ethyl)-7-(2-methylphenyl)-3-(3-(1-naphthyloxyl)propyl)-1H-indole-2-carboxylic acid $^1$H NMR (300 MHz, DMSO-$d_6$) 8.14-8.30 (m, 1H), 7.84-7.92 (m, 1H), 7.80 (d, J=7.9 Hz, 1H), 7.32-7.59 (m, 8H), 7.15 (t, J=7.7 Hz, 1H), 6.99 (d, J=5.9 Hz, 1H), 6.92 (d, J=6.3 Hz, 1H), 4.45-4.78 (m, 1H), 4.23 (t, J=5.6 Hz, 2H), 3.42 (s, 3H), 3.35-3.41 (m, 2H), 3.19-3.23 (m, 3H), 2.70-2.75 (m, 2H), 2.17-2.35 (m, 4H), 2.00 (s, 3H).

EXAMPLE 451

7-(1,1'-biphenyl-2-ylmethyl)-3-(3-(1-naphthyloxy)propyl)-1H-indole-2-carboxylic acid $^1$H NMR (300 MHz, DMSO-$d_6$) 12.99 (s, 1H), 11.25 (s, 1H), 8.15-8.33 (m, 1H), 7.76-7.95 (m, 1H), 7.47-7.57 (m, 2H), 7.23-7.47 (m, 11H), 7.05-7.11 (m, 1H), 6.80-6.91 (m, 2H), 6.58 (d, J=6.7 Hz, 1H), 4.26 (s, 2H), 4.17 (t, J=5.9 Hz, 2H), 3.28-3.36 (m, 2H), 2.15-2.26 (m, 2H).

EXAMPLE 452

7-(1,1'-biphenyl-3-ylmethyl)-3-(3-(1-naphthyloxy)propyl)-1H-indole-2-carboxylic acid $^1$H NMR (300 MHz, DMSO-$d_6$) 13.05 (s, 1H), 11.39 (s, 1H), 8.06-8.34 (m, 1H), 7.81-7.89 (m, 1H), 7.68 (s, 1H), 7.61 (d, J=7.1 Hz, 2H), 7.30-7.56 (m, 12H), 7.23-7.30 (m, 1H), 7.07 (d, J=6.3 Hz, 1H), 6.89-6.97 (m, 1H), 6.87 (d, J=7.5 Hz, 1H), 4.38 (s, 2H), 4.16 (t, =5.9 Hz, 2H), 3.27-3.31 (m, 2H), 2.14-2.23 (m, 2H).

EXAMPLE 453

7-(1-(2-(1-naphthyloxyl)ethyl)vinyl)-3-(3-(1-naphthyloxy)propyl)-1H-indole-2-carboxylic acid $^1$H NMR (300 MHz, DMSO-$d_6$) 13.03 (s, 1H), 10.51 (s, 1H), 8.14-8.30 (m, 1H), 7.92 (d, J=7.5 Hz, 1H), 7.83-7.89 (m, 1H), 7.81 (d, J=7.5 Hz, 1H), 7.62 (d, J=8.1 Hz, 1H), 7.28-7.54 (m, 8H), 7.18 (d, J=6.1 Hz, 1H), 6.94-7.03 (m, 1H), 6.87 (d, J=7.5 Hz, 2H), 5.51 (s, 1H), 5.37 (d, J=1.7 Hz, 1H), 4.11-4.26 (m, 4H), 3.32-3.37 (m, 2H), 3.16 (t, J=6.1 Hz, 2H), 2.15-2.26 (m, 2H).

EXAMPLE 454

3-(3-(1-naphthyloxy)propyl)-7-(2-(phenoxymethyl)benzyl)-1H-indole-2-carboxylic acid $^1$H NMR (300 MHz, DMSO-$d_6$) 13.01 (s, 1H), 11.24 (s, 1H), 8.09-8.34 (m, 1H), 7.72-7.94 (m, 1H), 7.41-7.58 (m, 5H), 7.32-7.41 (m, 1H), 7.17-7.30 (m, 4H), 7.00 (dd, J=6.6, 2.5 Hz, 1H), 6.87-6.96 (m, 5H), 6.79-6.87 (m, 1H), 5.13 (s, 2H), 4.39 (s, 2H), 4.17 (t, J=6.1 Hz, 2H), 3.32-3.40 (m, 2H), 2.15-2.25 (m, 2H).

EXAMPLE 455

3-(3-(1-naphthyloxy)propyl)-7-(2-(2-phenoxyethyl)phenyl)-1H-indole-2-carboxylic acid $^1$H NMR (300 MHz, DMSO-$d_6$) 12.95 (s, 1H), 10.60 (s, 1H), 10.60 (s, 1H), 8.17-8.32 (m, 1H), 7.82-7.91 (m, 1H), 7.70-7.78 (m, 1H), 7.29-7.58 (m, 7H), 7.20-7.27 (m, 1H), 7.04-7.15 (m, 4H), 6.89 (d, J=6.4 Hz, 1H), 6.79 (t, J=7.5 Hz, 1H), 6.52 (d, J=7.8 Hz, 2H), 4.21 (t, J=6.1 Hz, 2H), 3.93 (t, J=7.6 Hz, 2H), 3.36-3.45 (m, 2H), 2.70-2.95 (m, 2H), 2.16-2.31 (m, 2H).

EXAMPLE 456

3-(3-(1-naphthyloxy)propyl)-7-(3-(2-phenoxyethyl)phenyl)-1H-indole-2-carboxylic acid $^1$H NMR (300 MHz, DMSO-$d_6$) 13.06 (s, 1H), 10.34 (s, 1H), 8.10-8.33 (m, 1H), 7.80-7.98 (m, 1H), 7.70 (d, J=7.8 Hz, 1H), 7.59 (s, 1H), 7.34-7.56 (m, 8H), 7.22-7.31 (m, 3H), 7.05-7.13 (m, 1H), 6.95 (d, J=8.8 Hz, 2H), 6.85-6.93 (m, 2H), 4.26 (t, J=6.8 Hz, 2H), 4.19 (t, J=5.9 Hz, 2H), 3.35-3.43 (m, 2H), 3.14 (t, J=6.8 Hz, 2H), 2.16-2.32 (m, 2H).

EXAMPLE 457

3-(3-(1-naphthyloxy)propyl)-7-(2-(3-phenoxypropyl)phenyl)-1H-indole-2-carboxylic acid $^1$H NMR (300 MHz, DMSO-d$_6$) 12.92 (s, 1H), 10.50 (s, 1H), 8.09-8.41 (m, 1H), 7.82-8.01 (m, 1H), 7.70 (dd, J=6.4, 2.7 Hz, 1H), 7.47-7.57 (m, 2H), 7.45 (d, J=8.5 Hz, 1H), 7.33-7.42 (m, 2H), 7.25-7.32 (m, 1H), 7.18-7.24 (m, 2H), 7.12-7.18 (m, 2H), 7.01-7.09 (m, 2H), 6.88 (d, J=7.5 Hz, 1H), 6.83 (t, J=7.3 Hz, 1H), 6.66 (d, J=7.8 Hz, 2H), 4.20 (t, J=6.1 Hz, 2H), 3.56-3.75 (m, 2H), 3.29-3.41 (m, 2H), 2.63 (d, J=6.1 Hz, 2H), 2.18-2.31 (m, 2H), 1.68-1.84 (m, 2H).

EXAMPLE 458

3-(3-(1-naphthyloxy)propyl)-7-(3-(3-phenoxypropyl)phenyl)-1H-indole-2-carboxylic acid $^1$H NMR (300 MHz, DMSO-d$_6$) 13.03 (s, 1H), 10.32 (s, 1H), 8.05-8.32 (m, 1H), 7.80-7.98 (m, 1H), 7.69 (d, J=7.8 Hz, 1H), 7.34-7.56 (m, 7H), 7.22-7.32 (m, 3H), 7.20 (d, J=6.1 Hz, 1H), 7.03-7.11 (m, 1H), 6.86-6.97 (m, 4H), 4.19 (t, J=6.1 Hz, 2H), 4.01 (t, J=6.4 Hz, 2H), 3.37 (t, J=7.5 Hz, 2H), 2.80-2.90 (m, 2H), 2.16-2.32 (m, 2H), 2.01-2.16 (m, 2H).

EXAMPLE 459

3-(3-(3-hydroxy-2-methylphenoxy)propyl)-7-(2-methylphenyl)-1H-indole-2-carboxylic acid $^1$H NMR (300 MHz, DMSO-d$_6$) 12.88 (br. s, 1H), 10.44 (br. s, 1H), 9.17 (s, 1H), 7.66 (d, 1H), 7.20-7.36 (m, 4H), 7.11 (t, 1H), 7.02-7.06 (m, 1H), 6.88 (t, 1H), 6.42 (d, 1H), 6.35 (d, 1H), 3.96 (t, 2H), 3.25 (t, 2H), 2.04-2.12 (m, 5H), 2.02 (s, 3H).

EXAMPLE 460

3-(3-(3-(2-methoxyethoxy)-2-methylphenoxy)propyl)-7-(2-methylphenyl)-1H-indole-2-carboxylic acid $^1$H NMR (300 MHz, DMSO-d$_6$) 12.91 (br. s, 1H), 10.46 (s, 1H), 7.65 (d, 1H), 7.19-7.37 (m, 4H), 7.01-7.14 (m, 3H), 6.51-6.61 (m, 2H), 4.05-4.09 (m, 2H), 4.00 (t, 2H), 3.65-3.69 (m, 2H), 3.33 (s, 3H), 3.23-3.29 (m, 2H), 2.02-2.15 (m, 8H).

EXAMPLE 461

7-(1,2-dimethylprop-1-enyl)-3-(3-(1-naphthyloxy)propyl)-1H-indole-2-carboxylic acid $^1$H NMR (300 MHz, DMSO-d$_6$) 12.95 (br. s, 1H), 10.63 (s, 1H), 8.22-8.29 (m, 1H), 7.83-7.90 (m, 1H), 7.33-7.59 (m, 5H), 6.84-7.00 (m, 3H), 4.18 (t, 2H), 3.27-3.37 (m, 2H), 2.16-2.26 (m, 2H), 1.94 (s, 3H), 1.84 (s, 3H), 1.40 (s, 3H).

EXAMPLE 462

3-(3-(2-methyl-3-(2-morpholin-4-ylethoxy)phenoxy)propyl)-7-(2-methylphenyl)-1H-indole-2-carboxylic acid $^1$H NMR (300 MHz, DMSO-d$_6$) 12.88 (br. s, 1H), 10.50 (s, 1H), 7.65 (d, 1H), 7.16-7.36 (m, 4H), 7.02-7.16 (m, 3H), 6.58-6.68 (m, 2H), 4.33 (t, 2H), 3.99-4.04 (m, 4H), 3.49-3.75 (m, 6H), 3.23-3.28 (m, 4H), 2.07-2.14 (m, 5H), 2.05 (s, 3H).

EXAMPLE 463

3-(3-(2,3-dichlorophenoxyl)propyl)-7-(2-morpholin-4-ylphenyl)-1H-indole-2-carboxylic acid $^1$H NMR (300 MHz, DMSO-d$_6$) 13.04 (br. s, 1H), 10.04 (s, 1H), 7.71 (d, 1H), 7.31-7.45 (m, 3H), 7.27 (t, 1H), 7.09-7.22 (m, 4H), 7.00-7.07 (m, 1H), 4.09 (t, 2H), 3.18-3.34 (m, 6H), 2.73-2.81 (m, 4H), 2.09-2.19 (m, 2H).

EXAMPLE 464

1-(2-morpholin-4-ylethyl)-7-(2-morpholin-4-ylphenyl)-3-(3-(5,6,7,8-tetrahydronaphthalen-1-yloxy)propyl)-1H-indole-2-carboxylic acid $^1$H NMR (300 MHz, DMSO-d$_6$) 13.31 (br. s, 1H), 7.71-7.80 (m, 1H), 7.50-7.56 (m, 1H), 7.40-7.46 (m, 1H), 7.14-7.23 (m, 3H), 7.07 (d, 1H), 6.99 (t, 1H), 6.59-6.65 (m, 2H), 3.96 (t, 2H), 3.19-3.35 (m, 10H), 3.08-3.18 (m, 4H), 2.55-2.89 (m, 10H), 2.00-2.14 (m, 3H), 1.56-1.85 (m, 5H).

EXAMPLE 465

7-(2-methylphenyl)-3-(3-(1-naphthylthio)propyl)-1H-indole-2-carboxylic acid $^1$H NMR (300 MHz, DMSO-d$_6$) 12.89 (br. s, 1H), 10.48 (s, 1H), 8.23-8.28 (m, 1H), 7.92-7.97 (m, 1H), 7.78 (d, 1H), 7.54-7.64 (m, 3H), 7.46-7.50 (m, 1H), 7.42 (t, 1H), 7.30-7.35 (m, 2H), 7.24-7.29 (m, 1H), 7.19-7.23 (m, 1H), 7.08 (t, 1H), 7.01-7.05 (m, 1H), 3.24 (t, 2H), 3.11 (t, 2H), 2.04 (s, 3H), 1.94-2.02 (m, 2H).

EXAMPLE 466

3-(3-(3-(2-methoxyethoxy)-5-methylphenoxy)propyl)-7-(2-methylphenyl)-1H-indole-2-carboxylic acid $^1$H NMR (300 MHz, DMSO-d$_6$) 12.86 (br. s, 1H), 10.41 (s, 1H), 7.67 (d, 1H), 7.31-7.34 (m, 2H), 7.20-7.30 (m, 2H), 7.11 (t, 1H), 7.02-7.06 (m, 1H), 6.30-6.35 (m, 2H), 6.25-6.28 (m, 1H), 4.00-4.05 (m, 2H), 3.96 (t, 2H), 3.59-3.65 (m, 2H), 3.21 (t, 2H), 2.21 (s, 3H), 2.00-2.11 (m, 5H).

EXAMPLE 467

7-(2-morpholin-4-ylphenyl)-3-(3-(5,6,7,8-tetrahydronaphthalen-1-yloxy)propyl)-1H-indole-2-carboxylic acid $^1$H NMR (300 MHz, DMSO-d$_6$) 13.04 (br. s, 1H), 10.02 (s, 1H), 7.70 (d, 1H), 7.33-7.45 (m, 3H), 7.12-7.22 (m, 3H), 6.97 (t, 1H), 6.61 (t, 2H), 3.96 (t, 2H), 3.20-3.30 (m, 6H), 2.73-2.82 (m, 4H), 2.69 (t, 2H), 2.62 (t, 2H), 2.04-2.16 (m, 2H), 1.63-1.80 (m, 4H).

EXAMPLE 468

3-(3-(3-methyl-5-(3-morpholin-4-ylpropoxy)phenoxy)propyl)-7-(2-methylphenyl)-1H-indole-2-carboxylic acid $^1$H NMR (500 MHz, CDCl$_3$) δ 8.41 (s, 1H), 7.71 (s, 1H), 7.27-7.40 (m, 4H), 7.16-7.24 (m, 2H), 6.34 (s, 1H), 6.21-6.29

(m, 2H), 3.99-4.09 (m, 6H), 3.93 (t, 2H), 3.65-3.74 (m, 2H), 3.23-3.39 (m, 4H), 2.85-2.98 (m, 2H), 2.11-2.30 (m, 10H).

EXAMPLE 469

3-(3-(3-(3-cyclohexylpropoxy)-5-methylphenoxy)propyl)-7-(2-methylphenyl)-1H-indole-2-carboxylic acid

EXAMPLE 469A ethyl 7-bromo-3-(3-(3-hydroxy-5-methylphenoxy)propyl)-1H-indole-2-carboxylate A suspension of ethyl 7-bromo-3-(3-hydroxypropyl)-1H-indole-2-carboxylate (EXAMPLE 1C) (0.9 g), 5-methylbenzene-1,3-diol (1.028 g), triphenylphosphine (0.868 g), dibenzylazodicarboxylate (0.762 g) and tetrahydrofuran (40 ml) was stirred at room temperature for 19 hours. After removal of the solvent, the crude product was purified by flash chromatography silica gel, (Analogix, SF65-200 g) eluting with 0-10% ethyl acetate in hexane.

EXAMPLE 469B ethyl 7-bromo-3-(3-(3-hydroxy-5-methylphenoxy)propyl)-1H-indole-2-carboxylate A suspension of EXAMPLE 469A (0.067 g), 3-cyclohexylpropan-1-ol (0.22 g), triphenylphosphine (0.081 g), dibenzylazodicarboxylate (0.071 g) in tetrahydrofuran (3 ml) was stirred at room temperature for 2 hours. The sample was directly purified by flash chromatography, silica gel, (Analogix, SF25-40 g) eluting with 0 to 20% ethyl acetate in hexane.

EXAMPLE 469C 3-(3-(3-(3-cyclohexylpropoxy)-5-methylphenoxy)propyl)-7-(2-methylphenyl)-1H-indole-2-carboxylic acid The title compound was prepared according to the procedure for EXAMPLE 164G, substituting EXAMPLE 164F with EXAMPLE 469B. $^1$H NMR (500 MHz, CDCl$_3$) δ 8.41 (s, 1H), 7.68-7.76 (m, 1H), 7.28-7.39 (m, 4H), 7.16-7.23 (m, 2H), 6.24-6.35 (m, 3H), 4.00 (t, 2H), 3.88 (t, 2H), 3.33 (t, 2H), 2.15-2.28 (m, 8H), 1.61-1.79 (m, 7H), 1.09-1.35 (m, 6H), 0.83-0.96 (m, 2H).

EXAMPLE 470

3-(3-(3-(3-(2-carboxy-1H-indol-3-yl)propoxy)-5-methylphenoxy)propyl)-7-(2-morpholin-4-ylphenyl)-1H-indole-2-carboxylic acid $^1$H NMR (300 MHz, DMSO-d$_6$) 11.42 (s, 1H), 10.04 (s, 1H), 7.71 (d, 1H), 7.63 (d, 1H), 7.31-7.44 (m, 4H), 7.12-7.23 (m, 4H), 6.96-7.01 (m, 1H), 6.15-6.32 (m, 3H), 3.86-3.94 (m, 4H), 3.22-3.28 (m, 5H), 3.14-3.20 (m, 4H), 2.71-2.81 (m, 4H), 2.18 (s, 3H), 1.97-2.10 (m, 4H).

EXAMPLE 471

7-bromo-3-(3-(1-naphthyloxy)propyl)-1-(pyridin-4-ylmethyl)-1H-indole-2-carboxylic acid $^1$H NMR (300 MHz, DMSO-d$_6$) 8.66-8.77 (m, 2H), 8.12 (d, 1H), 7.88 (t, 2H), 7.36-7.56 (m, 7H), 7.01 (t, 1H), 6.89 (d, 1H), 6.34 (s, 2H), 4.21 (t, 2H), 3.38 (t, 2H), 2.20-2.29 (m, 2H).

EXAMPLE 473

7-(2-morpholin-4-ylphenyl)-3-(3-(1-naphthyloxy)propyl)-1-(pyridin-4-ylmethyl)-1H-indole-2-carboxylic acid $^1$H NMR (500 MHz, DMSO-d$_6$) 13.47 (br. s, 1H), 8.46 (d, 2H), 8.25-8.31 (m, 1H), 7.83-7.91 (m, 2H), 7.50-7.58 (m, 2H), 7.47 (d, 1H), 7.39 (t, 1H), 7.29-7.34 (m, 1H), 7.15 (t, 1H), 7.02-7.10 (m, 2H), 6.88 (d, 1H), 6.69-6.81 (m, 4H), 6.20 (d, 1H), 5.25 (d, 1H), 4.22 (t, 2H), 3.38-3.53 (m, 2H), 3.19-3.26 (m, 2H), 2.88-3.05 (m, 2H), 2.60-2.76 (m, 4H), 2.22-2.33 (m, 2H).

EXAMPLE 474

7-(1,1'-bi(cyclohexan)-2-en-2-yl)-3-(3-(1-naphthyloxy)propyl)-1H-indole-2-carboxylic acid $^1$H NMR (500 MHz, DMSO-d$_6$) 13.04 (br. s, 1H), 10.39 (s, 1H), 8.22-8.28 (m, 1H), 7.84-7.89 (m, 1H), 7.48-7.57 (m, 3H), 7.44 (d, 1H), 7.37 (t, 1H), 6.92-7.02 (m, 2H), 6.87 (d, 1H), 5.90-5.97 (m, 1H), 4.16 (t, 2H), 2.77-2.86 (m, 1H), 2.02-2.26 (m, 4H), 1.58-1.82 (m, 4H), 1.38-1.57 (m, 4H), 1.12-1.37 (m, 3H), 0.80-1.11 (m, 5H), 0.58-0.71 (m, 1H).

EXAMPLE 475

3-(3-(2,3-dichlorophenoxyl)propyl)-7-(1,2-dimethylprop-1-enyl)-1H-indole-2-carboxylic acid $^1$H NMR (500 MHz, DMSO-d$_6$) 12.88 (br. s, 1H), 10.63 (s, 1H), 7.50 (s, 1H), 7.28 (t, 1H), 7.17-7.21 (m, 1H), 7.04-7.08 (m, 1H), 6.97 (t, 1H), 6.88-6.92 (m, 1H), 4.09 (t, 2H), 3.22 (t, 2H), 2.05-2.14 (m, 2H), 1.94 (s, 3H), 1.83 (s, 3H), 1.40 (s, 3H).

EXAMPLE 476

7-(2-methylphenyl)-3-(3-(1-naphthyloxyl)propyl)-1-(pyridin-2-ylmethyl)-1H-indole-2-carboxylic acid $^1$H NMR (300 MHz, DMSO-d$_6$) 13.26 (br. s, 1H), 8.30-8.35 (m, 1H), 8.22-8.27 (m, 1H), 7.81-7.91 (m, 2H), 7.64-7.70 (m, 1H), 7.37-7.58 (m, 4H), 7.08-7.34 (m, 4H), 6.80-6.99 (m, 4H), 6.24-6.33 (m, 1H), 5.52 (d, 1H), 5.22 (d, 1H), 4.25 (t, 2H), 3.35-3.49 (m, 2H), 2.24-2.33 (m, 2H), 1.78 (s, 3H).

EXAMPLE 477

7-(2-methyl-4-(trifluoromethyl)phenyl)-3-(3-(2,3,5-trimethylphenoxyl)propyl)-1H-indole-2-carboxylic acid $^1$H NMR (300 MHz, DMSO-d$_6$) 12.74 (br. s, 1H), 10.96 (s, 1H), 7.65-7.73 (m, 2H), 7.57-7.62 (m, 1H), 7.42 (d, 1H), 7.13

(t, 1H), 7.06 (d, 1H), 6.54 (d, 2H), 3.97 (t, 2H), 3.23-3.30 (m, 2H), 2.15-2.20 (m, 6H), 2.05-2.14 (m, 8H).

EXAMPLE 478

7-(4-fluoro-2-methylphenyl)-3-(3-(2,3,5-trimethylphenoxyl)propyl)-1H-indole-2-carboxylic acid $^1$H NMR (500 MHz, DMSO-d$_6$) 12.89 (br. s, 1H), 10.69 (s, 1H), 7.66 (d, 1H), 7.13 (d, 5H), 6.54 (d, 2H), 3.97 (t, 2H), 3.25 (t, 2H), 2.14-2.20 (m, 6H), 2.00-2.13 (m, 8H).

EXAMPLE 479

7-(4-methoxy-2-methylphenyl)-3-(3-(2,3,5-trimethylphenoxyl)propyl)-1H-indole-2-carboxylic acid $^1$H NMR (400 MHz, DMSO-d$_6$) 10.30 (s, 1H), 7.60-7.66 (m, 1H), 7.05-7.17 (m, 2H), 6.99-7.03 (m, 1H), 6.89-6.92 (m, 1H), 6.82-6.87 (m, 1H), 6.51-6.57 (m, 2H), 3.97 (t, 2H), 3.81 (s, 3H), 2.15-2.20 (m, 6H), 2.02-2.10 (m, 8H).

EXAMPLE 480

7-(2-methylphenyl)-3-(3-(1-naphthyloxyl)propyl)-1-(pyridin-3-ylmethyl)-1H-indole-2-carboxylic acid $^1$H NMR (400 MHz, DMSO-d$_6$) 8.39-8.44 (m, 1H), 8.21-8.28 (m, 1H), 7.80-7.92 (m, 2H), 7.36-7.65 (m, 5H), 7.23-7.34 (m, 2H), 7.11-7.20 (m, 2H), 7.05 (t, 1H), 6.86-6.99 (m, 4H), 5.45 (d, 1H), 5.22 (d, 1H), 4.25 (t, 2H), 2.23-2.32 (m, 2H), 1.73 (s, 3H).

EXAMPLE 481

6-methyl-7-(2-methylphenyl)-3-(3-(1-naphthyloxy)propyl)-1H-indole-2-carboxylic acid $^1$H NMR (400 MHz, DMSO-d$_6$) 12.82 (br. s, 1H), 9.78 (s, 1H), 8.22-8.28 (m, 1H), 7.84-7.90 (m, 1H), 7.49-7.62 (m, 3H), 7.45 (d, 1H), 7.25-7.42 (m, 4H), 7.09 (d, 1H), 6.99 (d, 1H), 6.90 (d, 1H), 4.20 (t, 2H), 2.18-2.28 (m, 2H), 2.02 (s, 3H), 1.92 (s, 3H).

EXAMPLE 482

3-(3-(2,3-dichlorophenoxyl)propyl)-7-(2-methylphenyl)-1-(pyridin-2-ylmethyl)-1H-indole-2-carboxylic acid $^1$H NMR (400 MHz, DMSO-d$_6$) 12.96 (br. s, 1H), 8.22-8.27 (m, 1H), 7.76-7.84 (m, 1H), 7.50-7.57 (m, 1H), 7.30 (t, 1H), 7.05-7.26 (m, 6H), 6.99 (t, 1H), 6.91-6.95 (m, 1H), 6.83-6.88 (m, 1H), 6.06-6.12 (m, 1H), 5.46 (d, 1H), 5.19 (d, 1H), 4.16 (t, 2H), 2.09-2.21 (m, 2H), 1.76 (s, 3H).

EXAMPLE 483

7-(2-methylphenyl)-1-(2-morpholin-4-yl-2-oxoethyl)-3-(3-(1-naphthyloxyl)propyl)-1H-indole-2-carboxylic acid $^1$H NMR (400 MHz, DMSO-d$_6$) 8.23-8.30 (m, 1H), 7.84-7.90 (m, 1H), 7.76 (d, 1H), 7.49-7.59 (m, 2H), 7.31-7.49 (m, 4H), 7.22-7.30 (m, 1H), 7.02-7.15 (m, 2H), 6.88-6.95 (m, 2H), 5.00-5.13 (m, 1H), 4.66-4.81 (m, 1H), 4.23 (t, 2H), 3.07-3.30 (m, 2H), 2.65-2.86 (m, 2H), 2.16-2.29 (m, 2H), 1.95 (s, 3H).

EXAMPLE 484

3-(3-(3,5-dichlorophenoxyl)propyl)-7-(2-methylphenyl)-1H-indole-2-carboxylic acid $^1$H NMR (400 MHz, DMSO-d$_6$) 10.33 (s, 1H), 7.64 (d, 1H), 7.17-7.33 (m, 4H), 6.99-7.13 (m, 3H), 6.93-6.96 (m, 2H), 4.02 (t, 2H), 3.20 (t, 2H), 2.00-2.10 (m, 5H).

EXAMPLE 485

1-methyl-7-(2-methylphenyl)-3-(3-(1-naphthyloxy)propyl)-1H-indole-2-carboxylic acid $^1$H NMR (500 MHz, DMSO-d$_6$) 8.22-8.25 (m, 1H), 7.85-7.89 (m, 1H), 7.74 (d, 1H), 7.49-7.58 (m, 2H), 7.46 (d, 1H), 7.22-7.43 (m, 5H), 7.05-7.10 (m, 1H), 6.98 (d, 1H), 6.91 (d, 1H), 4.21 (t, 2H), 3.32 (s, 3H), 2.19-2.26 (m, 2H), 1.99 (s, 3H).

EXAMPLE 486

1-methyl-7-(2-morpholin-4-ylphenyl)-3-(3-(1-naphthyloxyl)propyl)-1H-indole-2-carboxylic acid $^1$H NMR (500 MHz, DMSO-d$_6$) 8.22-8.29 (m, 1H), 7.84-7.89 (m, 1H), 7.71 (d, 1H), 7.50-7.57 (m, 2H), 7.45 (d, 1H), 7.34-7.42 (m, 3H), 7.08-7.16 (m, 2H), 7.03 (t, 2H), 6.86 (d, 1H), 4.17 (t, 2H), 3.34-3.40 (m, 5H), 3.09-3.16 (m, 2H), 2.78-2.88 (m, 2H), 2.52-2.63 (m, 4H), 2.18-2.27 (m, 2H).

EXAMPLE 487

1-(3-(aminomethyl)benzyl)-7-(2-methylphenyl)-3-(3-(1-naphthyloxyl)propyl)-1H-indole-2-carboxylic acid $^1$H NMR (400 MHz, DMSO-d$_6$) 13.15 (br. s, 1H), 8.21-8.29 (m, 1H), 8.01 (s, 2H), 7.76-7.92 (m, 2H), 7.34-7.59 (m, 3H), 7.23-7.32 (m, 1H), 7.02-7.23 (m, 4H), 6.86-7.01 (m, 2H), 6.45 (s, 1H), 6.10 (d, 1H), 5.42 (d, 1H), 5.19 (d, 1H), 4.24 (t, 2H), 3.83 (dd, 2H), 3.40 (t, 2H), 2.20-2.33 (m, 2H).

EXAMPLE 488

1-(3-(aminomethyl)benzyl)-7-(2-morpholin-4-ylphenyl)-3-(3-(1-naphthyloxyl)propyl)-1H-indole-2-carboxylic acid $^1$H NMR (400 MHz, DMSO-d$_6$) 8.26-8.31 (m, 1H), 7.91-8.09 (m, 2H), 7.85-7.90 (m, 1H), 7.76-7.83 (m, 1H), 7.49-7.59 (m, 2H), 7.46 (d, 1H), 7.38 (t, 2H), 6.93-7.19 (m, 7H), 6.84 (d, 1H), 6.50 (s, 1H), 6.13 (d, 1H), 5.81 (d, 1H), 4.97 (d, 1H), 4.17 (t, 2H), 3.76-3.82 (m, 2H), 3.30-3.38 (m, 2H), 3.18-3.25 (m, 2H), 2.80-2.99 (m, 2H), 2.53-2.66 (m, 4H), 2.16-2.29 (m, 2H).

EXAMPLE 489

7-((E)-2-(2-((E)-2-cyclohexylvinyl)phenyl)vinyl)-3-(3-(1-naphthyloxyl)propyl)-1H-indole-2-carboxylic acid $^1$H NMR (400 MHz, DMSO-d$_6$) 11.66 (s, 1H), 8.18-8.23 (m, 1H), 7.92-8.03 (m, 2H), 7.81-7.88 (m, 1H), 7.68 (d, 1H), 7.32-7.63 (m, 7H), 7.17-7.32 (m, 2H), 7.01 (t, 1H), 6.80-6.90 (m, 2H), 6.02-6.12 (m, 1H), 4.16 (t, 2H), 2.15-2.29 (m, 2H), 1.57-1.85 (m, 5H), 1.11-1.37 (m, 6H).

EXAMPLE 490

7-(2-(3-carboxyphenyl)ethyl)-3-(3-(1-naphthyloxyl)propyl)-1H-indole-2-carboxylic acid $^1$H NMR (400 MHz, DMSO-d$_6$) 11.42 (s, 1H), 8.20-8.25 (m, 1H), 7.95 (s, 1H), 7.82-7.88 (m, 1H), 7.77 (d, 1H), 7.58 (d, 1H), 7.47-7.55 (m, 3H), 7.32-7.46 (m, 3H), 7.06 (d, 1H), 6.84-6.92 (m, 1H), 4.16 (t, 2H), 2.93-3.01 (m, 2H), 2.14-2.25 (m, 2H).

EXAMPLE 491

3-(3-(1-naphthyloxy)propyl)-7-((E)-2-(2-pyridin-3-ylphenyl)vinyl)-1H-indole-2-carboxylic acid $^1$H NMR (400 MHz, DMSO-d$_6$) 11.74 (s, 1H), 8.72-8.76 (m, 2H), 8.04-8.25 (m, 4H), 7.82-7.88 (m, 1H), 7.71-7.78 (m, 1H), 7.26-7.62 (m, 9H), 7.06 (d, 1H), 6.93 (t, 1H), 6.86 (d, 1H), 4.16 (t, 2H), 3.34 (t, 2H), 2.16-2.25 (m, 2H).

EXAMPLE 492

3-(3-(1-naphthyloxyl)propyl)-7-(2-(3-(((phenylsulfonyl)amino)carbonyl)phenyl)ethyl)-1H-indole-2-carboxylic acid $^1$H NMR (400 MHz, DMSO-d$_6$) 12.52 (br. s, 1H), 11.43 (s, 1H), 8.21-8.26 (m, 1H), 7.99-8.06 (m, 2H), 7.90 (s, 1H), 7.84-7.88 (m, 1H), 7.62-7.77 (m, 4H), 7.48-7.60 (m, 4H), 7.34-7.47 (m, 3H), 7.06 (d, 1H), 6.85-6.93 (m, 2H), 4.16 (t, 2H), 3.19-3.25 (m, 2H), 2.92-2.98 (m, 2H), 2.16-2.24 (m, 2H).

EXAMPLE 493

7-(2-(3-((4-methylpiperidin-1-yl)carbonyl)phenyl)ethyl)-3-(3-(1-naphthyloxy)propyl)-1H-indole-2-carboxylic acid $^1$H NMR (400 MHz, DMSO-d$_6$) 12.95 (br. s, 1H), 11.37 (s, 1H), 7.83-7.89 (m, 1H), 7.42-7.57 (m, 4H), 7.30-7.42 (m, 3H), 7.27 (s, 1H), 7.14 (d, 1H), 7.03 (d, 1H), 6.85-6.91 (m, 2H), 4.17 (t, 2H), 3.32 (t, 2H), 3.22-3.28 (m, 2H), 2.94-3.00 (m, 2H), 2.63-2.92 (m, 2H), 2.14-2.25 (m, 2H), 1.39-1.75 (m, 3H), 0.93-1.13 (m, 2H), 0.90 (d, 3H).

EXAMPLE 494

3-(3-(1-naphthyloxyl)propyl)-7-(2-(3-(((2-pyrrolidin-1-ylethyl)amino)carbonyl)phenyl)ethyl)-1H-indole-2-carboxylic acid $^1$H NMR (400 MHz, DMSO-d$_6$) 12.96 (br. s, 1H), 11.42 (s, 1H), 9.36 (s, 1H), 8.60-8.66 (m, 1H), 8.20-8.26 (m, 1H), 7.81-7.91 (m, 2H), 7.67-7.72 (m, 1H), 7.48-7.59 (m, 4H), 7.33-7.48 (m, 3H), 7.06 (d, 1H), 6.85-6.93 (m, 2H), 4.17 (t, 2H), 3.56-3.69 (m, 4H), 2.95-3.12 (m, 4H), 2.15-2.25 (m, 2H), 1.97-2.07 (m, 2H), 1.80-1.92 (m, 2H).

EXAMPLE 495

7-(2-(3-(((2-morpholin-4-ylethyl)amino)carbonyl)phenyl)ethyl)-3-(3-(1-naphthyloxyl)propyl)-1H-indole-2-carboxylic acid $^1$H NMR (400 MHz, DMSO-d$_6$) 12.98 (br. s, 1H), 11.42 (s, 1H), 9.55 (s, 1H), 8.62-8.69 (m, 1H), 8.20-8.25 (m, 1H), 7.81-7.90 (m, 2H), 7.69 (d, 1H), 7.47-7.59 (m, 4H), 7.33-7.47 (m, 3H), 7.06 (d, 1H), 6.85-6.94 (m, 2H), 4.17 (t, 2H), 3.97-4.05 (m, 2H), 3.50-3.71 (m, 6H), 3.06-3.21 (m, 4H), 2.95-3.04 (m, 2H), 2.16-2.25 (m, 2H).

EXAMPLE 496

7-(2-(3-(((2-(dimethylamino)ethyl)amino)carbonyl)phenyl)ethyl)-3-(3-(1-naphthyloxy)propyl)-1H-indole-2-carboxylic acid $^1$H NMR (400 MHz, DMSO-d$_6$) 12.94 (br. s, 1H), 11.41 (s, 1H), 9.26 (s, 1H), 8.58-8.64 (m, 1H), 8.19-8.27 (m, 1H), 7.81-7.88 (m, 2H), 7.68 (d, 1H), 7.47-7.58 (m, 4H), 7.33-7.47 (m, 3H), 7.06 (d, 1H), 6.84-6.94 (m, 2H), 4.17 (t, 2H), 3.33 (t, 2H), 3.21-3.30 (m, 4H), 2.95-3.04 (m, 2H), 2.85 (s, 6H), 2.16-2.26 (m, 2H).

EXAMPLE 497

3-(3-(1-naphthyloxyl)propyl)-7-((E)-2-(3-(((phenylsulfonyl)amino)carbonyl)phenyl)vinyl)-1H-indole-2-carboxylic acid $^1$H NMR (400 MHz, DMSO-d$_6$) 13.10 (br. s, 1H), 12.59 (br. s, 1H), 11.71 (s, 1H), 8.13-8.27 (m, 3H), 7.95-8.07 (m, 3H), 7.82-7.89 (m, 1H), 7.60-7.77 (m, 6H), 7.47-7.57 (m, 3H), 7.44 (d, 1H), 7.29-7.41 (m, 2H), 7.02 (t, 1H), 6.88 (d, 1H), 4.17 (t, 2H), 3.35 (t, 2H), 2.17-2.27 (m, 2H).

EXAMPLE 498

3-(3-(1-naphthyloxy)propyl)-7-((E)-2-(2-pyridin-4-ylphenyl)vinyl)-1H-indole-2-carboxylic acid $^1$H NMR (400 MHz, DMSO-d$_6$) 13.13 (br. s, 1H), 11.75 (s, 1H), 8.81-8.88 (m, 2H), 8.15-8.27 (m, 3H), 7.83-7.89 (m, 1H), 7.76-7.80 (m, 2H), 7.56-7.64 (m, 2H), 7.42-7.55 (m, 5H), 7.32-7.40 (m, 2H), 7.10 (d, 1H), 6.94 (t, 1H), 6.86 (d, 1H), 4.16 (t, 2H), 3.34 (t, 2H), 2.16-2.26 (m, 2H).

EXAMPLE 499

7-((E)-2-(3-chlorophenyl)vinyl)-3-(3-(1-naphthyloxy)propyl)-1H-indole-2-carboxylic acid $^1$H NMR (400 MHz, DMSO-d$_6$) 13.11 (br. s, 1H), 11.68 (s, 1H), 8.12-8.27 (m, 2H), 7.83-7.89 (m, 2H), 7.60-7.72 (m, 3H), 7.48-7.57 (m, 2H), 7.26-7.47 (m, 5H), 6.99-7.08 (m, 1H), 6.88 (d, 1H), 4.18 (t, 2H), 3.35 (t, 2H), 2.17-2.28 (m, 2H).

EXAMPLE 500

7-((E)-2-(3-((cyclohexylamino)carbonyl)phenyl)vinyl)-3-(3-(1-naphthyloxy)propyl)-1H-indole-2-carboxylic acid $^1$H NMR (400 MHz, DMSO-d$_6$) 13.08 (br. s, 1H), 11.73 (s, 1H), 8.13-8.26 (m, 3H), 8.05-8.09 (m, 1H), 7.92-7.97 (m, 1H), 7.83-7.89 (m, 1H), 7.69 (d, 2H), 7.62 (d, 1H), 7.48 (d, 4H), 7.36 (d, 2H), 7.03 (t, 1H), 6.88 (d, 1H), 4.18 (t, 2H), 3.73-3.85 (m, 1H), 2.16-2.28 (m, 2H), 1.81-1.91 (m, 2H), 1.71-1.79 (m, 2H), 1.26-1.38 (m, 6H).

EXAMPLE 501

3-(3-(1-naphthyloxyl)propyl)-7-((E)-2-(3-(((2-phenoxyethyl)amino)carbonyl)phenyl)vinyl)-1H-indole-2-carboxylic acid $^1$H NMR (400 MHz, DMSO-d$_6$) 13.08 (br. s, 1H), 8.69-8.74 (m, 1H), 8.10-8.27 (m, 3H), 7.95 (d, 1H), 7.82-7.89 (m, 1H), 7.67-7.76 (m, 2H), 7.62 (d, 1H), 7.43-7.56 (m, 4H), 7.22-7.41 (m, 4H), 6.85-7.07 (m, 5H), 4.11-4.21 (m, 4H), 3.63-3.71 (m, 2H), 2.17-2.27 (m, 2H).

EXAMPLE 502

7-((E)-2-(3-(((2-(2-(2-aminoethoxyl)ethoxy)ethyl)amino)carbonyl)phenyl)vinyl)-3-(3-(1-naphthyloxyl)propyl)-1H-indole-2-carboxylic acid $^1$H NMR (400 MHz, DMSO-d$_6$) 13.12 (br. s, 1H), 11.70 (s, 1H), 8.52 (t, 1H), 8.13-8.27 (m, 2H), 8.10 (s, 1H), 7.98 (d, 1H), 7.83-7.90 (m, 1H), 7.58-7.83 (m, 5H), 7.42-7.57 (m, 4H), 7.28-7.41 (m, 2H), 7.03 (t, 1H), 6.88 (d, 1H), 4.17 (t, 2H), 3.44-3.50 (m, 2H), 3.35 (t, 2H), 2.90-3.02 (m, 2H), 2.15-2.28 (m, 2H).

EXAMPLE 503

7-((E)-2-(3-((4-benzylpiperidin-1-yl)carbonyl)phenyl)vinyl)-3-(3-(1-naphthyloxyl)propyl)-1H-indole-2-carboxylic acid $^1$H NMR (400 MHz, DMSO-d$_6$) 13.10 (br. s, 1H), 11.70 (s, 1H), 8.12-8.28 (m, 2H), 7.82-7.90 (m, 1H), 7.59-7.81 (m, 4H), 7.41-7.57 (m, 4H), 7.13-7.40 (m, 8H), 7.03 (t, 1H), 6.88 (d, 1H), 4.41-4.59 (m, 1H), 4.18 (t, 2H), 3.51-3.69 (m, 1H), 3.35 (t, 2H), 2.92-3.10 (m, 1H), 2.67-2.82 (m, 1H), 2.55 (d, 2H), 2.17-2.28 (m, 2H), 1.63-1.90 (m, 3H), 1.08-1.29 (m, 2H).

EXAMPLE 504

3-(3-(1-naphthyloxyl)propyl)-7-((E)-2-(3-((4-phenylpiperazin-1-yl)carbonyl)phenyl)vinyl)-1H-indole-2-carboxylic acid $^1$H NMR (400 MHz, DMSO-d$_6$) 11.72 (s, 1H), 8.17-8.25 (m, 2H), 7.80-7.90 (m, 3H), 7.71 (d, 1H), 7.62 (d, 1H), 7.42-7.56 (m, 4H), 7.30-7.41 (m, 3H), 7.24 (t, 2H), 7.03 (t, 1H), 6.98 (s, 2H), 6.88 (d, 1H), 6.82 (t, 1H), 4.17 (t, 2H), 3.75-3.86 (m, 2H), 3.50-3.58 (m, 2H), 3.12-3.26 (m, 4H), 2.18-2.26 (m, 2H).

EXAMPLE 505

7-((E)-2-(3-((3-methylpiperidin-1-yl)carbonyl)phenyl)vinyl)-3-(3-(1-naphthyloxyl)propyl)-1H-indole-2-carboxylic acid $^1$H NMR (500 MHz, DMSO-d$_6$) 11.72 (s, 1H), 8.21-8.24 (m, 1H), 8.18 (d, 1H), 7.85-7.88 (m, 1H), 7.74-7.81 (m, 2H), 7.71 (d, 1H), 7.62 (d, 1H), 7.43-7.56 (m, 4H), 7.32-7.40 (m, 2H), 7.24 (d, 1H), 7.03 (t, 1H), 6.88 (d, 1H), 4.17 (t, 2H), 2.19-2.26 (m, 2H), 1.11-1.85 (m, 5H), 0.84 (d, 3H).

EXAMPLE 506

7-(2-(3-(((2-(2-(2-aminoethoxyl)ethoxy)ethyl)amino)carbonyl)phenyl)ethyl)-3-(3-(1-naphthyloxyl)propyl)-1H-indole-2-carboxylic acid $^1$H NMR (500 MHz, DMSO-d$_6$) 12.97 (br. s, 1H), 11.45 (s, 1H), 8.47 (t, 1H), 8.21-8.27 (m, 1H), 7.83-7.90 (m, 2H), 7.77 (br. s, 2H), 7.66 (d, 1H), 7.29-7.58 (m, 7H), 7.07 (d, 1H), 6.86-6.94 (m, 2H), 4.17 (t, 2H), 3.59 (t, 6H), 3.55 (t, 2H), 3.41-3.47 (m, 2H), 3.34 (t, 2H), 3.23-3.29 (m, 2H), 2.92-3.03 (m, 4H), 2.16-2.26 (m, 2H).

EXAMPLE 507

3-(3-(1-naphthyloxyl)propyl)-7-((E)-2-(3-((E)-2-phenylvinyl)phenyl)vinyl)-1H-indole-2-carboxylic acid $^1$H NMR (500 MHz, DMSO-d$_6$) 13.13 (br. s, 1H), 11.69 (s, 1H), 8.21-8.25 (m, 1H), 8.18 (d, 1H), 7.85-7.92 (m, 2H), 7.69-7.75 (m, 2H), 7.61-7.66 (m, 3H), 7.49-7.56 (m, 3H), 7.35-7.47 (m, 6H), 7.27-7.34 (m, 3H), 7.04 (t, 1H), 6.89 (d, 1H), 4.18 (t, 2H), 3.36 (t, 2H), 2.18-2.27 (m, 2H).

EXAMPLE 508

7-((E)-2-(1,1'-biphenyl-3-yl)vinyl)-3-(3-(1-naphthyloxy)propyl)-1H-indole-2-carboxylic acid $^1$H NMR (500 MHz, DMSO-d$_6$) 11.68 (s, 1H), 8.18-8.27 (m, 2H), 8.04 (s, 1H), 7.85-7.91 (m, 1H), 7.71-7.82 (m, 4H), 7.65 (d, 1H), 7.49-7.61 (m, 6H), 7.34-7.49 (m, 4H), 7.06 (t, 1H), 6.90 (d, 1H), 4.20 (t, 2H), 2.20-2.30 (m, 2H).

EXAMPLE 509

3-(3-(1-naphthyloxyl)propyl)-7-((E)-2-(3-((1E)-3-phenylprop-1-enyl)phenyl)vinyl)-1H-indole-2-carboxylic acid $^1$H NMR (500 MHz, DMSO-d$_6$) 13.09 (br. s, 1H), 11.64 (s, 1H), 8.00-8.27 (m, 2H), 7.81-7.89 (m, 1H), 7.47-7.76 (m, 6H), 7.09-7.46 (m, 10H), 7.02 (t, 1H), 6.88 (d, 1H), 6.52 (s, 1H), 4.17 (t, 2H), 2.62-2.70 (m, 2H), 2.17-2.27 (m, 2H).

EXAMPLE 510

3-(3-(1-naphthyloxyl)propyl)-7-((E)-2-(4-((E)-2-phenylvinyl)phenyl)vinyl)-1H-indole-2-carboxylic acid $^1$H NMR (400 MHz, DMSO-d$_6$) 13.09 (s, 1H), 11.71 (s, 1H), 8.20-8.25 (m, 1H), 8.17 (d, 1H), 7.83-7.89 (m, 1H), 7.78

(d, 2H), 7.70 (d, 1H), 7.58-7.67 (m, 5H), 7.22-7.56 (m, 10H), 7.03 (t, 1H), 6.88 (d, 1H), 4.18 (t, 2H), 3.35 (t, 2H), 2.17-2.28 (m, 2H).

EXAMPLE 511

3-(3-(1-naphthyloxy)propyl)-7-((E)-2-(4-((1E)-3-phenylprop-1-enyl)phenyl)vinyl)-1H-indole-2-carboxylic acid $^1$H NMR (400 MHz, DMSO-d$_6$) 13.04 (br. s, 1H), 11.68 (s, 1H), 8.19-8.27 (m, 1H), 8.06-8.16 (m, 1H), 7.83-7.89 (m, 1H), 7.64-7.75 (m, 3H), 7.56-7.62 (m, 1H), 7.18-7.55 (m, 12H), 7.01 (t, 1H), 6.87 (d, 1H), 6.41-6.56 (m, 2H), 4.17 (t, 2H), 3.53-3.58 (m, 2H), 2.15-2.28 (m, 2H).

EXAMPLE 512

7-((E)-2-(1,1'-biphenyl-4-yl)vinyl)-3-(3-(1-naphthyloxy)propyl)-1H-indole-2-carboxylic acid $^1$H NMR (400 MHz, DMSO-d$_6$) 13.07 (br. s, 1H), 11.73 (s, 1H), 8.15-8.26 (m, 2H), 7.82-7.90 (m, 3H), 7.68-7.76 (m, 5H), 7.62 (d, 1H), 7.32-7.56 (m, 8H), 7.03 (t, 1H), 6.88 (d, 1H), 4.18 (t, 2H), 3.36 (t, 2H), 2.18-2.28 (m, 2H).

EXAMPLE 513

7-(2-(1,1'-biphenyl-3-yl)ethyl)-3-(3-(1-naphthyloxy)propyl)-1H-indole-2-carboxylic acid $^1$H NMR (400 MHz, DMSO-d$_6$) 12.95 (br. s, 1H), 11.36 (s, 1H), 8.21-8.26 (m, 1H), 7.83-7.89 (m, 1H), 7.56-7.66 (m, 3H), 7.30-7.56 (m, 11H), 7.10 (d, 1H), 6.84-6.95 (m, 2H), 4.17 (t, 2H), 2.97-3.05 (m, 2H), 2.15-2.26 (m, 2H).

EXAMPLE 514

3-(3-(1-naphthyloxy)propyl)-7-(2-(3-(3-phenylpropyl)phenyl)ethyl)-1H-indole-2-carboxylic acid $^1$H NMR (400 MHz, DMSO-d$_6$) 12.91 (br. s, 1H), 11.33 (s, 1H), 8.21-8.26 (m, 1H), 7.83-7.89 (m, 1H), 7.41-7.56 (m, 4H), 7.37 (t, 1H), 6.83-7.32 (m, 12H), 4.16 (t, 2H), 3.19-3.26 (m, 2H), 2.87-2.94 (m, 2H), 2.52-2.63 (m, 4H), 2.14-2.26 (m, 2H), 1.79-1.91 (m, 2H).

EXAMPLE 515

7-((E)-2-(2-chlorophenyl)vinyl)-3-(3-(1-naphthyloxyl)propyl)-1H-indole-2-carboxylic acid $^1$H NMR (400 MHz, DMSO-d$_6$) 13.07 (br. s, 1H), 11.75 (s, 1H), 8.13-8.24 (m, 3H), 7.82-7.88 (m, 1H), 7.67 (t, 2H), 7.28-7.57 (m, 8H), 7.04 (t, 1H), 6.88 (d, 1H), 4.17 (t, 2H), 3.35 (t, 2H), 2.17-2.28 (m, 2H).

EXAMPLE 516

7-((E)-2-(1,1'-biphenyl-2-yl)vinyl)-3-(3-(1-naphthyloxy)propyl)-1H-indole-2-carboxylic acid $^1$H NMR (400 MHz, DMSO-d$_6$) 13.08 (br. s, 1H), 11.73 (s, 1H), 8.06-8.24 (m, 3H), 7.82-7.89 (m, 1H), 7.28-7.62 (m, 13H), 7.21 (d, 1H), 7.10 (d, 1H), 6.92 (d, 1H), 6.86 (d, 1H), 4.16 (t, 2H), 2.14-2.27 (m, 2H).

EXAMPLE 517

3-(3-(1-naphthyloxy)propyl)-7-((E)-2-(2-((E)-2-phenylvinyl)phenyl)vinyl)-1H-indole-2-carboxylic acid $^1$H NMR (400 MHz, DMSO-d$_6$) 13.08 (br. s, 1H), 11.76 (s, 1H), 8.21-8.25 (m, 1H), 8.02-8.10 (m, 2H), 7.81-7.89 (m, 2H), 7.68-7.80 (m, 5H), 7.63 (d, 1H), 7.48-7.56 (m, 2H), 7.45 (d, 1H), 7.26-7.42 (m, 6H), 7.14 (d, 1H), 7.04 (t, 1H), 6.88 (d, 1H), 4.17 (t, 2H), 2.18-2.26 (m, 2H).

EXAMPLE 518

3-(3-(1-naphthyloxy)propyl)-7-(2-phenylethyl)-1H-indole-2-carboxylic acid $^1$H NMR (400 MHz, DMSO-d$_6$) 12.93 (br. s, 1H), 11.37 (s, 1H), 8.21-8.26 (m, 1H), 7.83-7.89 (m, 1H), 7.48-7.56 (m, 3H), 7.44 (d, 1H), 7.24-7.41 (m, 4H), 7.14-7.21 (m, 1H), 7.06 (d, 1H), 6.85-6.93 (m, 2H), 4.17 (t, 2H), 3.34 (t, 2H), 3.21-3.27 (m, 2H), 2.89-2.97 (m, 2H), 2.16-2.26 (m, 2H).

EXAMPLE 519

7-(2-(2-chlorophenyl)ethyl)-3-(3-(1-naphthyloxyl)propyl)-1H-indole-2-carboxylic acid $^1$H NMR (400 MHz, DMSO-d$_6$) 12.95 (br. s, 1H), 11.34 (s, 1H), 8.20-8.25 (m, 1H), 7.84-7.88 (m, 1H), 7.34-7.56 (m, 7H), 7.20-7.32 (m, 2H), 7.02 (d, 1H), 6.85-6.93 (m, 2H), 4.17 (t, 2H), 3.19-3.25 (m, 2H), 2.99-3.07 (m, 2H), 2.16-2.26 (m, 2H).

EXAMPLE 520

7-(2-(1,1'-biphenyl-4-yl)ethyl)-3-(3-(1-naphthyloxyl)propyl)-1H-indole-2-carboxylic acid $^1$H NMR (400 MHz, DMSO-d$_6$) 12.93 (br. s, 1H), 11.38 (s, 1H), 8.21-8.26 (m, 1H), 7.84-7.88 (m, 1H), 7.62-7.67 (m, 2H), 7.56-7.61 (m, 2H), 7.31-7.55 (m, 10H), 7.10 (d, 1H), 6.85-6.95 (m, 2H), 4.17 (t, 2H), 2.94-3.01 (m, 2H), 2.16-2.26 (m, 2H).

EXAMPLE 521

3-(3-(1-naphthyloxyl)propyl)-7-(2-(4-(2-phenylethyl)phenyl)ethyl)-1H-indole-2-carboxylic acid $^1$H NMR (400 MHz, DMSO-d$_6$) 12.93 (br. s, 1H), 11.33 (s, 1H), 8.20-8.26 (m, 1H), 7.84-7.88 (m, 1H), 7.42-7.57 (m, 4H), 7.37 (t, 1H), 7.09-7.30 (m, 9H), 7.04 (d, 1H), 6.85-6.93 (m, 2H), 4.17 (t, 2H), 2.82-2.93 (m, 6H), 2.15-2.25 (m, 2H).

EXAMPLE 522

3-(3-(1-naphthyloxy)propyl)-7-(2-(4-(3-phenylpropyl)phenyl)ethyl)-1H-indole-2-carboxylic acid $^1$H NMR (400 MHz, DMSO-d$_6$) 12.92 (br. s, 1H), 11.33 (s, 1H), 8.20-8.25 (m, 1H), 7.84-7.88 (m, 1H), 7.47-7.56 (m, 3H), 7.44 (d, 1H), 7.37 (t, 1H), 7.08-7.31 (m, 9H), 7.05 (d, 1H), 6.84-6.93 (m, 2H), 4.16 (t, 2H), 3.16-3.25 (m, 2H), 2.85-2.93 (m, 2H), 2.53-2.63 (m, 4H), 2.15-2.25 (m, 2H), 1.81-1.92 (m, 2H).

EXAMPLE 523

7-(4-carboxy-2-methylphenyl)-3-(3-((2-cyanoquinolin-8-yl)oxy)propyl)-1H-indole-2-carboxylic acid $^1$H NMR (300 MHz, DMSO-$d_6$) 10.85 (s, 1H), 8.51 (d, 1H), 8.18 (d, 1H), 8.04 (s, 1H), 7.89 (s, 1H), 7.80 (m, 3H), 7.58 (m, 2H), 7.32 (d, 1H), 7.24 (m, 1H), 7.04 (m, 2H), 4.26 (t, 2H), 2.26 (m, 2H), 2.10 (s, 3H).

EXAMPLE 524

3-(3-((2-acetyl-1-benzofuran-7-yl)oxy)propyl)-7-(4-carboxy-2-methylphenyl)-1H-indole-2-carboxylic acid $^1$H NMR (300 MHz, DMSO-$d_6$) 12.87 (s, 2H), 10.87 (s, 1H), 7.89 (s, 2H), 7.82 (dd, 1H), 7.73 (dd, 1H), 7.34 (m, 2H), 7.24 (t, 1H), 7.07 (m, 3H), 4.24 (t, 2H), 2.58 (s, 2H), 2.19 (m, 2H), 2.09 (s, 3H).

EXAMPLE 525

7-(4-carboxy-2-methylphenyl)-3-(3-((2,2-dimethyl-2,3-dihydro-1-benzofuran-7-yl)oxy)propyl)-1H-indole-2-carboxylic acid $^1$H NMR (300 MHz, DMSO-$d_6$) 12.86 (s, 2H), 10.85 (s, 1H), 7.89 (m, 1H), 7.82 (m, 1H), 7.71 (m, 1H), 7.32 (d, 1H), 7.06 (m, 2H), 6.71 (m, 3H), 3.98 (t, 2H), 3.20 (t, 2H), 3.00 (s, 2H), 2.07 (m, 5H), 1.43 (s, 6H).

EXAMPLE 526

7-(4-carboxy-2-methylphenyl)-3-(3-(2,3-difluorophenoxyl)propyl)-1H-indole-2-carboxylic acid $^1$H NMR (300 MHz, DMSO-$d_6$) 12.86 (m, 2H), 10.85 (s, 1H), 7.89 (m, 1H), 7.82 (m, 1H), 7.69 (m, 1H), 7.32 (d, 1H), 7.09 (m, 3H), 6.96 (m, 2H), 4.12 (t, 2H), 3.24 (m, 5H).

EXAMPLE 527

7-(4-carboxy-2-methylphenyl)-3-(3-(3-methyl-2-nitrophenoxy)propyl)-1H-indole-2-carboxylic acid $^1$H NMR (300 MHz, DMSO-$d_6$) 12.88 (m, 2H), 10.88 (s, 1H), 7.89 (m, 1H), 7.82 (m, 1H), 7.63 (m, 1H), 7.40 (t, 1H), 7.32 (d, 1H), 7.08 (m, 3H), 6.99 (m, 1H), 4.13 (t, 2H), 3.16 (t, 2H), 2.26 (m, 3H), 2.10 (m, 3H), 2.03 (m, 2H).

EXAMPLE 528

7-(4-carboxy-2-methylphenyl)-3-(3-(2-methyl-3-nitrophenoxy)propyl)-1H-indole-2-carboxylic acid $^1$H NMR (300 MHz, DMSO-$d_6$) 12.86 (m, 2H), 10.86 (m, 1H), 7.89 (m, 1H), 7.82 (m, 1H), 7.69 (m, 1H), 7.45 (m, 3H), 7.31 (d, 1H), 7.07 (m, 2H), 4.17 (t, 2H), 3.27 (t, 2H), 2.15 (m, 2H), 2.09 (s, 3H).

EXAMPLE 529

7-(4-carboxy-2-methylphenyl)-3-(3-(2-chloro-3-(trifluoromethyl)phenoxy)propyl)-1H-indole-2-carboxylic acid $^1$H NMR (300 MHz, DMSO-$d_6$) 12.86 (m, 2H), 10.86 (m, 1H), 7.90 (m, 1H), 7.82 (m, 1H), 7.69 (m, 1H), 7.34 (m, 4H), 7.10 (m, 2H), 4.12 (t, 2H), 2.29 (m, 3H), 2.14 (m, 2H), 2.10 (m, 3H).

EXAMPLE 530

7-(4-carboxy-2-methylphenyl)-3-(3-(2-fluoro-3-(trifluoromethyl)phenoxy)propyl)-1H-indole-2-carboxylic acid $^1$H NMR (300 MHz, DMSO-$d_6$) 12.87 (m, 1H), 7.89 (m, 1H), 7.89 (m, 1H), 7.82 (m, 1H), 7.82 (m, 1H), 7.68 (m, 1H), 7.46 (m, 1H), 7.29 (m, 3H), 7.08 (m, 2H), 4.15 (t, 2H), 3.25 (t, 2H), 2.14 (m, 2H), 2.09 (m, 3H)

EXAMPLE 531

7-(2-chlorophenyl)-3-(3-(ethyl(1-naphthyl)amino)propyl)-1H-indole-2-carboxylic acid

EXAMPLE 531A ethyl 7-bromo-3-(3-oxopropyl)-1H-indole-2-carboxylate

To a solution of ethyl 7-bromo-3-(4-hydroxypropyl)-1H-indole-2-carboxylate (EXAMPLE 1C) (3.4 g) and triethylamine (8.5 ml) in dichloromethane (100 ml) and dimethylsulfoxide (10 mL), cooled to 0° C., was added pyridine-2-sulfonate (9.54 g). The mixture was stirred for 3 hours and diluted with ethyl acetate (300 ml) and washed with 5% HCl, water, and brine. After drying the combined organic layers over Na$_2$SO$_4$, the filtrate was concentrated and the crude product was purified by flash chromatography on a silica gel, eluting with 10% ethyl acetate in hexane.

EXAMPLE 531B ethyl 7-bromo-3-(3-(ethyl(naphthalen-1-yl)amino)propyl)-1H-indole-2-carboxylate To a solution of EXAMPLE 531A (130 mg) and N-ethylnaphthalen-1-amine (82 mg) in dichloromethane (3 mL) was added sodium triacetoxyborohydride (2.35 g). The mixture was stirred at room temperature overnight. After this time the mixture was diluted with ethyl acetate (1500 mL) and washed with 1N NaOH, water, brine, and dried over Na$_2$SO$_4$. After filtration and concentration of the filtrate, the residue was purified by flash chromatography using silica gel and eluenting with 5% ethyl acetate in hexane.

EXAMPLE 531C 7-(2-chlorophenyl)-3-(3-(ethyl(1-naphthyl)amino)propyl)-1H-indole-2-carboxylic acid To a mixture of EXAMPLE 531B (192 mg) and 2-chlorophenylboronic acid (76 mg) in tetrahydrofuran (6 ml) was added tris(dibenzylideneacetone)dipalladium(0) (19 mg), tri-t-butyl-phosphonium tetrafluoroborate (12 mg) and cesium fluoride (200 mg). The mixture was purged with argon and stirred at room temperature for 24 hours. The mixture was diluted with ethyl acetate (200 mL) and washed with water, and brine and dried over $Na_2SO_4$. Concentration of the mixture and column purification of the crude material (5% ethyl acetate in hexane) provided the title compound. A portion of this material (50 mg) was dissolved in 1:1 tetrahydrofuran/methanol with a few drops of water and hydrolyzed with LiOH. Subsequent purification via RP HPLC afforded the title compound. $^1$H NMR (300 MHz, DMSO-$d_6$) δ 10.80 (m, 1H), 8.27 (m, 1H), 7.90 (m, 1H), 7.55 (m, 1H), 7.53 (m, 1H), 7.42 (m, 3H), 7.34 (m, 3H), 7.21 (m, 2H), 7.03 (m, 1H), 6.98 (m, 2H), 3.21 (m, 4H), 3.08 (t, 2H), 1.79 (m, 2H), 0.96 (t, 3H).

EXAMPLE 532

7-(4-(morpholin-4-ylcarbonyl)-2-(trifluormethyl) phenyl)-3-(4-(5-oxo-2,3,4,5-tetrahydro-1H-1-benzazepin-1-yl)butyl)-1H-indole-2-carboxylic acid $^1$H NMR (300 MHz, DMSO-$d_6$) δ 11.11 (m, 1H), 8.29 (m, 1H), 8.21 (m, 1H), 7.75 (m, 1H), 7.53 (m, 2H), 7.27 (m, 1H), 7.09 (m, 2H), 6.96 (m, 1H), 6.70 (m, 1H), 3.74 (m, 6 H), 3.49 (t, 2H), 3.16 (t, 4H), 2.55 (t, 2H), 2.07 (m, 3H).

EXAMPLE 533

7-(4-(morpholin-4-ylcarbonyl)-2-(trifluromethyl) phenyl)-3-(4-(2,3,4,5-tetrahydro-1H-1-benzazepin-1-yl)butyl)-1H-indole-2-carboxylic acid $^1$H NMR (300 MHz, DMSO-$d_6$) 11.09 (m, 1H), 8.29 (m, 1H), 8.20 (dd, 2H), 7.68 (dd, 1H), 7.52 (dd, 1H), 7.08 (m, 4H), 6.83 (m, 2H), 4.36 (m, 6 H), 3.13 (m, 4H), 2.76 (m, 3H), 1.59 (m, 8H).

EXAMPLE 534

3-(4-(2,3-dihydro-4H-1,4-benzothiazin-4-yl)butyl)-7-(4-(morpholin-4-ylcarbonyl)-2-(trifluoromethyl) phenyl)-1H-indole-2-carboxylic acid $^1$H NMR (300 MHz, DMSO-$d_6$) 11.10 (m, 1H), 8.29 (m, 1H), 8.21 (m, 1H), 7.74 (m, 1H), 7.54 (m, 1H), 7.10 (m, 2H), 6.89 (m, 2H), 6.64 (m, 1H), 6.49 (m, 1H), 3.52 (m, 2H), 3.30 (m, 8H), 3.14 (m, 2H), 1.68 (m, 4H).

EXAMPLE 535

3-(4-(3,4-dihydroquinolin-1(2H)-yl)butyl)-7-(2-methylphenyl)-1H-indole-2-carboxylic acid $^1$H NMR (300 MHz, DMSO-$d_6$) δ 10.41 (m, 1H), 7.68 (m, 1H), 7.28 (m, 4H), 7.08 (m, 2H), 6.88 (m, 2H), 6.46 (m, 2H), 3.18 (m, 6H), 2.64 (m, 2H), 2.05 (m, 3H), 1.68 (m, 6H).

EXAMPLE 536

3-(4-(2-methyl-3,4-dihydroquinolin-1(2H)-yl)butyl)-7-(2-methylphenyl)-1H-indole-2-carboxylic acid $^1$H NMR (300 MHz, DMSO-$d_6$) 10.38 (s, 1H), 7.69 (m, 1H), 7.29 (m, 4H), 7.09 (m, 2H), 6.90 (m, 2H), 6.44 (m, 2H), 3.38 (m, 3H), 3.14 (m, 3H), 2.69 (m, 2H), 2.05 (m, 3H), 1.65 (m, 6H), 1.02 (d, 3H).

EXAMPLE 537

3-(4-(6-methyl-3,4-dihydroquinolin-1(2H)-yl)butyl)-7-(2-methylphenyl)-1H-indole-2-carboxylic acid $^1$H NMR (300 MHz, DMSO-$d_6$) 10.38 (s, 1H), 7.68 (m, 1H), 7.28 (m, 5 H), 7.10 (m, 2H), 6.72 (m, 2H), 6.45 (m, 1H), 3.15 (m, 7 H), 2.61 (m, 2H), 2.11 (s, 3H), 2.05 (s, 3H), 1.69 (m, 5H).

EXAMPLE 538

3-(4-(8-methyl-3,4-dihydroquinolin-1(2H)-yl)butyl)-7-(2-methylphenyl)-1H-indole-2-carboxylic acid $^1$H NMR (300 MHz, DMSO-$d_6$) δ 10.41 (m, 1H), 7.70 (m, 1H), 7.24 (m, 8H), 7.03 (m, 2H), 3.13 (m, 4H), 2.78 (m, 4H), 2.25 (m, 4H), 2.03 (s, 3H), 1.75 (m, 5H).

EXAMPLE 539

3-(4-(2-methyl-2,3-dihydro-1H-indol-1-yl)butyl)-7-(2-methylphenyl)-1H-indole-2-carboxylic acid $^1$H NMR (300 MHz, DMSO-$d_6$) 10.37 (m, 1H), 7.68 (m, 1H), 7.32 (m, 2H), 7.24 (m, 2H), 7.15 (m, 1H), 7.05 (m, 1H), 6.93 (m, 2H), 6.49 (m, 1H), 6.32 (m, 1H), 3.08 (m, 6 H), 2.06 (s, 3H), 1.63 (m, 4H), 1.18 (d, 3H).

EXAMPLE 540

7-(2-methylphenyl)-3-(4-(2,3,4,5-tetrahydro-1H-1-benzazepin-1-yl)butyl)-1H-indole-2-carboxylic acid $^1$H NMR (300 MHz, DMSO-$d_6$) 10.35 (m, 1H), 7.62 (m, 1H), 7.27 (m, 4H), 7.07 (m, 4H), 6.83 (m, 2H), 3.07 (m, 5H), 2.77 (m, 4H), 2.08 (s, 3H), 1.63 (m, 8H).

EXAMPLE 541

3-(4-(3-methyl-3,4-dihydroquinolin-1(2H)-yl)butyl)-7-(2-methylphenyl)-1H-indole-2-carboxylic acid $^1$H NMR (300 MHz, DMSO-$d_6$) δ 10.36 (m, 1H), 7.67 (m, 1H), 7.27 (m, 4H), 7.09 (m, 2H), 6.86 (m, 2H), 6.47 (m, 2H), 3.22 (m, 6 H), 2.75 (m, 1H), 2.31 (m, 2H), 2.06 (m, 3H), 1.91 (m, 1H), 1.65 (m, 4H), 0.96 (d, 3H).

EXAMPLE 542

3-(4-(3-(hydroxymethyl)-3,4-dihydroquinolin-1 (2H)-yl)butyl)-7-(2-methylphenyl)-1H-indole-2-carboxylic acid $^1$H NMR (300 MHz, DMSO-$d_6$) 10.39 (m, 1H), 7.68 (m, 1H), 7.28 (m, 4H), 7.09 (m, 2H), 6.89 (m, 2H), 6.44 (m, 2H), 3.25 (m, 8H), 2.93 (m, 1H), 2.67 (m, 1H), 2.36 (m, 1H), 2.06 (s, 3H), 1.92 (m, 1H), 1.66 (m, 4H).

EXAMPLE 543

3-(4-(2,3-dihydro-4H-1,4-benzothiazin-4-yl)butyl)-7-(2-methylphenyl)-1H-indole-2-carboxylic acid $^1$H NMR (300 MHz, DMSO-$d_6$) 10.40 (m, 1H), 7.68 (m, 1H), 7.29 (m, 4H), 7.09 (m, 2H), 6.88 (m, 2H), 6.55 (m, 2H), 3.54 (m, 2H), 3.29 (m, 3H), 3.13 (m, 2H), 2.98 (m, 2H), 2.05 (m, 3H), 1.67 (m, 4H).

EXAMPLE 544

4-methoxy-7-(2-methylphenyl)-3-(3-(1-naphthyloxy)propyl)-1H-indole-2-carboxylic acid $^1$H NMR (300 MHz, DMSO-d$_6$) 10.23 (m, 1H), 8.23 (m, 1H), 7.86 (m, 1H), 7.47 (m, 4H), 7.23 (m, 4H), 6.94 (m, 2H), 6.59 (m, 2H), 4.23 (t, 2H), 3.87 (s, 3H), 3.49 (m, 2H), 2.24 (m, 2H), 2.06 (m, 3H).

EXAMPLE 545

3-(3-(((1R,4S)-8-hydroxy-1,2,3,4-tetrahydro-1,4-methanonaphthalen-5-yl)oxy)propyl)-7-(2-methylphenyl)-1H-indole-2-carboxylic acid $^1$H NMR (300 MHz, DMSO-d$_6$) 10.45 (m, 1H), 8.57 (m, 1H), 7.65 (m, 1H), 7.27 (m, 4H), 7.07 (m, 2H), 6.43 (m, 2H), 3.90 (m, 2H), 3.48 (m, 2H), 3.22 (m, 2H), 2.06 (s, 3H), 1.79 (m, 2H), 1.28 (m, 5 H).

EXAMPLE 546

7-(2-methylphenyl)-3-(3-((1R,4S)-1,2,3,4-tetrahydro-1,4-methanonaphthalen-5-yloxy)propyl)-1H-indole-2-carboxylic acid

EXAMPLE 546A

To a solution of 3',6'-Dihydroxybenzonorbornane (3.52 g) and imidazole (1.36 g) in N,N-dimethylformamide (150 ml) was added a solution of t-Butylchlorodimethylsilane (3.01 g) in N,N-dimethylformamide (30 ml) dropwise. After the addition, the mixture was stirred overnight at room temperature. After concentration of the solvent under vacuum, the residue was dissolved in ethyl acetate (300 ml) and washed with 5% HCl, water, and brine and dried over Na$_2$SO$_4$. After evaporation of the solvent, the residue was loaded on a silica gel column and eluted with 20% ethyl acetate in hexane to give the product.

EXAMPLE 546B

To a cooled (0° C.) solution of ethyl 7-bromo-3-(3-hydroxypropyl)-1H-indole-2-carboxylate (326 mg) and EXAMPLE 546A (290 mg) and triphenylphosphine (315 mg) in tetrahydrofuran (10 ml) was added di-tert-butyl azodicarboxylate (276 mg). The mixture was stirred at 0° C. for 1 hour and then stirred at room temperature for 14 hours. After this time, the mixture was diluted with ethyl acetate (200 ml) and washed with water, brine and dried over Na$_2$SO$_4$. Concentration of the solvent and column purification (10% ethyl acetate in hexane) gave the product.

EXAMPLE 546C

To a mixture of the EXAMPLE 1C (310 mg) and 2-tolueneboronic acid (84 mg) in dimethoxyethane (20 ml) and ethanol (10 ml) was added tetrakis(triphenylphosphine)palladium(0) (30 mg), and cesium fluoride (236 mg). The mixture was stirred under nitrogen at reflux for 4 hours. After this time the solvent was concentrated under vacuum and the residue was partitioned between ethyl acetate (300 mL) and water (100 ml). The organic phase was washed with water, brine and dried over Na$_2$SO$_4$. Evaporation of solvent and column purification (5% ethyl acetate in hexane) afforded the product.

EXAMPLE 546D ethyl 7-(2-methylphenyl)-3-(3-((8-(((trifluoromethyl)sulfonyl)oxy)-1,2,3,4-tetrahydro-1,4-methanonaphthalen-5-yl)oxy)propyl)-1H-indole-2-carboxylate To a mixture of EXAMPLE 546C (85 mg) in pyridine (2 ml) at 0° C. was added triflic anhydride (120 mg). The mixture was stirred at room temperature overnight. The mixture was partitioned between ethyl ether (300 mL) and 5% aqueous HCl (50 ml). The organic phase was washed with water and brine and dried over Na$_2$SO$_4$. After filtration and concentration of the filtrate the crude product was used in the next step without further purification.

EXAMPLE 546E ethyl 7-(2-methylphenyl)-3-(3-(1,2,3,4-tetrahydro-1,4-methanonaphthalen-5-yloxy)propyl)-1H-indole-2-carboxylate To a solution of EXAMPLE 546D (80 mg) in tetrahydrofuran and methanol (40 ml, 1:1) was added 10% palladium hydroxide (40 mg). The mixture was shaken under 30 psi of hydrogen for 4 hours. The catalyst was filtered off, the filtrate was concentrated and the residue was hydrolyzed with LiOH/tetrahydrofuran/methanol/H$_2$O. The product was purified by reverse phase HPLC.

EXAMPLE 546F 7-(2-methylphenyl)-3-(3-((1R,4S)-1,2,3,4-tetrahydro-1,4-methanonaphthalen-5-yloxy)propyl)-1H-indole-2-carboxylic acid The title compound was prepared according to the procedure for EXAMPLE 164G, substituting EXAMPLE 546E for EXAMPLE 164F. $^1$H NMR (300 MHz, DMSO-d$_6$) 10.45 (m, 1H), 7.65 (m, 1H), 7.28 (m, 4H), 7.02 (m, 3H), 6.78 (m, 1H), 6.63 (m, 1H), 4.00 (m, 2H), 2.07 (m, 5H), 1.87 (m, 2H), 1.30 (m, 7H).

EXAMPLE 547

3-(3-((4-methoxy-1-naphthyl)oxy)propyl)-7-(2-methylphenyl)-1H-indole-2-carboxylic acid $^1$H NMR (300 MHz, DMSO-d$_6$) 10.47 (m, 1H), 8.22 (m, 1H), 8.11 (m, 1H), 7.69 (m, 1H), 7.54 (m, 2H), 7.26 (m, 4H), 7.05 (m, 2H), 6.82 (m, 2H), 4.14 (m, 2H), 3.91 (s, 3H), 3.36 (m, 2H), 2.22 (m, 2H), 2.05 (s, 3H).

EXAMPLE 548

7-(2-methylphenyl)-3-(3-((2-nitro-1-naphthyl)oxy)propyl)-1H-indole-2-carboxylic acid $^1$H NMR (300 MHz, DMSO-d$_6$) 12.92 (m, 1H), 10.51 (m, 1H), 8.30 (m, 1H), 8.08 (m, 1H), 7.90 (m, 2H), 7.74 (m, 3H), 7.19 (m, 4H), 4.27 (m, 2H), 2.23 (m, 2H), 2.07 (s, 3H).

EXAMPLE 549

3-(3-((3-hydroxy-1-naphthyl)oxy)propyl)-7-(2-methylphenyl)-1H-indole-2-carboxylic acid $^1$H NMR (300 MHz, DMSO-d$_6$) δ 12.92 (m, 1H), 10.50 (m, 1H), 9.65 (m, 1H), 8.08 (m, 1H), 7.64 (m, 2H), 7.30 (m, 4H), 7.05 (m, 2H), 6.68 (m, 1H), 6.48 (m, 1H), 4.13 (m, 2H), 2.23 (m, 2H), 2.05 (s, 3H).

EXAMPLE 550

7-(3,5-dimethylisoxazol-4-yl)-3-(3-(2,3,6,7-tetrahydro-1H,5H-pyrido(3,2,1-ij)quinolin-8-yloxy)propyl)-1H-indole-2-carboxylic acid $^1$H NMR (300 MHz, DMSO-d$_6$) 11.25 (m, 1H), 7.67 (m, 1H), 7.11 (m, 2H), 6.62 (d, 1H), 6.08 (d, 1H), 3.22 (m, 2H), 3.04 (m, 4H), 2.62 (m, 4H), 2.22 (s, 3H), 2.05 (s, 3H), 2.04 (m, 4H), 1.86 (m, 4H).

EXAMPLE 551

7-(2-methylphenyl)-3-(3-(2,3,6,7-tetrahydro-1H,5H-pyrido(3,2,1-ij)quinolin-8-yloxy)propyl)-1H-indole-2-carboxylic acid $^1$H NMR (300 MHz, DMSO-d$_6$) 10.46 (m, 1H), 7.65 (m, 1H), 7.27 (m, 4H), 7.08 (m, 2H), 6.63 (d, 1H), 6.10 (d, 1H), 3.93 (m, 2H), 3.23 (m, 2H), 3.05 (m, 4H), 2.64 (m, 4H), 2.05 (m, 5H), 1.86 (m, 4H).

EXAMPLE 552

7-(2-methylphenyl)-3-(3-((2-nitroso-1-naphthyl)oxy)propyl)-1H-indole-2-carboxylic acid $^1$H NMR (300 MHz, DMSO-d$_6$) δ 10.64 (m, 1H), 8.13 (m, 2H), 7.72 (m, 5H), 7.27 (m, 4H), 7.04 (m, 2H), 3.71 (m, 2H), 2.03 (s, 3H), 1.40 (m, 2H).

EXAMPLE 553

3-(3-((5-hydroxy-1-naphthyl)oxy)propyl)-7-(2-methylphenyl)-1H-indole-2-carboxylic acid $^1$H NMR (300 MHz, DMSO-d$_6$) 12.92 (m, 1H), 10.46 (m, 1H), 9.99 (m, 1H), 7.69 (m, 3H), 7.28 (m, 6H), 7.06 (m, 2H), 6.88 (m, 2H), 4.17 (t, 2H), 3.35 (t, 2H), 2.22 (m, 2H), 2.06 (s, 3H).

EXAMPLE 554

7-(2-methylphenyl)-3-(3-(2,3,4-trifluorophenoxyl)propyl)-1H-indole-2-carboxylic acid $^1$H NMR (300 MHz, DMSO-d$_6$) δ 12.85 (m, 1H), 10.47 (m, 1H), 7.66 (d, 1H), 7.12 (m, 8H), 4.10 (t, 2H), 3.23 (t, 2H), 2.11 (m, 2H), 2.06 (s, 3H).

EXAMPLE 555

3-(3-(3-chloro-2-methylphenoxy)propyl)-7-(2-methylphenyl)-1H-indole-2-carboxylic acid $^1$H NMR (300 MHz, DMSO-d$_6$) δ 12.87 (m, 1H), 10.45 (m, 1H), 7.65 (d, 1H), 7.27 (m, 4H), 7.07 (m, 2H), 6.88 (d, 1H), 4.04 (t, 2H), 3.27 (t, 2H), 2.24 (s, 3H), 2.12 (m, 2H), 2.06 (s, 3H).

EXAMPLE 556

3-(3-((8-hydroxy-1-naphthyl)oxy)propyl)-7-(2-methylphenyl)-1H-indole-2-carboxylic acid $^1$H NMR (300 MHz, DMSO-d$_6$) 10.53 (m, 1H), 9.56 (m, 1H), 7.68 (d, 1H), 7.44 (d, 1H), 7.34 (m, 6H), 7.24 (m, 2H), 7.07 (m, 2H), 6.93 (d, 1H), 6.81 (dd, 1H), 4.33 (t, 2H), 2.24 (m, 2H), 2.06 (s, 3H).

EXAMPLE 557

3-(3-(3-chloro-2-cyanophenoxy)propyl)-7-(2-methylphenyl)-1H-indole-2-carboxylic acid $^1$H NMR (300 MHz, DMSO-d$_6$) 12.88 (m, 1H), 10.48 (m, 1H), 7.70 (d, 1H), 7.63 (t, 1H), 7.27 (m, 5H), 7.18 (d, 1H), 7.07 (m, 2H), 4.20 (t, 2H), 3.26 (t, 2H), 2.13 (m, 2H), 2.05 (s, 3H).

EXAMPLE 558

3-(3-(2-bromo-3-methylphenoxy)propyl)-7-(2-methylphenyl)-1H-indole-2-carboxylic acid $^1$H NMR (300 MHz, DMSO-d$_6$) 12.88 (m, 1H), 10.46 (m, 1H), 7.70 (d, 1H), 7.32 (m, 2H), 7.25 (m, 2H), 7.18 (d, 1H), 7.06 (m, 2H), 6.93 (d, 1H), 6.86 (d, 1H), 4.06 (t, 2H), 3.27 (t, 2H), 2.38 (s, 3H), 2.11 (m, 2H), 2.05 (s, 3H).

EXAMPLE 559

7-(2-methylphenyl)-3-(3-(3-methyl-2-vinylphenoxy)propyl)-1H-indole-2-carboxylic acid $^1$H NMR (300 MHz, DMSO-d$_6$) 12.88 (m, 1H), 10.47 (m, 1H), 7.65 (d, 1H), 7.32 (m, 2H), 7.24 (m, 3H), 7.08 (m, 3H), 6.80 (d, 2H), 5.81 (dd, 1H), 5.53 (dd, 1H), 4.02 (t, 2H), 3.25 (m, 2H), 2.32 (m, 3H), 2.11 (m, 2H), 2.06 (s, 3H).

EXAMPLE 560

3-(3-(3-methyl-2-nitrophenoxy)propyl)-7-(2-methylphenyl)-1H-indole-2-carboxylic acid $^1$H NMR (300 MHz, DMSO-d$_6$) 12.89 (m, 1H), 10.51 (m, 1H), 7.60 (d, 1H), 7.40 (t, 1H), 7.32 (m, 2H), 7.24 (m, 3H), 4.13 (t, 2H), 3.15 (t, 2H), 2.26 (s, 3H), 2.05 (s, 3H), 2.03 (m, 2H).

EXAMPLE 561

3-(3-(2-amino-3-methylphenoxy)propyl)-7-(2-methylphenyl)-1H-indole-2-carboxylic acid $^1$H NMR (300 MHz, DMSO-d$_6$) 10.49 (m, 1H), 7.69 (d, 1H), 7.33 (m, 2H), 7.25 (m, 3H), 7.08 (m, 3H), 6.73 (m, 3H), 4.04 (t, 2H), 3.26 (t, 2H), 2.18 (s, 3H), 2.12 (m, 2H), 2.06 (s, 3H).

EXAMPLE 562

7-(4-(morpholin-4-ylcarbonyl)-2-(trifluoromethyl)phenyl)-3-(3-(1-naphthyloxyl)propyl)-1H-indole-2-carboxylic acid $^1$H NMR (300 MHz, DMSO-d$_6$) 11.10 (m, 1H), 8.25 (m, 2H), 7.86 (m, 2H), 7.73 (m, 3H), 7.53 (m, 3H), 7.43 (m, 4H), 7.07 (m, 3H), 6.90 (d, 1H), 4.21 (t, 2H), 3.61 (m, 6H), 2.24 (m, 2H).

EXAMPLE 563

3-(3-((6-amino-1-naphthyl)oxy)propyl)-7-(2-methylphenyl)-1H-indole-2-carboxylic acid

EXAMPLE 563A ethyl 3-(3-(6-aminonaphthalen-1-yloxy)propyl)-7-bromo-1H-indole-2-carboxylate To a mixture of ethyl 7-bromo-3-(3-hydroxypropyl)-1H-indole-2-carboxylate (EXAMPLE 1C) (100 mg), 6-aminonaphthalen-1-ol (98 mg) and triphenylphosphine, polymer supported (204 mg 0.613 mmol) in tetrahydrofuran (4 ml) was added di-tert-butyl diazene-1,2-dicarboxylate (141 mg). The reaction mixture was stirred at room temperature for 3 hours. The insoluble material was filtered off and the filtrate was concentrated. The residue was purified by flash chromatography (ethyl acetate in hexanes) to provide the title compound.

EXAMPLE 563B 3-(3-((6-amino-1-naphthyl)oxy)propyl)-7-(2-methylphenyl)-1H-indole-2-carboxylic acid A mixture of EXAMPLE 563A (45 mg), o-tolylboronic acid (15.7 mg), $K_2CO_3$ (1 M, 0.17 ml) and bis(triphenylphosphine)palladium(II) dichloride (7.2 mg, 0.01 mmol) in a mixture of dimethoxyethane (2.2 ml), ethanol (0.6 ml) and water (0.9 ml) was heated at 160° C. in a microwave reactor (CEM Discover) for 10 minutes. The reaction mixture was acidified with a diluted trifluoroacetic acid methanol solution and concentrated. The residue was suspended in a mixture of DMSO and methanol (1:1) and filtered. The filtrate was purified by RP HPLC to provide the desired product. $^1$H NMR (400 MHz, DMSO-$D_6$) δ 10.43 (s, 1 H), 8.08 (d, J=8.90 Hz, 1 H), 7.69 (d, J=6.75 Hz, 1 H), 7.31-7.34 (m, 2 H), 7.18-7.29 (m, 5 H), 7.02-7.11 (m, 5 H), 6.64 (d, J=7.67 Hz, 1 H), 4.15 (t, J=5.98 Hz, 2 H), 2.49-2.53 (m, 2 H), 2.17-2.25 (m, 2 H), 2.06 (s, 3 H).

EXAMPLE 564

7-(2-methylphenyl)-3-(3-(1,2,3,4-tetrahydronaphthalen-1-yloxy)prop-1-ynyl)-1H-indole-2-carboxylic acid

EXAMPLE 564A ethyl 7-o-tolyl-1H-indole-2-carboxylate

To a mixture of ethyl 7-(4,4,5,5-tetramethyl-1,3,2-dioxaborolan-2-yl)-1H-indole-2-carboxylate (Paul et al. *J. Am. Chem. Soc.* 2006, 128, 15552-15553) (1.6 g), tri-(t-butyl)phosphonium tetrafluoroborate (0.074 g), tris(dibenzylideneacetone)dipalladium(0) (0.116 g) and cesium fluoride (2.313 g) was added ortho-iodotoluene (0.781 ml), then dioxane (200 ml) and methanol (20 ml). The reaction mixture was immediately purged with nitrogen and stirred at room temperature for 2 hours. Additional amounts of (dibenzylideneacetone)dipalladium(0) (0.116 g), ortho-iodotoluene (0.781 ml), CsF (2.313 g), and tri-(t-butyl)phosphonium tetrafluoroborate (0.074 g) were added at the same time. The resulting solution was stirred at room temperature overnight. The insoluble material was filtered off and the filtrate was concentrated and the residue was purified by flash chromatography, eluting with 0-100% dichloromethane in hexane to provide the title compound.

EXAMPLE 564B ethyl 3-iodo-7-o-tolyl-1H-indole-2-carboxylate

To a solution of EXAMPLE 564A (944 mg, 3.38 mmol) in dichloromethane (10 mL) was added 1-iodopyrrolidine-2,5-dione (798 mg, 3.55 9 mmol). The reaction mixture was stirred at room temperature for 3 hours and directly loaded on a flash column, eluting with hexane first and then with 0-50% hexane in dichloromethane. The title compound was obtained as a white solid.

EXAMPLE 564C 7-(2-methylphenyl)-3-(3-(1,2,3,4-tetrahydronaphthalen-1-yloxy)prop-1-ynyl)-1H-indole-2-carboxylic acid To a solution of EXAMPLE 564B (180 mg) and 1-(prop-2-ynyloxy)-1,2,3,4-tetrahydronaphthalene (165 mg) in triethylamine (5 ml) was added bis(triphenylphosphine)palladium(II) dichloride (18.71 mg) and copper(I) iodide (4.23 mg). The reaction mixture was stirred at 70° C. for 3 hours, cooled and concentrated. The residue was dissolved in dichloromethane and purified by flash chromatography, eluting with dichloromethane, to provide ethyl 3-(3-(1,2,3,4-tetrahydronaphthalen-1-yloxy)prop-1-ynyl)-7-o-tolyl-1H-indole-2-carboxylate. This ester was hydrolyzed with aqueous NaOH in tetrahydrofuran and methanol to provide the title compound. $^1$H NMR (400 MHz, methanol-$d_4$) 7.76 (dd, J=7.98, 1.23 Hz, 1 H), 7.52 (dd, J=6.75, 2.46 Hz, 1 H), 7.34-7.40 (m, 2 H), 7.27-7.31 (m, 2 H), 7.26 (d, J=7.98 Hz, 1 H), 7.13-7.19 (m, 3 H), 7.07-7.12 (m, 1 H), 4.97 (t, =3.99 Hz, 1 H), 4.52-4.71 (m, 2 H), 2.79-2.90 (m, 1 H), 2.68-2.78 (m, 1 H), 2.14-2.21 (m, 1 H), 2.12 (s, 3 H), 1.91-2.06 (m, 2 H), 1.73-1.84 (m, 1 H).

EXAMPLE 565

3-(3-((6-(acryloylamino)-1-naphthyl)oxy)propyl)-7-(2-methylphenyl)-1H-indole-2-carboxylic acid

EXAMPLE 565A

To a mixture of ethyl 7-bromo-3-(3-hydroxypropyl)-1H-indole-2-carboxylate (1 g mmol), 6-aminonaphthalen-1-ol (0.732 g), triphenylphosphine, polymer supported (1.230 g) in tetrahydrofuran (4 ml) was added di-t-butyl azodicarboxylate (1.059 g, 4.60 mmol). The reaction was stirred at room temperature for 3 h. The insoluble material was removed by filtration and extensively washed with ethyl acetate. The combined filtrate was concentrated. The residue was purified by flash chromatography, eluting with CH2Cl2/ethyl acetate (20:1) to provide the title compound.

EXAMPLE 565B

The title compound was prepared according to the procedure for EXAMPLE 564A by substituting ethyl 7-(4,4,5,5-tetramethyl-1,3,2-dioxaborolan-2-yl)-1H-indole-2-carboxylate with o-tolylboronic acid, and ortho-iodotoluene with EXAMPLE 565A, respectively.

EXAMPLE 565C 3-(3-((6-(acryloylamino)-1-naphthyl)oxy)propyl)-7-(2-methylphenyl)-1H-indole-2-carboxylic acid To a mixture of EXAMPLE 565B (62.8 mg), acrylic acid (9.91 µl) and 2-(1H-7-azabenzotriazol-1-yl)-1,1,3,3-tetramethyl uronium hexafluorophosphate Methanaminium (HATU, 54.9 mg) in tetrahydrofuran (3 ml) was added triethylamine (36.6 µl). The reaction was stirred at room temperature overnight, diluted with ethyl acetate and washed with water. The organic layer was dried over sodium sulfate, filtered and concentrated. The residue was purified by flash chromatography, eluting with dichloromethane, to provide ethyl 3-(3-(6-acrylamidonaphthalen-1-yloxy)propyl)-7-o-tolyl-1H-indole-2-carboxylate. This ester was hydrolyzed with aqueous NaOH in tetrahydrofuran and methanol to provide the title compound. $^1$H NMR (500 MHz, methanol-$d_4$) δ 8.22-8.25 (m, 2 H), 7.68 (dd, J=5.95, 3.20 Hz, 1 H), 7.59 (dd, J=9.15, 2.14 Hz, 1 H), 7.25-7.37 (m, 6 H), 7.05-7.08 (m, 2 H), 6.74 (dd, J=6.10, 2.44 Hz, 1 H), 6.46-6.55 (m, 1 H), 6.38-6.44 (m, 1 H), 5.80 (dd, J=10.07, 1.83 Hz, 1 H), 4.20 (t, J=5.95 Hz, 2 H), 3.40-3.56 (m, 2 H), 2.34 (t, J=6.71 Hz, 2 H), 2.11 (s, 3 H).

EXAMPLE 566

7-(2-methylphenyl)-3-(3-((6-(propionylamino)-1-naphthyl)oxy)propyl)-1H-indole-2-carboxylic acid $^1$H NMR (500 MHz, methanol-$d_4$) 8.21 (d, J=9.15 Hz, 1 H), 8.14 (d, J=1.83 Hz, 1 H), 7.67 (dd, J=6.26, 2.90 Hz, 1 H), 7.53 (dd, J=9.15, 2.14 Hz, 1 H), 7.24-7.37 (m, 6 H), 7.04-7.07 (m, 2 H), 6.71 (dd, J=5.03, 3.51 Hz, 1 H), 4.19 (t, J=5.95 Hz, 2 H), 3.42-3.49 (m, 2 H), 2.45 (q, J=7.63 Hz, 2 H), 2.29-2.37 (m, 2 H), 2.11 (s, 3 H), 1.25 (t, J=7.63 Hz, 3 H).

EXAMPLE 567

7-(2-methylphenyl)-3-(3-(1,2,3,4-tetrahydronaphthalen-1-yloxy)propyl)-1H-indole-2-carboxylic acid A mixture of EXAMPLE 564 (50 mg) and Raney-Ni (wet, 240 mg) in tetrahydrofuran (5 ml) and methanol (3 ml) was stirred under hydrogen at 30° C. for 1 hour. The insoluble material was filtered off. To the filtrate was added 10% NaOH (1 ml) and the resulting mixture was stirred overnight and acidified with HCl. The mixture was concentrated and the residue was purified by reverse phase HPLC (mobile phase: 10%-100% acetonitrile in 0.1% TFA aqueous solution during 60 min) to provide the title compound. $^1$H NMR (400 MHz, methanol-$d_4$) δ 7.69 (dd, J=7.98, 1.23 Hz, 1 H), 7.31-7.38 (m, 3 H), 7.27-7.30 (m, 2 H), 7.13-7.17 (m, 3 H), 7.07-7.12 (m, 2 H), 4.43 (t, J=4.60 Hz, 1 H), 3.71-3.76 (m, 1 H), 3.59-3.65 (m, 1 H), 3.23-3.27 (m, 2 H), 2.79-2.86 (m, 1 H), 2.67-2.75 (m, 1 H), 2.12 (s, 3 H), 1.94-2.06 (m, 4 H), 1.85-1.93 (m, 1 H), 1.69-1.77 (m, 1 H).

EXAMPLE 568

3-(3-((6-methoxy-1-naphthyl)oxy)propyl)-7-(2-methylphenyl)-1H-indole-2-carboxylic acid $^1$H NMR (500 MHz, dichloromethane-$d_2$) 8.49 (s, 1 H), 8.22 (d, J=9.76 Hz, 1 H), 7.75 (d, J=7.32 Hz, 1 H), 7.27-7.38 (m, 7 H), 7.16-7.21 (m, 2 H), 7.12 (s, 2 H), 6.64 (dd, J=5.80, 2.75 Hz, 1 H), 4.19 (t, J=6.10 Hz, 2 H), 3.89 (s, 3 H), 3.46 (t, J=7.48 Hz, 2 H), 2.32-2.38 (m, 2 H), 2.15 (s, 3 H).

EXAMPLE 569

1-(4-methoxybenzyl)-7-(2-methylphenyl)-3-(3-(1-naphthyloxy)prop-1-ynyl)-1H-indole-2-carboxylic acid $^1$H NMR (400 MHz, DMSO-$d_6$) δ 13.50 (s, 1 H), 8.21-8.24 (m, 1 H), 7.89-7.92 (m, 1 H), 7.63 (dd, J=7.98, 1.23 Hz, 1 H), 7.49-7.57 (m, 4 H), 7.28-7.33 (m, 2 H), 7.24 (t, J=7.67 Hz, 2 H), 7.14 (t, J=7.52 Hz, 1 H), 7.01-7.04 (m, 2 H), 6.61-6.65 (m, 2 H), 6.18 (s, 1 H), 6.16 (s, 1 H), 5.39 (s, 2 H), 5.29 (d, J=15.96 Hz, 1 H), 5.11 (d, J=16.26 Hz, 1 H), 3.62 (s, 3 H), 1.72 (s, 3 H).

EXAMPLE 570

3-(3-((2,3,4,5,6,7,8-heptafluoro-1-naphthyl)oxy)propyl)-7-(2-methylphenyl)-1H-indole-2-carboxylic acid $^1$H NMR (500 MHz, DMSO-$d_6$) 12.84 (s, 1 H), 10.51 (s, 1 H), 7.70 (d, J=7.93 Hz, 1 H), 7.33 (d, J=3.97 Hz, 2 H), 7.25-7.30 (m, 1 H), 7.21-7.23 (m, 1 H), 7.13-7.16 (m, 1 H), 7.05 (d, J=6.71 Hz, 1 H), 4.29 (t, J=6.41 Hz, 2 H), 3.25-3.29 (m, 2 H), 2.14-2.20 (m, 2 H), 2.05 (s, 3 H).

EXAMPLE 571

3-(3-(1-benzothien-7-yloxy)propyl)-7-(2-methylphenyl)-1H-indole-2-carboxylic acid $^1$H NMR (500 MHz, DMSO-$d_6$) 12.91 (s, 1 H), 10.50 (s, 1 H), 7.75 (d, J=5.49 Hz, 1 H), 7.69 (d, J=7.93 Hz, 1 H), 7.45-7.48 (m, 2 H), 7.25-7.33 (m, 4 H), 7.21-7.23 (m, 1 H), 7.08 (t, J=7.48 Hz, 1 H), 7.02-7.04 (m, 1 H), 6.87 (d, J=7.93 Hz, 1 H), 4.23 (t, J=6.10 Hz, 2 H), 3.27-3.32 (m, 2 H), 2.14-2.20 (m, 2 H), 2.06 (s, 3 H).

EXAMPLE 572

3-(3-((4-fluoro-1-naphthyl)oxy)propyl)-7-(2-methylphenyl)-1H-indole-2-carboxylic acid $^1$H NMR (500 MHz, DMSO-$d_6$) 12.97 (s, 1 H), 10.46 (s, 1 H), 8.28 (d, J=7.93 Hz, 1 H), 8.00 (d, J=7.63 Hz, 1 H), 7.61-7.69 (m, 3 H), 7.33 (d, J=3.66 Hz, 2 H), 7.24-7.29 (m, 1 H), 7.19-7.23 (m, 2 H), 7.02-7.08 (m, 2 H), 6.84 (dd, J=8.54, 3.97 Hz, 1 H), 4.19 (t, J=6.10 Hz, 2 H), 3.32-3.37 (m, 2 H), 2.20-2.26 (m, 2 H), 2.06 (s, 3 H).

EXAMPLE 573

3-(3-((8-fluoro-1-naphthyl)oxy)propyl)-7-(2-methylphenyl)-1H-indole-2-carboxylic acid $^1$H NMR (500 MHz, DMSO-da) 10.46 (s, 1 H), 7.69-7.72 (m, 2 H), 7.42-7.52 (m, 3 H), 7.33 (d, J=3.66 Hz, 2 H), 7.21-7.29 (m, 3 H), 7.02-7.07 (m, 2 H), 6.97 (d, J=7.63 Hz, 1 H), 4.15 (t, J=6.10 Hz, 2 H), 3.32-3.36 (m, 2 H), 2.16-2.22 (m, 2 H), 2.06 (s, 3 H).

EXAMPLE 574

3-(3-((5-fluoro-1-naphthyl)oxy)propyl)-7-(2-methylphenyl)-1H-indole-2-carboxylic acid $^1$H NMR (500 MHz, DMSO-da) 10.43 (s, 1 H), 8.07 (d, J=8.54 Hz, 1 H), 7.68 (d, J=7.32 Hz, 1 H), 7.57-7.59 (m, 1 H), 7.48-7.52 (m, 2 H), 7.36 (dd, J=10.98, 7.63 Hz, 1 H), 7.33 (d, J=3.66 Hz, 2 H), 7.25-7.29 (m, 1 H), 7.21-7.23 (m, 1 H), 7.05-7.09 (m, 1 H), 7.01-7.04 (m, 2 H), 4.23 (t, J=6.10 Hz, 2 H), 3.22-3.31 (m, 2 H), 2.21-2.27 (m, 2 H), 2.06 (s, 3 H).

EXAMPLE 575

7-fluoro-3-(2-isopropylphenyl)-1-(3-(1-naphthyloxy)propyl)-1H-indole-2-carboxylic acid $^1$H NMR (400 MHz, DMSO-da) 12.87 (s, 1 H), 8.06 (d, J=8.29 Hz, 1 H), 7.84 (d, J=7.98 Hz, 1 H), 7.50 (t, J=6.90 Hz, 1 H), 7.32-7.47 (m, 5 H), 7.12-7.20 (m, 2 H), 6.99-7.05 (m, 2 H), 6.88 (d, J=8.59 Hz, 2 H), 5.03 (t, J=8.13 Hz, 2 H), 4.18 (t, J=5.83 Hz, 2 H), 2.63-2.70 (m, 1 H), 2.38-2.46 (m, 2 H), 1.00 (d, J=6.75 Hz, 3 H), 0.93 (d, J=6.75 Hz, 3 H).

EXAMPLE 576

7-fluoro-3-(2-methylphenyl)-1-(3-(1-naphthyloxy)propyl)-1H-indole-2-carboxylic acid $^1$H NMR (400 MHz, DMSO-$d_6$) 8.09 (d, J=8.90 Hz, 1 H), 7.85 (d, J=8.29 Hz, 1 H), 7.49-7.53 (m, 1 H), 7.36-7.47 (m, 3 H), 7.09-7.31 (m, 5 H), 6.99-7.04 (m, 1 H), 6.88-6.91 (m, 2 H), 5.02 (t, J=7.21 Hz, 2 H), 4.20 (t, J=5.68 Hz, 2 H), 2.38-2.45 (m, 2 H), 1.99 (s, 3 H).

EXAMPLE 577

3-(3-((5-fluoro-1-naphthyl)oxy)propyl)-7-(1,3,5-trimethyl-1H-pyrazol-4-yl)-1H-indole-2-carboxylic acid $^1$H NMR (400 MHz, DMSO-$d_6$) 10.51 (s, 1 H), 8.07 (d, J=8.59 Hz, 1 H), 7.65 (d, J=6.75 Hz, 1 H), 7.56-7.60 (m, 1 H), 7.46-7.53 (m, 2 H), 7.36 (dd, J=11.05, 6.75 Hz, 1 H), 7.04-7.08 (m, 1 H), 7.01-7.03 (m, 2 H), 4.23 (t, J=6.14 Hz, 2 H), 3.75 (s, 3 H), 3.33-3.37 (m, 2 H), 2.19-2.27 (m, 2 H), 2.05 (s, 3 H), 2.00 (s, 3 H).

EXAMPLE 578

3-(3-(1-naphthyloxyl)propyl)-1-(pyridin-4-ylmethyl)-7-(1,3,5-trimethyl-1H-pyrazol-4-yl)-1H-indole-2-carboxylic acid $^1$H NMR (400 MHz, DMSO-$d_6$) 8.62 (d, J=6.44 Hz, 2 H), 8.23-8.28 (m, 1 H), 7.83-7.90 (m, 2 H), 7.45-7.57 (m, 3 H), 7.38-7.44 (m, 1 H), 7.12-7.18 (m, 1 H), 6.90-6.96 (m, 4 H), 5.79 (d, J=18.41 Hz, 1 H), 5.58 (d, J=18.10 Hz, 1 H), 4.28 (t, J=5.98 Hz, 2 H), 3.59 (s, 3 H), 3.39-3.46 (m, 2 H), 2.25-2.33 (m, 2 H), 1.65 (s, 3 H), 1.58 (s, 3 H).

EXAMPLE 579

3-(3-(1-naphthyloxyl)propyl)-1-(pyridin-2-ylmethyl)-7-(1,3,5-trimethyl-1H-pyrazol-4-yl)-1H-indole-2-carboxylic acid $^1$H NMR (400 MHz, DMSO-$d_6$) 8.43 (d, J=4.30 Hz, 1 H), 8.24-8.27 (m, 1 H), 7.86-7.89 (m, 1 H), 7.81 (d, J=7.06 Hz, 1 H), 7.74 (t, J=8.29 Hz, 1 H), 7.49-7.56 (m, 2 H), 7.44-7.48 (m, 1 H), 7.38-7.42 (m, 1 H), 7.30-7.35 (m, 1 H), 7.09-7.14 (m, 1 H), 6.92 (t, J=7.36 Hz, 1 H), 6.89 (dd, J=7.06, 0.92 Hz, 1 H), 6.31 (d, J=7.67 Hz, 1 H), 5.73 (d, J=18.10 Hz, 1 H), 5.49 (d, J=17.49 Hz, 1 H), 4.26 (t, J=6.14 Hz, 2 H), 3.59 (s, 3 H), 3.36-3.44 (m, 2 H), 2.24-2.31 (m, 2 H), 1.67 (s, 3 H), 1.56 (s, 3 H).

EXAMPLE 580

3-(3-(1-naphthyloxyl)propyl)-1-(pyridin-3-ylmethyl)-7-(1,3,5-trimethyl-1H-pyrazol-4-yl)-1H-indole-2-carboxylic acid

EXAMPLE 580A ethyl 3-(3-(naphthalen-1-yloxy)propyl)-7-(1,3,5-trimethyl-1H-pyrazol-4-yl)-1H-indole-2-carboxylate To a mixture of ethyl 7-bromo-3-(3-(naphthalen-1-yloxy)propyl)-1H-indole-2-carboxylate (EXAMPLE 1C) (1.605 g) and 1,3,5-trimethyl-4-(4,4,5,5-tetramethyl-1,3,2-dioxaborolan-2-yl)-1H-pyrazole (0.838 g) in toluene (25 ml) was added diacetoxypalladium (0.080 g), dicyclohexyl(2',6'-dimethoxybiphenyl-2-yl)phosphine (0.291 g), and K$_3$PO$_4$ (2.259 g). The resulting mixture was stirred at 110° C. overnight. Silica gel (25 g) was added and the mixture was carefully dried on house vacuum overnight. The gel powder was loaded onto a flash column and eluted with 0-50% ethyl acetate in dichloromethane to provide the title compound.

EXAMPLE 580B 3-(3-(1-naphthyloxyl)propyl)-1-(pyridin-3-ylmethyl)-7-(1,3,5-trimethyl-1H-pyrazol-4-yl)-1H-indole-2-carboxylic acid A mixture of EXAMPLE 580A (90 mg), 3-(bromomethyl)pyridine hydrobromide (47.3 mg) and cesium carbonate (183 mg) in N,N-dimethylformamide (3.5 ml) was stirred at room temperature overnight. The insoluble material was filtered off and the filtrate was concentrated. The residue was suspended in tetrahydrofuran-methanol, and 10% NaOH was added. The resulting mixture was stirred at room temperature overnight and concentrated. The residue was dissolved in a mixture of DMSO and methanol. The solution was purified by reverse phase HPLC (mobile phase: 10%-100% acetonitrile in 0.1% TFA aqueous solution during 60 minutes) to provide the title compound. $^1$H NMR (400 MHz, DMSO-$d_6$) δ 8.55 (d, J=5.22 Hz, 1 H), 8.23-8.28 (m, 1 H), 7.85-7.90 (m, 1 H), 7.80-7.85 (m, 2 H), 7.49-7.57 (m, 3 H), 7.45-7.49 (m, 1 H), 7.38-7.43 (m, 1 H), 7.19 (d, J=7.67 Hz, 1 H), 7.10-7.15 (m, 1 H), 6.92 (t, J=7.67 Hz, 2 H), 5.65 (d, J=17.49 Hz, 1 H), 5.44 (d, J=17.80 Hz, 1 H), 4.26 (t, J=5.98 Hz, 2 H), 3.62 (s, 3 H), 3.35-3.49 (m, 2 H), 2.24-2.32 (m, 2 H), 1.67 (s, 3 H), 1.59 (s, 3 H).

EXAMPLE 581

7-(2-methylphenyl)-3-(3-(1-naphthyloxyl)propyl)-2-(1H-tetraazol-5-yl)-1H-indole

EXAMPLE 581A ethyl 7-bromo-1-(4-methoxybenzyl)-3-(3-(naphthalen-1-yloxy)propyl)-1H-indole-2-carboxylate To a solution of ethyl 7-bromo-3-(3-(naphthalen-1-yloxy)propyl)-1H-indole-2-carboxylate (2.39 g, prepared in a similar manner as described herein) in N,N-dimethylamide (20 mL) was added 1-(chloromethyl)-4-methoxybenzene (1.0 g) and Cs$_2$CO$_3$ (5.16 g). The mixture was stirred overnight at

EXAMPLE 581B 7-bromo-1-(4-methoxybenzyl)-3-(3-(naphthalen-1-yloxy)propyl)-1H-indole-2-carboxamide To a solution of EXAMPLE 581A (1 g) in oxalyl chloride (10 mL) was added a few drops of N,N-dimethylamide. The mixture was stirred for 3 hours at room temperature. The mixture was concentrated under vacuum and the residue was dissolved in dichloromethane (20 ml) and added to cooled (0° C.) concentrated $NH_3H_2O$ (30 ml). After the addition, the mixture was stirred for 2 hours before extraction with ethyl acetate (200 ml). The organic extract was washed with water, brine and dried over $Na_2SO_4$. After filtration, evaporation of solvent gave Example 581B.

EXAMPLE 581C 7-bromo-1-(4-methoxybenzyl)-3-(3-(naphthalen-1-yloxy)propyl)-1H-indole-2-carbonitrile To a cooled (0° C.) solution of EXAMPLE 581B (545 mg) in tetrahydrofuran (5 mL) and dichloromethane (1 ml) was added triethylamine (1 ml) followed by trifluoroacetic acid (1 ml) dropwise. After the addition, the mixture was stirred for 3 hours at 0° C. The mixture was diluted with ethyl acetate (200 mL) and water (80 mL). The aqueous layer was extracted with ether. The combined organic extracts were washed with water (×3), brine and dried over $Na_2SO_4$. After filtration, concentration of the solvent gave Example 581C.

EXAMPLE 581D 1-(4-methoxybenzyl)-3-(3-(naphthalen-1-yloxy)propyl)-7-o-tolyl-1H-indole-2-carbonitrile To a mixture of EXAMPLE 581C (300 mg) and o-tolylboronic acid (93 mg) in 1,2-dimethoxyethane (10 ml) and methanol (5 ml) was added tetrakis(triphenylphosphine)palladium(0) (33 mg) and CsF (260 mg). The mixture was stirred at reflux under nitrogen for 4 hours. The mixture was concentrated under vacuum and the residue was partitioned between ethyl acetate (300 mL) and water (100 ml). The aqueous layer was further extracted with ethyl acetate and the combined extracts were washed with water, brine and dried over $Na_2SO_4$. After filtration, concentration of the solvent and column purification (5 to 10% ethyl acetate in hexane) gave Example 581D.

EXAMPLE 581E 7-(2-methylphenyl)-3-(3-(1-naphthyloxyl)propyl)-2-(1H-tetraazol-5-yl)-1H-indole To a mixture of EXAMPLE 581D (232 mg) in N,N-dimethylamide (10 ml) was added $NaN_3$ (281 mg) and $NH_4Cl$ (231 mg). The mixture was stirred at reflux overnight. The mixture was concentrated under vacuum and the residue was partitioned between ethyl acetate (200 ml) and water (60 ml). The organic phase was washed with brine and dried over $Na_2SO_4$. Concentration of the solvent gave crude product which was dissolved in dichloromethane/trifluoroacetic acid (1:1, 4 ml) and heated to 125° C. in a microwave (CEM Discover) for 20 minutes. The mixture was concentrated and the residue was dissolved in dimehtylsulfoxide/methanol (1/1,2 ml) and loaded on HPLC for purification. $^1H$ NMR (300 MHz, DMSO-$d_6$) δ 10.63 (m, 1H), 8.26 (m, 1H), 7.86 (m, 1H), 7.74 (d, 1H), 7.53 (m, 2H), 7.42 (m, 5 H), 7.33 (m, 2H), 7.11 (m, 3H), 6.90 (d, 1H), 4.23 (t, 2H), 2.29 (m, 2H), 2.13 (s, 3H).

EXAMPLE 582

1-(4-methoxybenzyl)-7-(2-methylphenyl)-3-(3-(1-naphthyloxy)propyl)-2-(1H-tetraazol-5-yl)-1H-indole $^1H$ NMR (300 MHz, DMSO-$d_6$) δ 8.08 (d, 1H), 7.84 (m, 2H), 7.52 (m, 2H), 7.45 (d, 1H), 7.39 (d, 1H), 7.32 (m, 1H), 7.25 (d, 1H), 7.17 (m, 2H), 7.10 (d, 1H), 6.96 (d, 1H), 6.85 (d, 1H), 6.51 (d, 2H), 6.02 (d, 2H), 4.89 (dd, 2H), 4.14 (t, 2H), 3.57 (s, 3H), 3.16 (m, 2H), 2.20 (m, 2H), 1.80 (s, 3H).

EXAMPLE 585

7-(1-methyl-1H-imidazol-5-yl)-3-(3-(1-naphthyloxy)propyl)-1H-indole-2-carboxylic acid $^1H$ NMR (300 MHz, DMSO-$d_6$) δ 14.39 (s, 1H), 13.21 (s, 1H), 11.52 (s, 1H), 9.23 (s, 1H), 8.12-8.32 (m, 1H), 7.83-7.97 (m, 2H), 7.80 (d, J=1.7 Hz, 1H), 7.33-7.69 (m, 5H), 7.30 (d, J=6.1 Hz, 1H), 7.07-7.22 (m, 1H), 6.89 (d, J=6.4 Hz, 1H), 4.19 (t, J=6.1 Hz, 2H), 3.55 (s, 3H), 3.38 (t, J=7.3 Hz, 2H), 2.11-2.34 (m, 2H).

EXAMPLE 586

1-(2-(dimethylamino)-2-oxoethyl)-3-(3-(3-(1-naphthyloxyl)propyl)-7-(1,3,5-trimethyl-1H-pyrazol-4-yl)-1H-indole-2-carboxylic acid $^1H$ NMR (400 MHz, DMSO-$d_6$) 13.01 (s, 1 H), 8.26-8.30 (m, 1 H), 7.84-7.90 (m, 1 H), 7.73 (d, J=7.06 Hz, 1 H), 7.50-7.55 (m, 2 H), 7.44-7.48 (m, 1 H), 7.40 (t, J=7.98 Hz, 1 H), 7.03-7.08 (m, 1 H), 6.92 (d, J=7.36 Hz, 1 H), 6.88 (d, J=6.14 Hz, 1 H), 5.07-5.24 (m, 2 H), 4.23 (t, J=6.14 Hz, 2 H), 3.74 (s, 3 H), 3.31-3.38 (m, 2 H), 2.69 (s, 3 H), 2.56 (s, 3 H), 2.19-2.26 (m, 2 H), 1.91 (s, 3 H), 1.84 (s, 3 H).

EXAMPLE 587

1-(2-(4-methylpiperazin-1-yl)-2-oxoethyl)-3-(3-(1-naphthyloxy)propyl)-7-(1,3,5-trimethyl-1H-pyrazol-4-yl)-1H-indole-2-carboxylic acid $^1H$ NMR (500 MHz, pyridine-$d_5$) 8.64-8.68 (m, 1 H), 8.01 (d, J=7.02 Hz, 1 H), 7.87-7.90 (m, 1 H), 7.48-7.53 (m, 3 H), 7.36-7.40 (m, 1 H), 7.30-7.33 (m, 1 H), 7.19-7.21 (m, 1 H), 6.87 (d, J=7.32 Hz, 1 H), 6.05 (s, br, 1 H), 5.79 (s, br, 1 H), 4.28 (t, J=6.26 Hz, 2 H), 3.74-3.87 (m, 6 H), 3.24-3.52 (m, 3 H), 2.40-2.56 (m, 5 H), 2.35 (s, br, 1 H), 2.31 (s, 3 H), 2.22 (s, 3 H), 2.02 (s, 3 H).

EXAMPLE 588

7-(4,6-dimethylpyrimidin-5-yl)-1-(2-morpholin-4-yl-2-oxoethyl)-3-(3-(1-naphthyloxyl)propyl)-1H-indole-2-carboxylic acid $^1H$ NMR (400 MHz, DMSO-$d_6$) 9.01 (s, 1H), 8.27-8.29 (m, 1H), 7.84-7.88 (m, 2H), 7.45-7.56 (m, 3H), 7.39 (t, J=7.98

Hz, 1H), 7.16 (t, J=7.67 Hz, 1H), 7.01 (d, J=6.44 Hz, 1H), 6.92 (d, J=7.67 Hz, 1H), 4.92 (br, 2H), 4.24 (t, J=6.14 Hz, 2H), 3.07 (br, 2H), 3.35-3.40 (m, 4H), 3.22 (br, 2H), 2.93 (br, 2H), 2.15-2.28 (m, 2H), 2.09 (s, 6H).

EXAMPLE 589

1-(2-(4-methylpiperazin-1-yl)ethyl)-3-(3-(1-naphthyloxyl)propyl)-7-(1,3,5-trimethyl-1H-pyrazol-4-yl)-1H-indole-2-carboxylic acid $^1$H NMR (500 MHz, pyridine-$d_5$) 8.66 (d, J=7.93 Hz, 1 H), 8.01 (dd, J=8.09, 1.07 Hz, 1 H), 7.89-7.91 (m, 1 H), 7.48-7.55 (m, 3H), 7.32-7.42 (m, 2 H), 7.18-7.21 (m, 1 H), 6.91 (d, J=7.63 Hz, 1 H), 4.96-5.03 (m, 1 H), 4.71-4.78 (m, 1 H), 4.33 (t, J=6.10 Hz, 2 H), 3.84 (s, 3 H), 3.77 (t, J=7.48 Hz, 2 H), 2.98 (s, 3 H), 2.58 (s, 3 H), 2.42-2.58 (m, 6 H), 2.23 (s, 3 H), 2.21-2.27 (m, 1 H), 2.14 (s, 3 H), 2.10 (d, J=7.93 Hz, 1 H).

EXAMPLE 590

1-(2-morpholin-4-ylethyl)-3-(3-(1-naphthyloxyl)propyl)-7-(1,3,5-trimethyl-1H-pyrazol-4-yl)-1H-indole-2-carboxylic acid $^1$H NMR (500 MHz, pyridine-$d_5$) 8.66-8.69 (m, 1 H), 8.00-8.03 (m, 1 H), 7.89 (d, J=7.32 Hz, 1 H), 7.47-7.55 (m, 3 H), 7.31-7.43 (m, 2 H), 7.21 (m, 1 H), 6.92 (d, J=7.63 Hz, 1 H), 4.95-5.03 (m, 1 H), 4.83-4.89 (m, 1 H), 4.34 (t, J=6.26 Hz, 2 H), 3.76-3.81 (m, 2 H), 3.76 (s, 3 H), 3.61 (t, J=4.73 Hz, 4 H), 2.55-2.61 (m, 2 H), 2.39-2.44 (m, 1 H), 2.27 (s, 3 H), 2.20-2.30 (m, 5 H), 2.09 (s, 3 H).

EXAMPLE 591

1-(2-morpholin-4-yl-2-oxoethyl)-3-(3-(1-naphthyloxy)propyl)-7-(1,3,5-trimethyl-1H-pyrazol-4-yl)-1H-indole-2-carboxylic acid $^1$H NMR (500 MHz, methanol-$d_4$) 8.31-8.37 (m, 1 H), 7.74-7.81 (m, 2 H), 7.46-7.50 (m, 2 H), 7.36-7.41 (m, 1 H), 7.33 (t, J=7.93 Hz, 1 H), 7.01-7.07 (m, 1 H), 6.91-6.97 (m, 1 H), 6.80-6.83 (m, 1 H), 5.27 (s, 2 H), 4.20-4.24 (m, 2 H), 3.85-3.88 (m, 1 H), 3.85-3.90 (m, 1 H), 3.82-3.85 (m, 3 H), 3.82-3.84 (m, 3 H), 3.55-3.62 (m, 4 H), 3.44-3.50 (m, 3 H), 3.34-3.40 (m, 2 H), 3.16-3.24 (m, 3 H), 2.31-2.37 (m, 2 H), 1.93-2.03 (m, 6 H).

EXAMPLE 592

1-(2-(dimethylamino)ethyl)-3-(3-(1-naphthyloxyl)propyl)-7-(1,3,5-trimethyl-1H-pyrazol-4-yl)-1H-indole-2-carboxylic acid $^1$H NMR (500 MHz, pyridine-$d_5$) 8.65-8.69 (m, 1 H), 8.01 (d, J=7.02 Hz, 1 H), 7.89-7.91 (m, 1 H), 7.49-7.55 (m, 3 H), 7.40 (t, J=7.93 Hz, 1 H), 7.30-7.36 (m, 1 H), 7.19 (m, 1 H), 6.91 (d, J=7.63 Hz, 1 H), 5.01 (t, J=7.93 Hz, 2 H), 4.33 (t, J=6.10 Hz, 2 H), 3.81 (s, 3 H), 3.75-3.79 (m, 2 H), 2.86-2.99 (m, 2 H), 2.50-2.58 (m, 2 H), 2.47 (s, 6 H), 2.21 (s, 3 H), 2.12 (s, 3 H).

EXAMPLE 593

7-(2-methylimidazo(1,2-a)pyridin-3-yl)-3-(3-(1-naphthyloxyl)propyl)-1H-indole-2-carboxylic acid $^1$H NMR (400 MHz, DMSO-$d_6$) 13.16 (s, 1H), 11.35 (s, 1H), 8.14-8.36 (m, 1H), 7.91-8.08 (m, 4H), 7.84-7.90 (m, 1H), 7.37-7.57 (m, 5H), 7.34 (t, J=6.3 Hz, 1H), 7.22-7.29 (m, 1H), 6.92 (d, J=7.1 Hz, 1H), 4.23 (t, J=6.1 Hz, 2H), 3.37-3.46 (m, 2H), 2.37 (s, 3H), 2.21-2.31 (m, 2H),

EXAMPLE 594

7-(2-(1H-imidazol-1-yl)-4-methylpyridin-3-yl)-3-(3-(1-naphthyloxyl)propyl)-1-(pyridin-2-ylmethyl)-1H-indole-2-carboxylic acid $^1$H NMR (400 MHz, DMSO-$d_6$) 13.31 (s, 1H), 8.72 (s, 1H), 8.55 (d, J=4.7 Hz, 1H), 8.22-8.33 (m, 1H), 8.19 (d, J=4.1 Hz, 1H), 7.83-7.96 (m, 2H), 7.44-7.59 (m, 5H), 7.35-7.43 (m, 1H), 7.32 (s, 1H), 7.19 (s, 1H), 7.06-7.16 (m, 3H), 6.89 (d, J=6.8 Hz, 1H), 6.40 (d, J=7.8 Hz, 1H), 5.44 (d, J=17.3 Hz, 1H), 5.22 (d, J=17.3 Hz, 1H), 4.20 (t, J=6.1 Hz, 2H), 3.26-3.43 (m, 2H), 2.17-2.30 (m, 2H), 1.83 (s, 3H).

EXAMPLE 595

7-(2-ethyl-4-methylpyridin-3-yl)-3-(3-(1-naphthyloxyl)propyl)-1-(pyridin-2-ylmethyl)-1H-indole-2-carboxylic acid $^1$H NMR (400 MHz, DMSO-$d_6$) 8.63-8.67 (m, 1H) 8.22-8.28 (m, 2H) 7.96 (d, 1H) 7.85-7.90 (m, 1H) 7.34-7.72 (m, 6H) 7.15-7.27 (m, 2H) 7.03 (d, 1H) 6.92 (d, 1H) 6.37 (d, 1H) 5.40 (d, 1H) 5.18 (d, 1H) 4.27 (t, 2H) 2.26-2.35 (m, 2H) 1.97-2.15 (m, 2H) 1.86 (s, 3H) 0.90 (t, 3H).

EXAMPLE 596

7-(2-ethyl-4-methylpyridin-3-yl)-3-(3-(1-naphthyloxyl)propyl)-1-((1-(pyridin-4-ylmethyl)pyridinium-4-yl)methyl)-1H-indole-2-carboxylate $^1$H NMR (400 MHz, DMSO-$d_6$) 8.88-8.92 (m, 2H) 8.69-8.72 (m, 2H) 8.39-8.43 (m, 1H) 8.23-8.28 (m, 1H) 7.95-7.99 (m, 1H) 7.85-7.90 (m, 1H) 7.37-7.58 (m, 6H) 7.22-7.35 (m, 3H) 7.10-7.21 (m, 1H) 6.91-7.06 (m, 2H) 5.85 (s, 2H) 5.24-5.61 (m, 2H) 4.30 (t, 2H) 3.45 (t, 2H) 2.26-2.38 (m, 2H) 1.87-2.13 (m, 2H) 1.70-1.82 (m, 3H) 0.82 (t, 3H).

EXAMPLE 597

7-(2-ethyl-4-methylpyridin-3-yl)-3-(3-(1-naphthyloxyl)propyl)-1-(pyridin-4-ylmethyl)-1H-indole-2-carboxylic acid $^1$H NMR (400 MHz, DMSO-$d_6$) 8.60 (d, 1H) 8.43 (d, 2H) 8.22-8.28 (m, 1H) 7.99 (d, 1H) 7.85-7.91 (m, 1H) 7.37-7.59 (m, 5H) 7.25 (t, 1H) 7.02-7.07 (m, 1H) 6.94 (d, 1H) 6.69 (d, 2H) 5.38-5.51 (m, 1H) 5.14-5.28 (m, 1H) 4.29 (t, 2H) 3.46 (t, 2H) 2.27-2.37 (m, 2H) 1.92-2.13 (m, 2H) 1.85 (s, 3H) 0.88 (t, 3H).

EXAMPLE 598

7-(2-ethyl-4-methylpyridin-3-yl)-1-(2-morpholin-4-yl-2-oxoethyl)-3-(3-(1-naphthyloxyl)propyl)-1H-indole-2-carboxylic acid $^1$H NMR (400 MHz, DMSO-$d_6$) 12.96 (br. s, 1H) 8.60-8.67 (m, 1H) 8.24-8.29 (m, 1H) 7.84-7.90 (m, 2H) 7.49-7.59 (m, 3H) 7.46 (d, 1H) 7.39 (t, 1H) 7.19 (t, 1H) 7.03 (d, 1H) 6.91 (d, 1H) 4.24 (t, 2H) 2.18-2.40 (m, 4H) 2.01 (s, 3H) 1.02 (t, 3H).

EXAMPLE 599

1-(2-(dimethylamino)-2-oxoethyl)-7-(2-ethyl-4-methylpyridin-3-yl)-3-(3-(1-naphthyloxyl)propyl)-1H-indole-2-carboxylic acid $^1$H NMR (400 MHz, DMSO-d$_6$) 8.51-8.56 (m, 1H) 8.25-8.31 (m, 1H) 7.79-7.90 (m, 2H) 7.26-7.58 (m, 5H) 7.10-7.22 (m, 1H) 6.89-7.02 (m, 2H) 4.24 (t, 2H) 2.63 (s, 2H) 2.20-2.39 (m, 7H) 1.85-1.97 (m, 3H) 1.01 (t, 3H).

EXAMPLE 600

7-(2-ethyl-4-methylpyridin-3-yl)-1-(2-(4-methylpiperazin-1-yl)-2-oxoethyl)-3-(3-(1-naphthyloxyl)propyl)-1H-indole-2-carboxylic acid $^1$H NMR (400 MHz, DMSO-d$_6$) 10.19 (s, 1H) 8.62-8.77 (m, 1H) 8.21-8.32 (m, 1H) 7.82-7.95 (m, 2H) 7.33-7.74 (m, 5H) 7.18 (t, 1H) 7.02 (d, 1H) 6.90 (d, 1H) 4.23 (t, 2H) 3.34-3.40 (m, 6H) 2.61-2.97 (m, 6H) 2.15-2.41 (m, 3H) 2.01 (s, 3H) 1.02 (t, 3H).

EXAMPLE 601

7-(2-ethyl-4-methylpyridin-3-yl)-1-(2-morpholin-4-ylethyl)-3-(3-(1-naphthyloxy)propyl)-1H-indole-2-carboxylic acid $^1$H NMR (400 MHz, DMSO-d$_6$) 8.53-8.57 (m, 1H) 8.21-8.26 (m, 1H) 7.83-7.89 (m, 2H) 7.35-7.58 (m, 5H) 7.20 (t, 1H) 7.02 (d, 1H) 6.91 (d, 1H) 4.25 (t, 2H) 2.18-2.40 (m, 8H) 2.03 (s, 3H) 1.07 (t, 3H).

EXAMPLE 602

1-(2-(dimethylamino)ethyl)-7-(2-ethyl-4-methylpyridin-3-yl)-3-(3-(1-naphthyloxyl)propyl)-1H-indole-2-carboxylic acid $^1$H NMR (400 MHz, DMSO-d$_6$) 9.78 (s, 1H) 8.63 (d, 1H) 8.17-8.25 (m, 1H) 7.81-7.91 (m, 2H) 7.31-7.60 (m, 5H) 7.20 (t, 1H) 7.04 (d, 1H) 6.89 (d, 1H) 4.22 (t, 2H) 3.36 (t, 2H) 2.74-2.89 (m, 2H) 2.49 (s, 6H) 2.30-2.43 (m, 2H) 2.16-2.27 (m, 2H) 2.06 (s, 3H) 1.05 (t, 3H).

EXAMPLE 603

7-(2-ethyl-4-methylpyridin-3-yl)-1-(2-(4-methylpiperazin-1-yl)ethyl)-3-(3-(1-naphthyloxyl)propyl)-1H-indole-2-carboxylic acid $^1$H NMR (400 MHz, DMSO-d$_6$) 8.69 (d, 1H) 8.20-8.26 (m, 1H) 7.84-7.91 (m, 2H) 7.66 (d, 1H) 7.44-7.57 (m, 3H) 7.39 (t, 1H) 7.20 (t, 1H) 7.06 (d, 1H) 6.91 (d, 1H) 4.23 (t, 2H) 3.91-3.98 (m, 2H) 3.34 (t, 2H) 3.23-3.30 (m, 2H) 2.75-2.87 (m, 2H) 2.72 (s, 3H) 2.53-2.62 (m, 2H) 2.00-2.31 (m, 10H) 1.08 (t, 3H).

EXAMPLE 604

7-(2-((4-(4-carboxyphenyl)piperazin-1-yl)methyl)phenyl)-3-(3-(1-naphthyloxyl)propyl)-1H-indole-2-carboxylic acid $^1$H NMR (300 MHz, DMSO-d$_6$) δ 12.96 (s, 1H), 12.37 (s, 1H), 11.05 (s, 1H), 9.46 (s, 1H), 8.14-8.30 (m, 1H), 7.82-7.90 (m, 1H), 7.69-7.78 (m, 4H), 7.55-7.63 (m, 2H), 7.47-7.55 (m, 2H), 7.45 (d, J=8.1 Hz, 1H), 7.32-7.42 (m, 3H), 7.08-7.12 (m, 2H), 6.83-6.91 (m, 4H), 4.39 (d, J=16.7 Hz, 1H), 4.19 (t, J=5.9 Hz, 2H), 4.08 (d, J=16.7 Hz, 1H), 3.62-3.76 (m, 2H), 3.29-3.42 (m, 2H), 3.13-3.26 (m, 1H), 2.93-3.10 (m, 1H), 2.75-2.87 (m, 2H), 2.16-2.26 (m, 2H).

EXAMPLE 605

3-(3-(1-naphthyloxy)propyl)-7-(2-piperazin-1-ylpyridin-3-yl)-1H-indole-2-carboxylic acid $^1$H NMR (300 MHz, DMSO-d$_6$) δ 13.12 (s, 1H), 10.87 (s, 1H), 8.44 (s, 2H), 8.32 (dd, =4.7, 1.7 Hz, 1H), 8.22-8.29 (m, 1H), 7.84-7.90 (m, 1H), 7.70-7.80 (m, 2H), 7.48-7.58 (m, 2H), 7.46 (d, J=8.1 Hz, 1H), 7.35-7.43 (m, 1H), 7.31 (d, J=6.1 Hz, 1H), 7.07-7.16 (m, 2H), 6.89 (d, J=6.4 Hz, 1H), 4.19 (t, J=6.1 Hz, 2H), 3.12 (s, 4H), 2.59-2.71 (m, 2H), 2.16-2.31 (m, 2H).

EXAMPLE 606

1-(2-(dimethylamino)-2-oxoethyl)-7-(2-(1H-imidazol-1-yl)-4-methylpyridin-3-yl)-3-(3-(1-naphthyloxyl)propyl)-1H-indole-2-carboxylic acid $^1$H NMR (300 MHz, DMSO-d$_6$) δ 13.23 (s, 1H), 8.61 (d, J=4.7 Hz, 1H), 8.24-8.39 (m, 1H), 8.16-8.25 (m, 1H), 7.76-7.95 (m, 2H), 7.64 (d, J=5.1 Hz, 1H), 7.49-7.57 (m, 2H), 7.46 (d, J=8.1 Hz, 1H), 7.36-7.43 (m, 1H), 7.26 (s, 1H), 6.99-7.12 (m, 3H), 6.90 (d, J=7.5 Hz, 1H), 4.94 (s, 1H), 4.20 (t, J=6.3 Hz, 2H), 3.39-3.52 (m, 2H), 2.57 (s, 3H), 2.16-2.25 (m, 2H), 2.07 (s, 3H).

EXAMPLE 607

7-(2-(1H-imidazol-1-yl)-4-methylpyridin-3-yl)-3-(3-(1-naphthyloxyl)propyl)-1-(pyridin-3-ylmethyl)-1H-indole-2-carboxylic acid $^1$H NMR (300 MHz, DMSO-d$_6$) δ 13.44 (s, 1H), 8.55 (d, J=4.7 Hz, 1H), 8.14-8.37 (m, 3H), 7.90-7.98 (m, 1H), 7.84-7.90 (m, 1H), 7.36-7.58 (m, 6H), 7.08-7.21 (m, 4H), 6.98 (s, 1H), 6.91 (d, J=7.5 Hz, 1H), 6.69 (d, J=8.5 Hz, 1H), 5.52 (d, J=17.3 Hz, 1H), 4.97 (d, J=17.3 Hz, 1H), 4.21 (t, J=6.3 Hz, 2H), 3.38 (t, 2H), 3.11-3.21 (m, 2H), 2.16-2.30 (m, 2H), 1.68 (s, 3H).

EXAMPLE 608

7-(2-(1H-imidazol-1-yl)-4-methylpyridin-3-yl)-1-(2-morpholin-4-yl-2-oxoethyl)-3-(3-(1-naphthyloxyl)propyl)-1H-indole-2-carboxylic acid $^1$H NMR (300 MHz, DMSO-d$_6$) δ 13.26 (s, 1H), 8.66 (d, J=5.1 Hz, 1H), 8.41 (s, 1H), 8.23-8.31 (m, 1H), 7.80-7.91 (m, 2H), 7.71 (d, J=5.1 Hz, 1H), 7.49-7.57 (m, 2H), 7.46 (d, J=8.1 Hz, 1H), 7.36-7.43 (m, 1H), 7.31 (s, 1H), 7.15-7.23 (m, 1H), 7.00-7.10 (m, 2H), 6.90 (d, J=7.5 Hz, 1H), 4.88 (d, 2H), 4.20 (t, J=6.1 Hz, 2H), 3.34 (s, 4H), 3.17 (s, 2H), 3.04 (s, 2H), 2.14-2.25 (m, 2H), 2.09 (s, 3H).

EXAMPLE 609

7-(2-(1H-imidazol-1-yl)-4-methylpyridin-3-yl)-3-(3-(1-naphthyloxyl)propyl)-1-(2-oxo-2-piperazin-1-ylethyl)-1H-indole-2-carboxylic acid $^1$H NMR (300 MHz, DMSO-d$_6$) δ 13.22 (s, 2H), 8.57 (d, J=4.7 Hz, 1H), 8.24-8.31 (m, 1H), 7.82-7.91 (m, 2H), 7.49-7.61 (m, 3H), 7.47 (d, J=8.1 Hz, 1H), 7.35-7.44 (m, 1H), 7.10 (t, J=7.6 Hz, 3H), 6.89 (d, J=6.8 Hz, 2H), 6.47 (s, 1H), 5.01 (s, 1H), 4.21 (t, J=5.8 Hz, 2H), 3.12-3.29 (m, 4H), 2.81-3.06 (m, 4H), 2.16-2.25 (m, 2H), 2.03 (s, 3H).

The foregoing is meant to illustrate the invention but not to limit it. Variations and changes obvious to one skilled in the art are intended to be within the scope of the invention as defined in the appended claims.

We claim:

1. A compound, or a therapeutically acceptable salt thereof, wherein the compound is selected from the group consisting of:

3-(3-(3,4-dihydroquinolin-1(2H)-yl)propyl)-7-(2-(trifluoromethyl)phenyl)-1H-indole-2-carboxylic acid;

3-(4-(3,4-dihydroquinolin-1 (2H)-yl)butyl)-7-(2-(trifluoromethyl)phenyl)-1H-indole-2-carboxylic acid;

7-(4-carboxy-2-methylphenyl)-3-(4-(3,4-dihydroquinolin-1(2H)-yl)butyl)-1H-indole-2-carboxylic acid;

1-(carboxymethyl)-7-(2-methylphenyl)-3-(3-(1-naphthyloxyl)propyl)-1H-indole-2-carboxylic acid;

3-(4-(3,4-dihydroquinolin-1 (2H)-yl)butyl)-7-(4-(morpholin-4-ylcarbonyl)-2-(trifluoromethyl)phenyl)-1H-indole-2-carboxylic acid;

3-(4-(2-methyl-3,4-dihydroquinolin-1(2H)-yl)butyl)-7-(4-(morpholin-4-ylcarbonyl)-2-(trifluoromethyl)phenyl)-1H-indole-2-carboxylic acid;

3-(4-(6-methyl-3,4-dihydroquinolin-1(2H)-yl)butyl)-7-(4-(morpholin-4-ylcarbonyl)-2-(trifluoromethyl)phenyl)-1H-indole-2-carboxylic acid;

3-(4-(6-methoxy-3,4-dihydroquinolin-1(2H)-yl)butyl)-7-(4-(morpholin-4-ylcarbonyl)-2-(trifluoromethyl)phenyl)-1H-indole-2-carboxylic acid;

3-{4-(ethyl(1-naphthyl)amino)butyl}-7-(4-(morpholin-4-ylcarbonyl)-2-(trifluoromethyl)phenyl)-1H-indole-2-carboxylic acid;

3-(4-(2,3-dihydro-1H-indol-1-yl)butyl)-7-(4-(morpholin-4-ylcarbonyl)-2-(trifluoromethyl)phenyl)-1H-indole-2-carboxylic acid;

3-(4-(2-methyl-2,3-dihydro-1H-indol-1-yl)butyl)-7-(4-(morpholin-4-ylcarbonyl)-2-(trifluoromethyl)phenyl)-1H-indole-2-carboxylic acid;

7-(4-(morpholin-4-ylcarbonyl)-2-(trifluoromethyl)phenyl)-3-(4-(5-nitro-2,3-dihydro-1H-indol-1-yl)butyl)-1H-indole-2-carboxylic acid;

3-(4-(5-bromo-2,3-dihydro-1H-indol-1-yl)butyl)-7-(4-(morpholin-4-ylcarbonyl)-2-(trifluoromethyl)phenyl)-1H-indole-2-carboxylic acid;

3-(4-(2,3-dihydro-4H-1,4-benzoxazin-4-yl)butyl)-7-(4-(morpholin-4-ylcarbonyl)-2-(trifluoromethyl)phenyl)-1H-indole-2-carboxylic acid;

1-(tert-butoxycarbonyl)-7-(2-methylphenyl)-3-(3-(1-naphthyloxy)benzyl)-1H-indole-2-carboxylic acid;

7-(2-methylphenyl)-4-((E)-2-phenylvinyl)-1H-indole-2-carboxylic acid;

7-(2-methylphenyl)-4-(1-naphthyl)-1H-indole-2-carboxylic acid;

7-(2-methylphenyl)-4-(2-naphthyl)-1H-indole-2-carboxylic acid;

7-(2-methylphenyl)-4-(3-(2-naphthyloxy)propyl)-1H-indole-2-carboxylic acid;

7-(2-methylphenyl)-4-(4-(1-naphthyloxyl)butyl)-1H-indole-2-carboxylic acid;

7-(2-methylphenyl)-4-(4-(2-naphthyloxyl)butyl)-1H-indole-2-carboxylic acid;

7-(2-methylphenyl)-4-(2-(2-naphthyl)ethyl)-1H-indole-2-carboxylic acid;

7-(2-fluoro-5-methylpyridin-4-yl)-1-(2-morpholin-4-ylethyl)-3-(3-(1-naphthyloxy)propyl)-1H-indole-2-carboxylic acid;

1-ethyl-7-(ethyl(phenyl)amino)-3-(3-(1-naphthyloxy)propyl)-1H-indole-2-carboxylic acid;

7-(2-fluoro-5-methylpyridin-4-yl)-1-(2-(4-methylpiperazin-1-yl)ethyl)-3-(3-(1-naphthyloxy)propyl)-1H-indole-2-carboxylic acid;

3-(3-(1-naphthyloxy)propyl)-7-(phenyl(propyl)amino)-1-propyl-1H-indole-2-carboxylic acid;

1-butyl-7-(butyl(phenyl)amino)-3-(3-(1-naphthyloxy)propyl)-1H-indole-2-carboxylic acid;

7-(2-methylphenyl)-4-(2-(1-naphthyloxy)ethyl)-1H-indole-2-carboxylic acid;

7-(2-methylphenyl)-4-(2-(2-naphthyloxy)ethyl)-1H-indole-2-carboxylic acid;

4-(2-(2,3-dichlorophenoxy)ethyl)-7-(2-methylphenyl)-1H-indole-2-carboxylic acid;

4-{2-(2-chloro-3-(trifluoromethyl)phenoxy)ethyl}-7-(2-methylphenyl)-1H-indole-2-carboxylic acid;

1-methyl-3-{3-((1-methyl-1H-indol-4-yl)oxy)propyl}-7-(2-methylphenyl)-1H-indole-2-carboxylic acid;
3-bromo-7-(1,3-dimethyl-5-phenyl-1H-pyrazol-4-yl)-1H-indole-2-carboxylic acid;
3-bromo-7-{2-((E)-2-cyclohexylvinyl)-4-methylpyridin-3-yl}-1H-indole-2-carboxylic acid;
3-bromo-4-{2-((4-bromo-1-naphthyl)oxy)ethyl}-7-(2-methylphenyl)-1H-indole-2-carboxylic acid;
3-bromo-7-(2-methylphenyl)-4-(2-(1-naphthyloxy)ethyl)-1H-indole-2-carboxylic acid;
7-(2-methylphenyl)-4-(2-(1-naphthyloxy)ethyl)-3-vinyl-1H-indole-2-carboxylic acid;
7-(4,6-dimethylpyrimidin-5-yl)-1-(2-(4-methylpiperazin-1-yl)-2-oxoethyl)-3-(3-(1-naphthyloxy)propyl)-1H-indole-2-carboxylic acid;
1-(2-(dimethylamino)-2-oxoethyl)-7-(4,6-dimethylpyrimidin-5-yl)-3-(3-(1-naphthyloxy)propyl)-1H-indole-2-carboxylic acid;
7-(4,6-dimethylpyrimidin-5-yl)-1-(2-morpholin-4-ylethyl)-3-(3-(1-naphthyloxy)propyl)-1H-indole-2-carboxylic acid;
7-(4,6-dimethylpyrimidin-5-yl)-1-(2-(4-methylpiperazin-1-yl)ethyl)-3-(3-(1-naphthyloxy)propyl)-1H-indole-2-carboxylic acid;
1-(2-(dimethylamino)ethyl)-7-(4,6-dimethylpyrimidin-5-yl)-3-(3-(1-naphthyloxy)propyl)-1H-indole-2-carboxylic acid;
7-((1E)-1-ethylbut-1-enyl)-3-(3-(1-naphthyloxy)propyl)-1H-indole-2-carboxylic acid;
7-((Z)-2-carboxy-1-pentylvinyl)-3-(3-(1-naphthyloxy)propyl)-1H-indole-2-carboxylic acid;
1-(2-(dimethylamino)-2-oxoethyl)-7-(2-methylphenyl)-3-(3-(1-naphthyloxy)propyl)-1H-indole-2-carboxylic acid;
1-(2-(dimethylamino)ethyl)-7-(2-methylphenyl)-3-(3-(1-naphthyloxy)propyl)-1H-indole-2-carboxylic acid;
7-(1,2-dimethylprop-1-enyl)-3-(3-(1-naphthyloxy)propyl)-1H-indole-2-carboxylic acid;
7-bromo-3-(3-(1-naphthyloxy)propyl)-1-(pyridin-4-ylmethyl)-1H-indole-2-carboxylic acid;
3-(3-(2,3-dichlorophenoxyl)propyl)-7-(1,2-dimethylprop-1-enyl)-1H-indole-2-carboxylic acid;
6-methyl-7-(2-methylphenyl)-3-(3-(1-naphthyloxy)propyl)-1H-indole-2-carboxylic acid;
1-methyl-7-(2-methylphenyl)-3-(3-(1-naphthyloxy)propyl)-1H-indole-2-carboxylic acid;
1-methyl-7-(2-morpholin-4-ylphenyl)-3-(3-(1-naphthyloxy)propyl)-1H-indole-2-carboxylic acid;
7-(2-chlorophenyl)-3-{3-(ethyl(1-naphthyl)amino)propyl}-1H-indole-2-carboxylic acid;
7-(4-(morpholin-4-ylcarbonyl)-2-(trifluoromethyl)phenyl)-3-(4-(5-oxo-2,3,4,5-tetrahydro-1H-1-benzothiazin-1-yl)butyl)-1H-indole-2-carboxylic acid;
7-(4-(morpholin-4-ylcarbonyl)-2-(trifluoromethyl)phenyl)-3-(4-(2,3,4,5-tetrahydro-1H-1-benzazepin-1-yl)butyl)-1H-indole-2-carboxylic acid;
3-(4-(2,3-dihydro-4H-1,4-benzothiazin-4-yl)butyl)-7-(4-(morpholin-4-ylcarbonyl)-2-(trifluoromethyl)phenyl)-1H-indole-2-carboxylic acid;
3-(4-(3,4-dihydroquinolin-1(2H)-yl)butyl)-7-(2-methylphenyl)-1H-indole-2-carboxylic acid;
3-(4-(2-methyl-3,4-dihydroquinolin-1(2H)-yl)butyl)-7-(2-methylphenyl)-1H-indole-2-carboxylic acid;
3-(4-(6-methyl-3,4-dihydroquinolin-1(2H)-yl)butyl)-7-(2-methylphenyl)-1H-indole-2-carboxylic acid;
3-(4-(8-methyl-3,4-dihydroquinolin-1(2H)-yl)butyl)-7-(2-methylphenyl)-1H-indole-2-carboxylic acid;
3-(4-(2-methyl-2,3-dihydro-1H-indol-1-yl)butyl)-7-(2-methylphenyl)-1H-indole-2-carboxylic acid;
7-(2-methylphenyl)-3-(4-(2,3,4,5-tetrahydro-1H-1-benzazepin-1-yl)butyl)-1H-indole-2-carboxylic acid;
3-(4-(3-methyl-3,4-dihydroquinolin-1(2H)-yl)butyl)-7-(2-methylphenyl)-1H-indole-2-carboxylic acid;
3-{4-(3-(hydroxymethyl)-3,4-dihydroquinolin-1(2H)-yl)butyl}-7-(2-methylphenyl)-1H-indole-2-carboxylic acid;
3-(4-(2,3-dihydro-4H-1,4-benzothiazin-4-yl)butyl)-7-(2-methylphenyl)-1H-indole-2-carboxylic acid;
4-methoxy-7-(2-methylphenyl)-3-(3-(1-naphthyloxy)propyl)-1H-indole-2-carboxylic acid;
7-(2-methylphenyl)-3-(3-(1,2,3,4-tetrahydronaphthalen-1-yloxy)propyl)-1H-indole-2-carboxylic acid;
7-fluoro-3-(2-isopropylphenyl)-1-(3-(1-naphthyloxyl)propyl)-1H-indole-2-carboxylic acid;
7-fluoro-3-(2-methylphenyl)-1-(3-(1-naphthyloxy)propyl)-1H-indole-2-carboxylic acid;
7-(2-methylphenyl)-3-(3-(1-naphthyloxy)propyl)-2-(1H-tetraazol-5-yl)-1H-indole;
1-(4-methoxybenzyl)-7-(2-methylphenyl)-3-(3-(1-naphthyloxy)propyl)-2-(1H-tetraazol-5-yl)-1H-indole;
1-(2-(dimethylamino)-2-oxoethyl)-3-(3-(1-naphthyloxy)propyl)-7-(1,3,5-trimethyl-1H-pyrazol-4-yl)-1H-indole-2-carboxylic acid;
1-(2-(dimethylamino)ethyl)-3-(3-(1-naphthyloxy)propyl)-7-(1,3,5-trimethyl-1H-pyrazol-4-yl)-1H-indole-2-carboxylic acid;
1-(2-(dimethylamino)-2-oxoethyl)-7-(2-ethyl-4-methylpyridin-3-yl)-3-(3-(1-naphthyloxy)propyl)-1H-indole-2-carboxylic acid;
1-(2-(dimethylamino)ethyl)-7-(2-ethyl-4-methylpyridin-3-yl)-3-(3-(1-naphthyloxy)propyl)-1H-indole-2-carboxylic acid; and
1-(2-(dimethylamino)-2-oxoethyl)-7-(2-(1H-imidazol-1-yl)-4-methylpyridin-3-yl)-3-(3-(1-napthyloxy)propyl)-1H-indole-2-carboxylic acid.

2. A composition comprising an excipient and a therapeutically effective amount of the compound or therapeutically acceptable salt of claim 1.

* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<221> NAME/KEY: MOD_RES
<222> LOCATION: 1
<223> OTHER INFORMATION: Gly is modified with 6-FAM
<220> FEATURE:
<221> NAME/KEY: MOD_RES
<222> LOCATION: 20
<223> OTHER INFORMATION: Phe is modified with amide
<220> FEATURE:
<223> OTHER INFORMATION: Assay protein

<400> SEQUENCE: 1

Gly Glu Leu Glu Val Glu Phe Ala Thr Gln Leu Arg Arg Phe Gly Asp
1               5                   10                  15

Lys Leu Asn Phe
            20
```